US011174318B2

(12) United States Patent
Tassone

(10) Patent No.: US 11,174,318 B2
(45) Date of Patent: Nov. 16, 2021

(54) MONOCLONAL ANTIBODY TARGETING A UNIQUE SIALOGLYCOSYLATED CANCER-ASSOCIATED EPITOPE OF CD43

(71) Applicant: UNIVERSITÀ DEGLI STUDI MAGNA GRAECIA CATANZARO, Catanzaro (IT)

(72) Inventor: Pierfrancesco Tassone, Catanzaro (IT)

(73) Assignee: UNIVERSITÀ DEGLI STUDI MAGNA GRAECIA CATANZARO, Catanzaro (IT)

( * ) Notice: Subject to any disclaimer, the term of this patent is extended or adjusted under 35 U.S.C. 154(b) by 116 days.

(21) Appl. No.: 16/449,255

(22) Filed: Jun. 21, 2019

(65) Prior Publication Data

US 2020/0123268 A1   Apr. 23, 2020
US 2021/0155706 A9   May 27, 2021

Related U.S. Application Data

(63) Continuation-in-part of application No. PCT/EP2017/084482, filed on Dec. 22, 2017.

(30) Foreign Application Priority Data

Dec. 22, 2016  (DE) ..................... 10 2016 015 379.2

(51) Int. Cl.
| | |
|---|---|
| C07K 16/28 | (2006.01) |
| A61K 39/00 | (2006.01) |
| A61K 47/68 | (2017.01) |
| A61P 35/00 | (2006.01) |
| A61K 35/02 | (2015.01) |
| C07K 14/725 | (2006.01) |
| C07K 14/705 | (2006.01) |
| G01N 33/574 | (2006.01) |
| A61K 38/00 | (2006.01) |

(52) U.S. Cl.
CPC .......... *C07K 16/2896* (2013.01); *A61K 35/02* (2013.01); *A61K 47/6849* (2017.08); *A61K 47/6851* (2017.08); *A61P 35/00* (2018.01); *C07K 14/7051* (2013.01); *C07K 14/70521* (2013.01); *C07K 14/70578* (2013.01); *C07K 16/2809* (2013.01); *G01N 33/57407* (2013.01); *A61K 38/00* (2013.01); *A61K 2039/505* (2013.01); *C07K 2317/24* (2013.01); *C07K 2317/31* (2013.01); *C07K 2317/565* (2013.01); *C07K 2317/622* (2013.01); *C07K 2317/732* (2013.01); *C07K 2319/02* (2013.01); *C07K 2319/30* (2013.01); *C07K 2319/33* (2013.01)

(58) Field of Classification Search
CPC ............ C07K 16/2896; C07K 14/7051; C07K 2317/565; C07K 2317/622; A61K 47/6851; A61K 47/6849; A61K 2039/505; A61P 35/00
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 5,208,020 | A | 5/1993 | Chari et al. |
| 5,773,001 | A | 6/1998 | Hamann et al. |
| 5,965,726 | A | 10/1999 | Pavlakis et al. |
| 6,171,586 | B1 | 1/2001 | Lam et al. |
| 6,174,666 | B1 | 1/2001 | Pavlakis et al. |
| 6,291,664 | B1 | 9/2001 | Pavlakis et al. |
| 6,414,132 | B1 | 7/2002 | Pavlakis et al. |
| 6,685,940 | B2 | 2/2004 | Andya et al. |
| 6,794,498 | B2 | 9/2004 | Pavlakis et al. |
| 7,622,560 | B2 | 11/2009 | Park et al. |
| 7,745,394 | B2 | 6/2010 | Doronina et al. |
| 7,829,531 | B2 | 11/2010 | Senter et al. |

(Continued)

FOREIGN PATENT DOCUMENTS

| | | |
|---|---|---|
| EP | 1293514 B1 | 3/2003 |
| EP | 3363461 A1 | 8/2018 |

(Continued)

OTHER PUBLICATIONS

Abdollahpour-Alitappeh, M. et al., "Antibody-drug conjugates (ADCs) for cancer therapy: Strategies, challenges, and successes," Journal of Cellular Physiology, 2019, vol. 234, No. 5, pp. 5628-5642.

Agarwal, P. et al., "A Pictet-Spengler ligation for protein chemical modification," Proceedings of the National Academy of Sciences, 2013, vol. 110, No. 1, pp. 46-51.

Agarwal, P. et al., "Hydrazino-Pictet-Spengler ligation as a biocompatible method for the generation of stable protein conjugates," Bioconjugate Chemistry, 2013, vol. 24, No. 6, pp. 846-851.

(Continued)

*Primary Examiner* — Brad Duffy
*Assistant Examiner* — Cheom-Gil Cheong
(74) *Attorney, Agent, or Firm* — Fenwick & West LLP

(57) ABSTRACT

The present invention relates to a monoclonal mouse antibody produced by the hybridoma cell deposited under ICLC accession number ICLC PD n° 16001. Furthermore, the invention relates to an antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences GFTFSSFGMH (SEQ ID NO: 1), YISSGSGNFYYVDTVKG (SEQ ID NO: 43), STYYHGSRGAMDY (SEQ ID NO: 3), SASSSVSSMYWY (SEQ ID NO: 4), DTSKMAS (SEQ ID NO: 5), and QQWSSYPPIT (SEQ ID NO: 6), respectively. In addition, the invention relates to antibodies recognizing the same epitope.

20 Claims, 26 Drawing Sheets
(7 of 26 Drawing Sheet(s) Filed in Color)
Specification includes a Sequence Listing.

(56) References Cited

U.S. PATENT DOCUMENTS

| | | | |
|---|---|---|---|
| 8,163,888 | B2 | 4/2012 | Steeves et al. |
| 8,337,856 | B2 | 12/2012 | Blättler et al. |
| 8,420,081 | B2 | 4/2013 | Fraunhofer et al. |
| 8,426,555 | B2 | 4/2013 | Park et al. |
| 8,624,003 | B2 | 1/2014 | Kellogg et al. |
| 8,753,636 | B2 | 6/2014 | Park et al. |
| 8,821,865 | B2 | 9/2014 | Neu et al. |
| 8,945,865 | B2 | 2/2015 | Izumi et al. |
| 8,961,964 | B2 | 2/2015 | Liu et al. |
| 9,216,219 | B2 | 12/2015 | Cosenza et al. |
| 9,746,474 | B2 | 8/2017 | Park et al. |
| 2004/0197324 | A1 | 10/2004 | Liu et al. |
| 2005/0048549 | A1 | 3/2005 | Cao et al. |
| 2005/0074426 | A1 | 4/2005 | Corti et al. |
| 2007/0020179 | A1 | 1/2007 | Park et al. |
| 2007/0031436 | A1 | 2/2007 | Little et al. |
| 2014/0227256 | A1 | 8/2014 | Di Scala et al. |
| 2019/0002521 | A1 | 1/2019 | Maher et al. |

FOREIGN PATENT DOCUMENTS

| | | |
|---|---|---|
| WO | WO 1988/001649 A1 | 3/1988 |
| WO | WO 1990/012592 A1 | 11/1990 |
| WO | WO 1993/011161 A1 | 6/1993 |
| WO | WO 1994/004189 A1 | 3/1994 |
| WO | WO 1999/057150 A2 | 11/1999 |
| WO | WO 2004/003183 A1 | 1/2004 |
| WO | WO 2004/010957 A2 | 2/2004 |
| WO | WO 2004/067038 A1 | 8/2004 |
| WO | WO 2005/077090 A2 | 8/2005 |
| WO | WO 2005/082023 A2 | 9/2005 |
| WO | WO 2006/065533 A2 | 6/2006 |
| WO | WO 2007/030642 A2 | 3/2007 |
| WO | WO 2007/103288 A2 | 9/2007 |
| WO | WO 2009/073445 A2 | 6/2009 |
| WO | WO 2010/068759 A1 | 6/2010 |
| WO | WO 2010/138719 A1 | 12/2010 |
| WO | WO 2011/104381 A2 | 9/2011 |
| WO | WO 2012/171020 A1 | 12/2012 |
| WO | WO 2013/173337 A2 | 11/2013 |
| WO | WO 2014/008375 A1 | 1/2014 |
| WO | WO 2014/066468 A1 | 5/2014 |
| WO | WO 2014/093394 A1 | 6/2014 |
| WO | WO 2014/093640 A1 | 6/2014 |
| WO | WO 2014/160360 A1 | 10/2014 |
| WO | WO 2015/054659 A1 | 4/2015 |
| WO | WO 2015/057699 A2 | 4/2015 |
| WO | WO 2015/095755 A1 | 6/2015 |
| WO | WO 2015/123679 A1 | 8/2015 |
| WO | WO 2015/157286 A1 | 10/2015 |
| WO | WO 2015/195925 A1 | 12/2015 |
| WO | WO 2016/180941 A1 | 11/2016 |
| WO | WO 2017/015495 A1 | 1/2017 |
| WO | WO 2017/015496 A1 | 1/2017 |
| WO | WO 2017/015502 A1 | 1/2017 |
| WO | WO 2017/136623 A1 | 8/2017 |
| WO | WO 2017/160754 A1 | 9/2017 |
| WO | WO 2017/165851 A1 | 9/2017 |
| WO | WO 2018/115485 A1 | 6/2018 |

OTHER PUBLICATIONS

Arlotta, K.J et al., "Antibody and antibody derivatives as cancer therapeutics," Wiley Interdisciplinary Reviews: Nanomedicine and Nanobiotechnology, 2019, pp. e1556.

Barfield, R.M. et al., "ADC Development Using SMARTag™ Technology," Drug Development & Delivery, Apr. 2014, vol. 14, No. 3, pp. 34-41.

Bene, M.C et al., "Proposals for the immunological classification of acute leukemias. European Group for the Immunological Characterization of Leukemias (EGIL)," Leukemia, 1995, vol. 9, No. 10, pp. 1783-1786.

Bird, R.E et al., "Single-chain antigen-binding proteins," Science, 1988, vol. 242, No. 4877, pp. 423-426.

Brennan, M. et al., "Preparation of bispecific antibodies by chemical recombination of monoclonal immunoglobulin G1 fragments," Science, 1985, vol. 229, No. 4708, pp. 81-83.

Carrico, I. S. et al., "Introducing genetically encoded aldehydes into proteins," Nature Chemical Biology, 2007, vol. 3 No. 6, pp. 321-322.

Carter, P.J., "Potent antibody therapeutics by design," Nature Reviews Immunology, 2006, vol. 6, No. 5, pp. 343-357.

Cecco, L. et al., "Purification and characterization of a human sialoglycoprotein antigen expressed in immature thymocytes and fetal tissues," Tissue Antigens, 1998, vol. 51, No. 5, pp. 528-535.

Chmielewski, M. et al., "IL-12 release by engineered T cells expressing chimeric antigen receptors can effectively Muster an antigen-independent macrophage response on tumor cells that have shut down tumor antigen expression," Cancer Research, 2011, vol. 71, No. 17, pp. 5697-5706.

Chothia, C. et al., "Canonical structures for the hypervariable regions of immunoglobulins," Journal of Molecular Biology, 1987, vol. 196, No. 4, pp. 901-917.

Clackson, T et al., "Making antibody fragments using phage display libraries," Nature, Aug. 15, 1991, vol. 352, pp. 624-628.

Corvalan, J.R.F et al., "Tumour therapy with vinca alkaloids targeted by a hybrid-hybrid monoclonal antibody recognising both CEA and vinca alkaloids," International Journal of Cancer, 1988, vol. 41, pp. 22-25.

Curran, K.J. et al., "Enhancing Antitumor Efficacy of Chimeric Antigen Receptor T Cells Through Constitutive CD40L Expression," Molecular Therapy, Apr. 2015, vol. 23, No. 4, pp. 769-778.

De Laurentiis, A. et al., "Mass spectrometry-based identification of the tumor antigen UN1 as the transmembrane CD43 sialoglycoprotein," Molecular & Cellular Proteomics, 2011, vol. 10, No. 5, pp. M111-007898.

De Laurentiis, A. et al., "Partial purification and MALDI-TOF MS analysis of UN1, a tumor antigen membrane glycoprotein," International Journal of Biological Macromolecules, 2006, vol. 39, pp. 122-126.

Diamantis, N. et al., "Antibody-drug conjugates—an emerging class of cancer treatment," British Journal of Cancer, 2016, vol. 114, No. 4, pp. 362-367.

Drake, P.M. et al., "Aldehyde tag coupled with HIPS chemistry enables the production of ADCs conjugated site-specifically to different antibody regions with distinct in vivo efficacy and PK outcomes," Bioconjugate Chemistry, 2014, vol. 25, No. 7, pp. 1331-1341.

Drake, P.M. et al., "An emerging playbook for antibody-drug conjugates: lessons from the laboratory and clinic suggest a strategy for improving efficacy and safety," Current Opinion in Chemical Biology, 2015, vol. 28, pp. 174-180.

Eshhar, Z. et al., "Specific activation and targeting of cytotoxic lymphocytes through chimeric single chains consisting of antibody-binding domains and the gamma or zeta subunits of the immunoglobulin and T-cell receptors," Proceedings of the National Academy of Sciences, 1993, vol. 90, No. 2, pp. 720-724.

Fang, X. T. et al., "Efficient and inexpensive transient expression of multispecific multivalent antibodies in Expi293 cells," Biological Procedures Online, 2017, vol. 19, No. 11, pp. 1-9.

Finney, H.M. et al., "Activation of resting human primary T cells with chimeric receptors: costimulation from CD28, inducible costimulator, CD134, and CD137 in series with signals from the TCRζ chain," The Journal of Immunology, 2004, vol. 172, No. 1, pp. 104-113.

Finney, H.M. et al., "Chimeric receptors providing both primary and costimulatory signaling in T cells from a single gene product," The Journal of Immunology, 1998, vol. 161, No. 6, pp. 2791-2797.

Foster, A.E. et al., "Inducible MyD88/CD40 (iMC) Costimulation Provides Ligand-Dependent Tumor Eradication by CD123-Specific Chimeric Antigen Receptor T Cells," Blood, 2016, vol. 128, p. 4551.

Geiger, H. et al., "Age-and stage-specific regulation patterns in the hematopoietic stem cell hierarchy," Blood, 2001, vol. 98, No. 10, pp. 2966-2972.

(56) References Cited

OTHER PUBLICATIONS

Gillissen, M.A. et al., "Patient-derived antibody recognizes a unique CD43 epitope expressed on all AML and has antileukemia activity in mice," Blood Advances, Aug. 22, 2017, vol. 1, No. 19, pp. 1551-1564.

Grada, Z. et al., "TanCAR: A Novel Bispecific Chimeric Antigen Receptor for Cancer Immunotherapy," Moleculary Therapy—Nucleic Acids, 2013, vol. 2, pp. e105.

Hasegawa, K. et al., "Glycosylation Status of CD43 Protein Is Associated with Resistance of Leukemia Cells to CTL-Mediated Cytolysis," PLOS One, Mar. 24, 2016, vol. 11, No. 3, pp. e0152326.

Honda, S. et al., "A hyman hybrid hybridoma producing a bispecific monoclonal antibody that can target tumor cells for attack by Pseudomonas aeruginosa exotoxin A," Cytotechnology, 1990, vol. 4, No. 1, pp. 59-68.

Hudak. J.E. et al., "Synthesis of Heterobifunctional Protein Fusions Using Copper-Free Click Chemistry and the Aldehyde Tag," Angew. Chern. Int. Ed., 2012, vol. 51, pp. 4161-4165.

Huehls, A.M. et al., "Bispecific T-cell engagers for cancer immunotherapy," Immunology and Cell Biology, 2015, vol. 93, No. 3, pp. 290-296.

Imai, C. et al., "Chimeric receptors with 4-1BB signaling capacity provoke potent cytotoxicity against acute Tymphoblastic leukemia," Leukemia, 2004, vol. 18, No. 4, pp. 676-684.

Johnston, M.C. et al., "Antibody conjugated nanoparticles as a novel form of antibody drug conjugate chemotherapy," Drug Discovery Today: Technologies, 2018.

Kabat, E.A., et al. "Sequences of protein of immunological interest, National Institutes of Health." Public Health Service, US Department of Health and Human Services, Washington, DC (1991).

Kabat, E.A. et al., "Unusual distributions of amino acids in complementarity determining (hypervariable) segments of heavy and light chains of immunoglobulins and their possible roles in specificity of antibody-combining sites," Journal of Biological Chemistry, 1977, vol. 252, No. 19, pp. 6609-6616.

Kloss, C. et al., "Combinatorial antigen recognition with balanced signaling promotes selective tumor eradication by engineered T cells," Nature Biotechnology, 2013, vol. 31, No. 1, pp. 71-76.

Krause, A. et al., "Antigen-dependent CD28 signaling selectively enhances survival and proliferation in genetically modified activated human primary T lymphocytes," Journal of Experimental Medicine, 1998, vol. 188, No. 4, pp. 619-626.

Kutemeier, G et al., "Assembly of Humanized Antibody Genes from Synthetic Oligonucleotides Using a Single-Round PCR," BioTechniques, 1994, vol. 17, pp. 242-246.

Lambert, J.M. et al., "Antibody-drug conjugates (ADCs) for personalized treatment of solid tumors: a review," Advances in Therapy, 2017, vol. 34, No. 55, pp. 1015-1035.

Liang, S.I. et al., "A Molecular Approach for Assembling Aldehyde-Tagged Proteins on DNA Scaffolds," Journal of the American Chemical Society, 2014, vol. 136, p. 10850-10853.

Lyon, R., "Drawing lessons from the clinical development of antibody-drug conjugates," Drug Discovery Today: Technologies, 2018.

MacCallum, R.M. et al., "Antibody-antigen interactions: contact analysis and binding site topography," Journal of Molecular Biology, 1996, vol. 262, No. 5, pp. 732-745.

Maher, J. et al., "Human T-lymphocyte cytotoxicity and proliferation directed by a single chimeric TCRζ/CD28 receptor," Nature Biotechnology, 2002, vol. 20, No. 1, pp. 70-75.

Marks, J.D. et al., "By-Passing Immunization: Building High Affinity Human Antibodies By Chain Shuffling," Bio/Technology, 1992, vol. 10, pp. 779-783.

Milstein, C. et al., "Hybrid hybridomas and their use in immunohistochemistry," Nature, 1983, vol. 305, No. 5934, p. 537.

Modak, M. et al., "Engagement of distinct epitopes on CD43 induces different co-stimulatory pathways in human T cells," Immunology, 2016, vol. 149, pp. 280-296.

Orlandi, R. et al., "Cloning immunoglobulin variable domains for expression by the polymerase chain reaction," Proceedings of the National Academy of Sciences, 1989, vol. 86, No. 10, pp. 3833-3837.

Ostberg, J.R et al., "The Roman god Janus: a paradigm for the function of CD43," Immunology Today, 1998, vol. 19, No. 12, pp. 546-550.

Pastan, I. et al., "Immunotoxin treatment of cancer," Annu. Rev. Med., 2007, vol. 58, pp. 221-237.

Pegram, H.J.et al., "Tumor-targeted T cells modified to secrete IL-12 eradicate systemic tumors without need for prior conditioning," Blood, 2012, vol. 119, No. 19, pp. 4133-4141.

Pimm, M.V. et al., "A bispecific monoclonal antibody against methotrexate and a human tumour associated antigen augments cytotoxicity of methotrexate-carrier conjugate," British Journal of Cancer, 1990, vol. 61, No. 4, pp. 508-513.

Porter, D.L. et al., "Chimeric antigen receptor-modified T cells in chronic lymphoid leukemia," New England Journal of Medicine, 2011, vol. 365, No. 8, pp. 725-733.

Pulèe, M.A. et al., "A chimeric T cell antigen receptor that augments cytokine release and supports clonal expansion of primary human T cells," Molecular Therapy, 2005, vol. 12, No. 5, pp. 933-941.

Rabuka, D. et al., "Site-specific chemical protein conjugation using genetically encoded aldehyde tags," Nature Protocols, 2012, vol. 7, No. 6, p. 1052.

Rabuka, D., "Chemoenzymatic Methods for Site-Specific Protein Modification," Curr. Opin. Chem. Biol., Dec. 2010, vol. 14, No. 6, pp. 790-796.

Raso, V. et al., "Hybrid antibodies with dual specificity for the delivery of ricin to immunoglobulin-bearing target cells," Cancer Research, 1981, vol. 41, No. 6, pp. 2073-2078.

Roybal, K.T. et al., "Precision tumor recognition by T cells with combinatorial antigen-sensing circuits," Cell, 2016, vol. 164, No. 4, pp. 770-779.

Segal, D.M. et al., "Bispecific antibodies in cancer therapy," Current Opinion in Immunology, 1999, vol. 11, pp. 558-562.

Songsivilai, S. et al., "Bispecific antibody: a tool for diagnosis and treatment of disease," Clinical & Experimental Immunology, 1990, vol. 79, No. 3, pp. 315-321.

Stephan, M.T. et al., "T cell-encoded CD80 and 4-1BBL induce auto- and transcostimulation, resulting in potent tumor rejection," Nature Medicine, Dec. 2007, vol. 13, No. 12, pp. 1440-1449.

Storz, U., "Antibody-drug conjugates: Intellectual property considerations," MAbs, 2015, vol. 7., No. 6., pp. 989-1009.

Tassone, P. et al., "Differential Expression of UN1, Early Thymocyte-associated Sialoglycoprotein, in Breast Normal Tissue, Benign Disease and Carcinomas," Anticancer Research, 2022, vol. 22, pp. 2333-2340.

Tassone, P. et al., "Fetal ontogeny and tumor expression of the early thymic antigen UN1," International Journal of Oncology, 2002, vol. 20, No. 4, pp. 707-711.

Tassone, P. et al., "UN1, a murine monoclonal antibody recognizing a novel human thymic antigen," Tissue Antigens, 1994, vol. 44, No. 2, pp. 73-82.

Tuccillo, F.M. et al., "Aberrant Glycosylation as Biomarker for Cancer: Focus on CD43," BioMed Research International, 2014, pp. 1-14.

Tuccillo, F.M. et al., "Cancer-associated CD43 glycoforms as target of immunotherapy," Molecular Cancer Therapeutics, 2014, vol. 13, No. 3, pp. 752-762.

Van Spriel, A.B. et al., "Immunotherapeutic perspective for bispecific antibodies," Immunology Today, 2000, vol. 21, pp. 391-397.

Wilkie, S. et al., "Dual targeting of ErbB2 and MUC1 in breast cancer using chimeric antigen receptors engineered to provide complementary signaling," Journal of Clinical Immunology, 2012, vol. 32, No. 5, pp. 1059-1070.

Wilkie, S. et al., "Retargeting of human T cells to tumor-associated MUC1: the evolution of a chimeric antigen receptor," The Journal of Immunology, 2008, vol. 180, No. 7, pp. 4901-4909.

Wolska-Washer, A., et al., "Safety and tolerability of antibody-drug conjugates in cancer," Drug Safety, 2019, vol. 42, No. 2, pp. 295-314.

(56) References Cited

OTHER PUBLICATIONS

Wu, A.M. et al., "Arming antibodies: prospects and challenges for immunoconjugates," Nature Biotechnology, 2005, vol. 23, No. 9, pp. 1137-1146.

Wu, P. et al., "Site-specific chemical modification of recombinant proteins produced in mammalian cells by using the genetically encoded aldehyde tag," PNAS, Mar. 3, 2019, vol. 106, No. 9, pp. 3000-3005.

Xu, D. et al., "The development of CAR design for tumor CAR-T cell therapy," Oncotarget, 2018, vol. 9, No. 17, p. 13991-14004.

Yaghoubi. S. et al., "Potential drugs used in the antibody-drug conjugate (ADC) architecture for cancer therapy," Journal of Cellular Physiology, Jun. 18, 2019, pp. 1-34.

York, D. et al., "Generating aldehyde-tagged antibodies with high titers and high formylglycine yields by supplementing culture media with copper (II)," BMC Biotechnology, 2016, vol. 16, No. 1., pp. 23.

Zhao, Z. et al., "Structural design of engineered costimulation determines tumor rejection kinetics and persistence of CAR T cells," Cancer Cell, 2015, vol. 28, No. 4, pp. 415-428.

Zhukovsky, E.A. et al., "Bispecific antibodies and CARs: generalized immunotherapeutics harnessing T cell redirection," Current Opinion in Immunology, 2016, vol. 40, pp. 24-35.

Jeon, Y.K et al., "Targeting of a developmentally regulated epitope of CD43 for the treatment of acute leukemia," Cancer Immunol Immunother, vol. 60, Jun. 28, 2011, pp. 1697-1706.

PCT International Search Report and Written Opinion, PCT Application No. PCT/EP2020/067258, dated Aug. 27, 2020, 15 pages.

| | | | | 50 |
|---|---|---|---|---|
| MATLILILLGV | LVVSPDALGS | TTAVQTPTSG | EPLVSTSEPL | SSKMYTTISIT |
| 60 | 70 | 80 | 90 | 100 |
| SDPKADSTGD | QTSALPPSTS | INEGSPLWTS | IGASTGSPLP | EPTTYQEVSI |
| 110 | 120 | 130 | 140 | 150 |
| KMSSVPQETP | HATSHPAVPI | TANSLGSHTV | TGGTITTNSP | ETSSRTSGAP |
| 160 | 170 | 180 | 190 | 200 |
| VTTAASSLET | SRGTSGPPLT | MATVSLETSK | GTSGPPVTMA | TDSLETSTGT |
| 210 | 220 | 230 | 240 | 250 |
| TGPPVTMTTG | SLEPSSGASG | PQVSSVKLST | MMSPTTSTNA | STVPFRNPDE |
| 260 | 270 | 280 | 290 | 300 |
| NSRGMLPVAV | LVALLAVIVL | VALLLWRRR | QKRRTGALVL | SRGGKRNGVV |
| 310 | 320 | 330 | 340 | 350 |
| DAWAGPAQVP | EEGAVTVTVG | GSGGDKGSGF | PDGEGSSRRP | TLTTFFGRRK |
| 360 | 370 | 380 | 390 | 400 |
| SRQGSLAMEE | LKSGSGPSLK | GEEEPLVASE | DGAVDAPAPD | EPEGGDGAAP |

FIG. 15A

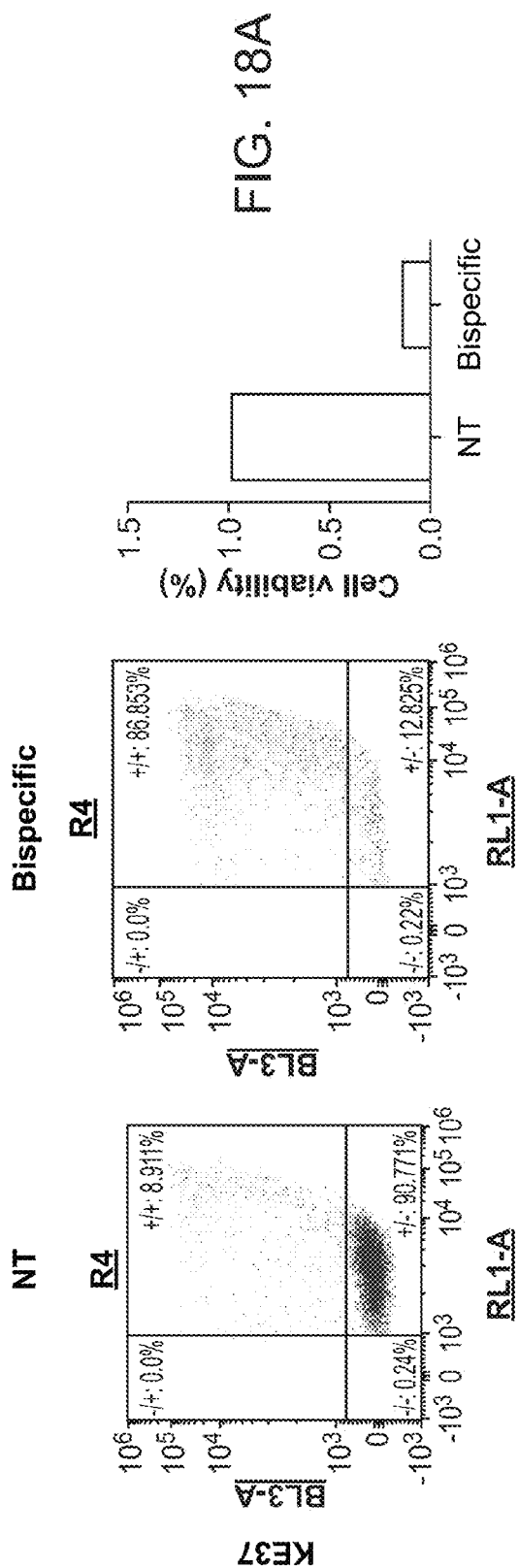
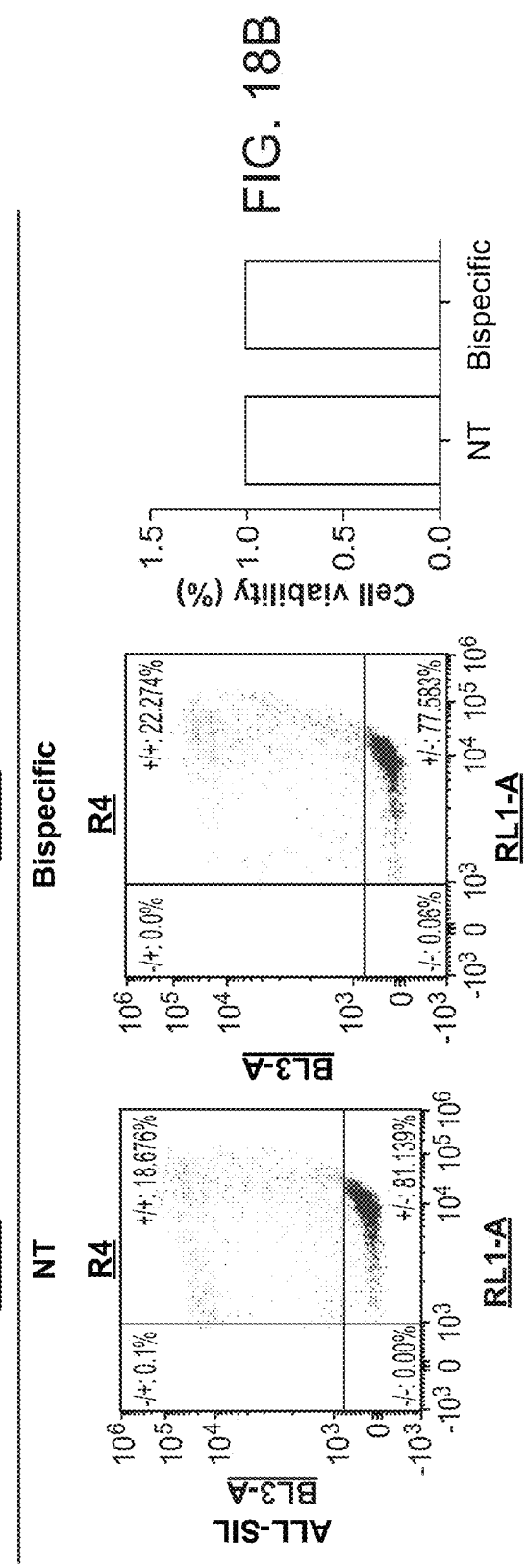
FIG. 18A
FIG. 18B

SEQUENCE LISTING

```
<160> NUMBER OF SEQ ID NOS: 45

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser Ser Phe Gly Met His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Tyr Ile Ser Ser Gly Ser Gly Asn Phe Tyr Tyr Val Asp Thr Val Lys
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Thr Tyr Tyr His Gly Ser Arg Gly Ala Met Asp Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Ser Ser Ser Val Ser Ser Met Tyr Trp Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Thr Ser Lys Met Ala Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Trp Ser Ser Tyr Pro Pro Ile Thr
1               5                   10

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Gln Leu Val Glu Ser Gly Gly Gly Leu Val Gln Pro Gly Gly
1               5                   10                  15

Ser Arg Lys Leu Ser Cys Val Ala Ser Gly Phe Thr Phe Ser Ser Phe
            20                  25                  30

Gly Met His Trp Val Arg Gln Ala Pro Glu Lys Gly Leu Glu Trp Val
        35                  40                  45
```

Ala Tyr Ile Ser Ser Gly Ser Gly Asn Phe Tyr Tyr Val Asp Thr Val
            50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                85                  90                  95

Ala Arg Ser Thr Tyr Tyr His Gly Ser Arg Gly Ala Met Asp Tyr Trp
            100                 105                 110

Gly Gln Gly Thr Ser Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ser Tyr Ile Ser Ser Gly Ser Gly Asn Phe Tyr Tyr Val Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Thr Tyr Tyr His Gly Ser Arg Gly Ala Met Asp Tyr Trp
            100                 105                 110

Gly Gln Gly Thr Leu Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ser Tyr Ile Ser Ser Gly Ser Gly Asn Phe Tyr Tyr Val Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

```
Ala Arg Ser Thr Tyr Tyr His Gly Ser Arg Gly Ala Met Asp Tyr Trp
            100                 105                 110

Gly Gln Gly Thr Leu Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Asn Phe Tyr Tyr Val Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Tyr His Gly Ser Arg Gly Ala Met Asp Tyr Trp
            100                 105                 110

Gly Gln Gly Thr Leu Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Val Val Gln Pro Gly Gly
1               5                   10                  15

Ser Leu Arg Leu Ser Cys Val Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Asn Phe Tyr Tyr Val Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Tyr His Gly Ser Arg Gly Ala Met Asp Tyr Trp
            100                 105                 110

Gly Gln Gly Thr Leu Val Thr Val Ser Ser
        115                 120

<210> SEQ ID NO 12
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ile Ala Leu Thr Gln Ser Pro Ala Ile Met Ser Ala Ser Pro Gly
1               5                   10                  15

Glu Lys Val Thr Met Thr Cys Ser Ala Ser Ser Ser Val Ser Ser Met
                20                  25                  30

Tyr Trp Tyr Gln Leu Lys Pro Gly Ser Ser Pro Arg Leu Leu Ile Tyr
            35                  40                  45

Asp Thr Ser Lys Met Ala Ser Gly Val Pro Ile Arg Phe Ser Gly Ser
        50                  55                  60

Gly Ser Gly Thr Ser Phe Ser Leu Thr Val Ser Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Ala Gly Ser Lys Leu Glu Leu Lys
                100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Met
                20                  25                  30

Tyr Trp Tyr Gln Gln Lys Pro Gly Leu Ala Pro Arg Leu Leu Ile Tyr
            35                  40                  45

Asp Thr Ser Lys Met Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Tyr Pro Pro Ile
                85                  90                  95

Thr Phe Gly Gln Gly Thr Arg Leu Glu Ile Lys
                100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Ala Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Met
                20                  25                  30
```

```
Tyr Trp Tyr Gln Leu Lys Pro Gly Leu Ala Pro Arg Leu Leu Ile Tyr
             35                  40                  45

Asp Thr Ser Lys Met Ala Ser Gly Ile Pro Ile Arg Phe Ser Gly Ser
 50                  55                  60

Gly Ser Gly Thr Asp Phe Thr Leu Thr Val Ser Arg Val Glu Pro Glu
 65                  70                  75                  80

Asp Phe Ala Val Tyr Tyr Cys Gln Gln Trp Ser Ser Tyr Pro Pro Ile
                 85                  90                  95

Thr Phe Gly Gln Gly Thr Arg Leu Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Val Met Thr Gln Ser Pro Ala Phe Leu Ser Val Thr Pro Gly
 1               5                  10                  15

Glu Lys Val Thr Ile Thr Cys Ser Ala Ser Ser Ser Val Ser Ser Met
             20                  25                  30

Tyr Trp Tyr Gln Gln Lys Pro Asp Gln Ala Pro Lys Leu Leu Ile Tyr
             35                  40                  45

Asp Thr Ser Lys Met Ala Ser Gly Val Pro Ser Arg Phe Ser Gly Ser
 50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Ser Ser Tyr Pro Pro Ile
                 85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Val Met Thr Gln Ser Pro Ala Phe Leu Ser Val Thr Pro Gly
 1               5                  10                  15

Glu Lys Val Thr Ile Thr Cys Ser Ala Ser Ser Ser Val Ser Ser Met
             20                  25                  30

Tyr Trp Tyr Gln Leu Lys Pro Asp Gln Ala Pro Lys Leu Leu Ile Tyr
             35                  40                  45

Asp Thr Ser Lys Met Ala Ser Gly Val Pro Ile Arg Phe Ser Gly Ser
 50                  55                  60

Gly Ser Gly Thr Asp Phe Thr Phe Thr Val Ser Ser Val Glu Ala Glu
 65                  70                  75                  80

Asp Ala Ala Thr Tyr Tyr Cys Gln Gln Trp Ser Ser Tyr Pro Pro Ile
                 85                  90                  95

Thr Phe Gly Gly Gly Thr Lys Val Glu Ile Lys
            100                 105
```

<210> SEQ ID NO 17
<211> LENGTH: 400
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Ala Thr Leu Leu Leu Leu Gly Val Leu Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Ala
50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
        115                 120                 125

Thr Val Thr Gly Gly Thr Ile Thr Thr Asn Ser Pro Glu Thr Ser Ser
130                 135                 140

Arg Thr Ser Gly Ala Pro Val Thr Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
        195                 200                 205

Thr Gly Ser Leu Glu Pro Ser Ser Gly Ala Ser Gly Pro Gln Val Ser
210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
        275                 280                 285

Val Leu Ser Arg Gly Gly Lys Arg Asn Gly Val Val Asp Ala Trp Ala
290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
            340                 345                 350

Gln Gly Ser Leu Ala Met Glu Glu Leu Lys Ser Gly Ser Gly Pro Ser
        355                 360                 365

Leu Lys Gly Glu Glu Pro Leu Val Ala Ser Asp Gly Ala Val
    370                 375                 380

Asp Ala Pro Ala Pro Asp Pro Glu Gly Asp Gly Ala Ala Pro
385                 390                 395                 400

<210> SEQ ID NO 18
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Pro Leu Val Ser Thr Ser Glu Pro Leu Ser Ser Lys Met Tyr Thr
1               5                   10                  15

Thr Ser Ile Thr Ser Asp Pro Lys Ala Asp Ser Thr Gly Asp Gln Thr
            20                  25                  30

Ser Ala Leu Pro Pro Ser Thr Ser Ile Asn Glu Gly Ser Pro Leu Trp
        35                  40                  45

Thr Ser Ile Gly Ala Ser Thr Gly Ser Pro Leu Pro Glu Pro Thr Thr
    50                  55                  60

Tyr Gln Glu Val Ser Ile Lys Met Ser Ser Val Pro Gln Glu Thr Pro
65                  70                  75                  80

His Ala Thr Ser His Pro Ala Val Pro Ile Thr Ala Asn Ser Leu Gly
                85                  90                  95

Ser His Thr Val Thr Gly Gly Thr Ile Thr Thr Asn Ser Pro Glu Thr
            100                 105                 110

Ser Ser Arg Thr Ser Gly Ala Pro Val Thr Thr Ala Ala Ser Ser Leu
        115                 120                 125

Glu Thr Ser Arg Gly Thr Ser Gly Pro Pro Leu Thr Met Ala Thr Val
    130                 135                 140

Ser Leu Glu Thr Ser Lys Gly Thr Ser Gly Pro Pro Val Thr Met Ala
145                 150                 155                 160

Thr Asp Ser Leu Glu Thr Ser Thr Gly Thr Thr Gly Pro Pro Val Thr
                165                 170                 175

Met Thr Thr Gly Ser Leu Glu Pro Ser Ser Gly Ala Ser Gly Pro Gln
            180                 185                 190

Val Ser Ser Val Lys Leu Ser Thr Met Met Ser Pro Thr Thr Ser Thr
        195                 200                 205

Asn Ala Ser Thr Val Pro Phe Arg Asn Pro Asp Glu Asn Ser Arg Gly
    210                 215                 220

Met Leu Pro Val Ala Val Leu Val Ala Leu Leu Ala Val Ile Val Leu
225                 230                 235                 240

Val Ala Leu Leu Leu Leu Trp Arg Arg Arg Gln Lys Arg Arg Thr Gly
                245                 250                 255

Ala Leu Val Leu Ser Arg Gly Gly Lys Arg Asn Gly Val Val Asp Ala
            260                 265                 270

Trp Ala Gly Pro Ala Gln Val Pro Glu Glu Gly Ala Val Thr Val Thr
        275                 280                 285

Val Gly Gly Ser Gly Gly Asp Lys Gly Ser Gly Phe Pro Asp Gly Glu
    290                 295                 300

Gly Ser Ser Arg Arg Pro Thr Leu Thr Thr Phe Phe Gly Arg Arg Lys
305                 310                 315                 320

Ser Arg Gln Gly Ser Leu Ala Met Glu Glu Leu Lys Ser Gly Ser Gly

```
                    325                 330                 335
Pro Ser Leu Lys Gly Glu Glu Pro Leu Val Ala Ser Glu Asp Gly
        340                 345                 350

Ala Val Asp Ala Pro Ala Pro Asp Glu Pro Glu Gly Gly Asp Gly Ala
        355                 360                 365

Ala Pro
    370

<210> SEQ ID NO 19
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Thr Ser Ala Leu Pro Pro Ser Thr Ser Ile Asn Glu Gly Ser Pro
1               5                   10                  15

Leu Trp Thr Ser Ile Gly Ala Ser Thr Gly Ser Pro Leu Pro Glu Pro
            20                  25                  30

Thr Thr Tyr Gln Glu Val Ser Ile Lys Met Ser Ser Val Pro Gln Glu
        35                  40                  45

Thr Pro His Ala Thr Ser His Pro Ala Val Pro Ile Thr Ala Asn Ser
    50                  55                  60

Leu Gly Ser His Thr Val Thr Gly Gly Thr Ile Thr Thr Asn Ser Pro
65                  70                  75                  80

Glu Thr Ser Ser Arg Thr Ser Gly Ala Pro Val Thr Thr Ala Ala Ser
                85                  90                  95

Ser Leu Glu Thr Ser Arg Gly Thr Ser Gly Pro Pro Leu Thr Met Ala
            100                 105                 110

Thr Val Ser Leu Glu Thr Ser Lys Gly Thr Ser Gly Pro Pro Val Thr
        115                 120                 125

Met Ala Thr Asp Ser Leu Glu Thr Ser Thr Gly Thr Thr Gly Pro Pro
    130                 135                 140

Val Thr Met Thr Thr Gly Ser Leu Glu Pro Ser Ser Gly Ala Ser Gly
145                 150                 155                 160

Pro Gln Val Ser Ser Val Lys Leu Ser Thr Met Met Ser Pro Thr Thr
                165                 170                 175

Ser Thr Asn Ala Ser Thr Val Pro Phe Arg Asn Pro Asp Glu Asn Ser
            180                 185                 190

Arg Gly Met Leu Pro Val Ala Val Leu Val Ala Leu Leu Ala Val Ile
        195                 200                 205

Val Leu Val Ala Leu Leu Leu Leu Trp Arg Arg Arg Gln Lys Arg Arg
    210                 215                 220

Thr Gly Ala Leu Val Leu Ser Arg Gly Gly Lys Arg Asn Gly Val Val
225                 230                 235                 240

Asp Ala Trp Ala Gly Pro Ala Gln Val Pro Glu Glu Gly Ala Val Thr
                245                 250                 255

Val Thr Val Gly Gly Ser Gly Gly Asp Lys Gly Ser Gly Phe Pro Asp
            260                 265                 270

Gly Glu Gly Ser Ser Arg Arg Pro Thr Leu Thr Thr Phe Phe Gly Arg
        275                 280                 285

Arg Lys Ser Arg Gln Gly Ser Leu Ala Met Glu Glu Leu Lys Ser Gly
    290                 295                 300
```

```
Ser Gly Pro Ser Leu Lys Gly Glu Glu Pro Leu Val Ala Ser Glu
305                 310                 315                 320

Asp Gly Ala Val Asp Ala Pro Ala Pro Asp Glu Pro Glu Gly Gly Asp
            325                 330                 335

Gly Ala Ala Pro
            340

<210> SEQ ID NO 20
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Thr Ser Ala Leu Pro Pro Ser Thr Ser Ile Asn Glu Gly Ser Pro
1               5                   10                  15

Leu Trp Thr Ser Ile Gly Ala Ser Thr Gly Ser Pro Leu Pro Glu Pro
            20                  25                  30

Thr Thr Tyr Gln Glu Val Ser Ile Lys Met Ser Ser Val Pro Gln Glu
            35                  40                  45

Thr Pro His Ala Thr Ser His Pro Ala Val Pro Ile Thr Ala Asn Ser
    50                  55                  60

Leu Gly Ser His Thr Val Thr Gly Gly Thr Ile Thr Thr Asn Ser Pro
65                  70                  75                  80

Glu Thr Ser Ser Arg Thr Ser Gly Ala Pro Val Thr Thr Ala Ala Ser
                85                  90                  95

Ser Leu Glu Thr Ser Arg Gly Thr Ser Gly Pro Pro Leu Thr Met Ala
            100                 105                 110

Thr Val Ser Leu Glu Thr Ser Lys Gly Thr Ser Gly Pro Pro Val Thr
        115                 120                 125

Met Ala Thr Asp Ser Leu Glu Thr Ser Thr Gly Thr Thr Gly Pro Pro
    130                 135                 140

Val Thr Met Thr Thr Gly Ser Leu Glu Pro Ser Ser Gly Ala Ser Gly
145                 150                 155                 160

Pro Gln Val Ser Ser Val Lys Leu Ser Thr Met Met Ser Pro Thr Thr
                165                 170                 175

Ser Thr Asn Ala Ser Thr Val Pro Phe Arg Asn Pro Asp Glu Asn Ser
            180                 185                 190

Arg Gly Met Leu Pro Val Ala Val Leu Val Ala Leu Leu Ala Val Ile
        195                 200                 205

Val Leu Val Ala Leu Leu Leu Leu Trp Arg Arg Arg Gln Lys Arg Arg
210                 215                 220

Thr Gly Ala Leu Val Leu Ser Arg Gly Gly Lys Arg Asn Gly Val Val
225                 230                 235                 240

Asp Ala Trp Ala Gly Pro Ala Gln Val Pro Glu Glu Gly Ala Val Thr
                245                 250                 255

Val Thr Val Gly Gly Ser Gly Gly Asp Lys Gly Ser Gly Phe Pro Asp
            260                 265                 270

Gly Glu Gly Ser Ser Arg Arg Pro Thr Leu Thr Thr Phe Phe Gly Arg
        275                 280                 285

Arg Lys Ser Arg Gln Gly Ser Leu Ala Met Glu Glu Leu Lys Ser Gly
    290                 295                 300

Ser Gly Pro Ser Leu Lys Gly Glu Glu Pro Leu Val Ala Ser Glu
305                 310                 315                 320
```

Asp Gly Ala Val Asp Ala Pro Ala Pro Asp Glu Pro Glu Gly Gly Asp
            325                 330                 335

Gly Ala Ala Pro
            340

<210> SEQ ID NO 21
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Pro Thr Thr Tyr Gln Glu Val Ser Ile Lys Met Ser Ser Val Pro
1               5                   10                  15

Gln Glu Thr Pro His Ala Thr Ser His Pro Ala Val Pro Ile Thr Ala
            20                  25                  30

Asn Ser Leu Gly Ser His Thr Val Thr Gly Gly Thr Ile Thr Thr Asn
        35                  40                  45

Ser Pro Glu Thr Ser Ser Arg Thr Ser Gly Ala Pro Val Thr Thr Ala
50                  55                  60

Ala Ser Ser Leu Glu Thr Ser Arg Gly Thr Ser Gly Pro Pro Leu Thr
65                  70                  75                  80

Met Ala Thr Val Ser Leu Glu Thr Ser Lys Gly Thr Ser Gly Pro Pro
                85                  90                  95

Val Thr Met Ala Thr Asp Ser Leu Glu Thr Ser Thr Gly Thr Thr Gly
            100                 105                 110

Pro Pro Val Thr Met Thr Thr Gly Ser Leu Glu Pro Ser Ser Gly Ala
        115                 120                 125

Ser Gly Pro Gln Val Ser Ser Val Lys Leu Ser Thr Met Met Ser Pro
130                 135                 140

Thr Thr Ser Thr Asn Ala Ser Thr Val Pro Phe Arg Asn Pro Asp Glu
145                 150                 155                 160

Asn Ser Arg Gly Met Leu Pro Val Ala Val Leu Val Ala Leu Leu Ala
                165                 170                 175

Val Ile Val Leu Val Ala Leu Leu Leu Leu Trp Arg Arg Arg Gln Lys
            180                 185                 190

Arg Arg Thr Gly Ala Leu Val Leu Ser Arg Gly Gly Lys Arg Asn Gly
        195                 200                 205

Val Val Asp Ala Trp Ala Gly Pro Ala Gln Val Pro Glu Glu Gly Ala
210                 215                 220

Val Thr Val Thr Val Gly Gly Ser Gly Gly Asp Lys Gly Ser Gly Phe
225                 230                 235                 240

Pro Asp Gly Glu Gly Ser Ser Arg Arg Pro Thr Leu Thr Thr Phe Phe
                245                 250                 255

Gly Arg Arg Lys Ser Arg Gln Gly Ser Leu Ala Met Glu Glu Leu Lys
            260                 265                 270

Ser Gly Ser Gly Pro Ser Leu Lys Gly Glu Glu Glu Pro Leu Val Ala
        275                 280                 285

Ser Glu Asp Gly Ala Val Asp Ala Pro Ala Pro Asp Glu Pro Glu Gly
290                 295                 300

Gly Asp Gly Ala Ala Pro
305                 310

```
<210> SEQ ID NO 22
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

Met Ala Thr Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Thr
50                  55                  60

Ser Ile Gly Ala Ser Thr Gly Ser Pro Leu Pro Glu Pro Thr Thr Tyr
65                  70                  75                  80

Gln Glu Val Ser Ile Lys Met Ser Ser Val Pro Gln Glu Thr Pro His
                85                  90                  95

Ala Thr Ser His Pro Ala Val Pro Ile Thr Ala Asn Ser Leu Gly Ser
            100                 105                 110

His Thr Val Thr Gly Gly Thr Ile Thr Thr Asn Ser Pro Glu Thr Ser
        115                 120                 125

Ser Arg Thr Ser Gly Ala Pro Val Thr Thr Ala Ala Ser Ser Leu Glu
130                 135                 140

Thr Ser Arg Gly Thr Ser Gly Pro Pro Leu Thr Met Ala Thr Val Ser
145                 150                 155                 160

Leu Glu Thr Ser Lys Gly Thr Ser Gly Pro Pro Val Thr Met Ala Thr
                165                 170                 175

Asp Ser Leu Glu Thr Ser Thr Gly Thr Thr Gly Pro Pro Val Thr Met
            180                 185                 190

Thr Thr Gly Ser Leu Glu Pro Ser Ser Gly Ala Ser Gly Pro Gln Val
        195                 200                 205

Ser Ser Val Lys Leu Ser Thr Met Met Ser Pro Thr Thr Ser Thr Asn
210                 215                 220

Ala Ser Thr Val Pro Phe Arg Asn Pro Asp Glu Asn Ser Arg Gly Met
225                 230                 235                 240

Leu Pro Val Ala Val Leu Val Ala Leu Leu Ala Val Ile Val Leu Val
                245                 250                 255

Ala Leu Leu Leu Leu Trp Arg Arg Arg Gln Lys Arg Arg Thr Gly Ala
            260                 265                 270

Leu Val Leu Ser Arg Gly Gly Lys Arg Asn Gly Val Val Asp Ala Trp
        275                 280                 285

Ala Gly Pro Ala Gln Val Pro Glu Glu Gly Ala Val Thr Val Thr Val
290                 295                 300

Gly Gly Ser Gly Gly Asp Lys Gly Ser Gly Phe Pro Asp Gly Glu Gly
305                 310                 315                 320

Ser Ser Arg Arg Pro Thr Leu Thr Thr Phe Phe Gly Arg Arg Lys Ser
                325                 330                 335

Arg Gln Gly Ser Leu Ala Met Glu Glu Leu Lys Ser Gly Ser Gly Pro
            340                 345                 350

Ser Leu Lys Gly Glu Glu Glu Pro Leu Val Ala Ser Glu Asp Gly Ala
        355                 360                 365

```
Val Asp Ala Pro Ala Pro Asp Glu Pro Glu Gly Gly Asp Gly Ala Ala
            370                 375                 380

Pro
385

<210> SEQ ID NO 23
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Thr Leu Leu Leu Leu Gly Val Leu Val Ser Pro Asp
1               5                   10                  15

Ala Leu Gly Ser Thr Thr Ala Val Gln Thr Pro Thr Ser Gly Glu Pro
                20                  25                  30

Leu Val Ser Thr Ser Glu Pro Leu Ser Ser Lys Met Tyr Thr Thr Ser
            35                  40                  45

Ile Thr Ser Asp Pro Lys Ala Asp Ser Thr Gly Asp Gln Thr Ser Ala
        50                  55                  60

Leu Pro Pro Ser Ser Ile Asn Glu Gly Ser Pro Leu Trp Thr Ser Ile
65                  70                  75                  80

Gly Ala Ser Thr Gly Ser Pro Leu Pro Glu Pro Thr Thr Tyr Gln Glu
                85                  90                  95

Val Ser Ile Lys Met Ser Ser Val Pro Gln Glu Thr Pro His Ala Thr
            100                 105                 110

Ser His Pro Ala Val Pro Ile Thr Ala Asn Ser Leu Gly Ser His Thr
        115                 120                 125

Val Thr Gly Gly Thr Ile Thr Thr Asn Ser Pro Glu Thr Ser Ser Arg
130                 135                 140

Thr Ser Gly Ala Pro Val Thr Thr Ala Ala Ser Ser Leu Glu Thr Ser
145                 150                 155                 160

Arg Gly Thr Ser Gly Pro Pro Leu Thr Met Ala Thr Val Ser Leu Glu
                165                 170                 175

Thr Ser Lys Gly Thr Ser Gly Pro Pro Val Thr Met Ala Thr Asp Ser
            180                 185                 190

Leu Glu Thr Ser Thr Gly Thr Thr Gly Pro Pro Val Thr Met Thr Thr
        195                 200                 205

Gly Ser Leu Glu Pro Ser Ser Gly Ala Ser Gly Pro Gln Val Ser Ser
210                 215                 220

Val Lys Leu Ser Thr Met Met Ser Pro Thr Thr Ser Thr Asn Ala Ser
225                 230                 235                 240

Thr Val Pro Phe Arg Asn Pro Asp Glu Asn Ser Arg Gly Met Leu Pro
                245                 250                 255

Val Ala Val Leu Val Ala Leu Leu Ala Val Ile Val Leu Val Ala Leu
            260                 265                 270

Leu Leu Leu Trp Arg Arg Arg Gln Lys Arg Arg Thr Gly Ala Leu Val
        275                 280                 285

Leu Ser Arg Gly Gly Lys Arg Asn Gly Val Val Asp Ala Trp Ala Gly
290                 295                 300

Pro Ala Gln Val Pro Glu Glu Gly Ala Val Thr Val Thr Val Gly Gly
305                 310                 315                 320

Ser Gly Gly Asp Lys Gly Ser Gly Phe Pro Asp Gly Glu Gly Ser Ser
                325                 330                 335
```

```
Arg Arg Pro Thr Leu Thr Thr Phe Phe Gly Arg Arg Lys Ser Arg Gln
            340                 345                 350

Gly Ser Leu Ala Met Glu Glu Leu Lys Ser Gly Ser Gly Pro Ser Leu
            355                 360                 365

Lys Gly Glu Glu Glu Pro Leu Val Ala Ser Asp Gly Ala Val Asp
            370                 375                 380

Ala Pro Ala Pro Asp Glu Pro Glu Gly Gly Asp Gly Ala Ala Pro
385                 390                 395

<210> SEQ ID NO 24
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Thr Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
            35                  40                  45

Ile Thr Ser Asp Pro Lys Ala Asp Ser Thr Gly Asp Gln Thr Ser Ala
        50                  55                  60

Leu Pro Pro Ser Asn Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
            115                 120                 125

Thr Val Thr Gly Gly Thr Ile Thr Thr Asn Ser Pro Glu Thr Ser Ser
130                 135                 140

Arg Thr Ser Gly Ala Pro Val Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
            195                 200                 205

Thr Gly Ser Leu Glu Pro Ser Ser Gly Ala Ser Gly Pro Gln Val Ser
        210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
            275                 280                 285

Val Leu Ser Arg Gly Gly Lys Arg Asn Gly Val Val Asp Ala Trp Ala
```

```
                  290                 295                 300
Gly Pro Ala Gln Val Pro Glu Glu Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
                340                 345                 350

Gln Gly Ser Leu Ala Met Glu Glu Leu Lys Ser Gly Ser Gly Pro Ser
                355                 360                 365

Leu Lys Gly Glu Glu Glu Pro Leu Val Ala Ser Glu Asp Gly Ala Val
                370                 375                 380

Asp Ala Pro Ala Pro Asp Glu Pro Glu Gly Gly Asp Gly Ala Ala Pro
385                 390                 395                 400

<210> SEQ ID NO 25
<211> LENGTH: 1203
<212> TYPE: DNA
<213> ORGANISM: Homo sapiens

<400> SEQUENCE: 25
atggccacgc ttctccttct ccttggggtg ctggtggtaa gcccagacgc tctggggagc      60
acaacagcag tgcagacacc cacctccgga gagccttggg tctctactag cgagcccctg     120
agctcaaaga tgtacaccac ttcaataaca agtgacccta aggccgacag cactggggac     180
cagacctcag ccctacctcc ctcaacttcc atcaatgagg atccccttct ttggacttcc     240
attggtgcca gcactggttc cccttttacct gagccaacaa cctaccagga agtttccatc     300
aagatgtcat cagtgcccca ggaaaccccct catgcaacca gtcatcctgc tgttcccata     360
acagcaaact ctctaggatc ccacaccgtg acaggtggaa ccataacaac gaactctcca     420
gaaacctcca gtaggaccag tggagcccct gttaccacgg cagctagctc tctggagacc     480
tccagaggca cctctggacc ccctcttacc atggcaactg tctctctgga acttccaaa      540 ggcacctctg accccctgt taccatggca actgactctc tggagacctc cactgggacc     600 actggaccc ctgttaccat gacaactggc tctctggagc cctccagcgg ggccagtgga     660
ccccaggtct ctagcgtaaa actatctaca atgatgtctc caacgacctc caccaacgca     720
agcactgtgc ccttccggaa cccagatgag aactcacgag gcatgctgcc agtggctgtg     780
cttgtggccc tgctggcggt catagtcctc gtggctctgc tcctgctgtg gcgccggcgg     840
cagaagcggc ggactggggc cctcgtgctg agcagaggcg gcaagcgtaa cggggtggtg     900
gacgcctggg ctgggccagc ccaggtccct gaggaggggg ccgtgacagt gaccgtggga     960
gggtccgggg gcgacaaggg ctctgggttc cccgatgggg aggggtctag ccgtcggccc    1020
acgctcacca ctttctttgg cagacggaag tctcgccagg ctccctggc gatggaggag    1080 ctgaagtctg ggtcaggccc cagcctcaaa ggggaggagg agccactggt ggccagtgag    1140
gatggggctg tggacgcccc agctcctgat gagcccgaag ggggagacgg ggctgccct     1200 taa                                                                  1203

<210> SEQ ID NO 26
<211> LENGTH: 400
<212> TYPE: PRT
<213> ORGANISM: Homo sapiens

<400> SEQUENCE: 26

Met Ala Thr Leu Leu Leu Leu Leu Gly Val Leu Val Val Ser Pro Asp
```

```
  1               5                   10                  15
Ala Leu Gly Ser Thr Thr Ala Val Gln Thr Pro Thr Ser Gly Glu Pro
                 20                  25                  30

Leu Val Ser Thr Ser Glu Pro Leu Ser Ser Lys Met Tyr Thr Thr Ser
                 35                  40                  45

Ile Thr Ser Asp Pro Lys Ala Asp Ser Thr Gly Asp Gln Thr Ser Ala
 50                  55                  60

Leu Pro Pro Ser Thr Ser Ile Asn Glu Gly Ser Pro Leu Trp Thr Ser
 65                  70                  75                  80

Ile Gly Ala Ser Thr Gly Ser Pro Leu Pro Glu Pro Thr Thr Tyr Gln
                 85                  90                  95

Glu Val Ser Ile Lys Met Ser Ser Val Pro Gln Glu Thr Pro His Ala
                100                 105                 110

Thr Ser His Pro Ala Val Pro Ile Thr Ala Asn Ser Leu Gly Ser His
                115                 120                 125

Thr Val Thr Gly Gly Thr Ile Thr Thr Asn Ser Pro Glu Thr Ser Ser
                130                 135                 140

Arg Thr Ser Gly Ala Pro Val Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
                180                 185                 190

Ser Leu Glu Thr Ser Thr Gly Thr Thr Gly Pro Pro Val Thr Met Thr
                195                 200                 205

Thr Gly Ser Leu Glu Pro Ser Ser Gly Ala Ser Gly Pro Gln Val Ser
                210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
                260                 265                 270

Leu Leu Leu Leu Trp Arg Arg Arg Gln Lys Arg Arg Thr Gly Ala Leu
                275                 280                 285

Val Leu Ser Arg Gly Gly Lys Arg Asn Gly Val Val Asp Ala Trp Ala
                290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
                340                 345                 350

Gln Gly Ser Leu Ala Met Glu Glu Leu Lys Ser Gly Ser Gly Pro Ser
                355                 360                 365

Leu Lys Gly Glu Glu Glu Pro Leu Val Ala Ser Glu Asp Gly Ala Val
                370                 375                 380

Asp Ala Pro Ala Pro Asp Glu Pro Glu Gly Gly Asp Gly Ala Ala Pro
385                 390                 395                 400

<210> SEQ ID NO 27
<211> LENGTH: 1437
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 27

| | | | | | |
|---|---|---|---|---|---|
| gcggccgcca | tgaattttgg | actgaggctg | attttcctgg | tgctgaccct | gaaaggcgtc | 60 |
| cagtgtgacg | tgcagctggt | cgagagtggc | ggagggctgg | tgcagcccgg | tggcagccga | 120 |
| aagctgtctt | gcgtcgctag | tggtttcacc | ttttccagct | tcggcatgca | ctgggtgagg | 180 |
| caggcacctg | agaaaggact | ggaatgggtc | gcctacatct | ctagtggaag | cgggaacttc | 240 |
| tactatgtgg | acactgtcaa | ggggaggttt | accatttctc | gggataaccc | aaaaaataca | 300 |
| ctgtttctgc | aaatgacttc | actgagatcc | gaagacaccg | ccatgtacta | ttgtgctaga | 360 |
| tcaacatact | accacggctc | cagggggcgct | atggactatt | ggggtcaggg | cacctctgtg | 420 |
| acagtctcga | gcgctagcac | aaagggccct | agtgtgtttc | ctctggctcc | ctcttccaaa | 480 |
| tccacttctg | gtggcactgc | tgctctggga | tgcctggtga | aggattactt | tcctgaacct | 540 |
| gtgactgtct | catggaactc | tggtgctctg | acttctggtg | tccacacttt | ccctgctgtg | 600 |
| ctgcagtcta | gtggactgta | ctctctgtca | tctgtggtca | ctgtgccctc | ttcatctctg | 660 |
| ggaacccaga | cctacatttg | taatgtgaac | cacaaaccat | ccaacactaa | agtggacaaa | 720 |
| aaagtggaac | ccaaatcctg | tgacaaaacc | cacacctgcc | caccttgtcc | tgcccctgaa | 780 |
| ctgctgggag | gaccttctgt | gtttctgttc | ccccccaaac | caaggatac | cctgatgatc | 840 |
| tctagaaccc | ctgaggtgac | atgtgtggtg | gtggatgtgt | ctcatgagga | ccctgaggtc | 900 |
| aaattcaact | ggtacgtgga | tggagtggaa | gtccacaatg | ccaaaaccaa | gcctagagag | 960 |
| gaacagtaca | attcaaccta | cagagtggtc | agtgtgctga | ctgtgctgca | tcaggattgg | 1020 |
| ctgaatggca | aggaatacaa | gtgtaaagtc | tcaaacaagg | ccctgcctgc | tccaattgag | 1080 |
| aaaacaatct | caaaggccaa | gggacagcct | agggaacccc | aggtctacac | cctgccacct | 1140 |
| tcaagagagg | aaatgaccaa | aaaccaggtg | tccctgacat | gctggtcaa | aggcttctac | 1200 |
| ccttctgaca | ttgctgtgga | gtgggagtca | aatggacagc | ctgagaacaa | ctacaaaaca | 1260 |
| accccccctg | tgctggattc | tgatggctct | ttctttctgt | actccaaact | gactgtggac | 1320 |
| aagtctagat | ggcagcaggg | gaatgtcttt | tcttgctctg | tcatgcatga | ggctctgcat | 1380 |
| aaccactaca | ctcagaaatc | cctgtctctg | tctcccggga | aatgatagta | aaagctt | 1437 |

<210> SEQ ID NO 28
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

| | | | | | |
|---|---|---|---|---|---|
| gcggccgcca | tgaattttgg | actgaggctg | attttcctgg | tgctgaccct | gaaaggcgtc | 60 |
| cagtgtcaga | tcgccctgac | ccagagtcct | gcaattatgt | cagcctcccc | gggcgagaag | 120 |
| gtgaccatga | catgctccgc | ttccagctct | gtcagttcaa | tgtactggta | tcagctgaag | 180 |
| cccggctcct | cccccaggct | gctgatctac | gacacaagca | aaatggcatc | tggcgtgccc | 240 |
| attcggttca | gcggctctgg | aagtgggact | tcatttttccc | tgaccgtgtc | cagagtcgag | 300 |
| gctgaagatg | ccgctacata | ctattgtcag | cagtggtcta | gttatccccc | tatcactttc | 360 |
| ggtgcaggca | gcaagctcga | gctgaaacgt | acggtcgcgg | cgccttctgt | gttcattttc | 420 |

| | | |
|---|---|---|
| cccccatctg atgaacagct gaaatctggc actgcttctg tggtctgtct gctgaacaac | 480 | |
| ttctacccta gagaggccaa agtccagtgg aaagtggaca atgctctgca gagtgggaat | 540 | |
| tcccaggaat ctgtcactga gcaggactct aaggatagca catactccct gtcctctact | 600 | |
| ctgacactga gcaaggctga ttacgagaaa cacaaagtgt acgcctgtga agtcacacat | 660 | |
| caggggctgt ctagtcctgt gaccaaatcc ttcaataggg gagagtgctg atagtaaaag | 720 | |
| ctt | 723 | |

<210> SEQ ID NO 29
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

| | | |
|---|---|---|
| gcggccgcca tgaattttgg actgaggctg attttcctgg tgctgaccct gaaaggcgtc | 60 | |
| cagtgtgagg tgcagctggt ggaatctggc ggagggctgg tgcagcccgg tggcagcctg | 120 | |
| agactgtctt gcgtcgccag tggattcacc ttttccagct tcgggatgca ctgggtcagg | 180 | |
| caggcacctg gaaaggggct ggagtgggtg gcctacatct ctagtggttc cggcaacttc | 240 | |
| tactatgtgg acactgtcaa gggcaggttt accattagcc gggataacgc taaaaattct | 300 | |
| ctgtatctgc aaatgaatag tctgagagcc gaagacacag ccgtgtacta ttgtgctaga | 360 | |
| tcaacttact atcatggttc ccgcggcgca atggattact ggggacaggg gaccctggtg | 420 | |
| acagtctcga gcgctagcac aaagggccct agtgtgtttc ctctggctcc ctcttccaaa | 480 | |
| tccacttctg gtggcactgc tgctctggga tgcctggtga aggattactt tcctgaacct | 540 | |
| gtgactgtct catggaactc tggtgctctg acttctggtg tccacacttt ccctgctgtg | 600 | |
| ctgcagtcta gtggactgta ctctctgtca tctgtggtca ctgtgccctc ttcatctctg | 660 | |
| ggaacccaga cctacatttg taatgtgaac cacaaaccat ccaacactaa agtggacaaa | 720 | |
| aaagtggaac ccaaatcctg tgacaaaacc cacacctgcc cacccttgtcc tgccctgaa | 780 | |
| ctgctgggag gaccttctgt gtttctgttc cccccaaaac caaggatac cctgatgatc | 840 | |
| tctagaaccc ctgaggtgac atgtgtggtg gtggatgtgt ctcatgagga ccctgaggtc | 900 | |
| aaattcaact ggtacgtgga tggagtggaa gtccacaatg ccaaaaccaa gcctagagag | 960 | |
| gaacagtaca attcaaccta cagagtggtc agtgtgctga ctgtgctgca tcaggattgg | 1020 | |
| ctgaatggca aggaatacaa gtgtaaagtc tcaaacaagg ccctgcctgc tccaattgag | 1080 | |
| aaaacaatct caaaggccaa gggacagcct agggaacccc aggtctacac cctgccacct | 1140 | |
| tcaagagagg aaatgaccaa aaaccaggtg tccctgacat gcctggtcaa aggcttctac | 1200 | |
| ccttctgaca ttgctgtgga gtgggagtca atggacagc tgagaacaa ctacaaaaca | 1260 | |
| accccccctg tgctggattc tgatggctct ttctttctgt actccaaact gactgtggac | 1320 | |
| aagtctagat ggcagcaggg gaatgtcttt tcttgctctg tcatgcatga ggctctgcat | 1380 | |
| aaccactaca ctcagaaatc cctgtctctg tctcccggga atgatagta aaagctt | 1437 | |

<210> SEQ ID NO 30
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
gcggccgcca tgaattttgg actgaggctg attttcctgg tgctgaccct gaaaggcgtc    60
cagtgtcagg tggtcatgac ccagtctcct gctttcctgt ccgtgacacc gggcgagaag   120
gtcaccatca catgctccgc atccagctct gtcagttcaa tgtactggta tcagctgaag   180
ccagaccagg cacccaaact gctgatctac gatacatcta aaatggccag tggcgtcccc   240
attaggttct cgggatcggg gagcggaact gacttcactt ttaccgtgtc gagcgtcgag   300
gccgaagatg ccgctaccta ctattgtcag cagtggtcta gttatccccc tatcacattt   360
ggcggaggga ctaaggtgga gattaagcgt acggtcgcgg cgccttctgt gttcattttc   420
cccccatctg atgaacagct gaaatctggc actgcttctg tggtctgtct gctgaacaac   480
ttctacccta gagaggccaa agtccagtgg aaagtggaca atgctctgca gagtgggaat   540
tcccaggaat ctgtcactga gcaggactct aaggatagca catactccct gtcctctact   600
ctgacactga gcaaggctga ttacgagaaa cacaaagtgt acgcctgtga agtcacacat   660
caggggctgt ctagtcctgt gaccaaatcc ttcaataggg agagtgctg atagtaaaag    720
ctt                                                                 723
```

<210> SEQ ID NO 31
<211> LENGTH: 1414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gcggccgcca tgaattttgg actgaggctg attttcctgg tgctgaccct gaaaggcgtc    60
cagtgtgacg tgcagctggt cgagagtggc ggagggctgg tgcagcccgg tggcagccga   120
aagctgtctt gcgtcgctag tggtttcacc ttttccagct tcggcatgca ctgggtgagg   180
caggcacctg agaaaggact ggaatgggtc gcctacatct ctagtggaag cgggaacttc   240
tactatgtgg acactgtcaa ggggaggttt accatttctc gggataaccc aaaaaataca   300
ctgtttctgc aaatgacttc actgagatcc gaagacaccg ccatgtacta ttgtgctaga   360
tcaacatact accacggctc caggggcgct atggactatt ggggtcaggg cacctctgtg   420
acagtctcga gcgcaaaaac aaccccctcca agcgtctacc ccctggcgcc tgggagcgcg   480
gcgcagacga actcgatggt cacgttgggg tgcctcgtca agggatattt cccggagcca   540
gtcacggtca cgtggaactc ggggagcctg tcgagcggcg tccacacgtt cccggcagtc   600
ctgcaaagcg acctgtacac gctgagctcg tcagtcacgg tcccgagctc gacgtggccg   660
tcggagacgg tcacgtgcaa cgtggcgcac ccggcgagct cgacgaaagt ggacaagaag   720
atcgtgccgc gggactgcgg gtgcaagcca tgcatatgca cggtcccgga agtgtcgagc   780
gtgttcatct cccgccgaa gccgaaggac gtgctgacga tcacgctgac gccgaaagtc   840
acgtgcgtcg tcgtagacat ctcgaaggac gacccggaag tccagttctc gtggttcgtc   900
gacgacgtgg aagtccacac ggcgcagacg cagccgcggg aggagcagtt caactcgacg   960
ttcaggagcg tgtcggagct gccgatcatg caccaggact ggctgaacgg gaaggagttc  1020
aagtgccgcg tcaactcggc ggcgttccca gcgccaattg agaagacgat ctcgaagacg  1080
aaggggcggc cgaaagcgcc gcaagtctac acgatcccgc cgccgaagga gcagatggcg  1140
aaggacaaag tctcgctgac gtgcatgatc acggacttct tcccggagga catcacggtc  1200
```

```
gagtggcagt ggaacgggca gcctgcagag aactacaaga acacgcagcc gatcatggac    1260
acggacggga gctacttcgt gtactcgaag ctgaacgtgc agaagtcgaa ctgggaggcg    1320
gggaacacgt tcacgtgctc agtcctgcac gaggggctgc acaaccacca cacggagaag    1380
agcctgtcgc actcgcccgg gaaatgataa gctt                                1414
```

<210> SEQ ID NO 32
<211> LENGTH: 718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gcggccgcca tgaattttgg actgaggctg attttcctgg tgctgaccct gaaaggcgtc     60
cagtgtcaga tcgccctgac ccagagtcct gcaattatgt cagcctcccc gggcgagaag    120
gtgaccatga catgctccgc ttccagctct gtcagttcaa tgtactggta tcagctgaag    180
cccggctcct cccccaggct gctgatctac gacacaagca aaatggcatc tggcgtgccc    240
attcggttca gcggctctgg aagtgggact tcatttcccc tgaccgtgtc cagagtcgag    300
gctgaagatg ccgctacata ctattgtcag cagtggtcta gttatccccc tatcactttc    360
ggtgcaggca gcaagctcga gctgaaacgg gctgacgcgg cgcctacagt ctccattttt    420
ccacctagta gcgaacagct gacatccggg ggggcttccg tcgtctgctt tctgaacaac    480 tttttacccca aggacatcaa cgtgaagtgg aaaattgatg gctccgagag cagaacggga    540
gtcctgaatt cttggaccga ccaggattct aaggacagta catattcaat gtccagcacc    600
ctgacactga ctaaagatga gtacgaacgg cacaatagct ataccctgcga ggcaaccccat    660 aaaacaagca caagcccaat cgtcaaatcc ttcaaccgta atgagtgttg ataagctt      718
```

<210> SEQ ID NO 33
<211> LENGTH: 2209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gcggccgcca tgaattttgg actgaggctg attttcctgg tgctgaccct gaaaggcgtc     60
cagtgtgagg tgcagctggt ggaatctggc ggagggctgg tgcagcccgg tggcagcctg    120
agactgtctt gcgtcgccag tggattcacc ttttccagct tcgggatgca ctgggtcagg    180
caggcacctg gaaaggggct ggagtgggtg gcctacatct ctagtggttc cggcaacttc    240
tactatgtgg acactgtcaa gggcaggttt accattagcc gggataacgc taaaaattct    300
ctgtatctgc aaatgaatag tctgagagcc gaagacacag ccgtgtacta ttgtgctaga    360
tcaacttact atcatggttc ccgcggcgca atggattact ggggacaggg gaccctggtg    420
acagtctcga gcgctagcac aaagggcccc agtgtgtttc ctctggctcc ctcttccaaa    480
tccacttctg gtggcactgc tgctctggga tgcctggtga aggattactt tcctgaacct    540
gtgactgtct catggaactc tggtgctctg acttctggtg tccacacttt ccctgctgtg    600
ctgcagtcta gtggactgta ctctctgtca tctgtggtca ctgtgccctc ttcatctctg    660
ggaacccaga cctacatttg taatgtgaac cacaaaccat ccaacactaa agtggacaaa    720
```

```
aaagtggaac ccaaatcctg tgacaaaacc cacacctgcc caccttgtcc tgcccctgaa      780
ctgctgggag gaccttctgt gtttctgttc ccaccaaaac caaagatacc cctgatgatc      840
tctagaaccc ctgaggtgac atgtgtggtg gtggatgtgt ctcatgagga ccctgaggtc      900
aaattcaact ggtacgtgga tggagtggaa gtccacaatg ccaaaaccaa gcctagagag      960
gaacagtaca attcaaccta cagagtggtc agtgtgctga ctgtgctgca tcaggattgg     1020
ctgaatggca aggaatacaa gtgtaaagtc tcaaacaagg ccctgcctgc tccaattgag     1080
aaaacaatct caaaggccaa gggacagcct agggaacccc aggtctacac cctgccacct     1140
tcaagagagg aaatgaccaa aaaccaggtg tccctgacat gcctggtcaa aggcttctac     1200
ccttctgaca ttgctgtgga gtgggagtca atggacagc ctgagaacaa ctacaaaaca      1260
accccccctg tgctggattc tgatggctct ttctttctgt actccaaact gactgtggac     1320
aagtctagat ggcagcaggg gaatgtcttt tcttgctctg tcatgcatga ggctctgcat     1380
aaccactaca ctcagaaatc cctgtctctg tctcctggca aaggcggcgg aggatccggg     1440 ggtggggaa gcggcggagg aggtagcgac atcaaactgc agcagagtgg agccgaactg     1500
gctagacctg gtgcttctgt gaaaatgtcc tgtaaaacct ccggttacac ctttacccgg     1560
tacacaatgc attgggtgaa acagaggcct ggacaggggc tggaatggat cggatacatc     1620
aaccctagtc ggggatacac aaactacaac cagaaattca agacaaggc caccctgaca     1680 accgacaaat cttcttctac tgcctacatg cagctgtcat ctctgacttc cgaggatagt     1740
gccgtctact actgtgctcg gtactacgat gatcattact gtctggacta ctggggccag     1800
ggaacaacac ttaccgtttc tagcgtcgag ggcggatctg gcggtagcgg tggatctgga     1860
ggctctggag gagtggatga tatccagctg acccagtctc ctgctatcat gtccgcttca     1920
cctggcgaaa aagtgaccat gacctgccgt gcttcatctt ccgtgtcata catgaattgg     1980
taccagcaga atctggcac atctcccaaa cgatggatct acgacacctc aaaagtcgct     2040
agtggcgtgc cttaccgttt ctccggttcc ggatctggaa catcatactc cctgaccatc     2100
tcttctatgg aggctgagga tgctgccaca tactactgtc agcagtggag tagcaatcct     2160
ctgacctttg gtgctgggac aaaactggag ctgaaatgat aagctttga                 2209
```

<210> SEQ ID NO 34
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Asp Val Gln Leu Val Glu Ser Gly Gly Gly Leu Val Gln Pro Gly Gly
1               5                   10                  15

Ser Arg Lys Leu Ser Cys Val Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Gly Asn Phe Tyr Tyr Val Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
            85                  90                  95
```

Ala Arg Ser Thr Tyr Tyr His Gly Ser Arg Gly Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 35
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ile Ala Leu Thr Gln Ser Pro Ala Ile Met Ser Ala Ser Pro Gly
1               5                   10                  15

Glu Lys Val Thr Met Thr Cys Ser Ala Ser Ser Ser Val Ser Ser Met
            20                  25                  30

Tyr Trp Tyr Gln Leu Lys Pro Gly Ser Ser Pro Arg Leu Leu Ile Tyr
        35                  40                  45

Asp Thr Ser Lys Met Ala Ser Gly Val Pro Ile Arg Phe Ser Gly Ser
    50                  55                  60

Gly Ser Gly Thr Ser Phe Ser Leu Thr Val Ser Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Ala Gly Ser Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Asn Phe Tyr Tyr Val Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Tyr His Gly Ser Arg Gly Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 37
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Ser Ser Met
            20                  25                  30
```

```
Tyr Trp Tyr Gln Leu Lys Pro Asp Gln Ala Pro Lys Leu Leu Ile Tyr
            35                  40                  45

Asp Thr Ser Lys Met Ala Ser Gly Val Pro Ile Arg Phe Ser Gly Ser
 50                  55                  60

Gly Ser Gly Thr Asp Phe Thr Phe Thr Val Ser Ser Val Glu Ala Glu
 65                  70                  75                  80

Asp Ala Ala Thr Tyr Tyr Cys Gln Gln Trp Ser Ser Tyr Pro Pro Ile
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 38
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Gln Leu Val Glu Ser Gly Gly Gly Leu Val Gln Pro Gly Gly
 1               5                  10                  15

Ser Arg Lys Leu Ser Cys Val Ala Ser Gly Phe Thr Phe Ser Ser Phe
             20                  25                  30

Gly Met His Trp Val Arg Gln Ala Pro Glu Lys Gly Leu Glu Trp Val
            35                  40                  45

Ala Tyr Ile Ser Ser Gly Ser Gly Asn Phe Tyr Tyr Val Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Ser Thr Tyr Tyr His Gly Ser Arg Gly Ala Met Asp Tyr Trp
            100                 105                 110

Gly Gln Gly Thr Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175
```

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
        260                 265                 270

Gln Phe Ser Trp Phe Val Asp Asp Val Glu Val His Thr Ala Gln Thr
    275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
        340                 345                 350

Pro Lys Glu Gln Met Ala Lys Asp Lys Val Ser Leu Thr Cys Met Ile
    355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
            405                 410                 415

Glu Ala Gly Asn Thr Phe Thr Cys Ser Val Leu His Glu Gly Leu His
        420                 425                 430

Asn His His Thr Glu Lys Ser Leu Ser His Ser Pro Gly Lys
    435                 440                 445

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Ile Ala Leu Thr Gln Ser Pro Ala Ile Met Ser Ala Ser Pro Gly
1               5                   10                  15

Glu Lys Val Thr Met Thr Cys Ser Ala Ser Ser Ser Val Ser Ser Met
            20                  25                  30

Tyr Trp Tyr Gln Leu Lys Pro Gly Ser Ser Pro Arg Leu Leu Ile Tyr
        35                  40                  45

Asp Thr Ser Lys Met Ala Ser Gly Val Pro Ile Arg Phe Ser Gly Ser
    50                  55                  60

Gly Ser Gly Thr Ser Phe Ser Leu Thr Val Ser Arg Val Glu Ala Glu
65                  70                  75                  80

Asp Ala Ala Thr Tyr Tyr Cys Gln Gln Trp Ser Ser Tyr Pro Pro Ile

```
                        85                  90                  95
Thr Phe Gly Ala Gly Ser Lys Leu Glu Leu Lys Arg Ala Asp Ala Ala
                    100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
                210

<210> SEQ ID NO 40
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Gly Ser Gly Asn Phe Tyr Tyr Val Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Tyr His Gly Ser Arg Gly Ala Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220
```

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Ser Gly Gly Gly Ser Gly Gly
    450                 455                 460

Gly Gly Ser Asp Ile Lys Leu Gln Gln Ser Gly Ala Glu Leu Ala Arg
465                 470                 475                 480

Pro Gly Ala Ser Val Lys Met Ser Cys Lys Thr Ser Gly Tyr Thr Phe
            485                 490                 495

Thr Arg Tyr Thr Met His Trp Val Lys Gln Arg Pro Gly Gln Gly Leu
        500                 505                 510

Glu Trp Ile Gly Tyr Ile Asn Pro Ser Arg Gly Tyr Thr Asn Tyr Asn
    515                 520                 525

Gln Lys Phe Lys Asp Lys Ala Thr Leu Thr Thr Asp Lys Ser Ser Ser
530                 535                 540

Thr Ala Tyr Met Gln Leu Ser Ser Leu Thr Ser Glu Asp Ser Ala Val
545                 550                 555                 560

Tyr Tyr Cys Ala Arg Tyr Tyr Asp Asp His Tyr Cys Leu Asp Tyr Trp
            565                 570                 575

Gly Gln Gly Thr Thr Leu Thr Val Ser Ser Val Glu Gly Gly Ser Gly
        580                 585                 590

Gly Ser Gly Gly Ser Gly Gly Ser Gly Gly Val Asp Asp Ile Gln Leu
    595                 600                 605

Thr Gln Ser Pro Ala Ile Met Ser Ala Ser Pro Gly Glu Lys Val Thr
    610                 615                 620

Met Thr Cys Arg Ala Ser Ser Ser Val Ser Tyr Met Asn Trp Tyr Gln
625                 630                 635                 640

Gln Lys Ser Gly Thr Ser Pro Lys Arg Trp Ile Tyr Asp Thr Ser Lys
```

```
            645                 650                 655
Val Ala Ser Gly Val Pro Tyr Arg Phe Ser Gly Ser Gly Ser Gly Thr
        660                 665                 670

Ser Tyr Ser Leu Thr Ile Ser Ser Met Glu Ala Glu Asp Ala Ala Thr
        675                 680                 685

Tyr Tyr Cys Gln Gln Trp Ser Ser Asn Pro Leu Thr Phe Gly Ala Gly
        690                 695                 700

Thr Lys Leu Glu Leu Lys
705                 710

<210> SEQ ID NO 41
<211> LENGTH: 7842
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
```

| | | | | |
|---|---|---|---|---|
| acgcgtgtag | tcttatgcaa | tactcttgta | gtcttgcaac | atggtaacga tgagttagca | 60 |
| acatgcctta | caaggagaga | aaaagcaccg | tgcatgccga | ttggtggaag taaggtggta | 120 |
| cgatcgtgcc | ttattaggaa | ggcaacagac | gggtctgaca | tggattggac gaaccactga | 180 |
| attgccgcat | tgcagagata | ttgtatttaa | gtgcctagct | cgatacaata aacgggtctc | 240 |
| tctggttaga | ccagatctga | gcctgggagc | tctctggcta | actagggaac ccactgctta | 300 |
| agcctcaata | aagcttgcct | tgagtgcttc | aagtagtgtg | tgcccgtctg ttgtgtgact | 360 |
| ctggtaacta | gagatccctc | agacccttt | agtcagtgtg | gaaaatctct agcagtggcg | 420 |
| cccgaacagg | gacctgaaag | cgaaagggaa | accagagctc | tctcgacgca ggactcggct | 480 |
| tgctgaagcg | cgcacggcaa | gaggcgaggg | gcggcgactg | gtgagtacgc caaaaatttt | 540 |
| gactagcgga | ggctagaagg | agagagatgg | gtgcgagagc | gtcagtatta agcgggggag | 600 |
| aattagatcg | cgatgggaaa | aaattcggtt | aaggccaggg | ggaaagaaaa aatataaatt | 660 |
| aaaacatata | gtatgggcaa | gcagggagct | agaacgattc | gcagttaatc ctggcctgtt | 720 |
| agaaacatca | gaaggctgta | gacaaatact | gggacagcta | caaccatccc ttcagacagg | 780 |
| atcagaagaa | cttagatcat | tatataatac | agtagcaacc | ctctattgtg tgcatcaaag | 840 |
| gatagagata | aaagacacca | aggaagcttt | agacaagata | gaggaagagc aaaacaaaag | 900 |
| taagaccacc | gcacagcaag | cggccactga | tcttcagacc | tggaggagga gatatgaggg | 960 |
| acaattggag | aagtgaatta | tataaatata | aagtagtaaa | aattgaacca ttaggagtag | 1020 |
| cacccaccaa | ggcaaagaga | agagtggtgc | agagagaaaa | aagagcagtg ggaataggag | 1080 |
| ctttgttcct | tgggttcttg | ggagcagcag | gaagcactat | gggcgcagcc tcaatgacgc | 1140 |
| tgacggtaca | ggccagacaa | ttattgtctg | gtatagtgca | gcagcagaac aatttgctga | 1200 |
| gggctattga | ggcgcaacag | catctgttgc | aactcacagt | ctggggcatc aagcagctcc | 1260 |
| aggcaagaat | cctggctgtg | gaaagatacc | taaaggatca | acagctcctg ggatttggg | 1320 |
| gttgctctgg | aaaactcatt | tgcaccactg | ctgtgccttg | gaatgctagt tggagtaata | 1380 |
| aatctctgga | acagattgga | atcacacgac | ctggatggga | tgggacagag aaattaacaa | 1440 |
| ttacacaagc | ttaatacact | ccttaattga | agaatcgcaa | aaccagcaag aaaagaatga | 1500 |
| acaagaatta | ttggaattag | ataaatgggc | aagtttgtgg | aattggttta acataacaaa | 1560 |
| ttggctgtgg | tatataaaat | tattcataat | gatagtagga | ggcttggtag gtttaagaat | 1620 |

| | | | | | |
|---|---|---|---|---|---|
| agtttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcggtt | 1800 |
| aacttttaaa | agaaaagggg | ggattggggg | gtacagtgca | ggggaaagaa | tagtagacat | 1860 |
| aatagcaaca | gacatacaaa | ctaaagaatt | acaaaaacaa | attacaaaat | tcaaaatttt | 1920 |
| atcgatacta | gtattatgcc | cagtacatga | ccttatggga | ctttcctact | tggcagtaca | 1980 |
| tctacgtatt | agtcatcgct | attaccatgg | tgatgcggtt | ttggcagtac | atcaatgggc | 2040 |
| gtggatagcg | gtttgactca | cggggatttc | caagtctcca | ccccattgac | gtcaatggga | 2100 |
| gtttgttttg | gcaccaaaat | caacgggact | ttccaaaatg | tcgtaacaac | tccgccccat | 2160 |
| tgacgcaaat | gggcggtagg | cgtgtacggt | gggaggttta | tataagcaga | gctcgtttag | 2220 |
| tgaaccgtca | gatcgcctgg | agacgccatc | cacgctgttt | tgacctccat | agaagattct | 2280 |
| agagccgcca | ccatggccct | cccagtaacc | gccctcctgc | tccccttgc | tttgctgctg | 2340 |
| cacgccgcac | ggcccgctag | cgaagttcag | cttgtcgaat | ctgggggagg | gttggttcag | 2400 |
| ccggagggga | gtctgcgcct | ttcttgcgtg | gcttcaggct | ttaccttttc | cagttttggg | 2460 |
| atgcattggg | tacgacaagc | acctgggaaa | ggactggagt | gggtggcata | tatatcaagc | 2520 |
| ggcagcggaa | acttctacta | cgttgacact | gtaaaaggga | gattcaccat | ctcccgagac | 2580 |
| aacgctaaaa | actcactcta | tcttcaaatg | aatagcctgc | gagctgagga | tacggcggtt | 2640 |
| tactactgcg | cgcgatcaac | atattaccac | gggtccagag | gcgcgatgga | ctactggggg | 2700 |
| caagggactt | tggttactgt | gggtggcgga | ggcagcggcg | gtggtggttc | cggaggcggc | 2760 |
| ggttctcaag | tcgttatgac | ccaaagcccc | gcatttcttt | ctgtgactcc | aggcgagaag | 2820 |
| gtgacgataa | cctgttcagc | cagttccagt | gtctccagta | tgtattggta | tcaactgaaa | 2880 |
| ccagatcagg | caccgaagct | tttgatatat | gacacatcta | aaatggcatc | aggggtaccc | 2940 |
| ataaggttta | gcgggtccgg | ctcagggacc | gattttacgt | ttactgtctc | atccgtcgag | 3000 |
| gcggaagatg | cagcgaccta | ttactgccag | cagtggagta | gttatccccc | catcacgttt | 3060 |
| ggcggcggta | cgaaagtgga | gataaaggac | tacaaagacg | atgacgacaa | gctcgagacc | 3120 |
| acgacgccag | cgccgcgacc | accaacaccg | gcgcccacca | tcgcgtcgca | gcccctgtcc | 3180 |
| ctgcgcccag | aggcgtgccg | gccagcggcg | ggggcgcag | tgcacacgag | ggggctggac | 3240 |
| ttcgcctgtg | atttttgggt | gctggtggtg | gttggtggag | tcctggcttg | ctatagcttg | 3300 |
| ctagtaacag | tggcctttat | tattttctgg | gtgaggagta | agaggagcag | gctcctgcac | 3360 |
| agtgactaca | tgaacatgac | tccccgccgc | cccgggccca | cccgcaagca | ttaccagccc | 3420 |
| tatgccccac | cacgcgactt | cgcagcctat | cgctccaaac | ggggcagaaa | gaaactcctg | 3480 |
| tatatattca | acaaccatt | tatgagacca | gtacaaacta | ctcaagagga | agatggctgt | 3540 |
| agctgccgat | ttccagaaga | agaagaagga | ggatgtgaac | tgagagtgaa | gttcagcagg | 3600 |
| agcgcagacg | cccccgcgta | ccagcagggc | cagaaccagc | tctataacga | gctcaatcta | 3660 |
| ggacgaagag | aggagtacga | tgttttggac | aagagacgtg | gccgggaccc | tgagatgggg | 3720 |
| ggaaagccga | gaaggaagaa | ccctcaggaa | ggcctgtaca | atgaactgca | gaaagataag | 3780 |
| atggcggagg | cctacagtga | gattgggatg | aaaggcgagc | gccggagggg | caaggggcac | 3840 |
| gatggccttt | accagggtct | cagtacagcc | accaaggaca | cctacgacgc | ccttcacatg | 3900 |
| caggccctgc | cccctcgcta | ataggaattc | gtcgacaatc | aacctctgga | ttacaaaatt | 3960 |
| tgtgaaagat | tgactggtat | tcttaactat | gttgctcctt | ttacgctatg | tggatacgct | 4020 |

```
gctttaatgc ctttgtatca tgctattgct tcccgtatgg ctttcatttt ctcctccttg    4080
tataaatcct ggttgctgtc tctttatgag gagttgtggc ccgttgtcag gcaacgtggc    4140
gtggtgtgca ctgtgtttgc tgacgcaacc cccactggtt ggggcattgc caccacctgt    4200
cagctccttt ccgggacttt cgctttcccc ctccctattg ccacggcgga actcatcgcc    4260
gcctgccttg cccgctgctg gacaggggct cggctgttgg gcactgacaa ttccgtggtg    4320
ttgtcgggga aatcatcgtc ctttccttgg ctgctcgcct gtgttgccac ctggattctg    4380
cgcgggacgt ccttctgcta cgtcccttcg gccctcaatc cagcggacct tccttcccgc    4440
ggcctgctgc cggctctgcg gcctcttccg cgtcttcgcc ttcgccctca gacgagtcgg    4500
atctcccttt gggccgcctc cccgcctggt acctttaaga ccaatgactt acaaggcagc    4560
tgtagatctt agccactttt taaaagaaaa gggggggactg gaagggctaa ttcactccca    4620
acgaaaataa gatctgcttt ttgcttgtac tgggtctctc tggttagacc agatctgagc    4680
ctgggagctc tctggctaac tagggaaccc actgcttaag cctcaataaa gcttgccttg    4740
agtgcttcaa gtagtgtgtg cccgtctgtt gtgtgactct ggtaactaga gatccctcag    4800 accctttttag tcagtgtgga aaatctctag cagtagtagt tcatgtcatc ttattattca    4860
gtatttataa cttgcaaaga aatgaatatc agagagtgag aggaacttgt ttattgcagc    4920
ttataatggt tacaaataaa gcaatagcat cacaaatttc acaaataaag cattttttc     4980 actgcattct agttgtggtt tgtccaaact catcaatgta tcttatcatg tctggctcta    5040
gctatcccgc ccctaactcc gcccagttcc gcccattctc cgccccatgg ctgactaatt    5100
ttttttattt atgcagaggc cgaggccgcc tcggcctctg agctattcca gaagtagtga    5160
ggaggctttt ttggaggcct agacttttgc agagacggcc caaattcgta atcatggtca    5220
tagctgtttc ctgtgtgaaa ttgttatccg ctcacaattc cacacaacat acgagccgga    5280
agcataaagt gtaaagcctg gggtgcctaa tgagtgagct aactcacatt aattgcgttg    5340
cgctcactgc ccgctttcca gtcgggaaac ctgtcgtgcc agctgcatta atgaatcggc    5400
caacgcgcgg ggagaggcgg tttgcgtatt gggcgctctt ccgcttcctc gctcactgac    5460
tcgctgcgct cggtcgttcg gctgcggcga gcggtatcag ctcactcaaa ggcggtaata    5520
cggttatcca cagaatcagg ggataacgca ggaaagaaca tgtgagcaaa aggccagcaa    5580
aaggccagga accgtaaaaa ggccgcgttg ctggcgtttt tccataggct ccgcccccct    5640
gacgagcatc acaaaaatcg acgctcaagt cagaggtggc gaaacccgac aggactataa    5700
agataccagg cgtttccccc tggaagctcc ctcgtgcgct ctcctgttcc gaccctgccg    5760
cttaccggat acctgtccgc ctttctccct tcgggaagcg tggcgctttc tcatagctca    5820
cgctgtaggt atctcagttc ggtgtaggtc gttcgctcca agctgggctg tgtgcacgaa    5880
ccccccgttc agcccgaccg ctgcgcctta tccggtaact atcgtcttga gtccaacccg    5940
gtaagacacg acttatcgcc actggcagca gccactggta acaggattag cagagcgagg    6000
tatgtaggcg gtgctacaga gttcttgaag tggtggccta actacggcta cactagaagg    6060
acagtatttg gtatctgcgc tctgctgaag ccagttacct tcggaaaaag agttggtagc    6120
tcttgatccg gcaaacaaac caccgctggt agcggtggtt ttttgtttg caagcagcag    6180 attacgcgca gaaaaaaagg atctcaagaa gatcctttga tcttttctac ggggtctgac    6240
gctcagtgga acgaaaactc acgttaaggg attttggtca tgagattatc aaaaaggatc    6300
ttcacctaga tccttttaaa ttaaaaatga agttttaaat caatctaaag tatatatgag    6360
```

-continued

```
taaacttggt ctgacagtta ccaatgctta atcagtgagg cacctatctc agcgatctgt    6420
ctatttcgtt catccatagt tgcctgactc cccgtcgtgt agataactac gatacgggag    6480
ggcttaccat ctggccccag tgctgcaatg ataccgcgag acccacgctc accggctcca    6540
gatttatcag caataaacca gccagccgga agggccgagc gcagaagtgg tcctgcaact    6600
ttatccgcct ccatccagtc tattaattgt tgccgggaag ctagagtaag tagttcgcca    6660
gttaatagtt tgcgcaacgt tgttgccatt gctacaggca tcgtggtgtc acgctcgtcg    6720
tttggtatgg cttcattcag ctccggttcc caacgatcaa ggcgagttac atgatccccc    6780
atgttgtgca aaaagcggtt agctccttcg gtcctccga tcgttgtcag aagtaagttg     6840
gccgcagtgt tatcactcat ggttatggca gcactgcata attctcttac tgtcatgcca    6900
tccgtaagat gcttttctgt gactggtgag tactcaacca agtcattctg agaatagtgt    6960
atgcggcgac cgagttgctc ttgcccggcg tcaatacggg ataataccgc gccacatagc    7020
agaactttaa aagtgctcat cattggaaaa cgttcttcgg ggcgaaaact ctcaaggatc    7080
ttaccgctgt tgagatccag ttcgatgtaa cccactcgtg cacccaactg atcttcagca    7140
tcttttactt tcaccagcgt ttctgggtga gcaaaaacag gaaggcaaaa tgccgcaaaa    7200
aagggaataa gggcgacacg gaaatgttga atactcatac tcttcctttt tcaatattat    7260
tgaagcattt atcagggtta ttgtctcatg agcggataca tatttgaatg tatttagaaa    7320
aataaacaaa taggggttcc gcgcacattt ccccgaaaag tgccacctga cgtctaagaa    7380
accattatta tcatgacatt aacctataaa aataggcgta tcacgaggcc ctttcgtctc    7440
gcgcgtttcg gtgatgacgg tgaaaacctc tgacacatgc agctcccgga gacggtcaca    7500
gcttgtctgt aagcggatgc cgggagcaga caagcccgtc agggcgcgtc agcgggtgtt    7560
ggcgggtgtc ggggctggct taactatgcg gcatcagagc agattgtact gagagtgcac    7620
catatgcggt gtgaaatacc gcacagatgc gtaaggagaa ataccgcat caggcgccat     7680 tcgccattca ggctgcgcaa ctgttgggaa gggcgatcgg tgcgggcctc ttcgctatta    7740
cgccagctgg cgaaagggg atgtgctgca aggcgattaa gttgggtaac gccagggttt     7800
tcccagtcac gacgttgtaa aacgacggcc agtgccaagc tg                      7842
```

<210> SEQ ID NO 42
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Ser Thr Thr Ala Val Gln Thr Pro Thr Ser Gly Glu Pro Leu Val Ser
1               5                   10                  15

Thr Ser Glu Pro Leu Ser Ser Lys Met Tyr Thr Thr Ser Ile Thr Ser
            20                  25                  30

Asp Pro Lys Ala Asp Ser Thr Gly Asp Gln Thr Ser Ala Leu Pro Pro
        35                  40                  45

Ser Thr Ser Ile Asn Glu Gly Ser Pro Leu Trp Thr Ser Ile Gly Ala
    50                  55                  60

Ser Thr Gly Ser Pro Leu Pro Glu Pro Thr Thr Tyr Gln Glu Val Ser
65                  70                  75                  80

Ile Lys Met Ser Ser Val Pro Gln Glu Thr Pro His Ala Thr Ser His
                85                  90                  95

```
Pro Ala Val Pro Ile Thr Ala Asn Ser Leu Gly Ser His Thr Val Thr
                100                 105                 110

Gly Gly Thr Ile Thr Thr Asn Ser Pro Glu Thr Ser Ser Arg Thr Ser
            115                 120                 125

Gly Ala Pro Val Thr Thr Ala Ala Ser Ser Leu Glu Thr Ser Arg Gly
        130                 135                 140

Thr Ser Gly Pro Pro Leu Thr Met Ala Thr Val Ser Leu Glu Thr Ser
145                 150                 155                 160

Lys Gly Thr Ser Gly Pro Pro Val Thr Met Ala Thr Asp Ser Leu Glu
                165                 170                 175

Thr Ser Thr Gly Thr Thr Gly Pro Pro Val Thr Met Thr Thr Gly Ser
            180                 185                 190

Leu Glu Pro Ser Ser Gly Ala Ser Gly Pro Gln Val Ser Ser Val Lys
        195                 200                 205

Leu Ser Thr Met Met Ser Pro Thr Thr Ser Thr Asn Ala Ser Thr Val
210                 215                 220

Pro Phe Arg Asn Pro Asp Glu Asn Ser Arg
225                 230
```

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Tyr Ile Ser Ser Gly Ser Gly Asn Phe Tyr Tyr Val Asp Thr Val Lys
1               5                   10                  15

Gly
```

<210> SEQ ID NO 44
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Val Gln Val Glu Ser Gly Gly Gly Leu Val Gln Pro Gly Gly Ser
1               5                   10                  15

Arg Lys Leu Ser Cys Val Ala Ser Gly Phe Thr Phe Ser Ser Phe Gly
            20                  25                  30

Met His Trp Val Arg Gln Ala Pro Glu Lys Gly Leu Glu Trp Val Ala
        35                  40                  45

Tyr Ile Ser Ser Gly Ser Gly Asn Phe Tyr Tyr Val Asp Thr Val Lys
    50                  55                  60

Gly Arg Phe Thr Ile Ser Arg Asp Asn Pro Lys Asn Thr Leu Phe Leu
65                  70                  75                  80

Gln Met Thr Ser Leu Arg Ser Glu Asp Thr Ala Met Tyr Tyr Cys Ala
                85                  90                  95

Arg Ser Thr Tyr Tyr His Gly Ser Arg Gly Ala Met Asp Tyr Trp Gly
            100                 105                 110

Gln Gly Thr Ser Val Thr Val Ser Ser
        115                 120
```

```
<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Val Glu Ser Gly Gly Leu Val Gln Pro Gly Gly Ser
1               5                   10                  15

Leu Arg Leu Ser Cys Ala Ala Ser Gly Phe Thr Phe Ser Ser Phe Gly
            20                  25                  30

Met His Trp Val Arg Gln Ala Pro Gly Lys Gly Leu Glu Trp Val Ser
        35                  40                  45

Tyr Ile Ser Ser Gly Ser Gly Asn Phe Tyr Tyr Val Asp Thr Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Thr Tyr Tyr His Gly Ser Arg Gly Ala Met Asp Tyr Trp Gly
            100                 105                 110

Gln Gly Thr Leu Val Thr Val Ser Ser
            115                 120
```

MONOCLONAL ANTIBODY TARGETING A UNIQUE SIALOGLYCOSYLATED CANCER-ASSOCIATED EPITOPE OF CD43

1. CROSS-REFERENCE TO RELATED APPLICATIONS

This application is a continuation-in-part of and claims benefit under 35 U.S.C. §§ 365(c) and 120 to PCT/EP2017/084482 filed on Dec. 22, 2017, which claims priority under 35 U.S.C. §§ 365(b) and 119(a) to foreign application DE 10 2016 015379.2 filed on Dec. 22, 2016, the disclosures of which are incorporated herein by reference in their entireties.

2. SEQUENCE LISTING

The instant application contains a Sequence Listing which has been submitted via EFS-Web and is hereby incorporated herein by reference in its entirety. Said ASCII copy, created on Jul. 16, 2019, is named 41782US_CRF_sequencelisting.txt, and is 96,382 bytes in size.

3. BIOLOGICAL DEPOSIT

A hybridoma secreting mAb UMG1 was deposited under the terms of the Budapest Treaty on Aug. 4, 2016 at the Centro di Biotecnologie Avanzate (CBA) Interlab Cell Line Collection (ICLC) under ICLC accession number ICLC PD n° 16001. Access to deposited material will be available, during pendency of a patent application making reference to it, to anyone determined by the Director to be entitled to access under 37 CFR 1.14 and 35 USC 122 (35 USC 114). Subject to paragraph (b) of 37 CFR 1.808, all restrictions imposed by the depositor on the availability to the public of the deposited material will be irrevocably removed upon the granting of the patent.

4. BACKGROUND

CD43 is a leukocyte marker normally restricted to cells of the hematopoietic lineage. CD43 is widely expressed on most peripheral and bone marrow-derived cell components. The precursor form of CD43 migrates with an apparent molecular weight of 54 kD. In its mature form, CD43 is heavily glycosylated, having a molecular weight between 115 and 200 kD. $CD4^+$ thymocytes and monocytes express the 115 kD form, while activated $CD4^+$ and $CD8^+$ T cells, B cells, neutrophils and platelets express a 130 kD form. CD43 is involved in multiple functions, such as cell adhesion, apoptosis and migration (Ostberg et al., *Immunology Today* 19:546-50, 1998).

A murine anti-human CD43 monoclonal antibody, UN1, was first described 25 years ago. Originally selected for high reactivity against human immature thymocytes (Tassone et al., Tissue Antigens 44:73-82, 1994), the UN1 mAb was later shown to bind not only to immature thymocytes, but also to various fetal tissues (Cecco et al., *Tissue Antigens* 51:528-535, 1998; Tassone et al., *Int. J. Oncology* 20:707-711, 2002) and to a variety of solid tumors, including breast, colon, gastric, and squamous cell lung carcinomas, but not to normal tissues and benign lesions (Tassone et al., *Int. J. Oncol.* 20:707-11, 2002; Tassone et al., *Anticancer Res.* 22:2333-40, 2002). In addition, the expression level of the UN1 epitope in breast cancer cells was shown to correlate with the progression stage of the disease (Tassone et al., *Anticancer Res.* 22:2333-40, 2002). The evidence that the epitope recognized by UN1 was an oncofetal antigen expressed in cancer tissues but not in most non-neoplastic adult tissues made the UN1 mAb an attractive tool for tumor detection and immunotherapy (reviewed in Tuccillo et al., *Mol. Cancer Ther.* 13(3), 2014).

Using immunoprecipitation and tandem mass spectrometry, the UN1 antibody was shown to recognize an epitope on CD43 that includes the monosaccharide, GalNAc, O-linked to the polypeptide chain of CD43 (de Laurentiis et al., *Int. J. Biological Macromol.* 39:122-126, 2006; de Laurentiis et al., *Molecular & Cellular Proteomics* 10:1-12, 2011).

However, despite extensive functional characterization, the UN1 antibody CDR sequences were never determined. The hybridoma secreting the UN1 antibody was never deposited in a biological repository and no UN1 hybridoma master cell bank or working cell bank was made. There is a need for antibodies that bind to the same or similar epitope as the UN1 antibody for use in cancer treatment, in particular for treating T cell acute lymphoblastic leukemias/lymphoblastic lymphomas, and for use in cancer diagnostics.

5. SUMMARY

Over the past 25 years, we have propagated cells that ultimately derive from the original UN1 hybridoma. A recent subclone secretes a monoclonal antibody, termed UMG1, that retains certain of the binding characteristics of the original UN1 antibody, but not all, and that has a distinct binding specificity that provides particular advantages.

In brief, the UMG1 antibody binds to a small subset of lymphocytes in peripheral blood mononuclear cells (PBMCs) from healthy human donors (Example 1). The UMG1 positive lymphocytes are almost all $CD45^+CD3^+CD4^+CD8^-CD127^+CCR7^+$ T lymphocytes (Example 2).

Like UN1, the UMG1 antibody binds to T-ALL cell lines belonging to EGIL T3 classification (Example 3). Unlike the UN1 antibody, however, the UMG1 antibody does not bind to breast cancer cells (Example 3). UMG1 also does not directly stain the cancer cells in lung cancer, colorectal cancer, and breast cancer tumors (Example 12), in contrast to prior observations with UN1 (see de Laurentiis et al., *Molecular & Cellular Proteomics* 10:1-12, 2011, FIG. 9). UMG1 does, however, bind to cellular immune infiltrates in lung cancer, colorectal cancer, and breast cancer tumors (Example 12). Although UMG1 does not bind to myeloid-derived cells in PBMCs from healthy donors (Example 1), the UMG1 epitope is expressed in tumor-associated macrophages, and UMG1 epitope expression is elevated when macrophages are co-cultured and interact with cancer cells (Example 13).

UMG1 also binds to Waldenström's macroglobulinemia cell lines (Example 3).

Chimeric antibodies constructed by fusing the variable regions of the UMG1 murine antibody to human IgG Fc regions (ch-UMG1) were capable of inducing antibody-dependent cell-mediated cytotoxicity (ADCC) against the T-ALL cell line HPB-ALL and T lymphoma cell line H9 in the presence of effector cells from human PBMCs (Example 9). ch-UMG1 antibodies were also capable of inducing ADCC against Waldenström's Macroglobulinemia cells (Example 13). Humanized antibodies constructed by grafting the CDRs from the UMG1 heavy and light chains into human frameworks (h-UMG1) were able to reduce growth of HPB-ALL tumors in an NSG mouse model (Example 16). Finally, third generation chimeric antigen receptor (CAR) T cells in which the CAR targeting moiety is a scFv having all 6 CDRs of the UMG1 antibody were activated in the presence of H9 T lymphoma cells (Example 17), predicting that UMG1-directed CAR-T therapy will be effective in treating T cell lymphoma.

The specificity of the UMG1 antibody makes it uniquely useful in treatment of T-ALL, T cell lymphoma, Waldenström's macroglobulinemia, and solid tumors in which depletion of tumor-associated macrophages would prove therapeutically beneficial.

Accordingly, in a first aspect, antibodies and antigen-binding fragments of antibodies are provided. The antibodies and antigen-binding fragments comprise a heavy chain variable domain (VH) and a light chain variable domain (VL). The VH comprises framework regions and the UMG1 heavy chain complementarity determining regions (CDRs), and the VL comprises framework regions and the UMG1 light chain CDRs.

The current disclosure, provides a novel humanized and mouse CD43 antibodies, that notably have different properties in comparison to the previously developed CD43 antibodies.

The present disclosure provides mouse and humanized CD43 antibodies and binding molecules, coding nucleic acid molecules, expression vectors, host cells and the method for expressing the antibody of the antibody. Additionally, the disclosure provides various pharmacological composition and methods of treatments for patients suffering from a disease.

The object of the present invention is to provide an antibody allowing the detection of an oncofetal epitope (OE) and the development of novel immunotherapeutic approaches.

The problem is solved by an antibody according to the invention. The data shown in the examples indicate that due to the specific pattern of restricted expression in fetal tissues and re-expression in malignancies, the epitope recognized by the antibody produced by the hybridoma cell deposited according to the invention can be considered to be an OE. The latter represents therefore a potentially suitable target for innovative immunotherapeutic strategies for treatment of human cancer.

Further, a chimeric antigen receptor (CAR) comprising the scFv of a binding molecule based on the antibody according to the invention linked to an intracellular region comprising the CD3 chain, the signaling region of the T cell receptor, and the two co-stimulatory domains CD28 and 41BB was developed. CD3+ lymphocytes expressing the CAR according to the invention induce significant cytotoxicity against cells expressing the epitope recognized by the antibody produced by the hybridoma cell deposited according to the invention.

A mouse antibody produced by the hybridoma cell deposited under ICLC PD no 16001 is provided. In addition, an antibody, which recognizes the same epitope as the antibody produced by the hybridoma cell deposited under ICLC PD no 16001 is provided.

The invention further provides a UMG1 antibody, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences GFTFSSFGMH (SEQ ID NO: 1), YISSGSGNFYYVDTVKG (SEQ ID NO: 43), STYYHGSRGAMDY (SEQ ID NO: 3), SASSSVSSMYWY (SEQ ID NO: 4), DTSKMAS (SEQ ID NO: 5), and QQWSSYPPIT (SEQ ID NO: 6), respectively.

Preferably, said antibody is a monoclonal antibody.

Further, a binding molecule derived from the antibody produced by the hybridoma cell deposited under ICLC PD n° 16001 or from the above antibody of the invention is provided.

Moreover, a chimeric antigen receptor is provided, which comprises an scFv binding molecule according to the invention linked to an intracellular region comprising the CD3ζ chain, the signaling region of the T cell receptor, and to the two co-stimulatory domains CD28 and 41BB.

Furthermore, an expression vector is provided that comprises a nucleic acid sequence, which encodes the chimeric antigen receptor according to the invention, the antibody according to the invention or the binding molecule according to the invention.

The invention further provides a CD3+ lymphocyte, an NK lymphocyte, a Cytokine induced killer (CIK) cell, a gamma-delta lymphocyte, or an NKT cell comprising the chimeric antigen receptor according to the invention or the expression vector according to the invention.

A pharmaceutical composition is provided comprising the antibody according to the invention or the binding molecule according to the invention or the CD3+ lymphocyte an NK lymphocyte, a Cytokine induced killer (CIK) cell, a gamma-delta lymphocyte, or an NKT cell according to the invention.

A nucleic acid is provided, encoding the antibody according to the invention or the binding molecule according to the invention.

A hybridoma cell is provided that produces the antibody according to the invention.

A method for producing the antibody according to the invention is provided, which comprises isolating said antibody from the hybridoma cell deposited under ICLC PD no 16001.

A method for the identification or isolation of T-cell acute lymbhoblastic leukemia cells, T lymphoma cells, Waldenström's Macroglobulinemia cells or tumor-associated macrophages is provided, which comprises contacting a cell sample comprising said cells with the antibody according to the invention or with the binding molecule according to the invention.

A method for producing CD3+ lymphocytes, NK lymphocytes, Cytokine induced killer (CIK) cells, gamma-delta lymphocytes, or NKT cells expressing a chimeric antigen receptor according to the invention is provided comprising the introduction of the expression vector according to the invention into said CD3+ lymphocytes, NK lymphocytes, Cytokine induced killer (CIK) cells, gamma-delta lymphocytes, or an NKT cells.

In an aspect, the disclosure provides a CD43 binding protein, comprising: an antibody or antigen-binding fragment thereof, wherein the antibody or antigen-binding fragment comprises a heavy chain variable domain (VH) and a light chain variable domain (VL), wherein the VH comprises framework regions and complementarity determining regions (CDRs) having the sequences SEQ ID NO: 1; SEQ ID NO: 2; and SEQ ID NO: 3, and the VL comprises framework regions and CDRs having the sequences SEQ ID NO: 4; SEQ ID NO: 5; and SEQ ID NO: 6.

In some embodiments, the antibody or antigen-binding fragment comprises a VH sequence which is SEQ ID NO: 7 and a VL sequence which is SEQ ID NO: 12.

In some other embodiments, the antibody is a murine antibody produced by the hybridoma cell line deposited under ICLC accession number ICLC PD number 16001 (UMG1).

In some other embodiments, the antibody is a chimeric antibody further comprising human constant region domains.

In some embodiment, the chimeric antibody comprises a human constant region domains that are IgG domains. In some other embodiments, the chimeric antibody comprises a heavy chain sequence which is SEQ ID NO: 34 and the antibody light chain sequence which is SEQ ID NO: 35.

In some embodiments, the antibody or antigen-binding fragment comprises human variable domain framework regions.

In some embodiments, the humanized antibody or antigen-binding fragment comprises the VH and VL domains having the sequences selected from: SEQ ID NO: 8, SEQ ID NO: 9, SEQ ID NO: 10, and SEQ ID NO: 11; and SEQ ID NO: 13, SEQ ID NO: 14, SEQ ID NO: 15, and SEQ ID NO: 16, respectively.

In some embodiments, the antibody or antigen-binding fragment is a bivalent monospecific monoclonal antibody, a bivalent bispecific antibody, a trivalent trispecific antibody, an F(ab), an F(ab)'2, a scFv, a diabody, a single domain antibody, a tandab, or a flexibody.

In some embodiments, the antibody is a monoclonal antibody. In some embodiments, the antibody or antigen-binding fragment is a scFv. In some embodiments, the antibody binds an epitope within amino acids 61-91 of wild-type CD43.

In some embodiments, the antibody is capable of inducing antibody dependent cellular cytotoxicity (ADCC) against the EGIL T3 subgroup of T cell acute lymphoblastic leukemia (T-ALL) cells, against T cell lymphoblastic lymphoma cells and against Waldenström's macroglobulinemia (WM) cells, and against tumor-infiltrating macrophages.

In an aspect, the disclosure provides a pharmaceutical composition comprising the CD43 binding protein provided herein.

In some embodiments, the disclosure provides a polynucleotide or plurality of polynucleotides encodes the CD43 binding protein provided herein.

In some embodiments, the disclosure provides an expression vector comprising the polynucleotide or plurality of polynucleotides provided herein.

In some embodiments, the disclosure provides a cell that expresses the CD43 binding protein provided herein.

In some other embodiments, the cell has a CD43 binding protein that is expressed on the surface of the cell.

In some other embodiments, the cell comprises the expression vector provided herein.

In an aspect, the disclosure provides a method of producing the CD43 binding protein provided herein, comprising culturing a cell provided herein, under conditions in which the cell secretes the CD43 binding protein into the culture medium, and purifying the CD43 binding protein from the culture medium.

In an aspect, the disclosure provides a chimeric antigen receptor (CAR), the CAR comprising the scFv provided herein, at least one T cell signaling domain, and at least one costimulatory domain.

In some embodiments, the CAR comprises a CD3ζ signaling domain. In some embodiments, the CAR comprises a CD28 costimulatory domain. In some embodiments, the CAR comprises a 4-1BB costimulatory domain. In some embodiments, the CAR comprises both a CD28 costimulatory domain and a 4-1BB costimulatory domain. In some embodiments, the CAR is encoded by the sequence of SEQ ID NO: 41.

In an aspect, the disclosure provides a polynucleotide that encodes a CAR provided herein.

In an aspect, the disclosure provides an expression vector that comprises the polynucleotide provided herein.

In an aspect, the disclosure provides a CAR-T cell comprising the CAR provided herein. In some embodiments, the CAR-T cell is an CD3+ αβ T cell. In some embodiments, the CAR-T cell is a CD3+γδ T cell. In some embodiments, the CAR-T cell is an NK T cell.

In an aspect, the disclosure provides a method of treating T-cell lymphoma, T-cell acute lymphoblastic leukemia (T-ALL) or Waldenström's Macroglobulinemia, the method comprising: administering a therapeutically effective amount of the CD43 binding protein provided herein, wherein the binding protein is capable of inducing ADCC, to a patient with T-cell lymphoma, T-ALL, or Waldenström's Macroglobulinemia.

In an aspect, the disclosure provides a method of treating T-cell lymphoma, T-ALL, or Waldenström's Macroglobulinemia, the method comprising: administering a therapeutically effective amount of the CD43 binding protein provided herein, wherein the binding protein is conjugated to a toxic drug.

In an aspect, the disclosure provides a method of treating T-cell lymphoma, T-ALL, or Waldenström's Macroglobulinemia, the method comprising: administering a therapeutically effective amount of the CD43 binding protein provided herein, wherein the binding protein is bispecific, and the second binding specificity is for CD3.

In an aspect, the disclosure provides a method of treating T-cell lymphoma, T-ALL or Waldenström's Macroglobulinemia, the method comprising: administering a therapeutically effective amount of the CAR-T cell provided herein.

In an aspect, the disclosure provides a method of depleting tumor-associated macrophages, the method comprising: administering to a patient with a solid tumor that has infiltrating macrophages a therapeutically effective amount of the CD43 binding protein provided herein, wherein the binding protein is capable of inducing ADCC of said macrophages.

In an aspect, the disclosure provides a method of depleting tumor-associated macrophages, the method comprising: administering to a patient with a solid tumor that has infiltrating macrophages a therapeutically effective amount of the CD43 binding protein provided herein, wherein the binding protein is conjugated to a toxic drug.

In an aspect, the disclosure provides a method of depleting tumor-associated macrophages, the method comprising: administering to a patient with a solid tumor that has infiltrating macrophages a therapeutically effective amount of the CD43 binding protein provided herein, wherein the binding protein is bispecific, and the second binding specificity is for CD3.

In an aspect, the disclosure provides a method of depleting tumor-associated macrophages, the method comprising: administering to a patient with a solid tumor with infiltrating macrophages a therapeutically effective amount of the CAR-T cell provided herein.

In an aspect, the disclosure provides a method for identifying T-cell lymphoma, T-cell acute lymphoblastic leukemia (T-ALL) cells, Waldenström's Macroglobulinemia cells, tumor-associated macrophages, or CD45+, CD3+, CD8−, CD127+, CCR7+ T lymphocytes, the method comprising detectably contacting a cell sample comprising said cells with the CD43 binding protein provided herein.

6. BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the features and advantages of the disclosure will be obtained by reference to the following detailed description that sets forth illustrative embodiments, in which the principles of the invention are utilized, and the accompanying drawings of which:

FIGS. 1A and 1B demonstrate expression of the epitope recognized by the UMG1 antibody on peripheral blood mononuclear cells of a panel of healthy donors and comparison to a commercial CD43 antibody. The scatterplot of FIG. 1A presents data obtained by flow cytometry. The x-axis presents the forward scatter detected (FSC), the y-axis depicts the side scatter (SSC). Each dot corresponds to one cell. The histogram in FIG. 1B depicts on the x-axis the phycoerythrin signal intensity. The y-axis relates the signal intensities to the maximum signal intensity (i.e. 100%) of the unstained sample. The red curve represents the unstained control, the blue curve represents the scramble IgG1 stained cells (i.e. the negative control), the orange curve represents the mAb UMG1 stained cells and the green curve represents the commercial anti-CD43 antibody stained cells.

FIGS. 2A-2D show four representative scatterplots of cell populations recognized by the UMG1 antibody produced by the hybridoma cell deposited according to the invention. FIGS. 2A and 2C show two scatterplots belonging to lymphocytes. FIGS. 2B and 2D are from lymphocytes detected by the UMG1 antibody produced by the hybridoma cell deposited according to the invention. In FIGS. 2A and 2B, the x-axis represents CD4 signal intensity, while the y-axis depicts CD8 signal intensity. In FIGS. 2C and 2D, the x-axis represents CD45ro signal intensity and the y-axis represents CCR7 signal intensity.

FIGS. 3A-3B show two histograms. FIG. 3A presents UMG1 expression detected by UMG1 antibody on BCWM.1 cell line. FIG. 3B presents UMG1 expression on MWCL.1 cell line. The unfilled curve represents the unstained control, the curve filled with horizontal stripes represents the secondary mAb stained cells, the curve filled with vertical stripes represents the scramble IgG plus secondary mAb stained cells and the curve filled with diagonal stripes represents cells stained by mAb UMG1.

FIG. 4 shows tumor associated macrophages (TAM) recognized by the UMG1 antibody. The arrows indicate TAM infiltrating a specimen of colorectal carcinoma.

FIGS. 5A-5B show THP1-derived macrophages. FIG. 5A show THP1-derived macrophages stained with: control IgG1 in absence of tumor cells (first row), ch-UMG1 (chimeric antibody according to aspect 2 of this invention, where the original murine Fc region was replaced with a fully human IgG1 Fc region) in absence of tumor cells (second row) and ch-UMG1 in presence of PANC1 pancreatic cancer cell line (third row and shown in greater detail in FIG. 5B). The first column represents the DAPI staining, the second column the antibody plus Alexa-Fluor 488 labeled secondary antibody and the third column represents the superimposed image.

FIGS. 6A-6B are bar graphs showing the results of the degranulation assay to evaluate Antibody-Dependent Cell mediated Cytotoxicity (ADCC) in HPB-ALL (FIG. 6A) and H9 cell lines (FIG. 6B). The numbers on the x-axis represent the different samples tested: no target is indicated by (1), effector plus target cells (E+T) (2), Negative control (NC) 200 μg/ml (3), ch-UMG1 10 μg/ml (4), ch-UMG1 50 μg/ml (5), ch-UMG1 100 μg/ml (6), ch-UMG1 200 μg/ml (7), Positive control (PC) 200 μg/ml (8). The y-axis represents the percentage of CD107a$^+$ NK cells affected by ADCC related to the whole number of CD107a$^+$ NK cells tested per sample.

FIG. 7 is a bar graph showing the results of the degranulation assay to evaluate Antibody-Dependent Cell mediated Cytotoxicity (ADCC) in BCWM.1 cell line. The numbers on x-axis represent the different samples. The numbers on the x-axis represent the different samples tested: no target is indicated by (1), effector plus target cells (E+T) (2), Negative control (NC) 200 μg/ml (3), ch-UMG1 10 μg/ml (4), ch-UMG1 50 μg/ml (5), ch-UMG1 100 g/ml (6), ch-UMG1 200 μg/ml (7), Positive control (PC) 200 μg/ml (8). The y-axis represents the percentage of CD107a$^+$ NK cells affected by ADCC related to the whole number of CD107a$^+$ NK cells tested per sample.

FIG. 8 is a bar graph illustrating that the CD3$^+$ expressing lymphocytes (CAR-T) were able to release significantly higher amount of Interferon gamma (IFNγ) in the presence of H9 cells. The y-axis shows the concentration of IFNγ expressed in ng/ml. On the x-axis the numbers indicated represent the different cells tested: (1) indicates non-transduced T cells (negative control); (2) indicates, T cells transduced with a control CAR (vehicle control); and (3) indicated T cells transduced with CAR-UMG1.

FIG. 9 is a bar graph illustrating that the CAR-T were able to release significantly higher amount of Interleukin 2 (IL-2) in the presence of H9 cells. The y-axis represents the concentration of IL2 expressed in ng/ml. On the x-axis the numbers indicated represent the different cells tested: (1) indicates non-transduced T cells (negative control); (2) indicates, T cells transduced with a control CAR (vehicle control); and (3) indicated T cells transduced with CAR-UMG1.

FIG. 10 is a bar graph showing that the CAR-T were able to induce selective killing of H9 cells. The y-axis reports the dead/live cells ratio. The x-axis reports: H9 alone (1), H9 in the presence of non-transduced T cells (2), H9 in the presence of T cells transduced with a control CAR (3) and H9 in the presence of T cells transduced with CAR-UMG1, also referred to as UMG1-CAR (4).

FIG. 11 is a line graph representing the tumor volume curves of an in vivo experiment comparing a control IgG1 (Rituximab) versus the humanized version of UMG1-mAb (h-UMG1) and the afucosylated version of UMG1-mAb (a-h-UMG1). In the graph, h-UMG1 is indicated with a line with squares, a-h-UMG1 is indicated with (a line with triangles), and the control IgG1 is indicated with a line with circles.

FIGS. 12A and 12B show representative flow cytometry results of direct staining of h-UMG1-PE and three commercially available CD43 antibodies. FIG. 12A shows staining in the ALL-SIL human cell line. FIG. 12B shows staining in the KE-37 cell line.

FIGS. 13A and 13B show competitive binding assays. FIG. 13A shows representative results from a competitive binding assay between h-UMG1, h-UMG1-PE, and three commerically available CD43 antibodies on the CEM cell line. FIG. 13B shows representative results from a competitive binding assay between h-UMG1, h-UMG1-PE, and three commerically available CD43 antibodies on the HPB-ALL cell line.

FIGS. 14A-14C show representative images of m-UMG1 staining in the inflammatory infiltrate in three different human tumors. FIG. 14A shows m-UMG1 staining in colorectal adenocarcinoma. FIG. 14B shows m-UMG1 staining in lung cancer adenocarcinoma. FIG. 14C shows m-UMG1 staining in breast cancer.

FIGS. 15A-15F show representative results from Example 9. FIG. 15A shows the amino acid sequence of full-length CD43 (SEQ ID NO: 17). FIG. 15B is an illustration depicting CD43 protein variants used to transfect the HEK293T cells. FIGS. 15C and 15E show the western blot results on the protein lysates of transfected HEK293T cells. FIGS. 15D and 15F are bar graphs showing FACS results on transfected HEK293T cells.

FIG. 16 shows screening of the h-UMG1 antibodies for their affinity to the antigent on HPB-ALL and H9 cell lines, which are known to be positive for the UMG1 epitope.

FIGS. 17A-17B show comparative flow cytometric profiles ofh-UMG1 and UN1 in four different cell lines of the hematopoietic lineage. FIG. 17A shows the reported UN1 flow cytometric profiles in cell lines of the hematopoietic lineage as provided by (Tassone et al., *Tissue Antigens* 44:73-82, 1994). FIG. 17B shows UMG1 flow cytometric profiles in cell lines of the hematopoietic lineage as provided by Example 8.

FIGS. 18A-18B show representative FACS images of treatment with the UMG1-CD3 bispecific antibody to conduct T-cell cytotoxicity assays on cell lines ALL-SIL (FIG. 18B) and KE-37 (FIG. 18A), as provided by Example 18.

FIG. 19 shows evaluation of the binding kinetics of h-UMG1 mAb to recombinant human CD43 analyte (aa 20-253, SEQ ID NO: 42) expressed in *E. coli* vector, an unglycosylated-CD43 protein. See, Example 10a.

7. DETAILED DESCRIPTION

7.1. Definitions

Figure 1A:
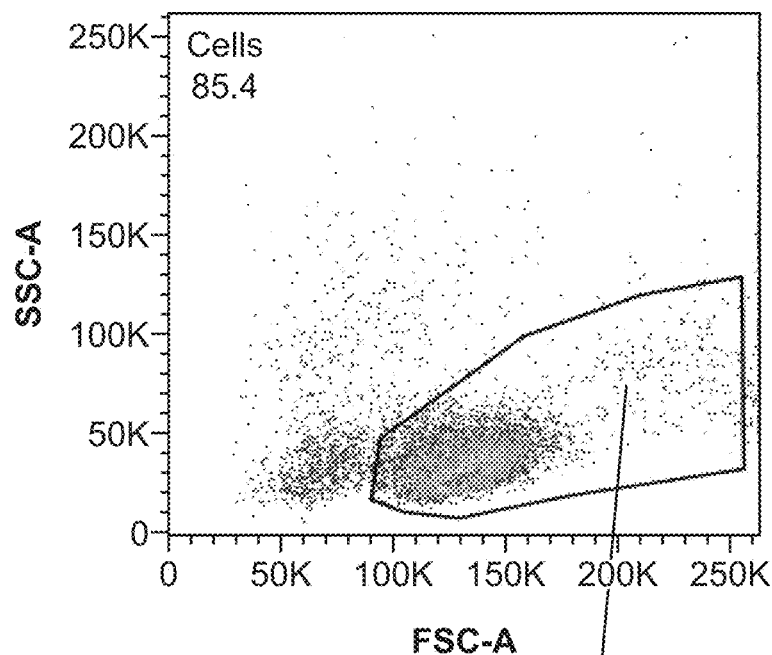

Unless otherwise defined, all terms of art, notations and other scientific terminology used herein are intended to have the meanings commonly understood by those of skill in the art.

Monoclonal antibody "UMG1" is a murine anti-human CD43 antibody produced by the hybridoma cell line deposited under ICLC accession number ICLC PD no 16001.

As used herein, unless otherwise qualified the term "antibody" has its broadest art-recognized meaning and includes all known formats, including, without limitation: bivalent monospecific monoclonal antibodies, bivalent bispecific antibodies, trivalent trispecific antibodies, F(ab) fragments, F(ab)'2 fragments, scFv fragments, diabodies, single domain antibodies, including camelid VHH single domain antibodies, tandabs, and flexibodies.

As used herein, the terms "treat" or "treatment" are used in their broadest accepted clinical sense. The terms include, without limitation, lessening a sign or symptom of disease; improving a sign or symptom of disease; alleviation of symptoms; diminishment of extent of disease; stabilization (i.e., not worsening) of the state of disease; delay or slowing of disease progression; amelioration or palliation of the disease state; remission (whether partial or total), whether detectable or undetectable; cure; prolonging survival as compared to expected survival if not receiving treatment. Unless explicitly stated otherwise, "treat" or "treatment" do not intend prophylaxis or prevention of disease.

By "subject" or "individual" is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on. Unless otherwise stated, "patient" intends a human "subject."

The term "sufficient amount" means an amount sufficient to produce a desired effect, e.g., an amount sufficient to modulate protein aggregation in a cell.

The term "therapeutically effective amount" is an amount that is effective to treat a disease. A "prophylactically effective amount" is an amount that is effective to slow onset of or prevent a disease.

In this disclosure, "comprises," "comprising," "containing," "having," "includes," "including," and linguistic variants thereof have the meaning ascribed to them in U.S. Patent law, permitting the presence of additional components beyond those explicitly recited.

As used herein, the singular forms "a," "an," and "the" include the plural referents unless the context clearly indicates otherwise. The terms "include," "such as," and the like are intended to convey inclusion without limitation, unless otherwise specifically indicated.

Ranges provided herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or otherwise apparent from context, as used herein the term "about" is understood as within a range of normal tolerance in the art.

7.2. General Overview

The current disclosure provides novel humanized and murine CD43 antibodies and binding molecules derived therefrom that have different expression and binding properties in comparison to the properties of other previously disclosed and commercially available CD43 antibodies.

7.3. CD43 Binding Proteins

7.3.1. Mouse Monoclonal UMG1 Antibodies

In a first aspect, the invention relates to a monoclonal mouse antibody produced by the hybridoma cell deposited under ICLC PD no 16001.

The hybridoma cell was deposited under the terms of the Budapest Treaty at Centro Biotecnologie Avanzate (CBA), Interlab Cell Line Collection (ICLC), Largo Rosanna, 10, 16132 Genova, Italy under accession number ICLC PD no 16001 on Aug. 4, 2016. The antibody was tested in the examples given below. As shown in the examples, the antibody binds to a specific epitope on CD43 in a portion of the protein that could be sialoglycosylated.

In this first aspect, the invention further relates to an antibody, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences GFTFSSFGMH (SEQ ID NO: 1), YIS-SGSGNFYYVDTVKG (SEQ ID NO: 43), STYYHGSR- GAMDY (SEQ ID NO: 3), SASSSVSSMYWY (SEQ ID NO: 4), DTSKMAS (SEQ ID NO: 5), and QQWSSYPPIT (SEQ ID NO: 6), respectively. These sequences are also given in SEQ IDs NO. 1-6.

In some embodiments, the antibody comprises all three heavy chain Complementary Determining Regions (CDRs) and all three light chain CDRs from: the antibody The CDR sequences mentioned above are the CDR sequences from the monoclonal mouse antibody produced by the hybridoma cell deposited under ICLC PD no 16001, as determined by sequencing.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

This monoclonal antibody may have framework sequences from any species. Preferably, it may have a mouse or human framework.

As used herein the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

Methods for producing a monoclonal antibody with the CDR sequences as mentioned above are known in the art and include the introduction of the nucleic acid sequences encoding the CDRs into suitable expression vectors encoding the desired framework sequences. Further methods are described below.

In a second aspect, the invention relates to an antibody which recognizes the same epitope as the antibody according to the first aspect.

Typically, and as generally known in the art, an antibody is a protein belonging to the protein family of immunoglobulins and is composed in its variable regions of framework regions and complementarity determining regions as defined above. Naturally, antibodies are produced by plasma cells in response to a certain antigen. In general, each antibody has two identical heavy chain immunoglobulins and two identical light chain immunoglobulins. Each heavy and each light chain may have a variable and a constant region. The constant region of a heavy chain may be one of five types of mammalian Ig heavy chains: α, δ, ε, γ and μ. The type of the heavy chain present usually defines the class (isotype) of the antibody: IgA, IgD, IgE, IgG and IgM antibodies, respectively. Similarly, the constant region of a light chain may be one of two types of mammalian Ig light chains: κ and λ. The variable regions of heavy and light chains are usually made of a unique combination of numerous protein sequences allowing the binding to a particular antigen.

According to the invention, the term "antibody" also covers an isolated antibody.

In general, each heavy chain is connected to one of the light chains, whereby the variable regions of a heavy and a light chain combine to form one of the two identical antigen-binding sites and their constant regions combine to form the constant region of the antibody. Further, both constructs of one heavy and one light chain may be connected via the constant regions of their heavy chains, forming a "Y"-shaped molecule, whereby the two arms depict the antigen-binding variable region and the stem depicts the constant region.

The antibody according to the second aspect may be a complete antibody, meaning that it usually comprises a heavy chain of three or four constant domains and a light chain of one constant domain as well as the respective variable domains, whereby each domain may comprise further modifications, such as mutations, deletions or insertions, which do not change the overall domain structure.

Further, the antibody according to the second aspect of the present invention may form a homo- or heterodimer or a homo- or heteromultimer, whereby "dimer" and "multimer" means that two and at least three antibodies, respectively, may combine to form a complex. The prefix "homo" means that a complex may be formed of identical antibody molecules, whereby the prefix "hetero" means that a complex may be formed of different antibody molecules.

In general, the term "antibody" is intended to comprise all above-mentioned immunoglobulin isotypes, i.e. the antibody may be an IgA, IgD, IgE, IgG or IgM antibody, including any subclass of these isotypes. Preferably, the antibody is an IgG antibody. Since the antibody may be expressed and produced recombinantly, the antibody may also comprise two different constant regions of heavy chains, e.g. one IgG1 and one IgG2 heavy chain, or heavy chains from different species. However, the heavy chains preferably are from the same species. Furthermore, the antibody may comprise either a lambda or a kappa light chain.

The antibody which recognizes the same epitope as one of the antibodies of the first aspect of the invention my further be an antibody, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 have the amino acid sequences GFTFSSFGMH (SEQ ID NO: 1), YIS-SGSGNFYYVDTVKG (SEQ ID NO: 43), STYYHGSR-GAMDY (SEQ ID NO: 3), SASSSVSSMYWY (SEQ ID NO: 4), DTSKMAS (SEQ ID NO: 5), and QQWSSYPPIT (SEQ ID NO: 6), respectively.

Furthermore, the antibody which recognizes the same epitope as one of the antibodies of the first aspect of the invention may be an antibody wherein the CDRs, in comparison to the sequences mentioned above has at least one conservative amino acid exchange, e.g., a similar amino acid with similar chemical structure and properties and/or function as the original amino acid.

The antibody which recognizes the same epitope as one of the antibodies of the first aspect of the invention may also be an antibody which has an increased or lowered affinity or specificity in comparison to one of the antibodies of the first aspect of the invention. Such antibodies are readily obtained by methods known in the art and further described herein below.

Generally, the antibody according to the second aspect of the invention may have a sequence, especially in its variable regions, that is at least 75%, 80%, 85%, 90%, 95%, or 100%

(e.g., at least 86, 87, 88, 89, 90, 91, 92, 93, 94, 95, 96, 97, 98 or 99%) identical to that of monoclonal mouse antibody produced by the hybridoma cell deposited under ICLC PD no 16001.

In some embodiments, the mouse antibody comprises a variable heavy chain to an amino acid sequence having 60-100% sequence identity to SEQ ID NO: 7, such as 70-100%, 80-100%, 85-100%, 90-100%, 95-100%, 97-100%, or 99-100% sequence identity to DVQVESGG-GLVQPGGSRKLSCVASGFTFSSFGMHWVRQA-PEKGLEW VAYISSGSGNFYYVDTVKGRFTIS-RDNPKNTLFLQMTSLRSEDTAMYYCARSTYYHG SRGAMDYWGQGTSVTVSS (SEQ ID NO: 44). In some embodiments, the mouse antibody comprises an amino acid sequence having 60% or greater sequence identity to SEQ ID NO: 7. In some embodiments, the mouse antibody comprises an amino acid sequence having 70% or greater sequence identity to SEQ ID NO: 7. In some embodiments, the mouse antibody comprises an amino acid sequence having 80% or greater sequence identity to SEQ ID NO: 7. In some embodiments, the mouse antibody comprises an amino acid sequence having 85% or greater sequence identity to SEQ ID NO: 7. In some embodiments, the mouse antibody comprises an amino acid sequence having 90% or greater sequence identity to SEQ ID NO: 7. In some embodiments, the mouse antibody comprises an amino acid sequence having 95% or greater sequence identity to SEQ ID NO: 7. In some embodiments, the mouse antibody comprises an amino acid sequence having 97% or greater sequence identity to SEQ ID NO: 7. In some embodiments, the mouse antibody comprises an amino acid sequence having 99% or greater sequence identity to SEQ ID NO: 7. In some embodiments, the mouse antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 7. In some embodiments, the mouse antibody comprises an amino acid sequence having 100% sequence identity to SEQ ID NO: 7.

In some embodiments, the mouse antibody comprises a variable light chain to an amino acid sequence having 60-100% sequence identity to SEQ ID NO: 12, such as 70-100%, 80-100%, 85-100%, 90-100%, 95-100%, 97-100%, or 99-100% sequence identity to QIALTQ-SPAIMSASPGEKVTMTCSASSSVSSMYWYQLKPGSSP RLLIYDTSKMASGVP IRFSGSGSGTSFSLTVSRVEAE-DAATYYCQQWSSYPPITFGAGSKLELK (SEQ ID NO: 12). In some embodiments, the mouse antibody comprises an amino acid sequence having 60% or greater sequence identity to SEQ ID NO: 12. In some embodiments, the mouse antibody comprises an amino acid sequence having 70% or greater sequence identity to SEQ ID NO: 12. In some embodiments, the mouse antibody comprises an amino acid sequence having 80% or greater sequence identity to SEQ ID NO: 12. In some embodiments, the mouse antibody comprises an amino acid sequence having 85% or greater sequence identity to SEQ ID NO: 12. In some embodiments, the mouse antibody comprises an amino acid sequence having 90% or greater sequence identity to SEQ ID NO: 12. In some embodiments, the mouse antibody comprises an amino acid sequence having 95% or greater sequence identity to SEQ ID NO: 12. In some embodiments, the mouse antibody comprises an amino acid sequence having 97% or greater sequence identity to SEQ ID NO: 12. In some embodiments, the mouse antibody comprises an amino acid sequence having 99% or greater sequence identity to SEQ ID NO: 12. In some embodiments, the mouse antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 12. In some embodiments, the mouse antibody comprises an amino acid sequence having 100% sequence identity to SEQ ID NO: 12.

In some embodiments, the mouse antibody comprises a variable heavy chain to an amino acid sequence having 60-100% sequence identity to SEQ ID NO: 7, such as 70-100%, 80-100%, 85-100%, 90-100%, 95-100%, 97-100%, or 99-100% sequence identity to DVQVESGG-GLVQPGGSRKLSCVASGFTFSSFGMHWVRQA-PEKGLEWV AYISSGSGNFYYVDTVKGRFTIS-RDNPKNTLFLQMTSLRSEDTAMYYCARSTYYHGS RGAMDYWGQGTSVTVSS (SEQ ID NO: 44) and a variable light chain to an amino acid sequence having 60-100% sequence identity to SEQ ID NO: 12, such as 70-100%, 80-100%, 85-100%, 90-100%, 95-100%, 97-100%, or 99-100% sequence identity to QIALTQSPAIM-SASPGEKVTMTCSASSSVSSMYWYQLKPGSSPR LLIYDTSKMASGVP IRFSGSGSGTSFSLTVSRVEAE-DAATYYCQQWSSYPPITFGAGSKLELK (SEQ ID NO: 12).

7.3.2. UMG1 Monospecific, Bispecific, and Multispecific Antibodies

Usually, the antibody according to the invention may be a monoclonal, a bispecific, or a multispecific antibody. Such antibodies are known in the art.

As used in the context of the present invention, the term "monoclonal" may be understood in the broadest sense describing antibodies produced by a single clone of B lymphocytes or antibodies having the same or a similar amino acid sequence.

The term "bispecific", as used herein, may be understood in the broadest sense describing antibodies interacting with two different epitopes. The bispecific antibody may be derived from two monoclonal antibodies. Optionally, these two different epitopes may be localized on the same antigen, but they may also be localized on two different antigens.

The term "multispecific", as used herein, may be understood in the broadest sense describing antibodies interacting with three or more different types of epitopes. Optionally, these epitopes may be localized on the same antigen or on two or more antigens.

Preferably, the antibody according to aspect two of the present invention is a monoclonal antibody.

Further, the antibody according to aspect two of the present invention preferably is a bispecific or a multispecific antibody.

Methods for the production of antibodies are well known to the person skilled in the art. Preferably, antibodies are produced by making hybridoma cells. Methods for the production of hybridoma cells as well as methods for the production of antibodies with the help of hybridoma cells are well-known to the person skilled in the art. Generally, mice are injected with the desired antigen and killed after a few days in order to isolate the spleen cells secreting the antibody against the desired antigen. In general, fusion of these antibody-secreting spleen cells with immortal non-secreting myeloma cells results to hybridoma cells. These hybridoma cells are then usually screened and the hybridoma producing the desired antibody is selected. The selected hybridoma may then be cultured in vivo or in vitro and the desired antibody can be isolated.

Bifunctional, or bispecific, antibodies may have antigen binding sites of different specificities. Various forms of bispecific antibodies and their production are known to the person skilled in the art. For example, these include BSIgG, which are IgG molecules comprising two distinct heavy chains and two distinct light chains that are secreted by so-called "hybrid hybridomas", and heteroantibody conjugates produced by the chemical conjugation of antibodies or antibody fragments of different specificities (Segal D M et al. Current Opin. Immunol. 1999, 11:558-562; Van Spriel A B et al. Immunology Today 2000, 21:391-397; each of which is incorporated by reference in its entirety).

Manufacture:

Bispecific antibodies may be generated to deliver cells, cytotoxins, or drugs to specific sites. An important use may be to deliver host cytotoxic cells, such as NK or cytotoxic T cells, to specific cellular targets. (P. J. Lachmann, Clin. Exp. Immunol. 1990, 79: 315, which is incorporated by reference in its entirety). Another important use may be the delivery of cytotoxic proteins to specific cellular targets (V. Raso, T. Griffin, Cancer Res. 1981, 41:2073; S. Honda et al., Cytotechnology, 1990, 4:59 each of which is incorporated by reference in its entirety). A further important use may be to deliver anti-cancer non-protein drugs to specific cellular targets (J. Corvalan et al., Intl. J. Cancer Suppl. 1988, 2:22; M. Pimm et al., British J. of Cancer 1990, 61:508; each of which is incorporated by reference in its entirety). Such bispecific antibodies may be prepared by chemical cross-linking (M. Brennan et al., 1985, Science 229:81; which is incorporated by reference in its entirety), disulfide exchange, or the production of hybrid-hybridomas (quadromas). Quadromas may be constructed by fusing hybridomas that secrete two different types of antibodies against two different antigens (Milstein and Cuello, Nature, 1983, 305: 537-539; which is incorporated by reference in its entirety).

The term "epitope", as used in the context of the present invention, may be understood in the broadest sense as a portion of a CD43 molecule capable of being recognized by and bound by the antibody produced by the hybridoma cell deposited under ICLC PD n° 16001 at one or more of the antibody's antigen binding regions. The part of an antibody that binds to the epitope is called a paratope. In many cases, epitopes have conformational properties that specifically generate binding sites for the paratope.

Epitopes usually consist of chemically active surface groupings of molecules such as amino acids or sugar side chains and generally have specific three dimensional structural characteristics as well as specific charge characteristics.

Further, it is understood and appreciated by one skilled in the art that the interaction between the epitope and the antibody may generally be based on the primary structure of the antigen, i.e. a continuous sequence of amino acids. Usually, the interaction may also be based on the secondary structure, the tertiary structure or the quaternary structure of the epitope as well as post-translational modifications, such as glycosylation. The interaction between the epitope and the antibody may further be based on the three-dimensional structure and resulting surface features of the antigen, which may involve a discontinuous section of the amino acid sequence comprising amino acids at distant locations into the interaction with the antibody.

An antibody recognizes "the same epitope" as the antibody according the first aspect, when the two antibodies recognize identical or sterically overlapping epitopes. In general, the most widely used and rapid methods for determining whether two epitopes recognize identical or sterically overlapping epitopes are competition assays, which usually may be configured in all number of different formats, using either labeled antigen or labeled antibody. For example, the antigen is immobilized on a 96-well plate, and the ability of unlabeled antibodies to block the binding of labeled antibodies is measured using radioactive or enzyme labels.

An antibody that recognizes "the same epitope" as the antibody according to the first aspect usually refers to an antibody that blocks binding of the reference antibody to its antigen in a competition assay by 50% or more, and conversely, the reference antibody usually blocks binding of the antibody to its antigen in a competition assay by 50% or more.

In general, the epitope recognized by and bound by the antibody produced by the hybridoma cell deposited under ICLC PD n° 16001 may be identified by any suitable epitope mapping method known in the art in combination with the antibody produced by the hybridoma cell deposited under ICLC PD n° 16001.

Examples of such a method include screening peptides of varying lengths derived from CD43 for binding to the antibody produced by the hybridoma cell deposited under ICLC PD n° 16001, whereby the smallest fragment that can specifically bind to the antibody usually contains the sequence of the epitope recognized by the antibody. In general, CD43 peptides may be produced synthetically or by proteolytic digestion of CD43. Methods for the identification of peptides binding to the antibody are well-known to the person skilled in the art, such as mass spectrometric analysis. In another example, NMR spectroscopy, can be used to identify residues which interact with an antibody of the present invention. For example, a CD43 peptide that has been uniformly 15N and 2H labelled can be mixed with an unlabelled antibody and those amino acids in the labelled peptide that interact with the unlabelled antibody can be detected as their position within the NMR spectra change. Typically, the difference between the two spectra enables the identification of the amino acids in CD43 that are involved in the interaction with the antibody. Preferably, mass spectrometric analysis is used for the identification of peptides binding to the antibody.

Exemplarily, the epitope recognized by and bound by the antibody produced by the hybridoma cell deposited under ICLC PD n° 16001 may also be identified by a method comprising amplification of various DNA fragments of CD43 DNA by polymerase chain reaction (PCR), integration of these fragments into an expression vector comprising their connection to a histidine fusion protein and, following protein expression, detection of the epitope, for example by western blot.

In a further example, in order to determine the site on CD43 recognized by and bound by the antibody produced by the hybridoma cell deposited under ICLC PD n° 16001, an expression vector cloned with CD43 may be introduced with deletion mutation by PCR method to prepare mutant series, such as *Escherichia coli* (*E. coli*) mutant series, that express proteins having various deleted sites in CD43. These *E. coli* mutants may be cultured and induced for expression. Western blot analysis may be carried out using the cell lysate as an antigen.

Further methods for the identification of the epitope recognized by and bound by the antibody produced by the hybridoma cell deposited under ICLC PD n° 16001 may comprise detection via immunoassays, such as enzyme-linked immunosorbent assay (ELISA).

The term "affinity", as used in the context of the present invention, may be understood in the broadest sense as the strength of the interaction between an epitope and an epitope-binding site of an antibody. Methods for determining an absolute value for antibody affinity, i.e. the affinity constant, are well known to the person skilled in the art. However, also relative values of antibody affinities may generally be determined, i.e. the affinity of two antibodies is compared without determining their absolute values. Methods for comparing the affinities of antibodies are well-known to the person skilled in the art. For example, flow cytometry may be used, whereby cells having the desired epitope may independently be brought into contact with different antibodies, which are subsequently marked with an immunofluorescent secondary antibody. Usually, after detection with flow cytometry, the intensity of the signals of the antibodies can be compared.

Screening Methods:

Methods for the identification of antibodies according to the second aspect, which recognize the same epitope as the antibody according to the antibody of the first aspect, are well-known to the person skilled in the art. For example, antibodies according to the second aspect may be identified by phage display based on antibody libraries.

Consequently, the antibody of the invention recognizing the same epitope may also be a human antibody.

In another preferred embodiment, the antibody according to the second aspect is a chimeric antibody. In a more preferred embodiment, the antibody according to the second aspect is a chimeric antibody according to the first aspect.

A chimeric antibody is an antibody, in which at least one region of an immunoglobulin of a species is fused to another region of an immunoglobulin of another species by genetic engineering in order to reduce its immunogenicity (see, e.g., U.S. Pat. Nos. 4,816,567 and 4,816,397).

7.3.3. Humanized UMG1 Antibodies

In another preferred embodiment, the antibody according to the second aspect is a humanized antibody. In a more preferred embodiment, the antibody according to the second aspect is a chimeric or humanized antibody according to the antibody of the first aspect.

In general, humanized antibodies are a particular type of chimeric antibodies. For example, humanized antibodies may be produced by grafting DNA of a human antibody into the mouse antibody framework coding DNA or by grafting DNA of a mouse antibody into human antibody framework coding DNA. Preferably, DNA of a human antibody is grafted into the mouse antibody framework coding DNA. In general, grafting of DNA comprises grafting of one or more DNA sequences into the target antibody framework coding DNA. Optionally, the variable and constant regions as well as heavy and light chains may be partially or fully humanized. Preferably, the heavy chain variable region and the light chain variable region of a mouse antibody are humanized. More preferably, the heavy chain variable region and the light chain variable region of a mouse antibody are humanized by changing a DNA sequence encoding 1 to 50, preferably, 1 to 30, more preferably 1 to 20 amino acids. In the DNA grafted may generally comprise DNA regions of the six hypervariable loops determining antigen specificity, also called complementarity-determining regions (CDR), or DNA regions not comprising a CDR, or both. Preferably, the humanization comprises grafting of DNA not comprising CDRs.

In general, the resulting DNA construct may then be used to express and produce antibodies that are usually less or not immunogenic in comparison to the non-human parental antibody. This includes the production of modified antibodies such as aglycosylated antibodies or afucosylated antibodies. Such methods are well-known in the art. Consequently, the antibody of the invention recognizing the same epitope may also be an aglycosylated antibody or a afucosylated antibody.

7.3.4. Engineered Humanized Antibodies

The disclosure also provides engineered humanized antibodies that recognize CD43. The h-UMG1 antibody can comprise one or more of the variable heavy or light regions provided in SEQ ID NOs: 8–11, and SEQ ID NOs:13-16, respectively. A person skilled in the art can generated various embodiments by making one or more conservative substitutions of amino acid residue provided by the present disclosure. A "conservative substitution" or a "conservative amino acid substitution," refers to the substitution an amino acid with a chemically or functionally similar amino acid.

In some embodiments, the antibody is IgG1, IgG2, IgG4, or IgM. In some embodiments, the antigen binding protein is an Fv fragment, a Fab fragment, a F(ab')$_2$ fragment, a Fab' fragment, an scFv fragment, an scFv-Fc fragment, and/or a single-domain antibody.

In some embodiments, the h-UMG1 antibody comprises an amino acid sequence having 60-100% sequence identity to SEQ ID NO: 8, such as 70-100%, 80-100%, 85-100%, 90-100%, 95-100%, 97-100%, or 99-100% sequence identity to EVQVESGGGLVQPGGSLRLS-CAASGFTFSSFGMHWVRQAPGKGLEWVSYISSGSGN FYYVDTVKGRFTISRDNAKNSLYLQMNSLRAED-TAVYYCARSTYYHGSRGAMDYW GQGTLVTVSS (SEQ ID NO: 45). In some embodiments, the h-UMG1 antibody comprises an amino acid sequence having 60% or greater sequence identity to SEQ ID NO: 8. In some embodiments, the h-UMG1 antibody comprises an amino acid sequence having 70% or greater sequence identity to SEQ ID NO: 8. In some embodiments, the h-UMG1 antibody comprises an amino acid sequence having 80% or greater sequence identity to SEQ ID NO: 8. In some embodiments, the h-UMG1 antibody comprises an amino acid sequence having 85% or greater sequence identity to SEQ ID NO: 8. In some embodiments, the h-UMG1 antibody comprises an amino acid sequence having 90% or greater sequence identity to SEQ ID NO: 8. In some embodiments, the h-UMG1 antibody comprises an amino acid sequence having 95% or greater sequence identity to SEQ ID NO: 8. In some embodiments, the h-UMG1 antibody comprises an amino acid sequence having 97% or greater sequence identity to SEQ ID NO: 8. In some embodiments, the h-UMG1 antibody the h-UMG1 antibody comprises an amino acid sequence having 99% or greater sequence identity to SEQ ID NO: 8. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8. In some embodiments, the h-UMG1 antibody comprises an amino acid sequence having 100% sequence identity to SEQ ID NO: 8.

In some embodiments, the h-UMG1 antibody comprises an amino acid sequence having 60-100% sequence identity to SEQ ID NO: 9, such as 70-100%, 80-100%, 85-100%, 90-100%, 95-100%, 97-100%, or 99-100% sequence identity to EVQLVESGG-GLVQPGGSLRLSCVASGFTFSSFGMHWVRQAPGK-GLEWVSYISSGSG NFYYVDTVKGRFTISRDNAKNSLYLQMNSLRAED-TAVYYCARSTYYHGSRGAMDY WGQGTLVTVSS (SEQ ID NO: 9). In some embodiments, the h-UMG1 antibody comprises an amino acid sequence having 60% or greater sequence identity to SEQ ID NO: 9. In some embodiments, the h-UMG1 antibody comprises an amino acid sequence having 70% or greater sequence identity to SEQ ID NO: 9. In some embodiments, the h-UMG1 antibody comprises an amino acid sequence having 80% or greater sequence identity to SEQ ID NO: 9. In some embodiments, the h-UMG1 antibody comprises an amino acid sequence having 85% or greater sequence identity to SEQ ID NO: 9. In some embodiments, the h-UMG1 antibody comprises an amino acid sequence having 90% or greater sequence identity to SEQ ID NO: 9. In some embodiments, the h-UMG1 antibody comprises an amino acid sequence having 95% or greater sequence identity to SEQ ID NO: 9. In some embodiments, the h-UMG1 antibody comprises an amino acid sequence having 97% or greater sequence identity to SEQ ID NO: 9. In some embodiments, the h-UMG1 antibody the h-UMG1 antibody comprises an amino acid sequence having 99% or greater sequence identity to SEQ ID NO: 9. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9. In some embodiments, the h-UMG1 antibody comprises an amino acid sequence having 100% sequence identity to SEQ ID NO: 9.

In some embodiments, the h-UMG1 antibody comprises an amino acid sequence having 60-100% sequence identity to SEQ ID NO: 10, such as 70-100%, 80-100%, 85-100%, 90-100%, 95-100%, 97-100%, or 99-100% sequence identity to EVQLVESGG-GLVQPGGSLRLSCVASGFTFSSFGMHWVRQAPGK-GLEWVAYISSGSG NFYYVDTVKGRFTISRDNAKNSLYLQMNSLRAED-TAVYYCARSTYYHGSRGAMDY WGQGTLVTVSS (SEQ ID NO: 10). In some embodiments, the h-UMG1 antibody comprises an amino acid sequence having 60% or greater sequence identity to SEQ ID NO: 10. In some embodiments, the h-UMG1 antibody comprises an amino acid sequence having 70% or greater sequence identity to SEQ ID NO: 10. In some embodiments, the h-UMG1 antibody comprises an amino acid sequence having 80% or greater sequence identity to SEQ ID NO: 10. In some embodiments, the h-UMG1 antibody comprises an amino acid sequence having 85% or greater sequence identity to SEQ ID NO: 10. In some embodiments, the h-UMG1 antibody comprises an amino acid sequence having 90% or greater sequence identity to SEQ ID NO: 10. In some embodiments, the h-UMG1 antibody comprises an amino acid sequence having 95% or greater sequence identity to SEQ ID NO: 10. In some embodiments, the h-UMG1 antibody comprises an amino acid sequence having 97% or greater sequence identity to SEQ ID NO: 10. In some embodiments, the h-UMG1 antibody comprises an amino acid sequence having 99% or greater sequence identity to SEQ ID NO: 10. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10. In some embodiments, the h-UMG1 antibody comprises an amino acid sequence having 100% sequence identity to SEQ ID NO: 10.

In some embodiments, the h-UMG1 antibody comprises an amino acid sequence having 60-100% sequence identity to SEQ ID NO: 11, such as 70-100%, 80-100%, 85-100%, 90-100%, 95-100%, 97-100%, or 99-100% sequence identity to QVQLVES-GGGVVQPGGSLRLSCVASGFTFSSFGMHW VRQAPGKGLEWVAYISSGSG NFYYVDTVKGRFTIS-RDNSKNTLYLQMNSLRAEDTAVYYCARSTYYHGSR-GAMDY WGQGTLVTVSS (SEQ ID NO: 11). In some embodiments, the h-UMG1 antibody comprises an amino acid sequence having 60% or greater sequence identity to SEQ ID NO: 11. In some embodiments, the h-UMG1 antibody comprises an amino acid sequence having 70% or greater sequence identity to SEQ ID NO: 11. In some embodiments, the h-UMG1 antibody comprises an amino acid sequence having 80% or greater sequence identity to SEQ ID NO: 11. In some embodiments, the h-UMG1 antibody comprises an amino acid sequence having 85% or greater sequence identity to SEQ ID NO: 11. In some embodiments, the h-UMG1 antibody comprises an amino acid sequence having 90% or greater sequence identity to SEQ ID NO: 11. In some embodiments, the h-UMG1 antibody comprises an amino acid sequence having 95% or greater sequence identity to SEQ ID NO: 11. In some embodiments, the h-UMG1 antibody comprises an amino acid sequence having 97% or greater sequence identity to SEQ ID NO: 11. In some embodiments, the h-UMG1 antibody the h-UMG1 antibody comprises an amino acid sequence having 99% or greater sequence identity to SEQ ID NO: 11. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11. In some embodiments, the h-UMG1 antibody comprises an amino acid sequence having 100% sequence identity to SEQ ID NO: 11.

In some embodiments, the h-UMG1 antibody comprises an amino acid sequence having 60-100% sequence identity to SEQ ID NO: 13, such as 70-100%, 80-100%, 85-100%, 90-100%, 95-100%, 97-100%, or 99-100% sequence identity to EIVLTQSPATLSLSPGER-ATLSCSASSSVSSMYWYQQKPGLAPRLLIYDTSK-MASGIPD RFSGSGSGTDFTLTISRLEPEDFAVYYCQQWSSYP-PITFGQGTRLEIK (SEQ ID NO: 13).

In some embodiments, the h-UMG1 antibody comprises an amino acid sequence having 60% or greater sequence identity to SEQ ID NO: 13. In some embodiments, the h-UMG1 antibody comprises an amino acid sequence having 70% or greater sequence identity to SEQ ID NO: 13. In some embodiments, the h-UMG1 antibody comprises an amino acid sequence having 80% or greater sequence identity to SEQ ID NO: 13. In some embodiments, the h-UMG1 antibody comprises an amino acid sequence having 85% or greater sequence identity to SEQ ID NO: 13. In some embodiments, the h-UMG1 antibody comprises an amino acid sequence having 90% or greater sequence identity to SEQ ID NO: 13. In some embodiments, the h-UMG1 antibody comprises an amino acid sequence having 95% or greater sequence identity to SEQ ID NO: 13. In some embodiments, the h-UMG1 antibody comprises an amino acid sequence having 97% or greater sequence identity to SEQ ID NO: 13. In some embodiments, the h-UMG1 antibody the h-UMG1 antibody comprises an amino acid sequence having 99% or greater sequence identity to SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 13. In some embodiments, the h-UMG1 antibody comprises an amino acid sequence having 100% sequence identity to SEQ ID NO: 13.

In some embodiments, the h-UMG1 antibody comprises an amino acid sequence having 60-100% sequence identity to SEQ ID NO: 14, such as 70-100%, 80-100%, 85-100%, 90-100%, 95-100%, 97-100%, or 99-100% sequence identity to EIALTQSPATLSLSPGER-ATLSCSASSSVSSMYWYQLKPGLAPRLLIYDTSK-MASGIPI RFSGSGSGTDFTLTVSRVEPEDFAVYYCQQWSSYP-PITFGQGTRLEIK (SEQ ID NO: 14).

In some embodiments, the h-UMG1 antibody comprises an amino acid sequence having 60% or greater sequence identity to SEQ ID NO: 14. In some embodiments, the h-UMG1 antibody comprises an amino acid sequence having 70% or greater sequence identity to SEQ ID NO: 14. In some embodiments, the h-UMG1 antibody comprises an amino acid sequence having 80% or greater sequence identity to SEQ ID NO: 14. In some embodiments, the h-UMG1 antibody comprises an amino acid sequence having 85% or greater sequence identity to SEQ ID NO: 14. In some embodiments, the h-UMG1 antibody comprises an amino acid sequence having 90% or greater sequence identity to SEQ ID NO: 14. In some embodiments, the h-UMG1 antibody comprises an amino acid sequence having 95% or greater sequence identity to SEQ ID NO: 14. In some embodiments, the h-UMG1 antibody comprises an amino acid sequence having 97% or greater sequence identity to SEQ ID NO: 14. In some embodiments, the h-UMG1 antibody the h-UMG1 antibody comprises an amino acid sequence having 99% or greater sequence identity to SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 14. In some embodiments, the h-UMG1 antibody comprises an amino acid sequence having 100% sequence identity to SEQ ID NO: 14.

In some embodiments, the h-UMG1 antibody comprises an amino acid sequence having 60-100% sequence identity to SEQ ID NO: 15, such as 70-100%, 80-100%, 85-100%, 90-100%, 95-100%, 97-100%, or 99-100% sequence identity to QVVMTQSPAFLSVTPGEKVTITCSASSSVSS MYWYQQKPDQAPKLLIYDTSKMASGV PSRFSGSGSGTDFTFTISSLEAEDAATYYCQQWSSYP-PITFGGGTKVEIK (SEQ ID NO: 15)

In some embodiments, the h-UMG1 antibody comprises an amino acid sequence having 60% or greater sequence identity to SEQ ID NO: 15. In some embodiments, the h-UMG1 antibody comprises an amino acid sequence having 70% or greater sequence identity to SEQ ID NO: 15. In some embodiments, the h-UMG1 antibody comprises an amino acid sequence having 80% or greater sequence identity to SEQ ID NO: 15. In some embodiments, the h-UMG1 antibody comprises an amino acid sequence having 85% or greater sequence identity to SEQ ID NO: 15. In some embodiments, the h-UMG1 antibody comprises an amino acid sequence having 90% or greater sequence identity to SEQ ID NO: 15. In some embodiments, the h-UMG1 antibody comprises an amino acid sequence having 95% or greater sequence identity to SEQ ID NO: 15. In some embodiments, the h-UMG1 antibody comprises an amino acid sequence having 97% or greater sequence identity to SEQ ID NO: 15. In some embodiments, the h-UMG1 antibody comprises an amino acid sequence having 99% or greater sequence identity to SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 15.

In some embodiments, the h-UMG1 antibody comprises an amino acid sequence having 100% sequence identity to SEQ ID NO: 15.

In some embodiments, the h-UMG1 antibody comprises an amino acid sequence having 60-100% sequence identity to SEQ ID NO: 16, such as 70-100%, 80-100%, 85-100%, 90-100%, 95-100%, 97-100%, or 99-100% sequence identity to QVVMTQSPAFLSVTPGEKVTITCSASSSVSS MYWYQLKPDQAPKLLIYDTSKMASGV PIRFSGSGSGTDFTFTVSSVEAEDAATYYCQQWSSYP-PITFGGGTKVEIK (SEQ ID NO: 16)

In some embodiments, the h-UMG1 antibody comprises an amino acid sequence having 60% or greater sequence identity to SEQ ID NO: 8 and SEQ ID NO: 13. In some embodiments, the h-UMG1 antibody comprises an amino acid sequence having 70% or greater sequence identity to SEQ ID NO: 8 and SEQ ID NO: 13. In some embodiments, the h-UMG1 antibody comprises an amino acid sequence having 80% or greater sequence identity to SEQ ID NO: 8 and SEQ ID NO: 13. In some embodiments, the h-UMG1 antibody comprises an amino acid sequence having 85% or greater sequence identity to SEQ ID NO: 8 and SEQ ID NO: 13. In some embodiments, the h-UMG1 antibody comprises an amino acid sequence having 90% or greater sequence identity to SEQ ID NO: 8 and SEQ ID NO: 13. In some embodiments, the h-UMG1 antibody comprises an amino acid sequence having 95% or greater sequence identity to SEQ ID NO: 8 and SEQ ID NO: 13. In some embodiments, the h-UMG1 antibody comprises an amino acid sequence having 97% or greater sequence identity to SEQ ID NO: 8 and SEQ ID NO: 13. In some embodiments, the h-UMG1 antibody comprises an amino acid sequence having 99% or greater sequence identity to SEQ ID NO: 8 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 13. In some embodiments, the h-UMG1 antibody comprises an amino acid sequence having 100% sequence identity to SEQ ID NO: 8 and SEQ ID NO: 13. In some embodiments, the h-UMG1 antibody comprises an amino acid sequence having 60% or greater sequence identity to SEQ ID NO: 8 and SEQ ID NO: 13. In some embodiments, the h-UMG1 antibody comprises an amino acid sequence having 70% or greater sequence identity to SEQ ID NO: 8 and SEQ ID NO: 13. In some embodiments, the h-UMG1 antibody comprises an amino acid sequence having 80% or greater sequence identity to SEQ ID NO: 8 and SEQ ID NO: 13. In some embodiments, the h-UMG1 antibody comprises an amino acid sequence having 85% or greater sequence identity to SEQ ID NO: 8 and SEQ ID NO: 13. In some embodiments, the h-UMG1 antibody comprises an amino acid sequence having 90% or greater sequence identity to SEQ ID NO: 8 and SEQ ID NO: 13. In some embodiments, the h-UMG1 antibody comprises an amino acid sequence having 95% or greater sequence identity to SEQ ID NO: 8 and SEQ ID NO: 13. In some embodiments, the h-UMG1 antibody comprises an amino acid sequence having 97% or greater sequence identity to SEQ ID NO: 8 and SEQ ID NO: 13. In some embodiments, the h-UMG1 antibody comprises an amino acid sequence having 99% or greater sequence identity to SEQ ID NO: 8 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 13. In some embodiments, the h-UMG1 antibody comprises an amino acid sequence having 100% sequence identity to SEQ ID NO: 8 and SEQ ID NO: 13.

In some embodiments, the h-UMG1 antibody comprises an amino acid sequence having 60% or greater sequence identity to SEQ ID NO: 8 and SEQ ID NO: 14. In some embodiments, the h-UMG1 antibody comprises an amino acid sequence having 70% or greater sequence identity to SEQ ID NO: 8 and SEQ ID NO: 14. In some embodiments, the h-UMG1 antibody comprises an amino acid sequence having 80% or greater sequence identity to SEQ ID NO: 8 and SEQ ID NO: 14. In some embodiments, the h-UMG1 antibody comprises an amino acid sequence having 85% or greater sequence identity to SEQ ID NO: 8 and SEQ ID NO: 14. In some embodiments, the h-UMG1 antibody comprises an amino acid sequence having 90% or greater sequence identity to SEQ ID NO: 8 and SEQ ID NO: 14. In some embodiments, the h-UMG1 antibody comprises an amino acid sequence having 95% or greater sequence identity to SEQ ID NO: 8 and SEQ ID NO: 14. In some embodiments, the h-UMG1 antibody comprises an amino acid sequence having 97% or greater sequence identity to SEQ ID NO: 8 and SEQ ID NO: 14. In some embodiments, the h-UMG1 antibody comprises an amino acid sequence having 99% or greater sequence identity to SEQ ID NO: 8 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 14. In some embodiments, the h-UMG1 antibody comprises an amino acid sequence having 100% sequence identity to SEQ ID NO: 8 and SEQ ID NO: 14. In some embodiments, the h-UMG1 antibody comprises an amino acid sequence having 60% or greater sequence identity to SEQ ID NO: 8 and SEQ ID NO: 14. In some embodiments, the h-UMG1 antibody comprises an amino acid sequence having 70% or greater sequence identity to SEQ ID NO: 8 and SEQ ID NO: 14. In some embodiments, the h-UMG1 antibody comprises an amino acid sequence having 80% or greater sequence identity to SEQ ID NO: 8 and SEQ ID NO: 14. In some embodiments, the h-UMG1 antibody comprises an amino acid sequence having 85% or greater sequence identity to SEQ ID NO: 8 and SEQ ID NO: 14. In some embodiments, the h-UMG1 antibody comprises an amino acid sequence having 90% or greater sequence identity to SEQ ID NO: 8 and SEQ ID NO: 14. In some embodiments, the h-UMG1 antibody comprises an amino acid sequence having 95% or greater sequence identity to SEQ ID NO: 8 and SEQ ID NO: 14. In some embodiments, the h-UMG1 antibody comprises an amino acid sequence having 97% or greater sequence identity to SEQ ID NO: 8 and SEQ ID NO: 14. In some embodiments, the h-UMG1 antibody comprises an amino acid sequence having 99% or greater sequence identity to SEQ ID NO: 8 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 14. In some embodiments, the h-UMG1 antibody comprises an amino acid sequence having 100% sequence identity to SEQ ID NO: 8 and SEQ ID NO: 14.

In some embodiments, the h-UMG1 antibody comprises an amino acid sequence having 60% or greater sequence identity to SEQ ID NO: 8 and SEQ ID NO: 15. In some embodiments, the h-UMG1 antibody comprises an amino acid sequence having 70% or greater sequence identity to SEQ ID NO: 8 and SEQ ID NO: 15. In some embodiments, the h-UMG1 antibody comprises an amino acid sequence having 80% or greater sequence identity to SEQ ID NO: 8 and SEQ ID NO: 15. In some embodiments, the h-UMG1 antibody comprises an amino acid sequence having 85% or greater sequence identity to SEQ ID NO: 8 and SEQ ID NO: 15. In some embodiments, the h-UMG1 antibody comprises an amino acid sequence having 90% or greater sequence identity to SEQ ID NO: 8 and SEQ ID NO: 15. In some embodiments, the h-UMG1 antibody comprises an amino acid sequence having 95% or greater sequence identity to SEQ ID NO: 8 and SEQ ID NO: 15. In some embodiments, the h-UMG1 antibody comprises an amino acid sequence having 97% or greater sequence identity to SEQ ID NO: 8 and SEQ ID NO: 15. In some embodiments, the h-UMG1 antibody comprises an amino acid sequence having 99% or greater sequence identity to SEQ ID NO: 8 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 15. In some embodiments, the h-UMG1 antibody comprises an amino acid sequence having 100% sequence identity to SEQ ID NO: 8 and SEQ ID NO: 15. In some embodiments, the h-UMG1 antibody comprises an amino acid sequence having 60% or greater sequence identity to SEQ ID NO: 8 and SEQ ID NO: 15. In some embodiments, the h-UMG1 antibody comprises an amino acid sequence having 70% or greater sequence identity to SEQ ID NO: 8 and SEQ ID NO: 15. In some embodiments, the h-UMG1 antibody comprises an amino acid sequence having 80% or greater sequence identity to SEQ ID NO: 8 and SEQ ID NO: 15. In some embodiments, the h-UMG1 antibody comprises an amino acid sequence having 85% or greater sequence identity to SEQ ID NO: 8 and SEQ ID NO: 15. In some embodiments, the h-UMG1 antibody comprises an amino acid sequence having 90% or greater sequence identity to SEQ ID NO: 8 and SEQ ID NO: 15. In some embodiments, the h-UMG1 antibody comprises an amino acid sequence having 95% or greater sequence identity to SEQ ID NO: 8 and SEQ ID NO: 15. In some embodiments, the h-UMG1 antibody comprises an amino acid sequence having 97% or greater sequence identity to SEQ ID NO: 8 and SEQ ID NO: 15. In some embodiments, the h-UMG1 antibody comprises an amino acid sequence having 99% or greater sequence identity to SEQ ID NO: 8 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 15. In some embodiments, the h-UMG1 antibody comprises an amino acid sequence having 100% sequence identity to SEQ ID NO: 8 and SEQ ID NO: 15.

In some embodiments, the h-UMG1 antibody comprises an amino acid sequence having 60% or greater sequence identity to SEQ ID NO: 8 and SEQ ID NO: 16. In some embodiments, the h-UMG1 antibody comprises an amino acid sequence having 70% or greater sequence identity to SEQ ID NO: 8 and SEQ ID NO: 16. In some embodiments, the h-UMG1 antibody comprises an amino acid sequence having 80% or greater sequence identity to SEQ ID NO: 8 and SEQ ID NO: 16. In some embodiments, the h-UMG1 antibody comprises an amino acid sequence having 85% or greater sequence identity to SEQ ID NO: 8 and SEQ ID NO: 16. In some embodiments, the h-UMG1 antibody comprises an amino acid sequence having 90% or greater sequence identity to SEQ ID NO: 8 and SEQ ID NO: 16. In some embodiments, the h-UMG1 antibody comprises an amino acid sequence having 95% or greater sequence identity to SEQ ID NO: 8 and SEQ ID NO: 16. In some embodiments, the h-UMG1 antibody comprises an amino acid sequence having 97% or greater sequence identity to SEQ ID NO: 8 and SEQ ID NO: 16. In some embodiments, the h-UMG1 antibody comprises an amino acid sequence having 99% or greater sequence identity to SEQ ID NO: 8 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 16. In some embodiments, the h-UMG1 antibody comprises an amino acid sequence having 100% sequence identity to SEQ ID NO: 8 and SEQ ID NO: 16. In some embodiments, the h-UMG1 antibody comprises an amino acid sequence having 60% or greater sequence identity to SEQ ID NO: 8 and SEQ ID NO: 16. In some embodiments, the h-UMG1 antibody comprises an amino acid sequence having 70% or greater sequence identity to SEQ ID NO: 8 and SEQ ID NO: 16. In some embodiments, the h-UMG1 antibody comprises an amino acid sequence having 80% or greater sequence identity to SEQ ID NO: 8 and SEQ ID NO: 16. In some embodiments, the h-UMG1 antibody comprises an amino acid sequence having 85% or greater sequence identity to SEQ ID NO: 8 and SEQ ID NO: 16. In some embodiments, the h-UMG1 antibody comprises an amino acid sequence having 90% or greater sequence identity to SEQ ID NO: 8 and SEQ ID NO: 16. In some embodiments, the h-UMG1 antibody comprises an amino acid sequence having 95% or greater sequence identity to SEQ ID NO: 8 and SEQ ID NO: 16. In some embodiments, the h-UMG1 antibody comprises an amino acid sequence having 97% or greater sequence identity to SEQ ID NO: 8 and SEQ ID NO: 16. In some embodiments, the h-UMG1 antibody comprises an amino acid sequence having 99% or greater sequence identity to SEQ ID NO: 8 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 8 and SEQ ID NO: 16. In some embodiments, the h-UMG1 antibody comprises an amino acid sequence having 100% sequence identity to SEQ ID NO: 8 and SEQ ID NO: 16.

In some embodiments, the h-UMG1 antibody comprises an amino acid sequence having 60% or greater sequence identity to SEQ ID NO: 9 and SEQ ID NO: 13. In some embodiments, the h-UMG1 antibody comprises an amino acid sequence having 70% or greater sequence identity to SEQ ID NO: 9 and SEQ ID NO: 13. In some embodiments, the h-UMG1 antibody comprises an amino acid sequence having 80% or greater sequence identity to SEQ ID NO: 9 and SEQ ID NO: 13. In some embodiments, the h-UMG1 antibody comprises an amino acid sequence having 85% or greater sequence identity to SEQ ID NO: 9 and SEQ ID NO: 13. In some embodiments, the h-UMG1 antibody comprises an amino acid sequence having 90% or greater sequence identity to SEQ ID NO: 9 and SEQ ID NO: 13. In some embodiments, the h-UMG1 antibody comprises an amino acid sequence having 95% or greater sequence identity to SEQ ID NO: 9 and SEQ ID NO: 13. In some embodiments, the h-UMG1 antibody comprises an amino acid sequence having 97% or greater sequence identity to SEQ ID NO: 9 and SEQ ID NO: 13. In some embodiments, the h-UMG1 antibody comprises an amino acid sequence having 99% or greater sequence identity to SEQ ID NO: 9 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 13. In some embodiments, the h-UMG1 antibody comprises an amino acid sequence having 100% sequence identity to SEQ ID NO: 9 and SEQ ID NO: 13.

In some embodiments, the h-UMG1 antibody comprises an amino acid sequence having 60% or greater sequence identity to SEQ ID NO: 9 and SEQ ID NO: 14. In some embodiments, the h-UMG1 antibody comprises an amino acid sequence having 70% or greater sequence identity to SEQ ID NO: 9 and SEQ ID NO: 14. In some embodiments, the h-UMG1 antibody comprises an amino acid sequence having 80% or greater sequence identity to SEQ ID NO: 9 and SEQ ID NO: 14. In some embodiments, the h-UMG1 antibody comprises an amino acid sequence having 85% or greater sequence identity to SEQ ID NO: 9 and SEQ ID NO: 14. In some embodiments, the h-UMG1 antibody comprises an amino acid sequence having 90% or greater sequence identity to SEQ ID NO: 9 and SEQ ID NO: 14. In some embodiments, the h-UMG1 antibody comprises an amino acid sequence having 95% or greater sequence identity to SEQ ID NO: 9 and SEQ ID NO: 14. In some embodiments, the h-UMG1 antibody comprises an amino acid sequence having 97% or greater sequence identity to SEQ ID NO: 9 and SEQ ID NO: 14. In some embodiments, the h-UMG1 antibody comprises an amino acid sequence having 99% or greater sequence identity to SEQ ID NO: 9 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 14. In some embodiments, the h-UMG1 antibody comprises an amino acid sequence having 100% sequence identity to SEQ ID NO: 9 and SEQ ID NO: 14. In some embodiments, the h-UMG1 antibody comprises an amino acid sequence having 60% or greater sequence identity to SEQ ID NO: 9 and SEQ ID NO: 14. In some embodiments, the h-UMG1 antibody comprises an amino acid sequence having 70% or greater sequence identity to SEQ ID NO: 9 and SEQ ID NO: 14. In some embodiments, the h-UMG1 antibody comprises an amino acid sequence having 80% or greater sequence identity to SEQ ID NO: 9 and SEQ ID NO: 14. In some embodiments, the h-UMG1 antibody comprises an amino acid sequence having 85% or greater sequence identity to SEQ ID NO: 9 and SEQ ID NO: 14. In some embodiments, the h-UMG1 antibody comprises an amino acid sequence having 90% or greater sequence identity to SEQ ID NO: 9 and SEQ ID NO: 14. In some embodiments, the h-UMG1 antibody comprises an amino acid sequence having 95% or greater sequence identity to SEQ ID NO: 9 and SEQ ID NO: 14. In some embodiments, the h-UMG1 antibody comprises an amino acid sequence having 97% or greater sequence identity to SEQ ID NO: 9 and SEQ ID NO: 14. In some embodiments, the h-UMG1 antibody comprises an amino acid sequence having 99% or greater sequence identity to SEQ ID NO: 9 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 14. In some embodiments, the h-UMG1 antibody comprises an amino acid sequence having 100% sequence identity to SEQ ID NO: 9 and SEQ ID NO: 14.

In some embodiments, the h-UMG1 antibody comprises an amino acid sequence having 60% or greater sequence identity to SEQ ID NO: 9 and SEQ ID NO: 15. In some embodiments, the h-UMG1 antibody comprises an amino acid sequence having 70% or greater sequence identity to SEQ ID NO: 9 and SEQ ID NO: 15. In some embodiments, the h-UMG1 antibody comprises an amino acid sequence having 80% or greater sequence identity to SEQ ID NO: 9 and SEQ ID NO: 15. In some embodiments, the h-UMG1 antibody comprises an amino acid sequence having 85% or greater sequence identity to SEQ ID NO: 9 and SEQ ID NO: 15. In some embodiments, the h-UMG1 antibody comprises an amino acid sequence having 90% or greater sequence identity to SEQ ID NO: 9 and SEQ ID NO: 15. In some embodiments, the h-UMG1 antibody comprises an amino acid sequence having 95% or greater sequence identity to SEQ ID NO: 9 and SEQ ID NO: 15. In some embodiments, the h-UMG1 antibody comprises an amino acid sequence having 97% or greater sequence identity to SEQ ID NO: 9 and SEQ ID NO: 15. In some embodiments, the h-UMG1 antibody comprises an amino acid sequence having 99% or greater sequence identity to SEQ ID NO: 9 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 15. In some embodiments, the h-UMG1 antibody comprises an amino acid sequence having 100% sequence identity to SEQ ID NO: 9 and SEQ ID NO: 15. In some embodiments, the h-UMG1 antibody comprises an amino acid sequence having 60% or greater sequence identity to SEQ ID NO: 9 and SEQ ID NO: 15. In some embodiments, the h-UMG1 antibody comprises an amino acid sequence having 70% or greater sequence identity to SEQ ID NO: 9 and SEQ ID NO: 15. In some embodiments, the h-UMG1 antibody comprises an amino acid sequence having 80% or greater sequence identity to SEQ ID NO: 9 and SEQ ID NO: 15. In some embodiments, the h-UMG1 antibody comprises an amino acid sequence having 85% or greater sequence identity to SEQ ID NO: 9 and SEQ ID NO: 15. In some embodiments, the h-UMG1 antibody comprises an amino acid sequence having 90% or greater sequence identity to SEQ ID NO: 9 and SEQ ID NO: 15. In some embodiments, the h-UMG1 antibody comprises an amino acid sequence having 95% or greater sequence identity to SEQ ID NO: 9 and SEQ ID NO: 15. In some embodiments, the h-UMG1 antibody comprises an amino acid sequence having 97% or greater sequence identity to SEQ ID NO: 9 and SEQ ID NO: 15. In some embodiments, the h-UMG1 antibody comprises an amino acid sequence having 99% or greater sequence identity to SEQ ID NO: 9 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 15. In some embodiments, the h-UMG1 antibody comprises an amino acid sequence having 100% sequence identity to SEQ ID NO: 9 and SEQ ID NO: 15.

In some embodiments, the h-UMG1 antibody comprises an amino acid sequence having 60% or greater sequence identity to SEQ ID NO: 9 and SEQ ID NO: 16. In some embodiments, the h-UMG1 antibody comprises an amino acid sequence having 70% or greater sequence identity to SEQ ID NO: 9 and SEQ ID NO: 16. In some embodiments, the h-UMG1 antibody comprises an amino acid sequence having 80% or greater sequence identity to SEQ ID NO: 9 and SEQ ID NO: 16. In some embodiments, the h-UMG1 antibody comprises an amino acid sequence having 85% or greater sequence identity to SEQ ID NO: 9 and SEQ ID NO: 16. In some embodiments, the h-UMG1 antibody comprises an amino acid sequence having 90% or greater sequence identity to SEQ ID NO: 9 and SEQ ID NO: 16. In some embodiments, the h-UMG1 antibody comprises an amino acid sequence having 95% or greater sequence identity to SEQ ID NO: 9 and SEQ ID NO: 16. In some embodiments, the h-UMG1 antibody comprises an amino acid sequence having 97% or greater sequence identity to SEQ ID NO: 9 and SEQ ID NO: 16. In some embodiments, the h-UMG1 antibody comprises an amino acid sequence having 99% or greater sequence identity to SEQ ID NO: 9 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 16. In some embodiments, the h-UMG1 antibody comprises an amino acid sequence having 100% sequence identity to SEQ ID NO: 9 and SEQ ID NO: 16. In some embodiments, the h-UMG1 antibody comprises an amino acid sequence having 60% or greater sequence identity to SEQ ID NO: 9 and SEQ ID NO: 16. In some embodiments, the h-UMG1 antibody comprises an amino acid sequence having 70% or greater sequence identity to SEQ ID NO: 9 and SEQ ID NO: 16. In some embodiments, the h-UMG1 antibody comprises an amino acid sequence having 80% or greater sequence identity to SEQ ID NO: 9 and SEQ ID NO: 16. In some embodiments, the h-UMG1 antibody comprises an amino acid sequence having 85% or greater sequence identity to SEQ ID NO: 9 and SEQ ID NO: 16. In some embodiments, the h-UMG1 antibody comprises an amino acid sequence having 90% or greater sequence identity to SEQ ID NO: 9 and SEQ ID NO: 16. In some embodiments, the h-UMG1 antibody comprises an amino acid sequence having 95% or greater sequence identity to SEQ ID NO: 9 and SEQ ID NO: 16. In some embodiments, the h-UMG1 antibody comprises an amino acid sequence having 97% or greater sequence identity to SEQ ID NO: 9 and SEQ ID NO: 16. In some embodiments, the h-UMG1 antibody comprises an amino acid sequence having 99% or greater sequence identity to SEQ ID NO: 9 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 9 and SEQ ID NO: 16. In some embodiments, the h-UMG1 antibody comprises an amino acid sequence having 100% sequence identity to SEQ ID NO: 9 and SEQ ID NO: 16.

In some embodiments, the h-UMG1 antibody comprises an amino acid sequence having 60% or greater sequence identity to SEQ ID NO: 10 and SEQ ID NO: 13. In some embodiments, the h-UMG1 antibody comprises an amino acid sequence having 70% or greater sequence identity to SEQ ID NO: 10 and SEQ ID NO: 13. In some embodiments, the h-UMG1 antibody comprises an amino acid sequence having 80% or greater sequence identity to SEQ ID NO: 10 and SEQ ID NO: 13. In some embodiments, the h-UMG1 antibody comprises an amino acid sequence having 85% or greater sequence identity to SEQ ID NO: 10 and SEQ ID NO: 13. In some embodiments, the h-UMG1 antibody comprises an amino acid sequence having 90% or greater sequence identity to SEQ ID NO: 10 and SEQ ID NO: 13. In some embodiments, the h-UMG1 antibody comprises an amino acid sequence having 95% or greater sequence identity to SEQ ID NO: 10 and SEQ ID NO: 13. In some embodiments, the h-UMG1 antibody comprises an amino acid sequence having 97% or greater sequence identity to SEQ ID NO: 10 and SEQ ID NO: 13. In some embodiments, the h-UMG1 antibody comprises an amino acid sequence having 99% or greater sequence identity to SEQ ID NO: 10 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 13. In some embodiments, the h-UMG1 antibody comprises an amino acid sequence having 100% sequence identity to SEQ ID NO: 10 and SEQ ID NO: 13. In some embodiments, the h-UMG1 antibody comprises an amino acid sequence having 60% or greater sequence identity to SEQ ID NO: 10 and SEQ ID NO: 13. In some embodiments, the h-UMG1 antibody comprises an amino acid sequence having 70% or greater sequence identity to SEQ ID NO: 10 and SEQ ID NO: 13. In some embodiments, the h-UMG1 antibody comprises an amino acid sequence having 80% or greater sequence identity to SEQ ID NO: 10 and SEQ ID NO: 13. In some embodiments, the h-UMG1 antibody comprises an amino acid sequence having 85% or greater sequence identity to SEQ ID NO: 10 and SEQ ID NO: 13. In some embodiments, the h-UMG1 antibody comprises an amino acid sequence having 90% or greater sequence identity to SEQ ID NO: 10 and SEQ ID NO: 13. In some embodiments, the h-UMG1 antibody comprises an amino acid sequence having 95% or greater sequence identity to SEQ ID NO: 10 and SEQ ID NO: 13. In some embodiments, the h-UMG1 antibody comprises an amino acid sequence having 97% or greater sequence identity to SEQ ID NO: 10 and SEQ ID NO: 13. In some embodiments, the h-UMG1 antibody comprises an amino acid sequence having 99% or greater sequence identity to SEQ ID NO: 10 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 13. In some embodiments, the h-UMG1 antibody comprises an amino acid sequence having 100% sequence identity to SEQ ID NO: 10 and SEQ ID NO: 13.

In some embodiments, the h-UMG1 antibody comprises an amino acid sequence having 60% or greater sequence identity to SEQ ID NO: 10 and SEQ ID NO: 14. In some embodiments, the h-UMG1 antibody comprises an amino acid sequence having 70% or greater sequence identity to SEQ ID NO: 10 and SEQ ID NO: 14. In some embodiments, the h-UMG1 antibody comprises an amino acid sequence having 80% or greater sequence identity to SEQ ID NO: 10 and SEQ ID NO: 14. In some embodiments, the h-UMG1 antibody comprises an amino acid sequence having 85% or greater sequence identity to SEQ ID NO: 10 and SEQ ID NO: 14. In some embodiments, the h-UMG1 antibody comprises an amino acid sequence having 90% or greater sequence identity to SEQ ID NO: 10 and SEQ ID NO: 14. In some embodiments, the h-UMG1 antibody comprises an amino acid sequence having 95% or greater sequence identity to SEQ ID NO: 10 and SEQ ID NO: 14. In some embodiments, the h-UMG1 antibody comprises an amino acid sequence having 97% or greater sequence identity to SEQ ID NO: 10 and SEQ ID NO: 14. In some embodiments, the h-UMG1 antibody comprises an amino acid sequence having 99% or greater sequence identity to SEQ ID NO: 10 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 14. In some embodiments, the h-UMG1 antibody comprises an amino acid sequence having 100% sequence identity to SEQ ID NO: 10 and SEQ ID NO: 14. In some embodiments, the h-UMG1 antibody comprises an amino acid sequence having 60% or greater sequence identity to SEQ ID NO: 10 and SEQ ID NO: 14. In some embodiments, the h-UMG1 antibody comprises an amino acid sequence having 70% or greater sequence identity to SEQ ID NO: 10 and SEQ ID NO: 14. In some embodiments, the h-UMG1 antibody comprises an amino acid sequence having 80% or greater sequence identity to SEQ ID NO: 10 and SEQ ID NO: 14. In some embodiments, the h-UMG1 antibody comprises an amino acid sequence having 85% or greater sequence identity to SEQ ID NO: 10 and SEQ ID NO: 14. In some embodiments, the h-UMG1 antibody comprises an amino acid sequence having 90% or greater sequence identity to SEQ ID NO: 10 and SEQ ID NO: 14. In some embodiments, the h-UMG1 antibody comprises an amino acid sequence having 95% or greater sequence identity to SEQ ID NO: 10 and SEQ ID NO: 14. In some embodiments, the h-UMG1 antibody comprises an amino acid sequence having 97% or greater sequence identity to SEQ ID NO: 10 and SEQ ID NO: 14. In some embodiments, the h-UMG1 antibody comprises an amino acid sequence having 99% or greater sequence identity to SEQ ID NO: 10 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 14. In some embodiments, the h-UMG1 antibody comprises an amino acid sequence having 100% sequence identity to SEQ ID NO: 10 and SEQ ID NO: 14.

In some embodiments, the h-UMG1 antibody comprises an amino acid sequence having 60% or greater sequence identity to SEQ ID NO: 10 and SEQ ID NO: 15. In some embodiments, the h-UMG1 antibody comprises an amino acid sequence having 70% or greater sequence identity to SEQ ID NO: 10 and SEQ ID NO: 15. In some embodiments, the h-UMG1 antibody comprises an amino acid sequence having 80% or greater sequence identity to SEQ ID NO: 10 and SEQ ID NO: 15. In some embodiments, the h-UMG1 antibody comprises an amino acid sequence having 85% or greater sequence identity to SEQ ID NO: 10 and SEQ ID NO: 15. In some embodiments, the h-UMG1 antibody comprises an amino acid sequence having 90% or greater sequence identity to SEQ ID NO: 10 and SEQ ID NO: 15. In some embodiments, the h-UMG1 antibody comprises an amino acid sequence having 95% or greater sequence identity to SEQ ID NO: 10 and SEQ ID NO: 15. In some embodiments, the h-UMG1 antibody comprises an amino acid sequence having 97% or greater sequence identity to SEQ ID NO: 10 and SEQ ID NO: 15. In some embodiments, the h-UMG1 antibody comprises an amino acid sequence having 99% or greater sequence identity to SEQ ID NO: 10 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 15. In some embodiments, the h-UMG1 antibody comprises an amino acid sequence having 100% sequence identity to SEQ ID NO: 10 and SEQ ID NO: 15. In some embodiments, the h-UMG1 antibody comprises an amino acid sequence having 60% or greater sequence identity to SEQ ID NO: 10 and SEQ ID NO: 15. In some embodiments, the h-UMG1 antibody comprises an amino acid sequence having 70% or greater sequence identity to SEQ ID NO: 10 and SEQ ID NO: 15. In some embodiments, the h-UMG1 antibody comprises an amino acid sequence having 80% or greater sequence identity to SEQ ID NO: 10 and SEQ ID NO: 15. In some embodiments, the h-UMG1 antibody comprises an amino acid sequence having 85% or greater sequence identity to SEQ ID NO: 10 and SEQ ID NO: 15. In some embodiments, the h-UMG1 antibody comprises an amino acid sequence having 90% or greater sequence identity to SEQ ID NO: 10 and SEQ ID NO: 15. In some embodiments, the h-UMG1 antibody comprises an amino acid sequence having 95% or greater sequence identity to SEQ ID NO: 10 and SEQ ID NO: 15. In some embodiments, the h-UMG1 antibody comprises an amino acid sequence having 97% or greater sequence identity to SEQ ID NO: 10 and SEQ ID NO: 15. In some embodiments, the h-UMG1 antibody comprises an amino acid sequence having 99% or greater sequence identity to SEQ ID NO: 10 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 15. In some embodiments, the h-UMG1 antibody comprises an amino acid sequence having 100% sequence identity to SEQ ID NO: 10 and SEQ ID NO: 15.

In some embodiments, the h-UMG1 antibody comprises an amino acid sequence having 60% or greater sequence identity to SEQ ID NO: 10 and SEQ ID NO: 16. In some embodiments, the h-UMG1 antibody comprises an amino acid sequence having 70% or greater sequence identity to SEQ ID NO: 10 and SEQ ID NO: 16. In some embodiments, the h-UMG1 antibody comprises an amino acid sequence having 80% or greater sequence identity to SEQ ID NO: 10 and SEQ ID NO: 16. In some embodiments, the h-UMG1 antibody comprises an amino acid sequence having 85% or greater sequence identity to SEQ ID NO: 10 and SEQ ID NO: 16. In some embodiments, the h-UMG1 antibody comprises an amino acid sequence having 90% or greater sequence identity to SEQ ID NO: 10 and SEQ ID NO: 16. In some embodiments, the h-UMG1 antibody comprises an amino acid sequence having 95% or greater sequence identity to SEQ ID NO: 10 and SEQ ID NO: 16. In some embodiments, the h-UMG1 antibody comprises an amino acid sequence having 97% or greater sequence identity to SEQ ID NO: 10 and SEQ ID NO: 16. In some embodiments, the h-UMG1 antibody comprises an amino acid sequence having 99% or greater sequence identity to SEQ ID NO: 10 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 16. In some embodiments, the h-UMG1 antibody comprises an amino acid sequence having 100% sequence identity to SEQ ID NO: 10 and SEQ ID NO: 16. In some embodiments, the h-UMG1 antibody comprises an amino acid sequence having 60% or greater sequence identity to SEQ ID NO: 10 and SEQ ID NO: 16. In some embodiments, the h-UMG1 antibody comprises an amino acid sequence having 70% or greater sequence identity to SEQ ID NO: 10 and SEQ ID NO: 16. In some embodiments, the h-UMG1 antibody comprises an amino acid sequence having 80% or greater sequence identity to SEQ ID NO: 10 and SEQ ID NO: 16. In some embodiments, the h-UMG1 antibody comprises an amino acid sequence having 85% or greater sequence identity to SEQ ID NO: 10 and SEQ ID NO: 16. In some embodiments, the h-UMG1 antibody comprises an amino acid sequence having 90% or greater sequence identity to SEQ ID NO: 10 and SEQ ID NO: 16. In some embodiments, the h-UMG1 antibody comprises an amino acid sequence having 95% or greater sequence identity to SEQ ID NO: 10 and SEQ ID NO: 16. In some embodiments, the h-UMG1 antibody comprises an amino acid sequence having 97% or greater sequence identity to SEQ ID NO: 10 and SEQ ID NO: 16. In some embodiments, the h-UMG1 antibody comprises an amino acid sequence having 99% or greater sequence identity to SEQ ID NO: 10 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 10 and SEQ ID NO: 16. In some embodiments, the h-UMG1 antibody comprises an amino acid sequence having 100% sequence identity to SEQ ID NO: 10 and SEQ ID NO: 16.

In some embodiments, the h-UMG1 antibody comprises an amino acid sequence having 60% or greater sequence identity to SEQ ID NO: 11 and SEQ ID NO: 13. In some embodiments, the h-UMG1 antibody comprises an amino acid sequence having 70% or greater sequence identity to SEQ ID NO: 11 and SEQ ID NO: 13. In some embodiments, the h-UMG1 antibody comprises an amino acid sequence having 80% or greater sequence identity to SEQ ID NO: 11 and SEQ ID NO: 13. In some embodiments, the h-UMG1 antibody comprises an amino acid sequence having 85% or greater sequence identity to SEQ ID NO: 11 and SEQ ID NO: 13. In some embodiments, the h-UMG1 antibody comprises an amino acid sequence having 90% or greater sequence identity to SEQ ID NO: 11 and SEQ ID NO: 13. In some embodiments, the h-UMG1 antibody comprises an amino acid sequence having 95% or greater sequence identity to SEQ ID NO: 11 and SEQ ID NO: 13. In some embodiments, the h-UMG1 antibody comprises an amino acid sequence having 97% or greater sequence identity to SEQ ID NO: 11 and SEQ ID NO: 13. In some embodiments, the h-UMG1 antibody comprises an amino acid sequence having 99% or greater sequence identity to SEQ ID NO: 11 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 13. In some embodiments, the h-UMG1 antibody comprises an amino acid sequence having 100% sequence identity to SEQ ID NO: 11 and SEQ ID NO: 13. In some embodiments, the h-UMG1 antibody comprises an amino acid sequence having 60% or greater sequence identity to SEQ ID NO: 11 and SEQ ID NO: 13. In some embodiments, the h-UMG1 antibody comprises an amino acid sequence having 70% or greater sequence identity to SEQ ID NO: 11 and SEQ ID NO: 13. In some embodiments, the h-UMG1 antibody comprises an amino acid sequence having 80% or greater sequence identity to SEQ ID NO: 11 and SEQ ID NO: 13. In some embodiments, the h-UMG1 antibody comprises an amino acid sequence having 85% or greater sequence identity to SEQ ID NO: 11 and SEQ ID NO: 13. In some embodiments, the h-UMG1 antibody comprises an amino acid sequence having 90% or greater sequence identity to SEQ ID NO: 11 and SEQ ID NO: 13. In some embodiments, the h-UMG1 antibody comprises an amino acid sequence having 95% or greater sequence identity to SEQ ID NO: 11 and SEQ ID NO: 13. In some embodiments, the h-UMG1 antibody comprises an amino acid sequence having 97% or greater sequence identity to SEQ ID NO: 11 and SEQ ID NO: 13. In some embodiments, the h-UMG1 antibody comprises an amino acid sequence having 99% or greater sequence identity to SEQ ID NO: 11 and SEQ ID NO: 13. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 13. In some embodiments, the h-UMG1 antibody comprises an amino acid sequence having 100% sequence identity to SEQ ID NO: 11 and SEQ ID NO: 13.

In some embodiments, the h-UMG1 antibody comprises an amino acid sequence having 60% or greater sequence identity to SEQ ID NO: 11 and SEQ ID NO: 14. In some embodiments, the h-UMG1 antibody comprises an amino acid sequence having 70% or greater sequence identity to SEQ ID NO: 11 and SEQ ID NO: 14. In some embodiments, the h-UMG1 antibody comprises an amino acid sequence having 80% or greater sequence identity to SEQ ID NO: 11 and SEQ ID NO: 14. In some embodiments, the h-UMG1 antibody comprises an amino acid sequence having 85% or greater sequence identity to SEQ ID NO: 11 and SEQ ID NO: 14. In some embodiments, the h-UMG1 antibody comprises an amino acid sequence having 90% or greater sequence identity to SEQ ID NO: 11 and SEQ ID NO: 14. In some embodiments, the h-UMG1 antibody comprises an amino acid sequence having 95% or greater sequence identity to SEQ ID NO: 11 and SEQ ID NO: 14. In some embodiments, the h-UMG1 antibody comprises an amino acid sequence having 97% or greater sequence identity to SEQ ID NO: 11 and SEQ ID NO: 14. In some embodiments, the h-UMG1 antibody comprises an amino acid sequence having 99% or greater sequence identity to SEQ ID NO: 11 and SEQ ID NO: 14. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 14. In some embodiments, the h-UMG1 antibody comprises an amino acid sequence having 100% sequence identity to SEQ ID NO: 11 and SEQ ID NO: 14.

In some embodiments, the h-UMG1 antibody comprises an amino acid sequence having 60% or greater sequence identity to SEQ ID NO: 11 and SEQ ID NO: 15. In some embodiments, the h-UMG1 antibody comprises an amino acid sequence having 70% or greater sequence identity to SEQ ID NO: 11 and SEQ ID NO: 15. In some embodiments, the h-UMG1 antibody comprises an amino acid sequence having 80% or greater sequence identity to SEQ ID NO: 11 and SEQ ID NO: 15. In some embodiments, the h-UMG1 antibody comprises an amino acid sequence having 85% or greater sequence identity to SEQ ID NO: 11 and SEQ ID NO: 15. In some embodiments, the h-UMG1 antibody comprises an amino acid sequence having 90% or greater sequence identity to SEQ ID NO: 11 and SEQ ID NO: 15. In some embodiments, the h-UMG1 antibody comprises an amino acid sequence having 95% or greater sequence identity to SEQ ID NO: 11 and SEQ ID NO: 15. In some embodiments, the h-UMG1 antibody comprises an amino acid sequence having 97% or greater sequence identity to SEQ ID NO: 11 and SEQ ID NO: 15. In some embodiments, the h-UMG1 antibody comprises an amino acid sequence having 99% or greater sequence identity to SEQ ID NO: 11 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 15. In some embodiments, the h-UMG1 antibody comprises an amino acid sequence having 100% sequence identity to SEQ ID NO: 11 and SEQ ID NO: 15. In some embodiments, the h-UMG1 antibody comprises an amino acid sequence having 60% or greater sequence identity to SEQ ID NO: 11 and SEQ ID NO: 15. In some embodiments, the h-UMG1 antibody comprises an amino acid sequence having 70% or greater sequence identity to SEQ ID NO: 11 and SEQ ID NO: 15. In some embodiments, the h-UMG1 antibody comprises an amino acid sequence having 80% or greater sequence identity to SEQ ID NO: 11 and SEQ ID NO: 15. In some embodiments, the h-UMG1 antibody comprises an amino acid sequence having 85% or greater sequence identity to SEQ ID NO: 11 and SEQ ID NO: 15. In some embodiments, the h-UMG1 antibody comprises an amino acid sequence having 90% or greater sequence identity to SEQ ID NO: 11 and SEQ ID NO: 15. In some embodiments, the h-UMG1 antibody comprises an amino acid sequence having 95% or greater sequence identity to SEQ ID NO: 11 and SEQ ID NO: 15. In some embodiments, the h-UMG1 antibody comprises an amino acid sequence having 97% or greater sequence identity to SEQ ID NO: 11 and SEQ ID NO: 15. In some embodiments, the h-UMG1 antibody comprises an amino acid sequence having 99% or greater sequence identity to SEQ ID NO: 11 and SEQ ID NO: 15. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 15. In some embodiments, the h-UMG1 antibody comprises an amino acid sequence having 100% sequence identity to SEQ ID NO: 9 and SEQ ID NO: 15.

In some embodiments, the h-UMG1 antibody comprises an amino acid sequence having 60% or greater sequence identity to SEQ ID NO: 11 and SEQ ID NO: 16. In some embodiments, the h-UMG1 antibody comprises an amino acid sequence having 70% or greater sequence identity to SEQ ID NO: 11 and SEQ ID NO: 16. In some embodiments, the h-UMG1 antibody comprises an amino acid sequence having 80% or greater sequence identity to SEQ ID NO: 11 and SEQ ID NO: 16. In some embodiments, the h-UMG1 antibody comprises an amino acid sequence having 85% or greater sequence identity to SEQ ID NO: 11 and SEQ ID NO: 16. In some embodiments, the h-UMG1 antibody comprises an amino acid sequence having 90% or greater sequence identity to SEQ ID NO: 11 and SEQ ID NO: 16. In some embodiments, the h-UMG1 antibody comprises an amino acid sequence having 95% or greater sequence identity to SEQ ID NO: 11 and SEQ ID NO: 16. In some embodiments, the h-UMG1 antibody comprises an amino acid sequence having 97% or greater sequence identity to SEQ ID NO: 11 and SEQ ID NO: 16. In some embodiments, the h-UMG1 antibody comprises an amino acid sequence having 99% or greater sequence identity to SEQ ID NO: 11 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 16. In some embodiments, the h-UMG1 antibody comprises an amino acid sequence having 100% sequence identity to SEQ ID NO: 11 and SEQ ID NO: 16. In some embodiments, the h-UMG1 antibody comprises an amino acid sequence having 60% or greater sequence identity to SEQ ID NO: 11 and SEQ ID NO: 16. In some embodiments, the h-UMG1 antibody comprises an amino acid sequence having 70% or greater sequence identity to SEQ ID NO: 11 and SEQ ID NO: 16. In some embodiments, the h-UMG1 antibody comprises an amino acid sequence having 80% or greater sequence identity to SEQ ID NO: 11 and SEQ ID NO: 16. In some embodiments, the h-UMG1 antibody comprises an amino acid sequence having 85% or greater sequence identity to SEQ ID NO: 11 and SEQ ID NO: 16. In some embodiments, the h-UMG1 antibody comprises an amino acid sequence having 90% or greater sequence identity to SEQ ID NO: 11 and SEQ ID NO: 16. In some embodiments, the h-UMG1 antibody comprises an amino acid sequence having 95% or greater sequence identity to SEQ ID NO: 11 and SEQ ID NO: 16. In some embodiments, the h-UMG1 antibody comprises an amino acid sequence having 97% or greater sequence identity to SEQ ID NO: 11 and SEQ ID NO: 16. In some embodiments, the h-UMG1 antibody comprises an amino acid sequence having 99% or greater sequence identity to SEQ ID NO: 11 and SEQ ID NO: 16. In some embodiments, the h-UMG1 antibody comprises an amino acid sequence having 85%, 86%, 87%, 88%, 89%, 90%, 91%, 92%, 93%, 94%, 95%, 96%, 97%, 98%, 99%, or 100% sequence identity to SEQ ID NO: 11 and SEQ ID NO: 16. In some embodiments, the h-UMG1 antibody comprises an amino acid sequence having 100% sequence identity to SEQ ID NO: 11 and SEQ ID NO: 16.

In another preferred embodiment, the monoclonal antibody according to the antibody of aspect two is capable of inducing antibody dependent cellular cytotoxicity (ADCC) against the EGIL T3 subgroup of T cell acute lymphoblastic leukemia (T-ALL), against T cell lymphoblastic lymphoma cells and against Waldenström's macroglobulinemia (WM) cells.

Lymphocytes belong to the group of white blood cells and are mediators of humoral and cell-mediated immunity. There are two groups of lymphocytes, B-cells and T-cells.

Just like many other cell types, B- and T-cells, can abnormally develop to B- and T-cell tumors. Due to the numerous developmental stages of developing B- and T-cells, there are various kinds of tumors. Both, B-cells and T-cells, originate from lymphoid progenitor cells.

In the case of B-cells, this lymphoid progenitor cell develops via many B cell developmental stages each comprising a certain definable cell type until a plasma cell is formed. One of these stages includes the so-called "IgM-secreting B cell", which finally develops into an antibody-producing plasma cell. A tumor originating from an "IgM-secreting B-cell" is called "Waldenström's macroglobulinemia" (WM). WM is a rare, indolent and incurable disease. It is characterized by bone marrow accumulation of clonal IgM secreting lymphoplasmacytic cells.

T-cells develop from lymphoid progenitor cells to mature T-cells in only a few developmental stages. Tumors may especially evolve from mature T-cells or lymphoid progenitor cells, the latter leading to B- or T-cell acute lymphoblastic leukemia, (B-ALL) and (T-ALL), respectively. The T-cell phenotype T-ALL accounts for about 20% of all acute lymphoblastic leukemia cases and occurs more often in adults than in children. T-ALL is closely related to T-cell lymphoblastic lymphoma (T-LBL) and differential diagnosis between the two diseases is based on prevalent localization in specific sites, such as bone marrow in T-ALL or secondary lymphoid organ in T-LBL. The European Group for the Immunological Characterization of Leukemias (EGIL) classified T-ALL in four subgroups according to their immunophenotype (Bene M C, Leukemia 1995; 9:1783):

1) EGIL T1 (pro-), characterized by cytoplasmic positivity for CD3 (cCD3) and surface expression of CD7;

2) EGIL T2 (pre-) characterized by positivity for cCD3, CD7 and positivity of CD2 or CD5;

3) EGIL T3 (cortical) characterized by positivity for cCD3, CD1a and the presence or the absence of surface CD3 (sCD3) and 4) EGIL T4 (mature leukemia), characterized by the positivity for cCD3 and sCD3 and negative for CD1a.

The term "Antibody-dependent cellular cytotoxicity (ADCC)", as used herein, is the killing of a cell bound and marked by antibodies by a cytotoxic effector cell, such as natural killer (NK) cells.

In order to examine, whether an antibody is capable of inducing ADCC, the following assay can be used. A degranulation assay by co-culturing peripheral blood mononuclear cells (PBMCs) from healthy donors, which include the effector cells, with target cells expressing the epitope in the presence of different antibody concentrations is performed. $4 \times 10^4$ target cells are seeded in 96 wells round-bottom plate and cultured for 30 minutes at 37° C. 5% $CO_2$ in the presence of different concentrations of antibody (0, 10, 50, 100, and 200 μg/ml) or control IgG1. Subsequently, $0.4 \times 10^6$ PBMCs (fixed effector cells (E): target cells (T)=10: 1) from the same donor are added to each well together with 20 μl/ml of Phycoerythrin (PE)-conjugated anti-CD107a monoclonal antibody (mAb) (BD) and cells are then incubated at 37° C. 5% $CO_2$ for 3 h. After 1 h, 6 μg/ml monensin is added to each well (GolgiStop, BD). At the end of the incubation period, cells are stained with Allophycocyanin (APC)-conjugated anti-CD56 and Peridinin Chlorophyll Protein Complex (PerCp)-conjugated anti-CD3 and analyzed on an ATTUNE NxT flow cytometer (THERMO Scientific). By detecting $CD3^-/CD56^+/CD107a^+$ cells, NK cells ($CD3^-/CD56^+$) inducing target cells lysis ($CD107a^+$) are measured. An increase of $CD3^-/CD56^+/CD107a^+$ cells according to increasing antibody concentrations therefore confirms the potential of an antibody to induce ADCC. The resulting data allow to design immune targeting approaches, which e.g. are an urgent and unmet clinical need in T cell acute lymphoblastic leukemias/lymphoblastic lymphomas. Further methods to examine, whether an antibody is capable of inducing ADCC, can also be used and are well-known to the person skilled in the art.

7.3.5. UMG1 Binding Molecules

In a third aspect, the invention provides a binding molecule derived from an UMG1 antibody according to aspect one or aspect two.

According to the invention, a binding molecule is a molecule derived from the monoclonal mouse UMG1 antibody produced by the hybridoma cell deposited under ICLC PD n° 16001. Preferably, the binding molecule is an immunoglobulin comprising molecule, i.e. it comprises at least one Immunoglobulin (Ig) domain.

In a preferred embodiment the binding molecule of the invention is being selected from the group consisting of single chain antibodies. In a more preferred embodiment, the binding molecule is being selected from the group consisting of a single chain variable fragment (scFv), a multimer of a scFv, such as a diabody, a triabody or a tetrabody, antibody fragments, preferably a Fab, a tandab, and a flexibody.

The structure of an antibody and especially the function of its CDRs are generally known in the art (Carter P J. Potent antibody therapeutics by design. Nature Rev. Immunol. 6:343-357, 2006, which is incorporated by reference in its entirety). Single chain Fv (scFv) and multimers thereof, tandabs, diabodies and flexibodies are in general standard antibody formats known in the art, e.g. from WO 1988/001649 A1, WO 1993/011161 A1, WO 1999/057150 A2 and EP1293514B1, each of which is incorporated by reference in its entirety.

In a scFv, the two antigen binding variable regions of the light and heavy chain (VH Fv and VL Fv) of an antibody are in general artificially connected by a linker peptide, designated as single chain variable fragment or single chain antibody (Bird, et al. (1988) Science 242:423-426; Orlandi, et al (1989) Proc Natl Acad Sci USA 86:3833-3837; Clarkson et al., Nature 352: 624-628 (1991), each of which are incorporated by reference in their entirety). The antigen binding site can be made up of the variable domains of light and heavy chains of a monoclonal antibody. Several investigations have shown that the scFv fragment may have indeed the full intrinsic antigen binding affinity of one binding site of the whole antibody.

In the context of this invention, diabodies are scFv with two binding specificities and can either be monospecific and bivalent or bispecific and bivalent.

Tandabs and flexibodies are further antibody formats which are e.g. defined in US2007031436 and EP1293514B1, respectively, which are incorporated by reference in their entirety.

Antibody fragments that contain the idiotypes of the protein can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments.

7.3.6. Antibody-Drug Conjugates (ADCs)

The antibody or binding molecule of the invention can further be linked to an active substance, preferably a toxin, a nanoparticle, a cytokine, or a radionucleotide. Such antibody drug conjugates (ADCs) are known in the art (Wu A M, Senter P D. Nature Biotechnol. 23:1137-1146, 2005, Pastan et al. Annu. Rev. Med. 58:221-237, 2007, WO 1990/012592 A1, WO 2007/030642 A2, WO 2004/067038 A1, WO 2004/003183 A1, US 2005/0074426 A1, WO 1994/004189 A1; each of which is incorporated by reference in its entirety). See also, Yaghoubi et al., "*Potential drugs used in the antibody-drug conjugate (ADC) architecture for cancer therapy*," J Cell Physiol. 2019 Jun. 18. doi: 10.1002/jcp.28967. [Epub ahead of print]; Arlotta et al., "*Antibody and antibody derivatives as cancer therapeutics*," Wiley Interdiscip Rev Nanomed Nanobiotechnol. 2019 Apr. 9:e1556. doi: 10.1002/wnan. 1556. [Epub ahead of print]; Wolska-Washer et al., "*Safety and Tolerability of Antibody-Drug Conjugates in Cancer*," Drug Saf. 2019 February; 42(2):295-314; Johnston et al., "*Antibody conjugated nanoparticles as a novel form of antibody drug conjugate chemotherapy*," Drug Discov Today Technol. 2018, 30:63-69; Lyon, "Drawing lessons from the clinical development of antibody-drug conjugates," Drug Discov Today Technol. 2018 December; 30:105-109; and Abdollahpour-Alitappeh et al., "*Antibody-drug conjugates (ADCs) for cancer therapy: Strategies, challenges, and successes*," J Cell Physiol. 2019 May; 234(5):5628-5642, the disclosures of which are incorporated herein by reference in their entireties.

In various embodiments, the binding molecule is conjugated to a therapeutic agent (i.e. drug) to form a binding molecule-drug conjugate. Therapeutic agents include, but are not limited to, chemotherapeutic agents, imaging agents (e.g. radioisotopes), immune modulators (e.g. cytokines, chemokines, or checkpoint inhibitors), and toxins (e.g. cytotoxic agents). In certain embodiments, the therapeutic agents are attached to the binding molecule through a linker peptide, as discussed in more detail below in Section 6.7.3.

Methods of preparing antibody-drug conjugates (ADCs) that can be adapted to conjugate drugs to the binding molecules disclosed herein are described, e.g., in U.S. Pat. No. 8,624,003 (pot method), U.S. Pat. No. 8,163,888 (one-step), U.S. Pat. No. 5,208,020 (two-step method), U.S. Pat. Nos. 8,337,856, 5,773,001, 7,829,531, 5,208,020, 7,745, 394, WO 2017/136623, WO 2017/015502, WO 2017/015496, WO 2017/015495, WO 2004/010957, WO 2005/077090, WO 2005/082023, WO 2006/065533, WO 2007/030642, WO 2007/103288, WO 2013/173337, WO 2015/

057699, WO 2015/095755, WO 2015/123679, WO 2015/ 157286, WO 2017/165851, WO 2009/073445, WO 2010/ 068759, WO 2010/138719, WO 2012/171020, WO 2014/ 008375, WO 2014/093394, WO 2014/093640, WO 2014/ 160360, WO 2015/054659, WO 2015/195925, WO 2017/ 160754, Storz (MAbs. 2015 November-December; 7(6): 989-1009), Lambert et a. (*Adv Ther.* 2017 34: 1015), Diamantis et al. (*British Journal of Cancer,* 2016, 114, 362-367). Carrico et al. (*Nat Chem Biol,* 2007. 3: 321-2), We et al. (*Proc Natl Acad Sci USA,* 2009, 106: 3000-5), Rabuka et al. (*Curr Opin Chem Biol.,* 2011 14: 790-6), Hudak et al. (*Angew Chem Int Ed Engl.,* 2012: 4161-5), Rabuka et al. (*Nat Protoc.,* 2012 7:1052-67), Agarwal et al. (*Proc Natl Acad Sci USA.,* 2013, 110: 46-51), Agarwal et al. (*Bioconjugate Chem.,* 2013, 24: 846-851), Barfield et al. (*Drug Dev. and D.,* 2014, 14:34-41), Drake et al. (*Bioconjugate Chem.,* 2014, 25:1331-41), Liang et al. (*J Am Chem Soc.,* 2014, 136:10850-3), Drake et al. (*Curr Opin Chem Biol.,* 2015, 28:174-80), and York et al. (*BMC Biotechnology,* 2016, 16(1):23), each of which is hereby incorporated by reference in its entirety for all that it teaches.

7.3.7. Chimeric Antigen Receptors (CARs)

The disclosure also provides a chimeric antigen receptor (CAR) comprising a binding molecule of aspect three linked to an intracellular domain preferably comprising one or more signaling domains.

Preferably, the invention relates to a chimeric antigen receptor (CAR) comprising the scFv of the preferred embodiment of the binding molecule of aspect three linked to an intracellular region comprising the CD3ζ chain, the signaling region of the T cell receptor, and to the two co-stimulatory domains CD28 and 4-1BB.

The CAR according to the invention is a relevant tool for targeting malignant cells bearing the epitope recognized and bound by the monoclonal antibody of aspect one or aspect two, when expressed in T-cells or NK cells. The term "Chimeric antigen receptors" (CAR), as used herein, refers to synthetic receptors comprising a targeting moiety that is associated with one or more signaling domains in a single fusion molecule. In general, the binding moiety of a CAR comprises scFv, but it may also comprise other binding entities. Binding moieties based on receptor or ligand domains have also been used successfully. The signaling domains for CARs can be derived from the cytoplasmic region of the CD3ζ or the Fc receptor gamma chains, but may also be derived from other cytoplasmic regions. First generation CARs have been shown to successfully redirect T-cell cytotoxicity. Signaling domains from co-stimulatory molecules, as well as transmembrane and hinge domains have been added to form CARs of second and third generations, leading to some successful therapeutic trials in humans, where T-cells could be redirected against malignant cells expressing CD19 (Porter D L et al., N Eng J Med, 2011).

7.3.7.1. CAR-T Embodiments

Those skilled in the art will appreciate that CAR-T provided by the disclosure can be designed for particular applications provided by the disclosure (D. Xu et al. *Oncotarget.* 2018 Mar. 2; 9(17)), which is hereby incorporated by reference in its entirety.

In various embodiments, the CAR is a $1^{st}$ generation CAR (Eshhar et al. Proc Natl Acad Sci USA (1993) 90(2)); in various embodiments, the CAR is a co-stimulatory CAR (Krause et al. J ExpMed. (1998) 188(4)); in various embodiments, the CAR is a 2nd generation CAR (Finney et al. J Immunol (1998) 161(6); Maher et al. Nat Biotechnol (2002) 20(1); Finney et al. (2004) J Immunol.172(1); Imai et al. (2004) Leukemia 18(4)); in various embodiments, the CAR is a 3rd generation CAR (Pule et al. (2005) MolTher. 12(5); Geiger et al. Blood (2001) 98; Wilkie et al. (2008) J Immunol. 180(7)); in various embodiments, the CAR is a 4th generation TRUCKS CAR (Chmielewski et al. Cancer Res (2011) 71.); in various embodiments, the CAR is an Armored CAR generation CAR (Pegram et al. (2012) Blood 119; Curran et al. (2015) MolTher. 2015 April; 23(4)); in various embodiments, the CAR is a engineered co-stimulation generation CAR (Zhao et al. (2015) Cancer Cell 28); in various embodiments, the CAR is a SynNotch/sequential AND gate generation CAR (Roybal et al. (2016) Cell 164); in various embodiments, the CAR is a co-stimulation in cis and in trans generation CAR (Stephan et al. (2007) Nat Med 13(12)); in various embodiments, the CAR is a dual-targeted generation CAR (Wilkie et al. (2012) J Clin Immunol. 32(5)); in various embodiments, the CAR is a Combinatorial CARs/AND gate generation CAR (Kloss et al. (2013) Nat Biotechnol 31(1)); in various embodiments, the CAR is a TanCAR generation CAR (Ahmed et al. (2013) MolTher Nucleic Acids. 2:e105); in various embodiments, the CAR is a Go-CART generation CAR (Foster et al, (2014)); the disclosures of which are incorporated herein by reference in their entireties.

In particular embodiments, the CAR is a pCAR, as described in US pre-grant publication US 2019/0002521, incorporated by reference herein in its entirety.

7.3.7.2. CAR Constructs (CAR-UMG1) with a Primary Intracellular Signaling Domain In some embodiments, the CAR construct comprises a primary intracellular signaling domain. A primary intracellular signaling domain produces an intracellular signal when an extracellular domain, e.g., an antigen binding domain, to which it is fused binds cognate antigen. The primary intracellular signaling domain is derived from a primary stimulatory molecule, e.g., it comprises intracellular sequence of a primary stimulatory molecule. The primary intracellular signaling domain comprises sufficient primary stimulatory molecule sequence to produce an intracellular signal, e.g., when an antigen binding domain to which it is fused binds cognate antigen.

A primary stimulatory molecule, is a molecule, that upon binding cognate ligand, mediates an immune effector response, e.g., in the cell in which it is expressed. Typically, it generates an intracellular signal that is dependent on binding to a cognate ligand that comprises antigen. The TCR/CD3 complex is an exemplary primary stimulatory molecule; it generates an intracellular signal upon binding to cognate ligand, e.g., an MHC molecule loaded with a peptide. Typically, e.g., in the case of the TCR/CD3 primary stimulatory molecule, the generation of an intracellular signal by a primary intracellular signaling domain is dependent on binding of the primary stimulatory molecule to antigen.

Primary stimulation can mediate altered expression of certain molecules, such as downregulation of TGF-β, and/or reorganization of cytoskeletal structures, and the like.

Stimulation, can, e.g., in the presence of co-stimulation, result in an optimization, e.g., an increase, in an immune effector function of the CART cell. Stimulation, e.g., in the context of a CART cell, can mediate a T cell response, e.g., proliferation, activation, differentiation, and the like.

In some embodiments, the primary intracellular signaling domain comprises a signaling motif, e.g., an immunoreceptor tyrosine-based activation motif or ITAMs. A primary intracellular signaling domain can comprise ITAM containing cytoplasmic signaling sequences from (for example)

TCR zeta (CD3 zeta, CDζ), common FcR gamma, (FCER1G), Fc gamma RIIa, FcR beta (Fc Epsilon Rib), CD3 gamma, CD3 delta, CD3 epsilon, CD5, CD22, CD79a, CD79b, CD278 (also known as "ICOS"), FcsRI, DAP10, DAP 12, and CD66d.

A primary intracellular signaling domain comprises a functional fragment, or analog, of a primary stimulatory molecule (e.g., CD3 zeta, CD3ζ). The primary intracellular signaling domain can comprise the entire intracellular region or a fragment of the intracellular region which is sufficient for generation of an intracellular signal when an antigen binding domain to which it is fused binds cognate antigen. In some examples, the primary intracellular signaling domain has at least 70, 75, 80, 85, 90, 95, 98, or 99% sequence identity with the entire intracellular region, or a fragment of the intracellular region which is sufficient for generation of an intracellular signal, of a naturally occurring primary stimulatory molecule, e.g., a human, or other mammalian, e.g., a nonhuman species, e.g., rodent, monkey, ape or murine intracellular primary stimulatory molecule.

In some embodiments, the primary intracellular signaling domain has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of the entire intracellular region, or a fragment of the intracellular region which is sufficient for generation of an intracellular signal, of a naturally occurring human primary stimulatory molecule, e.g., a naturally occurring human primary stimulatory molecule disclosed herein.

7.3.7.3. CAR Constructs (CAR-UMG1) with a Costimulatory Signaling Domain

In some embodiments, the CAR construct comprises a costimulatory signaling domain which produces an intracellular signal when an extracellular domain, e.g., an antigen binding domain, to which it is fused binds cognate ligand. The costimulatory signaling domain is derived from a costimulatory molecule. The costimulatory signaling domain comprises sufficient primary costimulatory molecule sequence to produce an intracellular signal, e.g., when an extracellular domain, e.g., an antigen binding domain, to which it is fused binds cognate ligand.

The costimulatory domain can be one which optimizes the performance, e.g., the persistence, or immune effector function, of a T cell that comprises a CAR which comprises the costimulatory domain.

Costimulatory molecules are cell surface molecules, other than antigen receptors or their counter ligands that promote an immune effector response. In some cases they are required for an efficient or enhanced immune response. Typically, a costimulatory molecule generates an intracellular signal that is dependent on binding to a cognate ligand that is, in certain embodiments, other than an antigen, e.g., the antigen recognized by an antigen binding domain of a CART cell. Typically, signaling from a primary stimulatory molecule and a costimulatory molecule contribute to an immune effector response, and in some cases both are required for efficient or enhanced generation of an immune effector response.

A costimulatory domain comprises a functional fragment, or analog, of a costimulatory molecule (e.g., ICOS, CD28, or 4-1BB). It can comprise the entire intracellular region or a fragment of the intracellular region which is sufficient for generation of an intracellular signal, e.g., when an antigen binding domain to which it is fused binds cognate antigen. In certain embodiments, the costimulatory domain has at least 70%, 75%, 80%, 85%, 90%, 95%, 98%, or 99% sequence identity with the entire intracellular region, or a fragment of the intracellular region which is sufficient for generation of an intracellular signal, of a naturally occurring costimulatory molecule, e.g., a human, or other mammalian, e.g., a nonhuman species, e.g., rodent, monkey, ape or murine intracellular costimulatory molecule.

Exemplary co-stimulatory domains include, but are no limited to, those selected from CD27, CD27, CD28, 4-1BB (CD137), QX40, CD30, CD40, ICQS (CD278), ICAM-1, LFA-1 (CD11a/CD18), CD2, CD7, LIGHT, NKG2C, B7-H3, a ligand that specifically binds with CD8, CDS, GITR, BAFFR, HVEM (LIGHTR), SLAMf7, NKP80 (KLRF1), CD160 (BY55), CD19, CD4, CD8 alpha, CD8 beta, IL2R beta, IL2R gamma, IL7R alpha, ITGA4, VLA1, CD49a, ITGA4, IA4, CD49D, ITGA6, VLA-6, C49f, ITGAD, CD11d, ITGAE, CD103, ITGAL, ITGAM, CD11b, ITGAX, CD11c, ITGB1, CD29, ITGB2, CD18, ITGB7, TNFR2, TRANCE/RANKL, DNAM1 (CD226), SLAMF4 (C244, 2B4), CD84, CD96 (Tactile), CEACAM1, CRTAM, Ly9 (CD229), PSGL1, C1OO (SEMA4D), CD69, SLAMF6 (NTB-A, Ly108), SLAM (SLAMF1, CD150, IPO-3), BLAME (SLAMF8), SELPLG (CD162), LTBR, LAT, GADS, and PAG/Cbp.

In some embodiments, the costimulatory signaling domain has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of the entire intracellular region, or a fragment of the intracellular region which is sufficient for generation of an intracellular signal, of, a naturally occurring human costimulatory molecule, e.g., a naturally occurring human costimulatory molecule disclosed herein.

7.3.7.4. Immune Effector Cell Comprising the Chimeric Antigen Receptor (CAR)

In a sixth aspect, the invention provides a CD3+ lymphocyte, an NK lymphocyte, a Cytokine induced killer (CIK) cell, a gamma-delta lymphocyte, an NKT cell or another immune effector cell comprising the chimeric antigen-ch-UMG1 according to aspect four or the expression vector according to aspect five.

Generally, CD3 is a complex of four signaling chains associated to the α:β heterodimer of the T-cell receptor in a functional T-cell receptor complex. The CD3 complex is usually required for T-cell receptor signaling. In general, the group of CD3+ lymphocytes exclusively contain thymocytes and T-cells. Detection of CD3+ cells can be achieved by e.g., flow-cytometry.

7.3.8. Bispecific T-Cell Engagers (BiTEs)

Two main approaches for T-cell redirection involve their genetic modification with chimeric antigen receptors (CAR), or the use of recombinant proteins designated bispecific T-cell engagers (BiTE).

The present disclosure provides various embodiments of BiTE-UMG1 constructs (Huehls A M et al., "*Bispecific T-cell engagers for cancer immunotherapy*" Immunol Cell Biol. 2015 March; 93(3):290-6; Zhukovsky E A et al., "*Bispecific antibodies and CARs: generalized immunotherapeutics harnessing T cell redirection.*" Curr Opin Immunol. 2016 June; 40:24-35), disclosures of which are incorporated herein by reference in their entireties.

Generally, BiTEs are constructed of two single-chain variable fragments (scFv) connected in tandem by a flexible linker. One scFv binds to a T-cell-specific molecule, usually CD3, whereas the second scFv binds to a tumor-associated antigen. This structure and specificity allows a BiTE to physically link a T cell to a tumor cell, ultimately stimulating T-cell activation, tumor killing and cytokine production.

In some embodiments, the BiTE-UMG1 constructs target a hematological cancer. In some embodiments, the BiTE-UMG1 constructs target a solid tumor cancer type. In some embodiments, the BiTE-UMG1 constructs target tumor-associated macrophages in a solid tumor.

7.4. Pharmaceutical Compositions of CD43 Binding Proteins

In a seventh aspect, the invention provides a pharmaceutical composition comprising the monoclonal UMG1 antibody according to aspects 1 or 2 or the UMG1 binding molecule according to aspect three or the CD3+ lymphocyte, the NK lymphocyte, the Cytokine induced killer (CIK) cell, the gamma-delta lymphocyte, the NKT cell or the other immune effector cell according to aspect six.

The term "pharmaceutical composition", as used herein, may be interchangeably used with the term "drug".

In some embodiments of the pharmaceutical composition, is an antibody or antigen-binding fragment thereof. In some embodiments, the antibody is monoclonal. In some embodiments, the monoclonal antibody is a chimeric antibody. In some embodiments, the monoclonal antibody is a humanized antibody. In some embodiments, the monoclonal antibody is a human antibody. In some embodiments, the pharmaceutical composition is an antibody-drug conjugate.

In various embodiments, the pharmaceutical compositions are described in more detail in U.S. Pat. Nos. 8,961,964, 8,945,865, 8,420,081, 6,685,940, 6,171,586, 8,821,865, 9,216,219, U.S. application Ser. No. 10/813,483, WO 2014/066468, WO 2011/104381, and WO 2016/180941, each of which is incorporated herein in its entirety.

7.5. Methods of Manufacturing

The UMG1 binding molecules (antibodies, protein, antigens, etc.) provided by the present disclosure can be manufactured using standard methods known in the art.

For example, UMG1 binding molecules can be made by expression using standard cell free translation, transient transfection, and stable transfection approaches currently used for antibody manufacture. In specific embodiments, Expi293 cells (ThermoFisher) can be used for production of the binding molecules using protocols and reagents from ThermoFisher, such as ExpiFectamine, or other reagents known to those skilled in the art, such as polyethylenimine as described in detail in Fang et al. (*Biological Procedures Online*, 2017, 19:11), which is incorporated herein in its entirety. Expressed proteins can be readily purified using standard methods known in the art such as, for example, a CH1 affinity resin, such as the CaptureSelect CH1 resin and provided protocol from ThermoFisher. Further purification can be accomplished using ion exchange chromatography as is routinely used in the art.

7.6. Administration

The UMG1 pharmaceutical composition provided by the present disclosure may be administered by any suitable route of administration. Suitable routes of administration include, but are not limited to, parenteral administration, including subcutaneous, intradermal, intravenous, intramuscular, intraperitoneal, nasal, and pulmonary routes.

7.7. Combination Therapeutics

The present disclosure also provides combination therapeutics. In some embodiments, the pharmaceutical composition provided herein is given in combination with another therapeutic treatment. The therapeutic treatment may be, surgical, radiation, holistic, cellular therapy, tissue regeneration, or another pharmaceutical composition known for the treatment of a cell proliferation disease or cancer.

Therapeutically-effective dosages vary in some embodiments when the pharmaceutical compositions provide by the present disclosure are used in treatment combinations. Methods for experimentally determining therapeutically-effective dosages of drugs and other agents for use in combination treatment regimens include the use of metronomic dosing, i.e., by providing more frequent, lower doses in order to minimize toxic side effects.

Combination treatment regimens encompass treatment regimens in which administration of a compound described herein is initiated prior to, during, or after treatment with a second agent described above, and continues until any time during treatment with the second agent or after termination of treatment with the second agent. Such regimens also include treatments in which a compound described herein and the second agent being used in combination are administered simultaneously or at different times and/or at decreasing or increasing intervals during the treatment period.

Combination treatments further include periodic treatments that start and stop at various times to assist with the clinical management of the patient. For example, a compound described herein in the combination treatment is administered weekly at the onset of treatment, decreasing to biweekly, and decreasing further as appropriate.

7.8. Formulations

The disclosure also provides various UMG1 pharmaceutical formulations comprising an effective amount of an UMG1 antigen, antibody, or binding molecule or protein.

In some embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising UMG1 antibody or UMG1 binding molecule are manufactured in a conventional manner, such as, by way of example only, by means of conventional mixing, dissolving, granulating, dragee-making, levigating, emulsifying, encapsulating, entrapping or compression processes.

UMG1 pharmaceutical compositions can optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances. Methods for the preparation of compositions comprising the compounds described herein include formulating the compounds with one or more inert, pharmaceutically acceptable excipients or carriers to form a solid, semi-solid or liquid.

Solid formulation of compositions include, but are not limited to, powders, tablets, dispersible granules, capsules, cachets, and suppositories.

Liquid formulation compositions include solutions in which a compound is dissolved, emulsions comprising a compound, or a solution containing liposomes, micelles, or nanoparticles comprising a compound as disclosed herein.

Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

The content of the antibody, the binding molecule or the CD3+ lymphocyte in the pharmaceutical composition is not limited as far as it is useful for treatment or prevention, but preferably contains 0.0000001-10% by weight per total composition. Further, the antibody, the binding molecule or the CD3+ lymphocyte described herein are preferably employed in a carrier. The choice of carrier may depend upon route of administration and concentration of the active agent(s) and the carrier may be in the form of a lyophilized composition or an aqueous solution. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilizers are non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co. The composition may also contain at least one further active compound, such as a chemotherapeutic agent.

Preferably, the antibody, the binding molecule, the CD3$^+$ lymphocyte and/or the active compound are included in an effective amount. The term "effective amount" refers to an amount sufficient to induce a detectable therapeutic response in the subject to which the pharmaceutical composition is to be administered.

7.9. Polynucleotides Encoding CD43 Binding Proteins

In an eighth aspect, the invention provides a nucleic acid or polynucleotide, encoding a UMG1 antibody according to aspects one or two or the UMG1 binding molecule according to aspect three.

Also provided herein are polynucleotides encoding an antibody that are optimized, e.g., by codon/RNA optimization, replacement with heterologous signal sequences, and elimination of mRNA instability elements. Methods to generate optimized nucleic acids encoding an antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly; each of which is incorporated by reference in its entirety. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an antibody encoded by polynucleotides that have not been optimized.

In certain embodiments, an optimized polynucleotide sequence encoding an antibody described herein or a fragment thereof (e.g., VL domain and/or VH domain) can hybridize to an antisense (e.g., complementary) polynucleotide of an unoptimized polynucleotide sequence encoding an antibody described herein or a fragment thereof (e.g., VL domain and/or VH domain). In specific embodiments, an optimized nucleotide sequence encoding an antibody described herein or a fragment hybridizes under high stringency conditions to antisense polynucleotide of an unoptimized polynucleotide sequence encoding an antibody described herein or a fragment thereof. In a specific embodiment, an optimized nucleotide sequence encoding an antibody described herein or a fragment thereof hybridizes under high stringency, intermediate or lower stringency hybridization conditions to an antisense polynucleotide of an unoptimized nucleotide sequence encoding an antibody described herein or a fragment thereof. Information regarding hybridization conditions has been described, see, e.g., U.S. Patent Application Publication No. US 2005/0048549 (e.g., paragraphs 72-73).

The polynucleotides of the invention can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6; which is incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding the antibodies of the invention described herein can be readily isolated and sequenced using conventional procedures (e.g., by using oligonucleotide probes that are capable of binding specifically to genes encoding the heavy and light chains of the antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of the antibodies in the recombinant host cells.

To generate whole antibodies, PCR primers including VH or VL nucleotide sequences, a restriction site, and a flanking sequence to protect the restriction site can be used to amplify the VH or VL sequences in scFv clones or other clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise a promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Site-directed or high-density mutagenesis of the variable region or other mutagenesis methods can be used to optimize specificity, affinity, etc. of a monoclonal antibody. Especially, affinity maturation strategies and chain shuffling strategies (Marks et al., 1992, Bio/Technology 10:779-783; each of which is incorporated by reference in its entirety) are known in the art and can be employed to generate high affinity human antibodies.

7.10. Hybridoma Cell that Produces the UMG1 Monoclonal Antibody

In a ninth aspect, the invention provides a hybridoma cell that produces the monoclonal antibody according to the antibody of aspects one or two.

7.11. Hybridoma Composition

The invention also provides a hybridoma composition, deposited under ICLC PD n° 16001.

7.12. Method for Producing the UMG1 Monoclonal Antibody

In an eleventh aspect, the invention provides a method for producing the monoclonal antibody according to aspects one or two, said method comprising isolating said antibody from the hybridoma cell deposited under ICLC PD n° 16001.

7.13. Isolation of Cells Using the UMG1 Antibody and/or Binding Molecules

In a twelfth aspect, the invention provides a method for the identification or isolation of T-cell acute lymbhoblastic leukemia cells, T lymphoma cells, Waldenström's Macroglobulinemia cells or tumor-associated macrophages, comprising contacting a cell sample comprising said cells with the monoclonal antibody according to aspects one or two or with the binding molecule according to aspect three.

In general, macrophages are the most represented non-malignant cells in the tumor microenvironment. Tumor associated macrophages (TAM) are considered to acquire a pro-tumoral inflammatory and immune-suppressive phenotype and to favor chemo-resistance, angiogenesis, cell motility and intra/extravasation. Therefore, targeting TAM may represent a novel therapeutic and still unexplored clinical option to improve the efficacy of current anticancer treatments.

Methods for the identification or isolation of specific cells, such as T-cell acute lymbhoblastic leukemia cells, T lymphoma cells, Waldenström's Macroglobulinemia cells or tumor-associated macrophages, based on antibodies or binding molecules in general are well-known to the person skilled in the art, such as methods based on fluorescent cell sorting by flow cytometry, magnetic cell isolation or single cell sorting, e.g. by cell sorters.

7.14. Method for Producing Immune Effector Cells

In a thirteenth aspect, the invention provides a method for producing CD3+ lymphocytes, NK lymphocyte, the Cytokine induced killer (CIK) cells, gamma-delta lymphocytes, NKT cells or the other immune effector cells expressing a chimeric antigen receptor according to the chimeric antigen receptor of aspect four comprising the introduction of the expression vector according to the expression vector of aspect five into said CD3+ lymphocytes, NK lymphocyte, the Cytokine induced killer (CIK) cells, gamma-delta lymphocytes, NKT cells or the other immune effector cells.

7.15. Expression Vector Compositions

In a fifth aspect, the invention provides an expression vector comprising a nucleic acid sequence which encodes the chimeric antigen receptor according to aspect four, the antibody according to the aspects one and two or the binding molecule according to the binding molecule according to aspect three.

Generally, expression vectors are plasmids which are used to introduce a desired nucleic acid sequence, such as a gene, into a target cell, resulting in the transcription and translation of the protein encoded by the nucleic acid sequence, i.e. the chimeric antigen receptor, the antibody or the binding molecule. Therefore, the expression vector in general comprises regulatory sequences, such as promoter and enhancer regions, as well as a polyadenylation site in order to direct efficient transcription of the nucleic acid sequence on the expression vector. The expression vector may further comprise additional necessary or useful regions, such as a selectable marker for selection in eukaryotic or prokaryotic cells, a purification tag for the purification of the resulting protein, a multiple cloning site or an origin of replication.

Usually, the expression vector may be a viral or a non-viral vector. In general, various kinds of viral vectors, such as retroviral vectors, e.g. lentiviral or adenoviral vectors, or plasmids may be used. In a preferred embodiment, the expression vector according to aspect five is a viral vector. In a more preferred embodiment, the expression vector is a lentiviral vector.

7.16. Methods of Treatment

In another aspect, methods of treatment are provided, the methods comprising administering a binding molecule or antibody as described herein to a patient in an amount effective to treat the patient.

In some embodiments, the method comprises administering a binding molecule or antibody as described herein to a patient in an amount effective to treat the patient using a CAR or CAR-T.

In some embodiments, the method comprises administering a binding molecule or antibody as described herein to a patient in an amount effective to treat the patient using a BiTE.

In some embodiments, the method comprises administering a binding molecule or antibody as described herein to a patient in an amount effective to treat the patient using an antibody-drug conjugate.

7.16.1. Indications

In some embodiments, an antibody or binding molecule of the present disclosure may be used to treat a proliferation disease or cancer. In some embodiments, the cancer is a solid tumor. In some embodiments, the cancer is a blood cancer including, but not limited to, T-cell malignancies, T-cell leukemia, T-cell lymphoma, T-cell acute lymphoblastic leukemia, multiple myeloma, B cell malignancies, myeloid malignancies, acute myeloid leukemia and chronic myeloid leukemia.

In some embodiments, the cancer or proliferation disease may be a cancer from the bladder, blood, blood immune cells (e.g., T-cell or B-cells, monocytes, and the like), bone, bone marrow, brain, breast, colon, colorectal, esophagus, gastrointestinal, gum, head, kidney, liver, lung, nasopharynx, neck, ovary, prostate, pancreas, skin, stomach, testis, tongue, or uterus.

In some embodiments, the cancer or tumor treated with the antibody or binding molecule of the present disclosure may be a neoplasm, malignant; non-malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia, and/or Waldenström's Macroglobulinemia.

In a thirteenth aspect, the invention provides a method for producing CD3+ lymphocytes, NK lymphocyte, the Cytokine induced killer (CIK) cells, gamma-delta lymphocytes, NKT cells or the other immune effector cells expressing a chimeric antigen receptor according to the chimeric antigen receptor of aspect four comprising the introduction of the expression vector according to the expression vector of aspect five into said CD3+ lymphocytes, NK lymphocyte, the Cytokine induced killer (CIK) cells, gamma-delta lymphocytes, NKT cells or the other immune effector cells.

7.17. Examples

The following examples are provided for the purpose of illustrating the invention, but should not be construed as limiting the invention. The examples comprise technical features and it will be appreciated that the invention also relates to any combinations of the technical features presented in the examples.

7.17.1. Example 1: UMG1 Binding Specificity—UMG1 Antibody Binds to Lymphocytes but not to Myeloid-Derived Cells in PBMC The binding of UMG1 to human peripheral blood mononuclear cells (PBMCs) from healthy donors was tested.

Methods: Peripheral blood mononuclear cells (PBMCs) from different healthy donors were obtained by Ficoll gradient separation. Subsequently, cells were seeded in 5 ml tubes and stained with 1 µg/ml of the UMG1 antibody or 1 µg/ml of a negative control "scramble" murine IgG1 antibody in 100 µl of binding solution (phosphate buffered saline (PBS)+0.5% fetal bovine serum (FBS)) and incubated at 4° C. for 30 minutes. Cells were then washed 2 times in binding solution and stained with a fluorescein isothiocyanate (FITC)-conjugated secondary antibody at 4° C. in the dark for 30 minutes. Subsequently, cells were washed 2 times in binding solution. Cell were analyzed on an ATTUNE NxT flow cytometer (THERMO Scientific). One tube for each donor was left unstained and one tube for each donor was stained with the FITC-conjugated secondary antibody only as a negative control.

Results:

The UMG1 antibody was able to recognize a lymphocyte subpopulation having variable prevalence (range: 0-15%) in different human donors. The UMG1 antibody did not show any reactivity with any other cell populations within the PBMCs, including myeloid-derived cells, demonstrating that myeloid-derived cells in PBMCs from healthy subjects are negative for expression of the UMG1 epitope (see FIG. 1A and FIG. 1B).

Figure 1B:
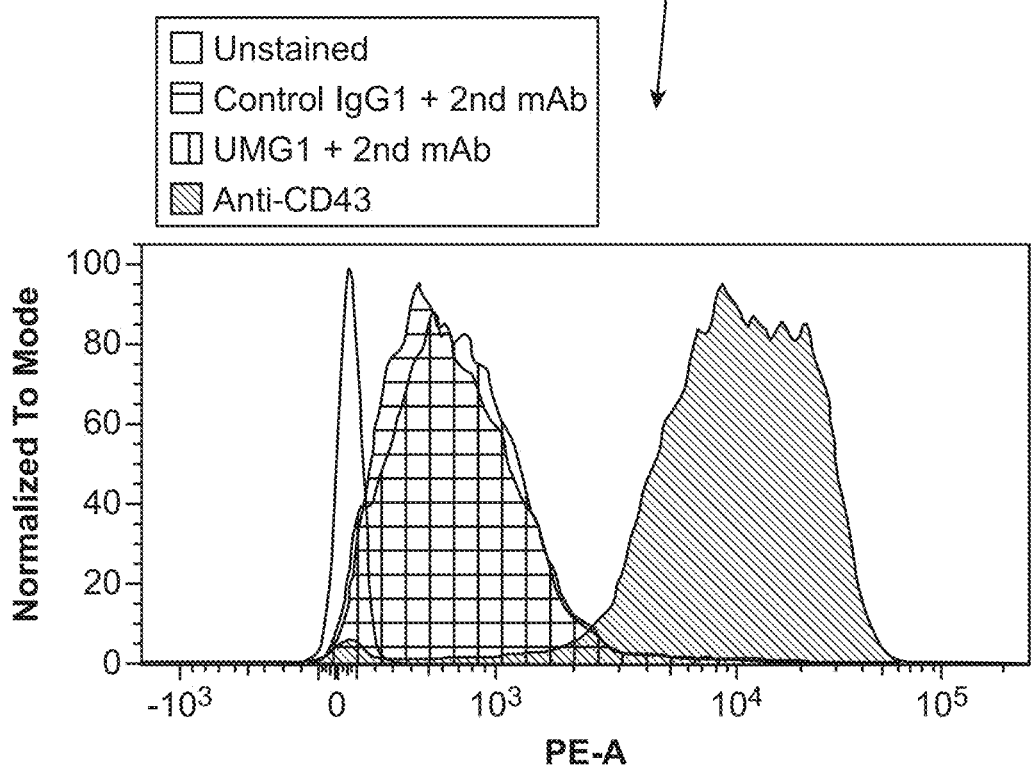
Figures 2A, 2B:
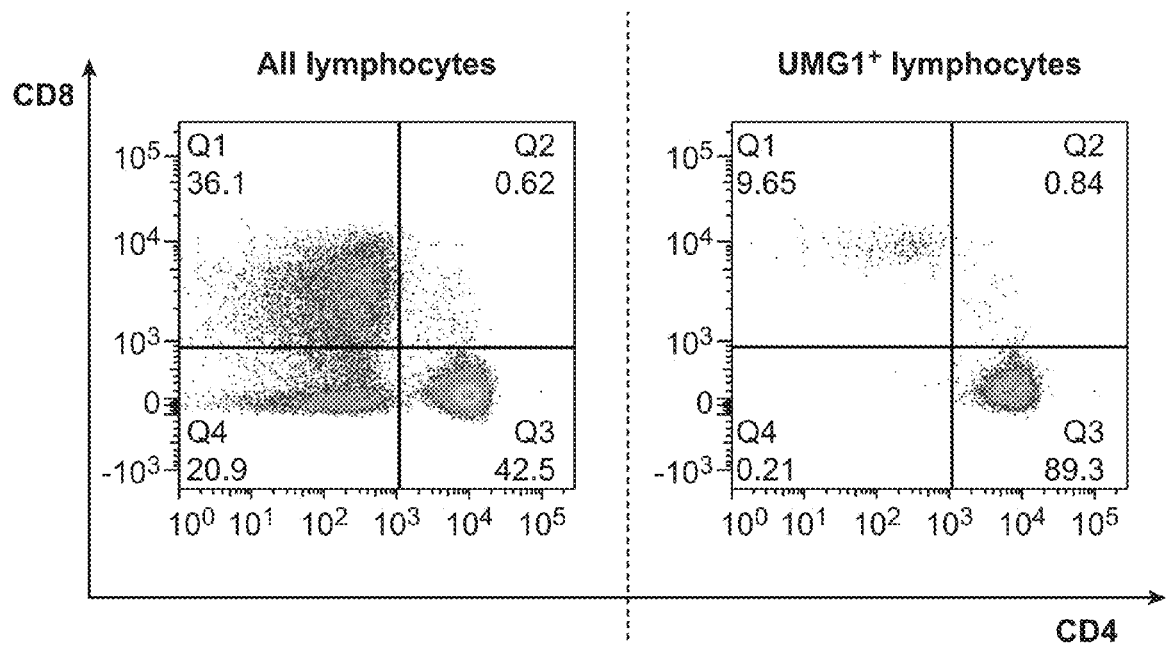
Figures 2C, 2D:
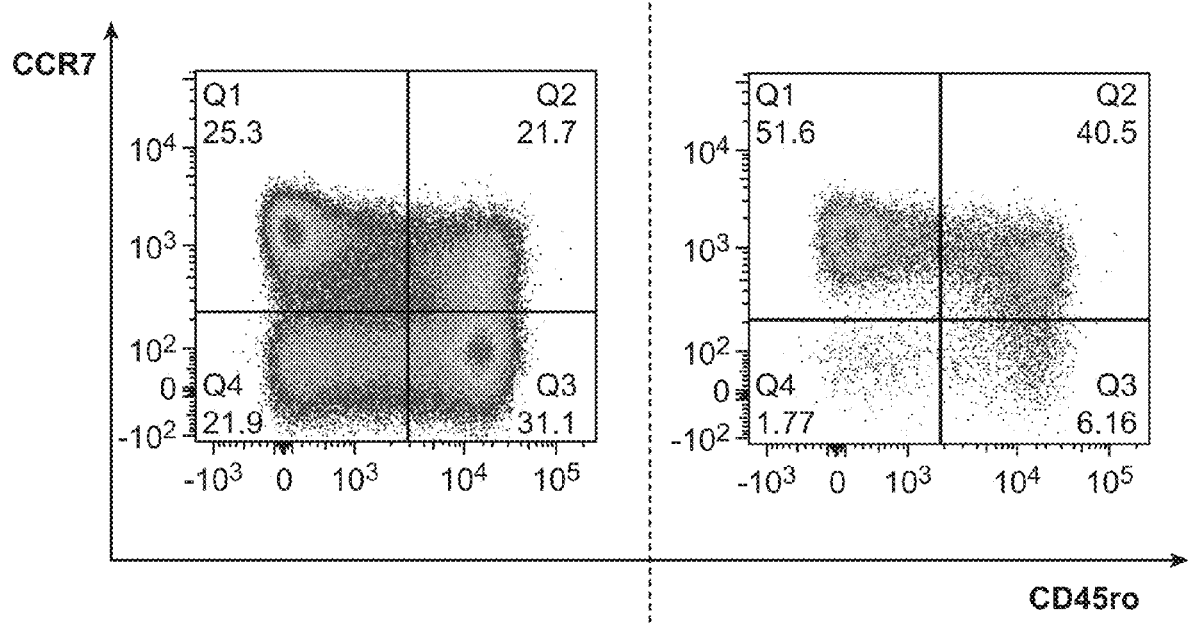

In contrast, when we assayed the same PBMCs for CD43 expression by using a commercial anti-CD43 antibody (S7 from Becton Dickinson), all lymphocytes and myeloid cells were found to be positive (see FIG. 1B).

Consequently, the epitope on CD43 recognized by the UMG1 antibody exhibits a specific, restricted, expression pattern in PBMC cells that is different from the pattern of expression of the epitope recognized by a commercial anti-CD43 antibody (S7).

7.17.2. Example 2: UMG1 Binding Specificity—PBMC T Lymphocyte Subsets Bound by the UMG1 Antibody This example further characterizes the lymphocyte subpopulation detected by the UMG1 antibody using an immune-magnetic sorting of the respective lymphocytes.

Methods:

Briefly, 15 µg of the UMG1 antibody were mixed with components provided by the manufacturer (EasySep™ "Do-it-yourself" Selection Kit, STEMCELL Technologies) to obtain a solution ready for immunomagnetic separation. This solution was added to PBMCs from 3 different donors having at least 10% of lymphocytes detected by the antibody, after FcR blocking, and cells were incubated at room temperature (r.t.) for 15 minutes. Subsequently, EasySep® Magnetic Nanoparticles were added to the solution and cells were incubated for further 10 minutes at r.t. The solution was then placed in a magnet and unbound cells were removed.

Results:

Cells detected by the UMG1 antibody were almost all $CD45^+CD3^+CD4^+CD8^-CD127^+CCR7^+$ T lymphocytes, (see FIGS. 2A-2D and Table 1).

TABLE 1

| Marker of UMG1 antigen-positive cells | |
| --- | --- |
| MARKER | +/− |
| CD45 | + |
| CD3 | + |
| CD4 | + |
| CD8 | − |
| CD127 | + |
| CCR7 | + |
| CD45ra | + |
| CD45ro | +/− (40% positive; see FIG. 2) |
| CD56 | − |

7.17.3. Example 3: UMG1 Binding Specificity—Only T-ALL and Waldenström's Macroglobulinemia Cancer Cell Lines Express the UMG1 Epitope In this experiment, various hematopoietic and non-hematopoietic cancer cell lines were evaluated for the expression of UMG1 epitope.

Methods:

Briefly, cells were seeded in 5 ml tubes and stained with 1 µg/ml of mAb UMG1 or 1 µg/ml of a scramble murine IgG1 antibody in 100 µl of binding solution (phosphate buffered saline (PBS)+0.5% fetal bovine serum (FBS)) and incubated at 4° C. for 30 minutes. Cells were then washed 2 times in binding solution and stained with a fluorescein isothiocyanate (FITC)-conjugated secondary antibody at 4° C. in the dark for 30 minutes. Subsequently, cells were washed 2 times in binding solution and acquired on an ATTUNE NxT flow cytometer (THERMO Scientific). One tube for each cell line was left unstained and one tube for each cell line was stained with the FITC-conjugated secondary antibody only.

Figure 3A:
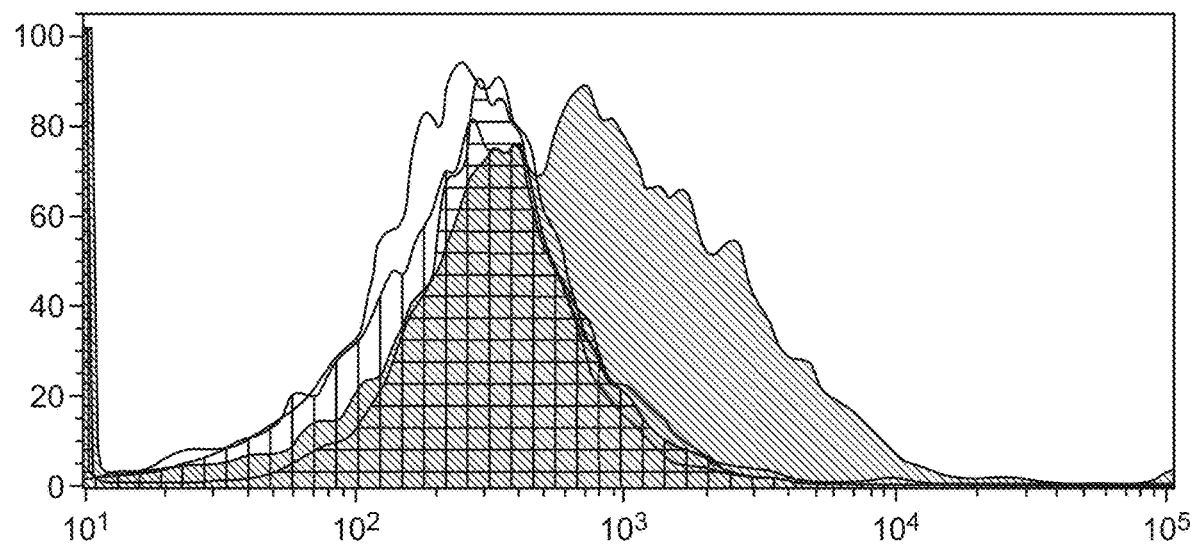
Figure 3B:
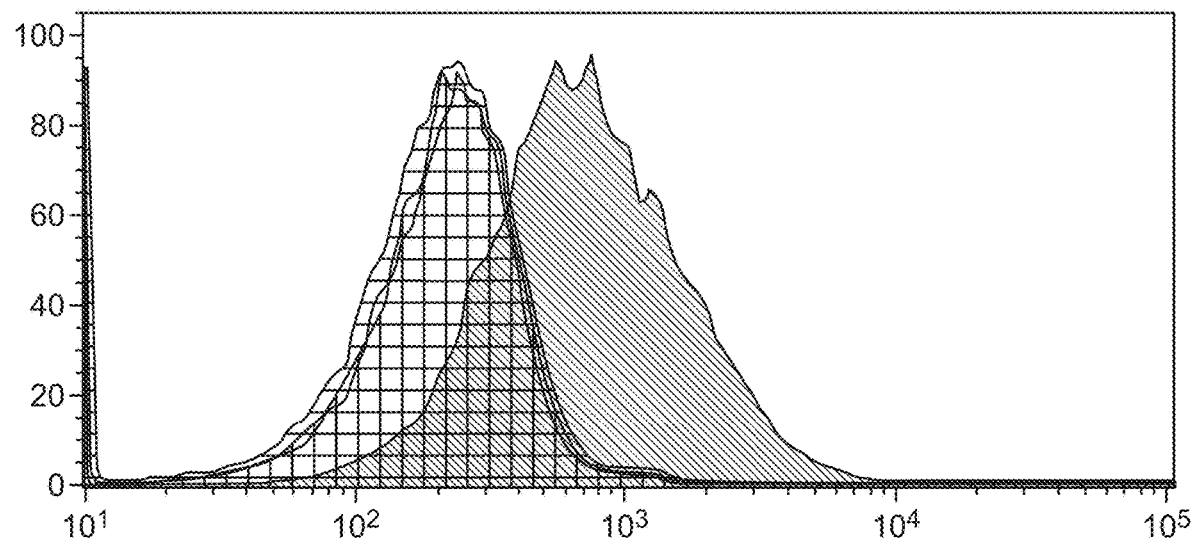
Figure 4:
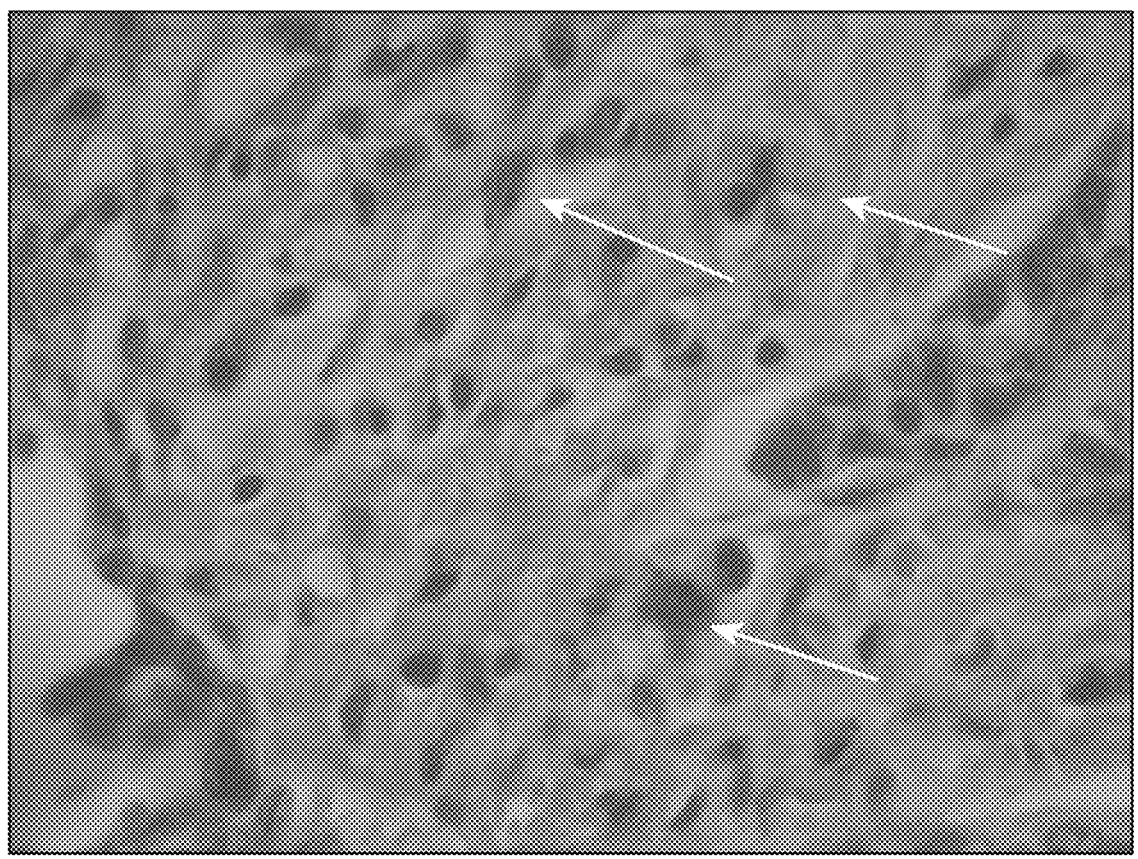

Results:

It was observed that T-ALL cell lines belonging to EGIL T3 classification and Waldenström's macroglobulinemia (FIGS. 3A-3B) were all positive for expression of the UMG1 epitope, while the other cell lines assayed were negative for the UMG1 epitope (see Table 2). The UMG1 antibody recognizes T-ALL and Waldenström's Macroglobulinemia cell lines, but not other hematopoietic cancers and non-hematopoietic tumors.

TABLE 2

UMG1 epitope expression in various cancer cell lines

| Cell lines | Cancer type | UMG1+/− |
|---|---|---|
| H929 | Multiple Myeloma (MM) | − |
| AMO | MM | − |
| U266 | MM | − |
| KMS11 | MM | − |
| 8226 | MM | − |
| BCWM.1 | Waldenström's Macroglobulinemia (WM) | + |
| MWCL.1 | WM | + |
| H9 | T lymphoma | + |
| HPB-ALL | T-ALL | + |
| MOLT-4 | T-ALL | + |
| JURKAT | T-ALL | − |
| CEM | T-ALL | +/− |
| HSB2 | T-ALL | − |
| THP-1 | Monocytic leukemia | − |
| MOJ | Glioblastoma | − |
| SKMEL | Melanoma | − |
| HCC | Breast | − |
| MCF-7 | Breast | − |
| 5637 | Bladder | − |
| CAPAN | Pancreatic | − |
| BXPC 3 | Pancreatic | − |

7.17.4. Example 4: UMG1 Binding Specificity—UMG1 Binds to T-ALL Human Cell Lines with Binding Pattern Different from Commercially Available CD43 Antibodies This example demonstrates the unique binding properties of the UMG1 antibody compared to commercially available CD43 antibodies in two different T-ALL human cell lines, ALL-SIL and KE-37.

Methods:

Commercially available CD43 antibodies: clones, CD43 1G10 (Becton Dickinson), CD43 MEM-59 (Invitrogen), and CD43 L-10 (Invitrogen) were compared to the UMG1 antibody.

Cells from various human cell lines (100,000 cells/tube) were collected. Cells were washed by adding 2 mL of cold staining buffer and centrifuging cells at 1,200 rpm for 5 minutes at room temperature and the supernatant was discarded. The primary antibody UMG1 was added at the concentration of (1 μg/ml in the final staining volume of 100 μL of cells. Cell were gently to mix by pulse vortex. Next, the cells were incubated for 15 minutes at 2-8° C., protected from light. Cells were washed twice, by adding 2 mL of staining buffer and centrifuge cells at 1,200 rpm for 5 minutes at room temperature and the supernatant was discarded. The secondary fluorochrome-labeled antibody was diluted following the manufacture's instructions in a final volume of 100 μL of cells and incubated for at least 15 minutes at 2-8° C., protect from light. Cells were washed twice as indicated above and then resuspend in 500 μL of PBS 1× and analyzed by flow cytometry.

Figures 12A, 12B:
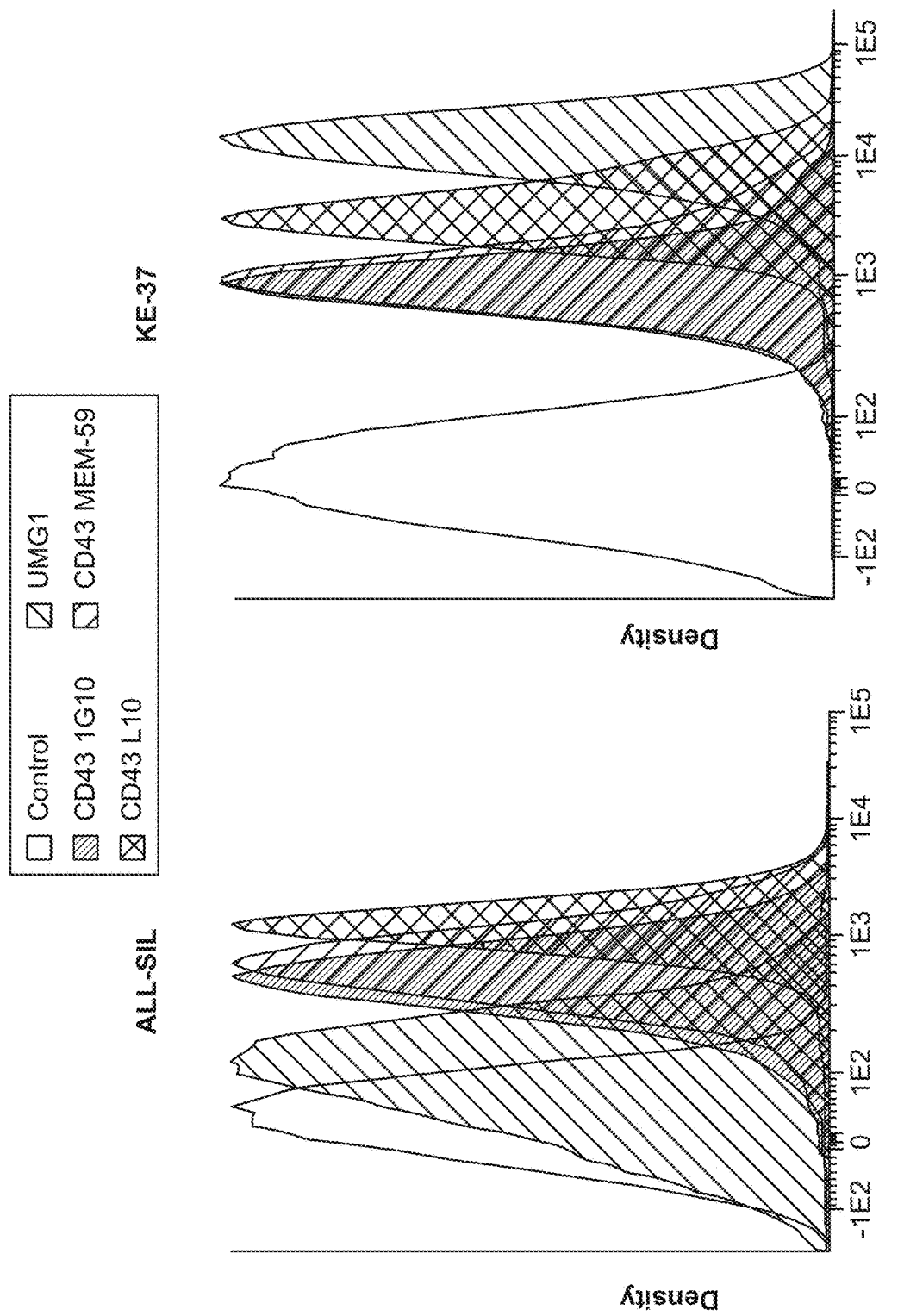

Results:

We observed different expression density and intensity by FACS analysis for the UMG1 antibody, and CD43 1G10 (Becton Dickinson), CD43 MEM-59 (Invitrogen), and CD43 L-10 (Invitrogen) in both ALL-SIL and KE-37 cell lines. See FIGS. 12A and 12B. These observations suggest that the UMG1 antibody has a different binding site on CD43 than three different CD43 commercial antibodies.

7.17.5. Example 5: UMG1 Binding Specificity—UMG1 is Reactive with the Tumor Immune Infiltrate This example demonstrates the unique binding properties and expression of m-UMG1 in human colon, lung, and breast cancer tissues compared to other characterized CD43 antibodies.

Methods:

Paraffin embedded tissue samples from three different human cancers were sectioned, de-paraffinized and then analyzed by immunohistochemistry for expression of the UMG1 epitope using the following protocol.

Samples were placed in a de-paraffinize in heater for 30 minutes at 65° C. Next, the sections were in soaked in (1) xylene for 10 minutes, (2) xylene for 5 minutes, and then re-hydrated through graded alcohols: 90% ethanol for 2 minutes; alcohols 70% ethanol for 2 minutes. Slides were washed in running tap water and then a final wash was conducted with de-ionized water.

Antigen unmasking was carried out using Novocastra Epitope Retrieval Solutions, pH 9 (Leica Biosystems) in Thermostatic bath at 98° C. for 30 minutes. Neutralize endogenous peroxidase using Peroxidase Block for 10 minutes. Peroxidase Block. 3/4%, (v/v) $H_2O_2$. Next, samples were washed in PBS for 2 times for 5 minutes each wash. After washing, the samples were incubated with Protein Block for 8 minutes. Protein Block, 0.4% Casein in phosphate-buffered saline. After blocking, the slides were washed in PBS for 2 times for 5 minutes for each wash.

The sections were stained using the primary antibody UMG1 ("m-UMG1") overnight at 4 C°, at a dilution of 1:300. Next, the stained sections were washed in PBS for 2 times for 5 minutes each wash. After washing, the samples were incubated with rabbit anti-mouse IgG from 30 mins and then washed in PBS for 2 times for 5 minutes each wash. After washing, the samples were incubated with Novolink Polymer for 30 minutes, anti-rabbit Poly-HRP-IgG, and then washed in PBS for 2 times for 5 minutes for each wash.

Staining on the sections was revealed by AEC (3-amino-9-ethylcarbazole) substrate-chromogen (Dako) and then rinsed in running tap water. Sections were counterstain using Hematoxylin for 5 minutes and then washed again in running tap water. Sections were mounted with the Ultramount Aqueous Permenent Mounting Medium (Dako). The tissue sections were analyzed for UMG1 staining under an optical microscope (Leica Microsystems), and microphotographs were collected using a digital camera (Leica).

Figure 14A:
Figure 14B:
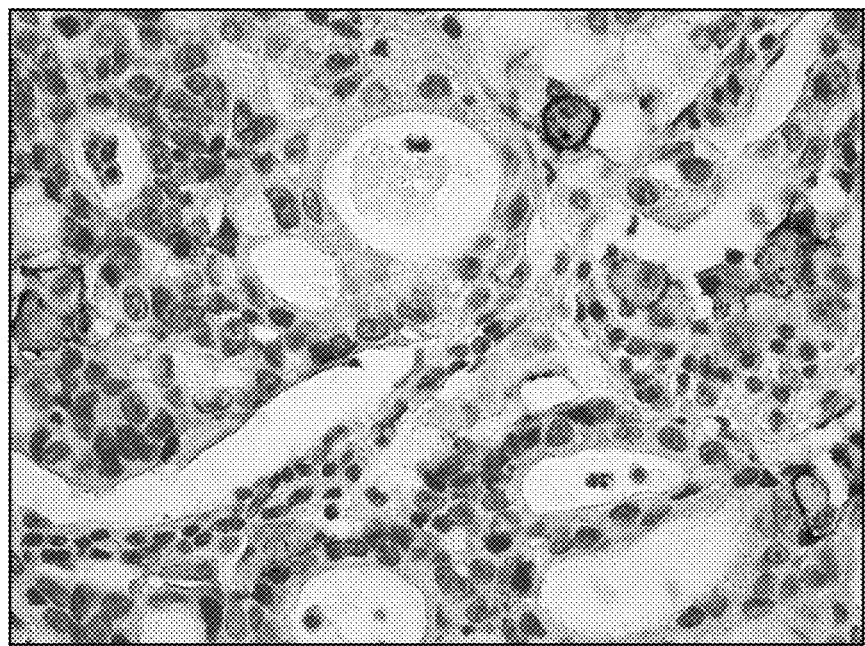
Figure 14C:
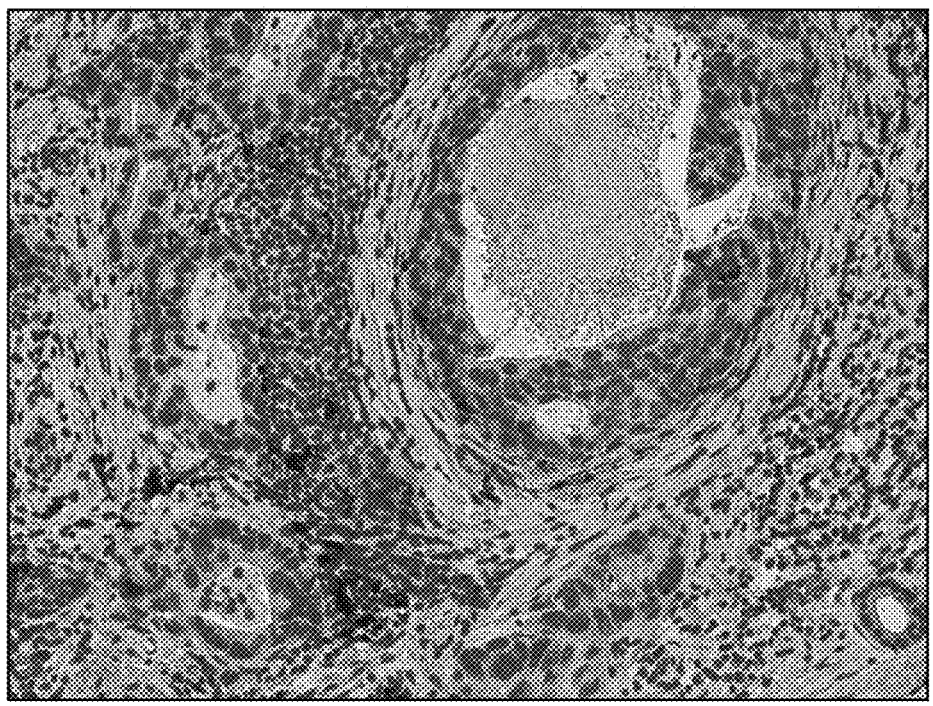

Results:

We observed UMG1 staining in the immune infiltrate of various solid tumors. More specifically, we saw significant reactivity with tumor associated macrophages in lung cancer, colorectal cancer, and breast cancer tissues. See, FIGS. 14A (colorectal adenocarcinoma (grade 2, G2), 14B (lung adenocarcinoma) and 14C (breast, Triple negative ductal infiltrating breast cancer (G2, basal-like)).

Figure 9:
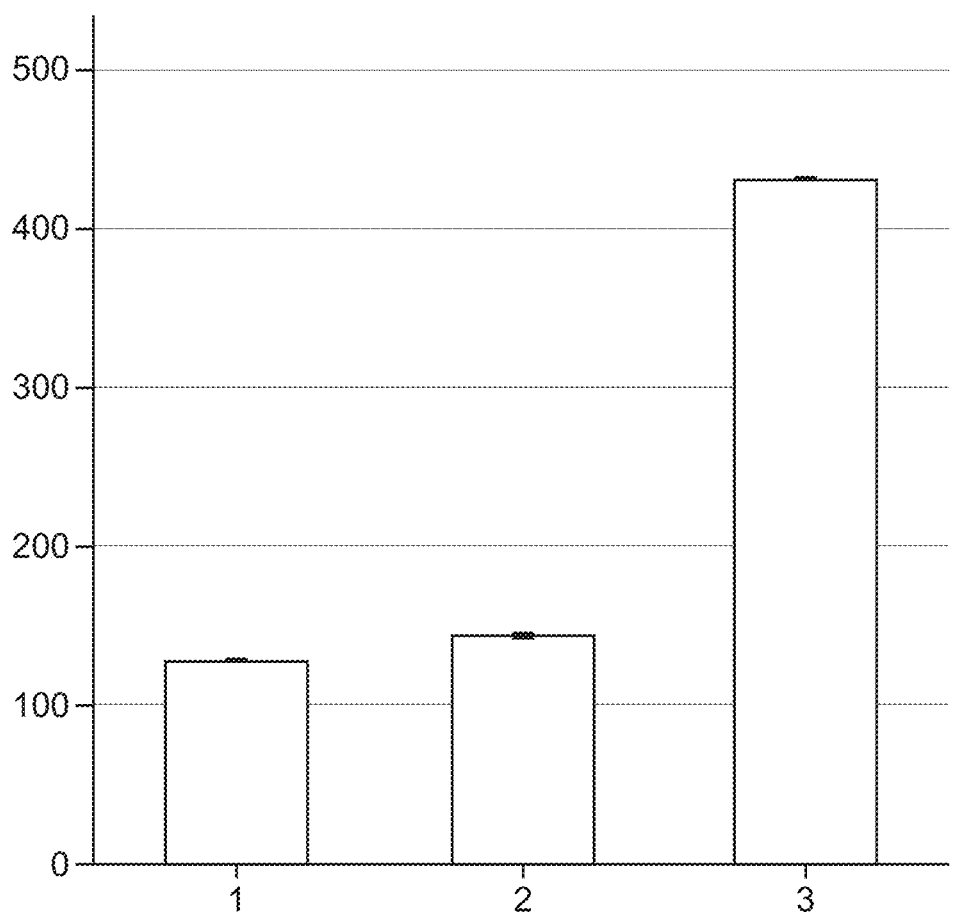

Significantly, UMG1 failed to stain the cancer cells directly, unlike other previously described CD43 antibodies, such as UN1 (See, UN1 staining in De Laurentiis, A. et al., *Molecular Cellular Proteomics*, 2011, FIG. 9).

These results demonstrate that the UMG1 antibody has a different binding profile to CD43 than other characterized CD43 antibodies, in particular UN1, which had previously been shown to bind CD43 in cancer cells.

7.17.6. Example 6: UMG1 Binding Specificity—UMG1 Epitope is Expressed in Tumor-Associated Macrophages, and UMG1 Epitope Expression is Elevated when Macrophages are Co-Cultured and Interact with Cancer Cells In this example, specimens from different kinds of cancer were assessed for expression of the UMG1 epitope by immunohistochemistry, and it was discovered that the specific CD43 epitope bound by UMG1 is highly expressed by tumor-associated macrophages (TAM).

Methods:

Different types of cancers were stained as outlined in the examples provided herein.

Results:

By evaluating specimens from different kinds of cancer through immunohistochemistry (Table 3, FIG. 4, and FIGS. 14A-14C), it was observed that UMG1+ macrophages are a high infiltrating component of most tumors, with a specific and particular high grade of infiltration in pancreatic and ovarian cancer, notwithstanding the absence of the UMG1 epitope in myeloid-derived cells in PBMCs of healthy subject.

TABLE 3

UMG1 + TAM infiltration in various tumors

| Cancer Type | UMG1 + TAM infiltration (+: low; ++: medium; +++: high) |
| --- | --- |
| Hodgkin Lymphoma | + |
| Non-Hodgkin Lymphoma | ++ |
| Plasmacytoma | ++ |
| Colorectal cancer | + |
| Pancreatic cancer | +++ |
| Lunc cancer | ++ |
| Prostate cancer | + |
| Breast cancer | ++ |
| Ovarian cancer | +++ |
| Bladder cancer | ++ |
| Melanoma | ++ |

To better understand the significance of UMG1 epitope in macrophages, in a second experiment UMG1 epitope expression changes were assessed in a model of macrophage differentiation in the presence or absence of co-cultured cancer cells. For this purpose, THP-1 monocytic leukemia cells were used; as shown in Example 3, these cells do not express the UMG1 epitope.

Methods:

To obtain differentiated human unpolarized MO macrophages (THP-1M), the cells were cultured for 48 h in complete appropriate medium in the presence of 50 ng/ml of phorbol 12-myristate 13-acetate (PMA). The media was then replaced with fresh medium without PMA. Next, PANC1 pancreatic cancer cell line cells were added at a 1:1 ratio selected wells and incubated for 48 hrs.

Cells were then prepared for immunofluorescence analysis. Briefly, after fixation, THP-1M cells were stained with a chimeric antibody derived from UMG1, ch-UMG1, which is further described in Example 11, or human IgG1 control, and incubated at 4° C. overnight. A FITC anti-human secondary mAb was then added to the cells for 2 hours. After washing, anti-fade mounting medium with DAPI (Vectashield®, Vectorlabs) was added to cells and coverslips and then analyzed.

Figure 5A:
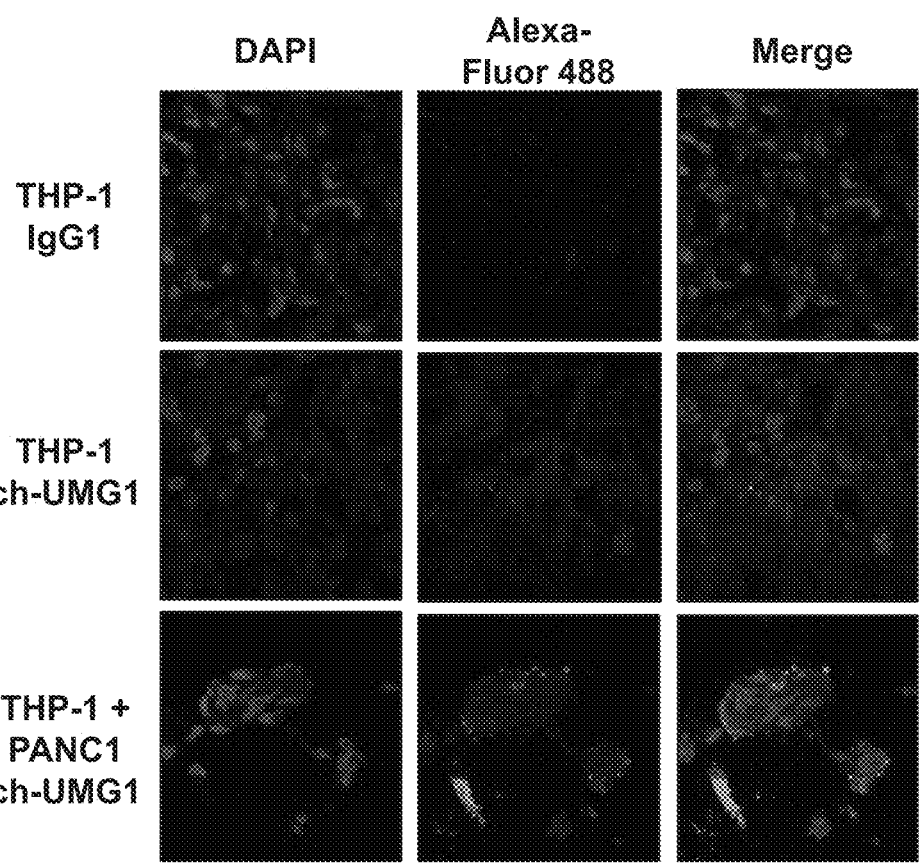

Results:

As shown in FIG. 5A, THP-1-derived macrophages stained with control IgG1 were completely negative, while those stained with ch-UMG1 were weakly (faint) positive. Interestingly, in the presence of PANC1 cells, THP1-derived macrophages showed strong (bright) UMG1 expression. One particular interaction between THP-1-derived macrophages (white arrow) and PANC1 cells (red arrow) is shown (FIG. 5A, on the left).

These findings demonstrate that the UMG1-specific epitope is significantly upregulated (i.e, elevated) when macrophages are co-cultured and interact with cancer cells within a reconstituted tumor microenvironment. This elevated expression means that the UMG1 epitope is a suitable target for therapeutic approaches focused on purging tumor-associated macrophages. Beyond this relevant potential as therapeutic tool, UMG1 might also prove useful for detection, analysis of prognostic role and predictive studies.

7.17.7. Example 7: UMG1 Binding Specificity—Competitive Binding Assays Suggest that the UMG1 Binding Site on CD43 is Unique Compared Commercially Available CD43 Antibodies To determine if the binding site of UMG1 is the same as or different from commercially available CD43 antibodies, competitive binding assays between (i) h-UMG1 (a humanized version of the UMG1 antibody, further described in Example 14, below) and phycoerythrin-conjugated h-UMG1 (h-UMG1-PE) and (ii) h-UMG1 and three commercially available CD43 antibodies were conducted on two different cell lines, CEM and HPB-ALL.

Methods:

Competitive binding assay was performed and analyzed by FACS analysis using the following antibodies: unconjugated h-UMG1, h-UMG1-PE, and commercially available CD43 antibodies: MEM-59 PE (Invitrogen), L-10 PE (Invitrogen), and 1G10 PE (Becton Dickinson). Briefly, CEM and HPB-ALL cells were incubated for 20 minutes, on ice, in the dark with h-UMG1 unconjugated at increasing concentrations (0.016 g/ml, 0.08 µg/ml, 0.4 µg/ml, 1 µg/ml, 2 µg/ml) in the presence of 1 µg/ml of one of the CD43 clones or h-UMG1-PE (positive control).

Approximately, 500,000 cells were collected and stained for each test. Cell were analyzed and measured with FACS Canto (Becton Dickinson) and analyzed by DIVA software (BD FACSDiva™ software). For each measurement 10,000 events were gated using the DIVA software. Each experiment was performed in triplicate.

Figure 13A:
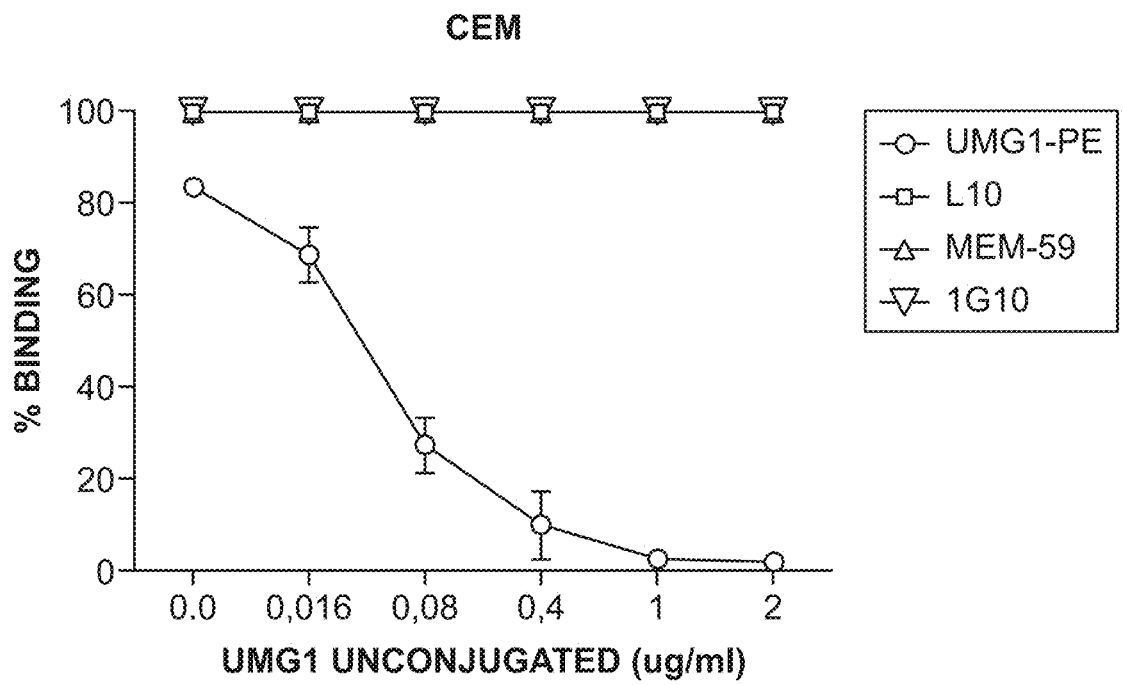
Figure 13B:
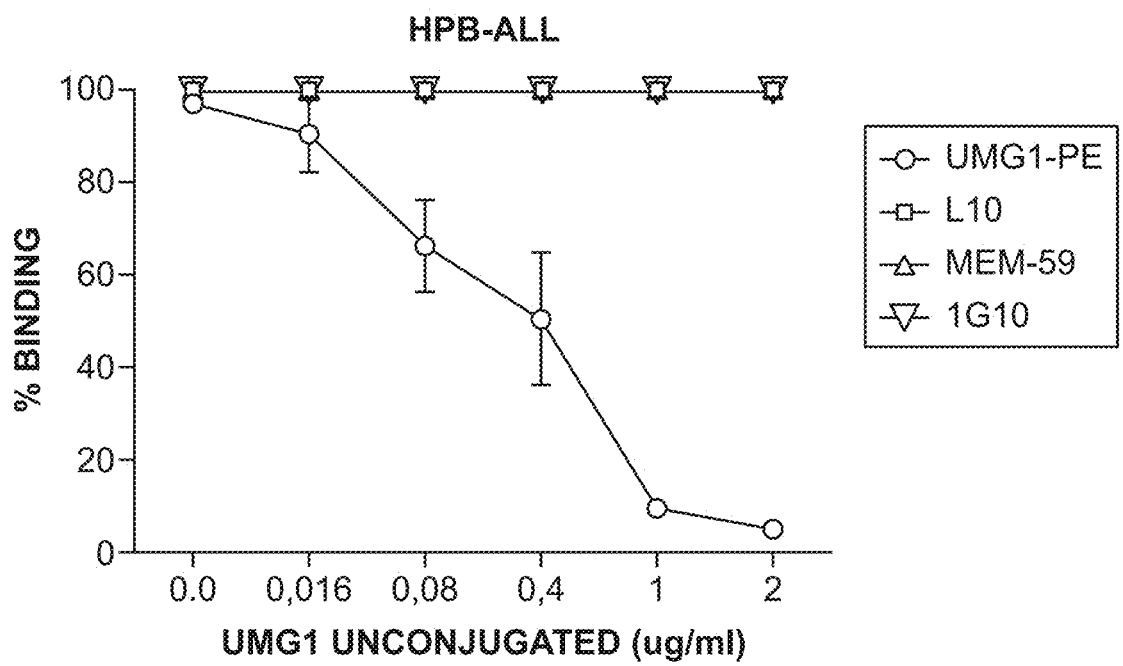

Results:

As expected, unconjugated h-UMG1 competes with h-UMG1-PE binding in both CEM and HPB-ALL cell lines. That is, the number of stained cells marked with h-UMG1-PE are reduced by increasing the concentrations of unstained h-UMG1. See, FIGS. 13A and 13B (line with circles).

In contrast, unconjugated h-UMG1 does not compete with the binding of other commercially available CD43 antibodies (MEM-59 (Invitrogen), L-10 (Invitrogen), and 1G10 (Becton Dickinson). Indeed, the number of stained cells marked with anti-CD43 was not reduced by increasing the concentration of unconjugated h-UMG1 antibody. See, FIGS. 13A and 13B (line with up-facing triangles, line with down-facing triangles, line with squares).

These results suggest that h-UMG1 antibody has a different binding site then three commercially available CD43 antibodies.

7.17.8. Example 8: UMG1 Binding Specificity—Flow Cytometric Profiles of h-UMG1 in Cell Lines of the Hematopoietic Lineage Compared to UN1 Historical Published Data As mentioned above, UN1 was reported in the literature to bind directly to various cancer lines, whereas in the experiments reported in Example 3 and Example 5 above, UMG1 does not. Instead, UMG1 binds to tumor-associated macrophage infiltrates into solid tumors.

Since the hybridoma that secretes the UN1 antibody was never deposited in a biological repository and no UN1 hybridoma master cell bank or working cell bank was made, precluding side-by-side experimental comparisons between the original UN1 antibody and UMG1, we further explored similarities and differences between UN1 and UMG1 binding by repeating experiments first reported in Tassone et al., Tissue Antigens 44:73-82, 1994. In this reference, binding of UN1 to various cell lines of the hematopoietic lineage—such as JURKAT, MOLT-4, CEM and HPB-ALL lines—was assessed by flow cytometry expression.

Methods:

Cells from human cell lines were collected at approximately 100,000 cells/tube. Cells were then washed by adding 2 mL of cold staining buffer and centrifuging the cells at 1,200 rpm for 5 minutes at room temperature to pellet and supernatant was discarded.

The h-UMG1 primary antibody was added at the concentration of 1 µg/ml in the final staining volume of 100 µL of cells. Next, cells were mixed by pulse vortex and incubated for 15 minutes at 2-8° C., protected from light. The excess primary antibody was then washed off twice, by adding 2 mL of staining buffer and centrifuge cells at 1,200 rpm for 5 minutes at room temperature to pellet, and the supernatant was discarded. The secondary fluorochrome-labeled antibody was added at the recommended dilution in a final volume of 100 µL of cells, and incubated for at least 15 minutes at 2-8° C., protected from light.

The excess secondary antibody was then washed off the cells twice, by adding 2 mL of staining buffer and centrifuging cells at 1,200 rpm for 5 minutes at room temperature to pellet and the supernatant was discarded. The washed pelleted cells were resuspended in 500 µL of PBS 1× and analyzed by flow cytometry.

Figure 17A:
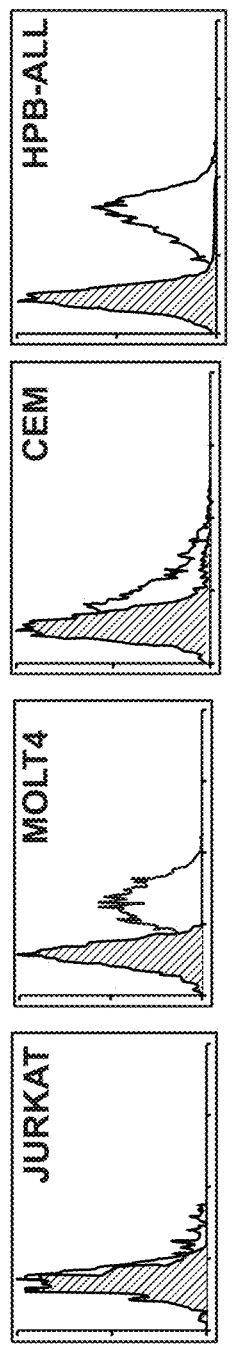
Figure 17B:
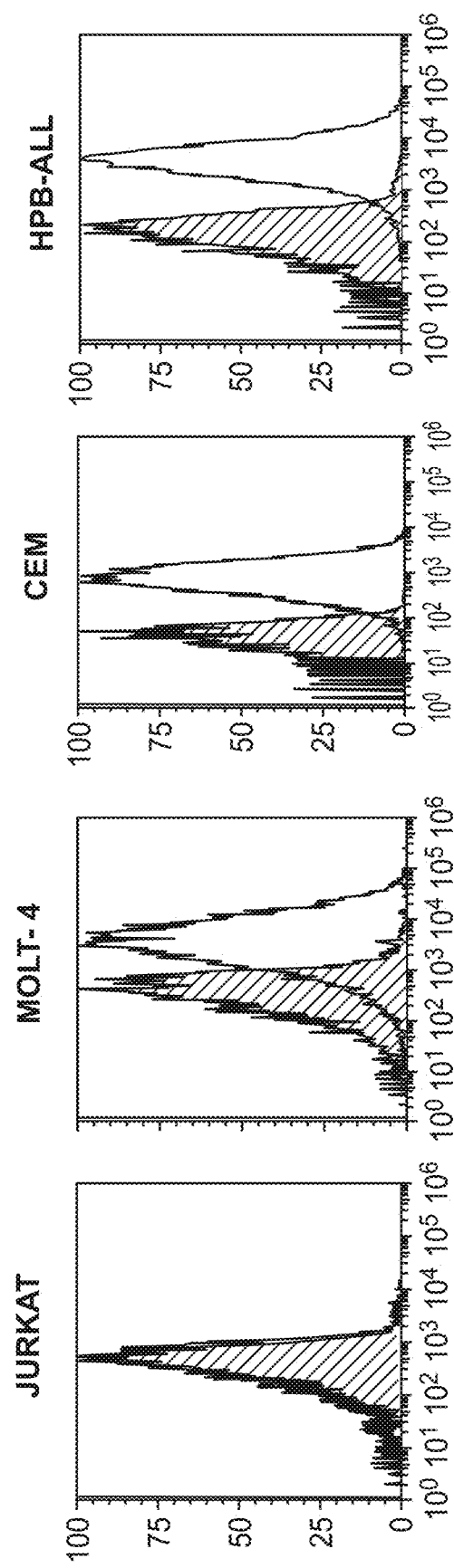

Results:

FIG. 17A shows the historical flow cytometric profiles of UN1 performed in 1994 by the Tassone lab (Tassone et al., Tissue Antigens 44:73-82, 1994), in JURKAT, MOLT-4, CEM, and HPB-ALL cell lines. FIG. 17B shows the results of flow cytometric profiles of h-UMG1 antibody in JURKAT, MOLT-4, CEM, and HPB-ALL cell lines.

The comparison indicates that both UMG1 and UN1 do not bind to JURKAT cells, but do bind to MOLT-4, CEM, and HPB-ALL cell lines.

Notably, UMG1's flow cytometric profile in the CEM cell line shows approximately 1 log shift in the curve compared to UN1. The difference in the UN1 and UMG1 curves suggest that there is a difference in binding affinity to CEM cells.

7.17.9. Example 9: UMG1 Binding Specificity—Epitope Binding Site on CD43

Various CD43 protein variants were tested for binding of the h-UMG1 antibody by western blot and FACS analysis to determine h-UMG1's binding site on CD43 in HEK293T-wild type cells that do not express CD43.

Figure 15B:
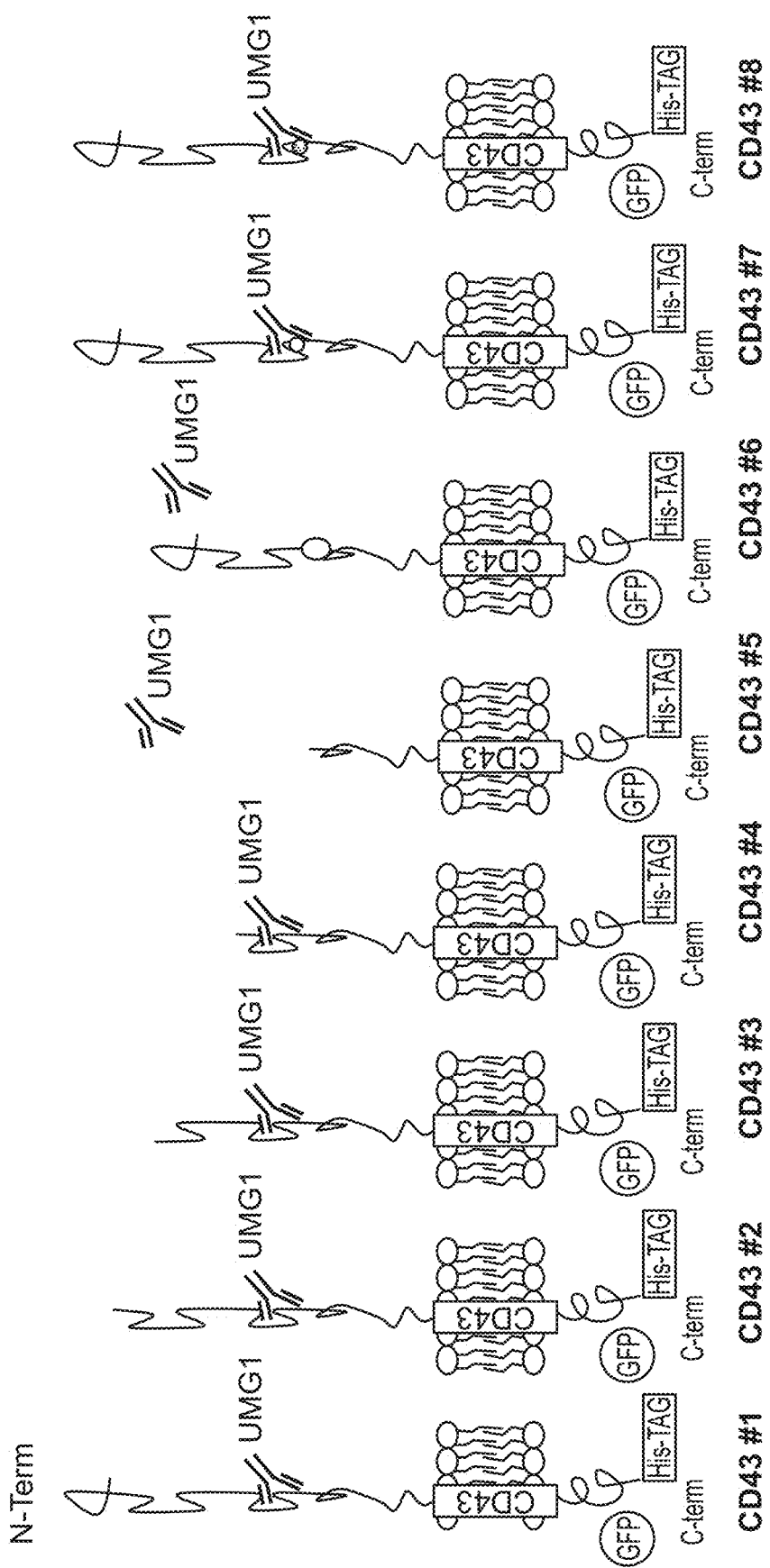

CD43 Protein Variants:

The sequences of CD43 protein clones tested are provide in FIG. 15A, Table 4 and in the sequence listing as SEQ ID NOs: 17-24. Wildtype CD43, indicated as "CD43 #1" was generated using the full 400 amino acid region. For engineering the CD43 protein variants, the N-terminal domain was sequentially truncated. The first CD43 truncated variant, "CD43 #2," was generated using aa from 31 to 400 of full-length CD43. The second CD43 variant indicated as, "CD43 #3" was generated using aa from 41 to 400 of the full length CD43. The third CD43 variant, indicated as "CD43 #4" was generated using aa from 61 to 400 from full-length CD43. The fourth CD43 variant, indicated as "CD43 #5", consists of aa 91-400 from full length CD43. The fifth CD43 variant, indicated as "CD43 #6", has a deletion from aa 64 to 78.

In addition, single amino acid deletion variants were also tested. The sixth CD43 variant, indicated as "CD43 #7" has a deletion of a single amino acid at aa 69, which is thought to be the GalNac site. The seventh CD43 variant, indicated as "CD43 #8" has a single amino acid substitution at aa 69, T changed into N, or "T69N".

TABLE 4

CD43 protein variants tested for UMG1 antibody binding

| Variant | Sequence Regions used (reference to wild type CD43) | SEQ ID NO: |
| --- | --- | --- |
| CD43 #1 (wt) | aa 1-400 | 17 |
| CD43 #2 | aa 31-400 | 18 |
| CD43 #3 | aa 41-400 | 19 |
| CD43 #4 | aa 61-400 | 20 |
| CD43 #5 | aa 91-400 | 21 |
| CD43 #6 | aa 1-63 | 79-400 | 22 |
| CD43 #7 | aa 1-68 | 70-400 | 23 |
| CD43 #8 | aa 1-400 (T69N) | 24 |

Constructs:

CD43 protein constructs were expressed using pLenti-CMV-(insert)-Histag-GFP-2A-Puro expression vectors from Applied Biological Materials (ABM) Inc. service (Vancouver, Canada). His-Tag and/or GFP detections served as a positive control for successful transfection and/or protein expression.

Transfection:

Each vector was transiently expressed in HEK293T cells by using Lipofectamine LTX (Thermo Fisher Scientific, MA, USA) according to the manufacturer's protocol. HEK293T cells were maintained at 37° C. and 5% $CO_2$ in DMEM supplemented with 10% FBS and 1% penicillin/streptomycin (ThermoFisher Scientific, MA, USA). 72 h after transfection, cells were subjected to western blot or flow cytometry (FACS) analysis.

Western Blot:

Western analysis with UMG1 antibody was conducted to determine if the UMG1 antibody could bind and detect the CD43 wildtype and CD43 protein variants at the expected kDa size. His-Tagged antibody was used as a positive control.

Briefly, whole cell protein extracts were obtained using NP40 lysis buffer complemented with Halt™ Protease and Phosphatase Inhibitor Cocktail (ThermoFisher Scientific, MA, USA). Bradford assay (Bio-Rad Laboratories, Berkeley, Calif., USA) was used to estimate protein concentration. Cell lysates were loaded at a concentration of 60 µg per lane and separated using NuPAGE™ 3-8% Tris-Acetate Protein Gels (Invitrogen, Thermo Scientific, MA, USA). Proteins were transferred by electro-transferred for 30 minutes with the Trans-Blot R Turbo™ Transfer System (Bio-Rad Laboratories, Berkeley, Calif., USA) and immunoblotted with anti-Actin antibody purchased from Cell Signaling (data not shown), anti-His-Tag antibody (#G020) from abm (Vancouver, Canada) and h-UMG1 primary antibody (both at 1:500 dilution). Goat anti-mouse and rabbit anti-human HRP-conjugated antibodies (Invitrogen) were used as secondary antibodies (1:3,000 dilution). Immunoreactive bands were revealed by enhanced chemiluminescence detection method using SuperSignal™ West Pico PLUS Chemiluminescent Substrate (Thermo Scientific, MA, USA).

Flow Cytometry (FACS) Analysis:

FACS was conducted to determine if the antibody could detect the CD43 wildtype and CD43 variants, as expressed in HEK293T cell line cells.

FACS assay was conducted following standard procedures, by using 1 ug/ml of h-UMG1-PE conjugated antibody to detect the percentage of h-UMG1 positive cells among the GFP positive cells. Samples were acquired by flow cytometry (LSRFortessa™ X-20, BD) and analyzed by DIVA software (BD FACSDiva™ software). A minimum of 20,000 events were gated for each measurement.

Figure 15C:
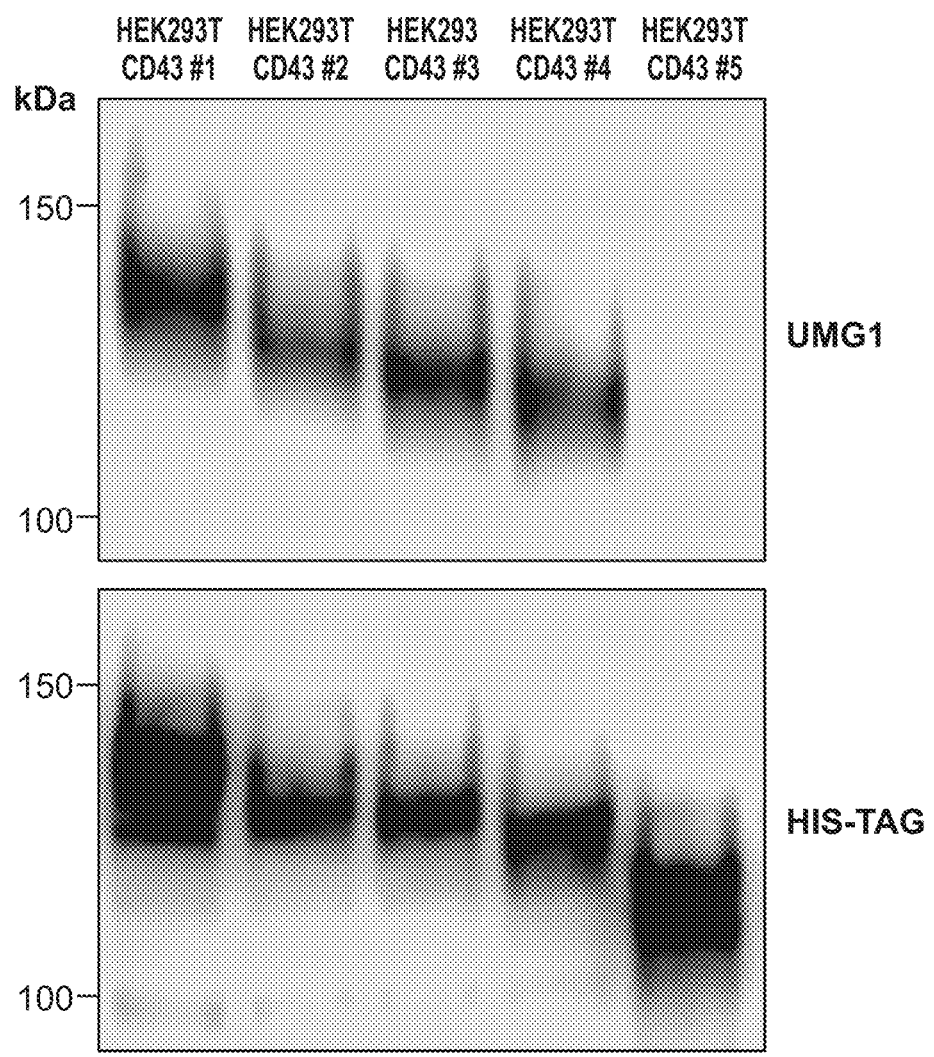
Figure 15D:
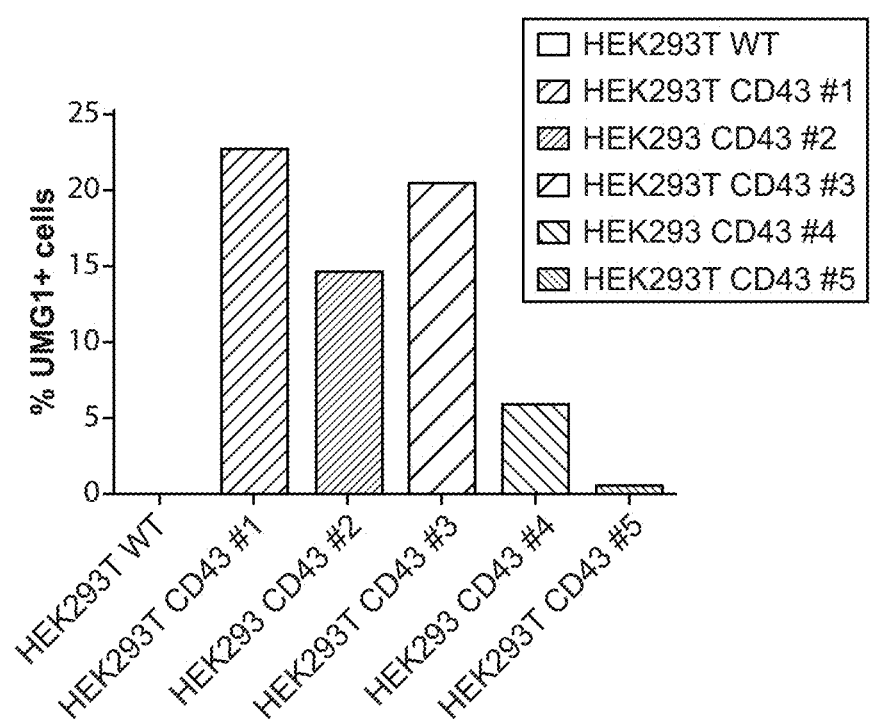
Figure 15E:
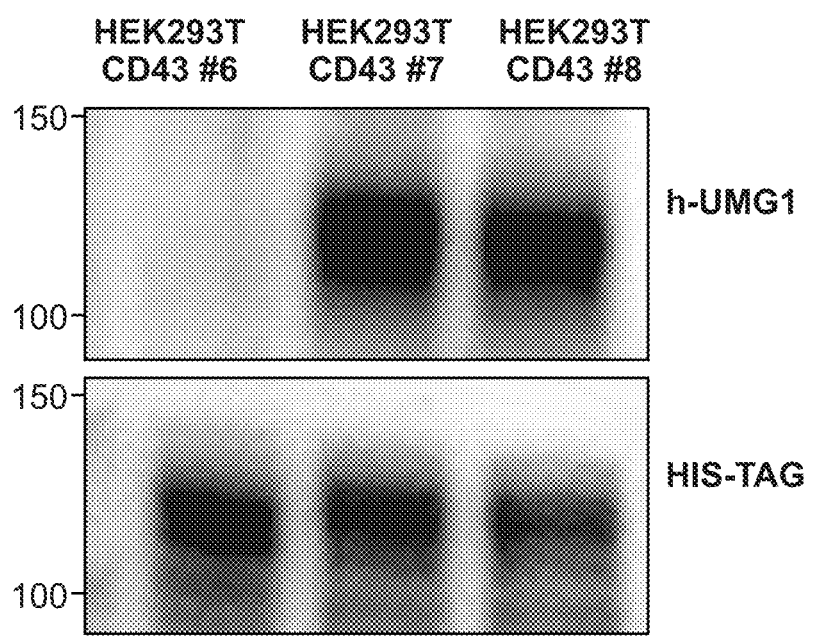

Results:

The results from the western analysis suggest that the UMG1 epitope binding site is located between aa 61 to 91 (as numbered in the wildtype CD43). See, boxed sequence in FIG. 15A, which shows the hypothesized binding site for the h-UMG1 antibody. Furthermore, these studies show that the UMG1 antibody binds specifically to UMG1 rather than to CD43 His-tagged proteins that lack of specific extracellular regions that UMG1 recognizes. See, FIGS. 15C and 15E.

Figure 15F:
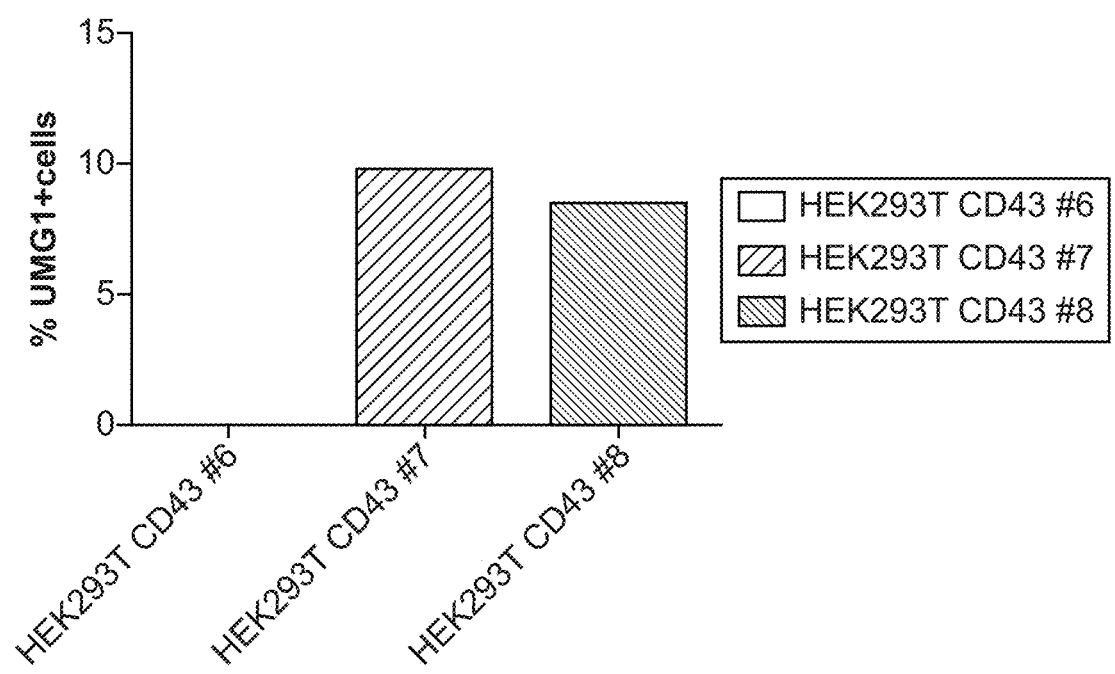

The FACS observations confirms the results observed in the western blots, that the UMG1 in epitope binding site is located between aa 61 to 91 on CD43 wild type because it cannot be detected in GFP-expressing cells of the CD43 #5 and CD43 #6 protein variants. See, FIGS. 15D and 15F. In addition, the western blot and FACS studies presented in FIGS. 15E and 15F suggest that the CD43 aa region from aa 61 to 91 is recognized by the h-UMG1 antibody in HEK293T cells with transgenic expression of CD43 also if the Treonine 69 is deleted (CD43 #7) or substituted with an amino acid that is not O-glycosylated (CD43 #8). These results in the binding of an epitope that should not have any sugar group. As expected, wild-type HEK293T cells that are not transformed with CD43, do not show any reactivity with the UMG1 antibody.

7.17.10. Example 10a: UMG1 Binding Specificity—Binding to the Aglycosylated Extracellular Portion of CD43 in Comparison to Other CD43 Antibodies This example shows the binding affinity measurement between a humanized-UMG1 (h-UMG1) (H3-L4) and of the extracellular portion of CD43 (aa 20-253). The result is reported as dissociation constant KD.

Methods:

Antibodies dissolved in water were manually printed onto the bare gold-coated (thickness 47 nm) PlexArray Nanocapture Sensor Chip (Plexera Bioscience, Seattle, Wash., US) at 40% humidity. Different concentration of the analytes (CD43) were tested for affinity. Each concentration was printed in replicate, and each spot contained 0.2 uL of sample solution. The chip was incubated in 80% humidity at 4° C. for overnight, and rinsed with 10×PBST for 10 min, 1×PBST for 10 min, and deionized water twice for 10 min. The chip was then blocked with 5% (w/v) non-fat milk in water overnight, and washed with 10×PBST for 10 min, 1x PBST for 10 min, and deionized water twice for 10 min before being dried under a stream of nitrogen prior to use. SPRi measurements were performed with PlexAray HT (Plexera Bioscience, Seattle, Wash., US). Collimated light (660 nm) passes through the coupling prism, reflects off the SPR-active gold surface, and is received by the CCD camera. Various concentrations of analyte (human recombinant CD43 extracellular portion (from aa 20-253) produced in *E. coli* vector of CD43; SEQ ID NO: 42) were used in the experiments (various concentrations of the analyte are shown by different colored lines in FIG. 19). Buffers and samples were injected by a non-pulsatile piston pump into the 30 µL flowcell that was mounted on the coupling prim. Each measurement cycle contained four steps: washing with PBST running buffer at a constant rate of 2 uL/s to obtain a stable baseline, sample injection at 5 uL/s for binding, surface washing with PBST at 2 uL/s for 300 s, and regeneration with 0.5% (v/v) H3PO4 at 2 uL/s for 300 s. All the measurements were performed at 25° C. The signal changes after binding and washing (in AU) are recorded as the assay value.

Selected protein-grafted regions in the SPR images were analyzed, and the average reflectivity variations of the chosen areas were plotted as a function of time. Real-time binding signals were recorded and analyzed by Data Analysis Module (DAM, Plexera Bioscience, Seattle, Wash., US). Kinetic analysis was performed using BIAevaluation 4.1 software (Biacore, Inc.).

Figure 19:
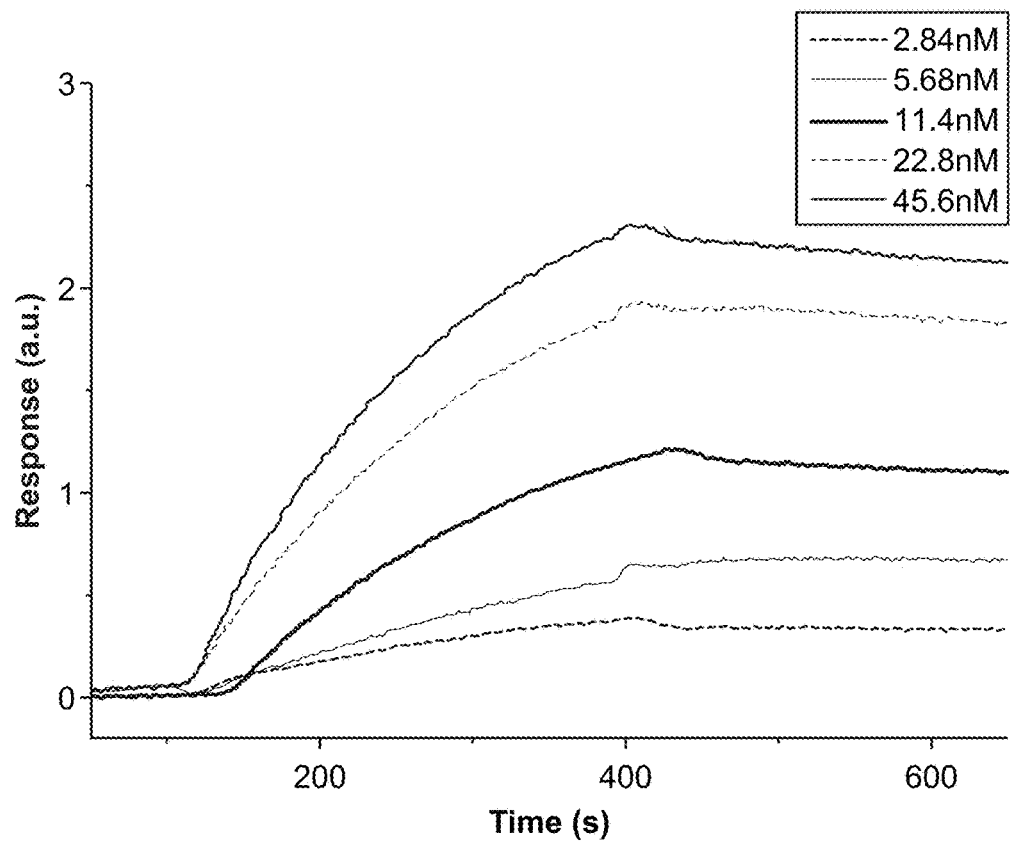

Results:

The SPR binding result showed a $K_D$ value of 99.4 nM between the extracellular portion of CD43 and h-UMG1 (FIG. 19). The result indicates strong binding affinity to the target.

Further, the binding to the aglycosylated extracellular portion of CD43 (produced in *E. coli*, without mammalian glycosylation) differentiate UMG1 from other anti-CD43 antibodies that bind only to glycosylated or neuraminidase-sensitive epitope, such as UN1 and MEM-59 respectively (de Laurentiis A, et al., Mol Cell Proteomics. 2011 May; 10(5)).

7.17.11. Example 10b: UMG1 Binding Specificity—Comparison of UMG1 Binding Characteristics to UN1 Historical Data As demonstrated in the Examples above, UMG1 and its chimeric and humanized derivatives, ch-UMG1 and h-UMG1, respectively, have several different binding properties as compared to other anti-CD43 antibodies, including historically reported data on UN1. Table 5 compares properties of UMG1 to historically reported data on UN1.

TABLE 5

Figure 5B:
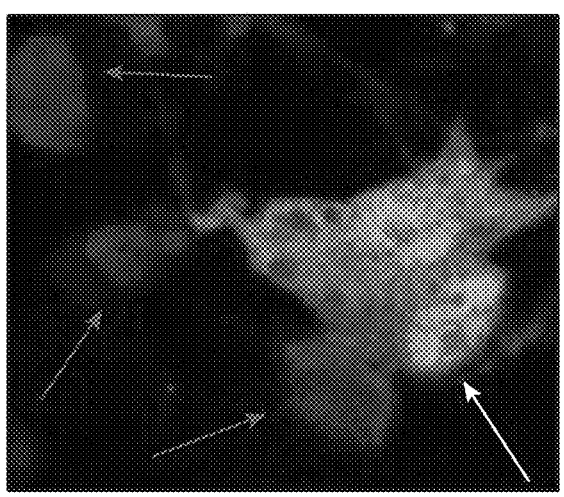
Figure 8:
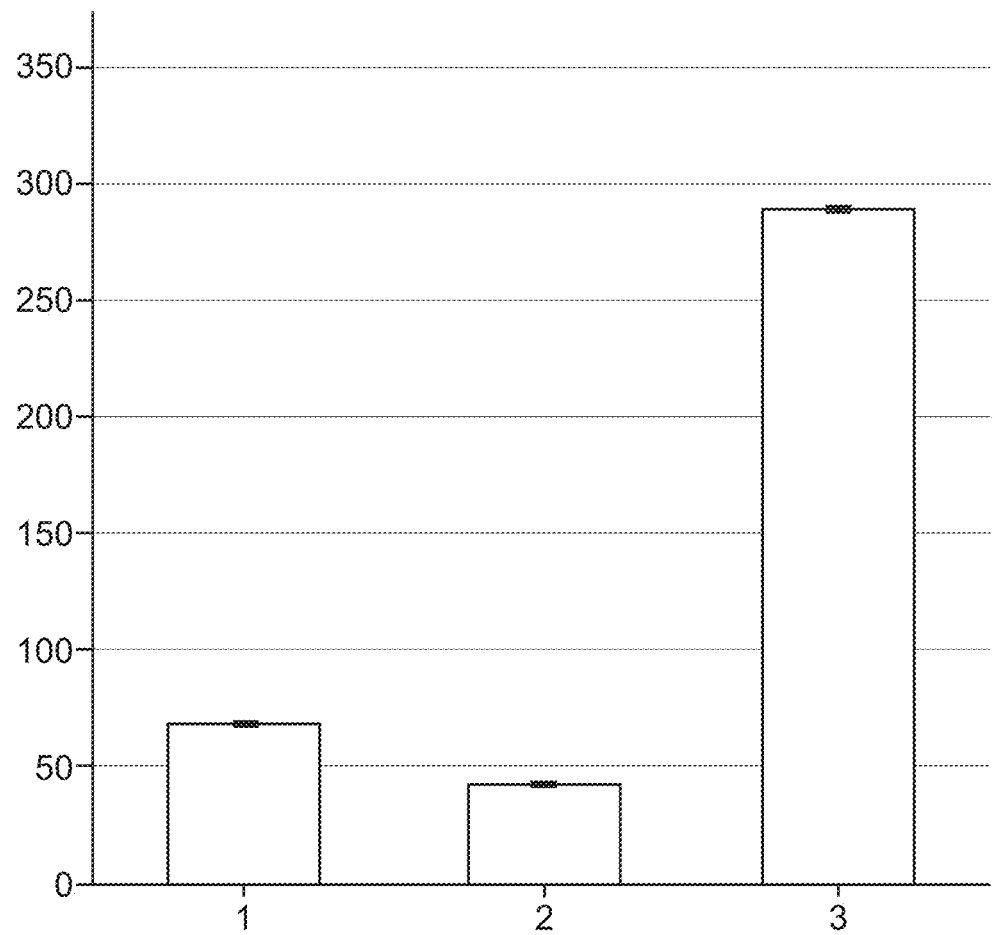

| Property | UN1 | UMG1 |
| --- | --- | --- |
| Hybridoma | No repository deposit, no frozen master cell bank, no frozen working cell bank | Deposited under ICLC accession number ICLC PD n° 16001 |
| Sequence of CDR | Never sequenced | Known SEQ ID Nos: 1-6 |
| Binding to glycosylated CD43 | Yes | Yes |
| Binding to unglycosylated CD43 | No (de Laurentiis et al., *Molecular & Cellular Proteomics* 10: 1-12, 2011; FIG. 8.) | Yes Data from Western Blot and FACS on residue T69 deleted or mutated form of CD43 (Example 9). Example 10a, FIG. 19, SPR data above |
| Binding to PBMCs | Positive for a subpopulation of lymphocytes; negative for monocytes and granulocytes (Tassone et al., *Tissue Antigens* 44: 73-82, 1994) | Positive for a subpopulation of lymphocytes; negative for myeloid-derived cells. See, Example 1, Example 2, Table 1, FIGS. 2A-2D |
| Binding to T lymphoma and T-ALL | Yes (Tassone et al., *Tissue Antigens* 44: 73-82, 1994) | Yes See, Example 3, Table 2 |
| Binding to Waldenström's Macro-globulinemia cells | Unknown | Yes See, Example 3, Table 2, FIGS. 3A-3B |
| Binding to cancer tissues | Yes (Cecco et al., Tissue Antigens 51: 528-535, 1998; Tassone et al., *Int. J. Oncology* 20: 707-711, 2002; Tuccillo et al., *Mol. Cancer Ther.* 13(3)). | No See, Example 4, Table 3, and FIG. 4 and Example 5, FIGS. 14A-14C |
| Binding to tumor associated macrophages (TAMs) | No de Laurentiis et al., *Molecular & Cellular Proteomics* 10: 1-12, 2011); FIG. 9. | Yes See, Example 4, Table 3, FIGS. 4 and 5A-5B; Example 5, FIGS. 14A-C |
| Binding to fetal tissues | Yes (Tassone et al., *Tissue Antigens* 44: 73-82; Tassone et al., *Int. J. Oncology* 20: 707-711, 2002). | Not described |
| Antibody dependent cellular cytotoxicity (ADCC) in HPB-ALL cell line | Yes (Tuccillo et al., *Mol. Cancer Ther.* 13(3), 2014). | Yes Example 12 |
| Flow Cytometric Profiles in cell lines of the hematopoietic lineage | Binds MOLT-4, CEM, and HPB-ALL but not Jurkat (Tassone et al., *Tissue Antigens* 44: 73-82, 1994) | Binds MOLT-4, CEM, and HPB-ALL but not Jurkat, but affinity different in CEM cells Example 8 |

7.17.12. Example 11: Construction of a Chimeric Antibody Having the Binding Specificity of UMG1

A chimeric antibody with the binding specificity of UMG1 (ch-UMG1) was constructed by fusing the murine UMG1 VH (SEQ ID NO: 34) to human VH constant region and the murine UMG1 VL (SEQ ID NO: 35) to a human light chain constant region using standard techniques.

7.17.13. Example 12: Ch-UMG1 Induces Antibody-Dependent Cell Mediate Cytotoxicity (ADCC) of T Cell Acute Lymphoblastic Leukemias/Lymphoblastic Lymphomas To determine the potential activity of mAb ch-UMG1 as an immunotherapeutic tool, its ability to induce antibody-dependent cell-mediated cytotoxicity (ADCC) was tested against two cell lines that had been shown in Example 3 to express the UMG1 epitope.

PBMCs from healthy donors (effector cells) were co-cultured with T-ALL cell line HPB-ALL or T lymphoma cell line H9 (target cells) in the presence of different concentration of the ch-UMG1 as follows.

Methods:
$4 \times 10^4$ target cells were seeded in 96 wells round-bottom plate and cultured for 30 minutes at 37° C. 5% $CO_2$ in the presence of different concentrations of mAb ch-UMG1 (0, 10, 50, 100, 200 µg/ml) or chimeric negative or positive control (NC and PC respectively, 200 µg/ml each) IgG1 at the highest dose (200 µg/ml). Subsequently, $0.4 \times 10^6$ PBMCs (fixed E:T=10: 1) from the same donor were added to each well together with 20 µl/ml of PE-conjugated anti-CD107a mAb (Becton Dickinson) and cells were then incubated at 37° C. 5% $CO_2$ for 3 h. After 1 h, 6 µg/ml monensin was added to each well (GolgiStop, BD). At the end of the incubation period, cells were stained with APC-conjugated anti-CD56 and PerCp-conjugated anti-CD3 and analyzed by FACS using ATTUNE NxT flow cytometer (THERMO Scientific).

Figure 6A:
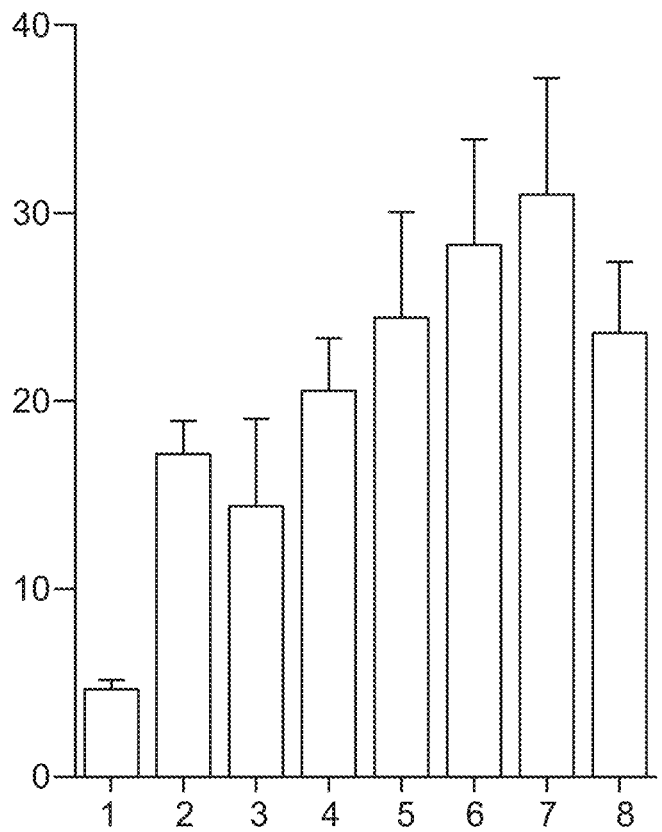
Figure 6B:
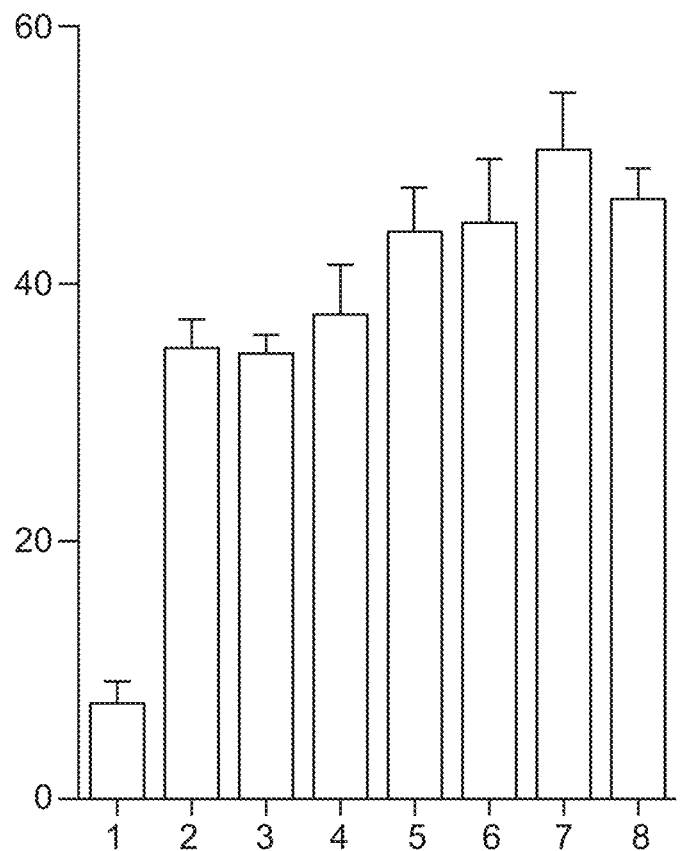

Results:
$CD3^-/CD56^+/CD107a^+$ cells were found to significantly increase according to the concentration of the ch-UMG1 antibody, confirming the potential of the ch-UMG1 antibody as an ADCC inducer (FIGS. 6A-6B).

Chimeric mAb ch-UMG1 is an active immunotherapeutic tool for T cell acute lymphoblastic leukemias/lymphoblastic lymphomas. These data allow to design immune targeting approaches, which are an urgent and unmet clinical need in T cell acute lymphoblastic leukemias/lymphoblastic lymphomas.

7.17.14. Example 13: Ch-UMG1 Induces Antibody-Dependent Cell Mediate Cytotoxicity (ADCC) of Waldenström's Macroglobulinemia Cells To further investigate the immunotherapeutic potential of ch-UMG1 antibody, its ability to induce antibody-dependent cell mediated cytotoxicity (ADCC) of Waldenström's macroglobulinemia cells was evaluated.

Methods:
We performed a degranulation assay by co-culturing purified NK cells from healthy donors (effector cells) and the BCWM.1 cell line (target cells) in the presence of different concentrations of ch-UMG1 antibody or negative/positive controls. We selected the mAb cetuximab as negative control and the mAb rituximab as positive control.

Specifically, $10^5$ target cells were seeded in 96 wells round-bottom plate and cultured for 30 minutes at 37° C. 5% $CO_2$ in the presence of different concentration of the ch-UMG1 antibody (0, 10, 50, 100, 200 µg/ml), 200 ug/ml cetuximab, or 200 µg/ml rituximab. Subsequently, $10^5$ NK cells (fixed E:T=1:1) from the same donor were added to each well together with 20 µl/ml of PE-conjugated anti-CD107a mAb (BD) and cells were then incubated at 37° C. 5% $CO_2$ for 2 h. After 1 h, 6 µg/ml monensin was added to each well (GolgiStop, BD). At the end of the incubation period cells were stained with APC-conjugated anti-CD56 and PerCp-conjugated anti-CD3 and analyzed on an ATTUNE NxT flow cytometer (THERMO Scientific).

Figure 7:
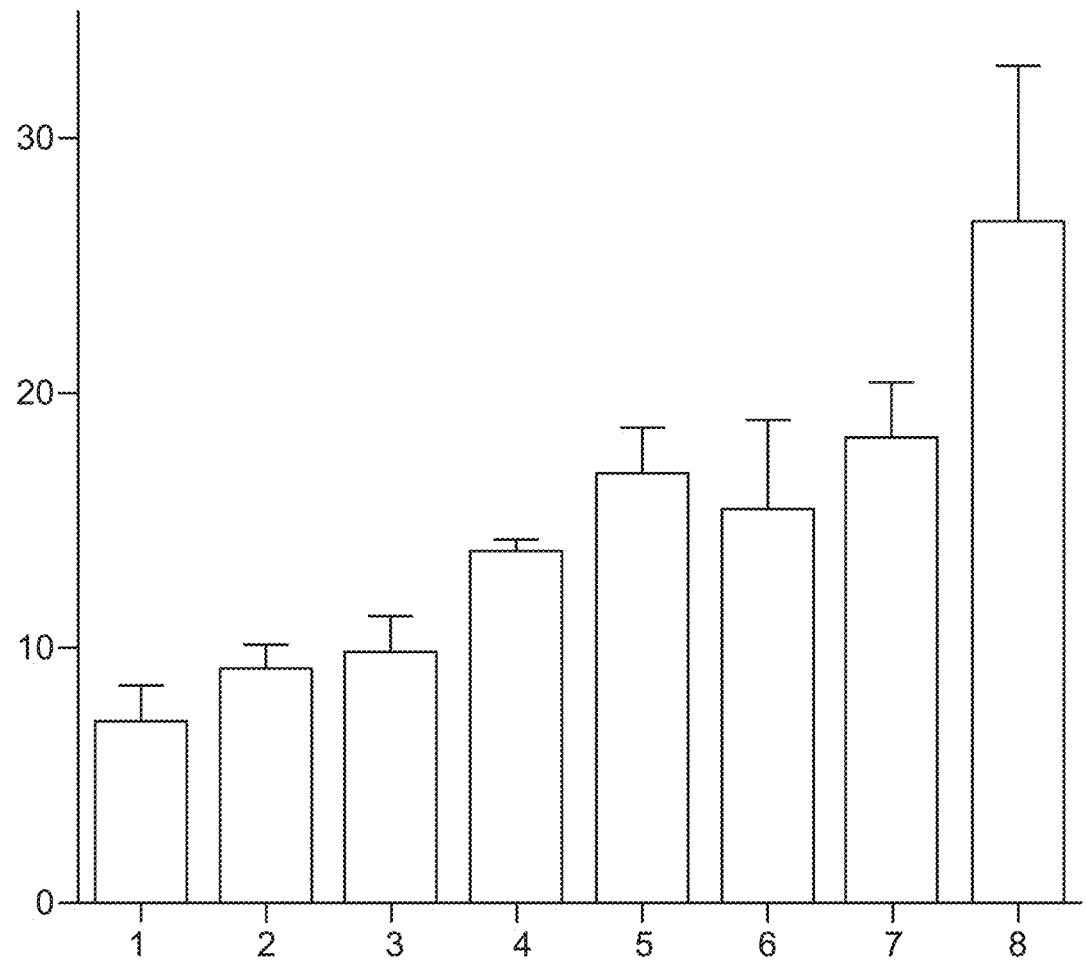

Results:
$CD3^-/CD56^+/CD107a^+$ cells were found to significantly increase according to ch-UMG1 antibody concentrations, reaching exactly the same effect obtained with rituximab. These results confirming the potential of the ch-UMG1 antibody as ADCC inducer (FIG. 7). Chimeric mAb ch-UMG1 is an active immunotherapeutic tool for Waldenström's Macroglobulinemia.

7.17.15. Example 14: Construction of Humanized UMG1 Monoclonal Antibodies

Humanized UMG1 antibodies were constructed using combination of human heavy chain SEQ ID NO: 8 to SEQ ID NO: 11 and human light chain SEQ ID NO:13 to SEQ ID NO: 16, provided herein.

Expression and Purification of the antibodies were conducted as follows: The corresponding cDNAs of the antibodies were cloned into vector system using conventional (non-PCR based) cloning techniques. The vector plasmids were gene synthesized. Plasmid DNA was prepared under low-endotoxin conditions based on anion exchange chromatography. DNA concentration was determined by measuring the absorption at a wavelength of 260 nm. Correctness of the sequences was verified with Sanger sequencing (with up to two sequencing reactions per plasmid depending on the size of the cDNA.)

Suspension-adapted CHO K1 cells (originally received from ATCC and adapted to serum-free growth in suspension culture) were used for production. For the afucosylated antibody (a-h-UMG1) the GlymaxX technology was used (ProBioGen) and it was transiently expressed in CHO cells (Evitria). The seed was grown in a chemically defined, animal-component free, serum-free medium. Cells were transfected with custom-made, proprietary transfection reagent, and cells were grown after transfection in an animal-component free, serum-free medium.

Supernatant was harvested by centrifugation and subsequent filtration (0.2 µm filter). The antibody was purified using MabSelect™ SuRe™. Purity was determined by analytical size exclusion chromatography with an Agilent AdvanceBio SEC column (300A 2.7 um 7.8×300 mm) and DPBS as running buffer at 0.8 ml/min.

Endotoxin content was measured with the Charles River Endosafe PTS system. Titers were measured with ForteBio Protein A biosensors (kinetic assay) and calculated based on a human IgG1 standard.

Putative h-UMG1 antibodies (constructed as described in Example 14) were tested for their affinity on HPB-ALL and H9 cell lines, which are known to be positive for the UMG1 epitope.

Methods:
Four humanized heavy chain (H 1-4) and four humanized light chain (L 1-4) variants were generated by identifying murine complementary determinant regions (CDRs) and grafting the CDRs into a human antibody framework by replacing selected residues in the closest human germ line sequence of the framework regions, with the aim to preserve potentially structurally important residues of the murine counterpart. 16 humanized antibodies were construction by combining each of the four humanized heavy chains (SEQ ID NOs: 8-11) with each of the four humanized light chains (SEQ ID NOs:13-16). The IgG1 isotype was used for all heavy chain variants.

Additionally, 8 hybrid CHL(1-4) and H(1-4)CL variants were generated. the 8 hybrids variants include 4 with the mouse heavy chain and a human light chain selected between L1-4 (SEQ NOs: 13-16) and 4 with the mouse light chain and a human heavy chain selected from H1-4 (SEQ NO: 8–11).

Recombinant genes were placed into the Evitria vector plasmid and transfected (with eviFect, Evitria) into CHO K1 cells. Cells were grown after transfection in animal-component free, serum-free medium (eviMake2, Evitria). Supernatant was harvested by centrifugation and subsequently sterile filtered (0.2 µm filter).

7.17.16. Example 15: Screening of h-UMG1 Antibodies for Binding to HPB-ALL and H9 Cell Lines Selection:

Each of the humanized antibodies was screened for its affinity to the target (estimated by mean fluorescence intensity, MFI) on 2 different cell lines (HPB-ALL and H9) and compared to binding of chimeric (ch-UMG1) and hybrid mAbs by flow cytometry (Attune NxT, Thermo Scientific). Each screening was performed twice, for a total of 4 replicates. All tests were performed under the same conditions: all mAbs were used at a final concentration of 1 µg/ml; Rituximab (Roche) has been used as IgG1 negative control; FITC Mouse Anti-Human IgG (BD Biosciences) was used as secondary mAb.

Figure 16:
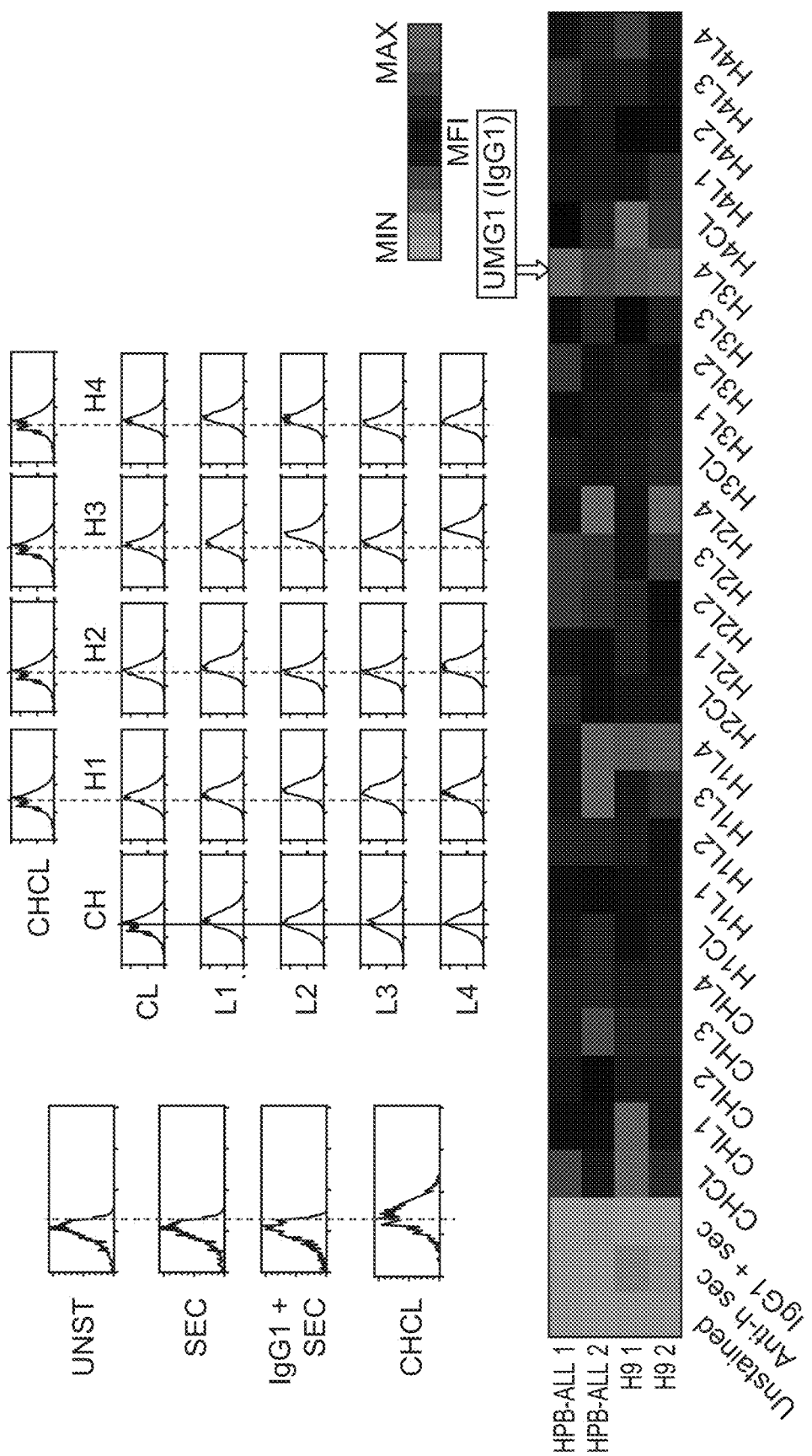

Results:

All the evaluated antibodies were able to bind the target with at least the same affinity of the chimeric mAb (ch-UMG1). See FIG. 16. One humanized antibody (H3-L4) achieved the highest MFI in the screening and was chosen for further development with the name of UMG1. See FIG. 16.

7.17.17. Example 16: Reduction of HPB-ALL Tumors in NSG Mouse Model by Humanized UMG1 (h-UMG1) and Afucosylated h-UMG1 (a-h-UMG1)

This example reports tumor volume curves of an in vivo experiment comparing a control IgG1 versus the humanized version of UMG1-mAb (h-UMG1) and an afucosylated version of UMG1-mAb (a-h-UMG1).

Figure 11:
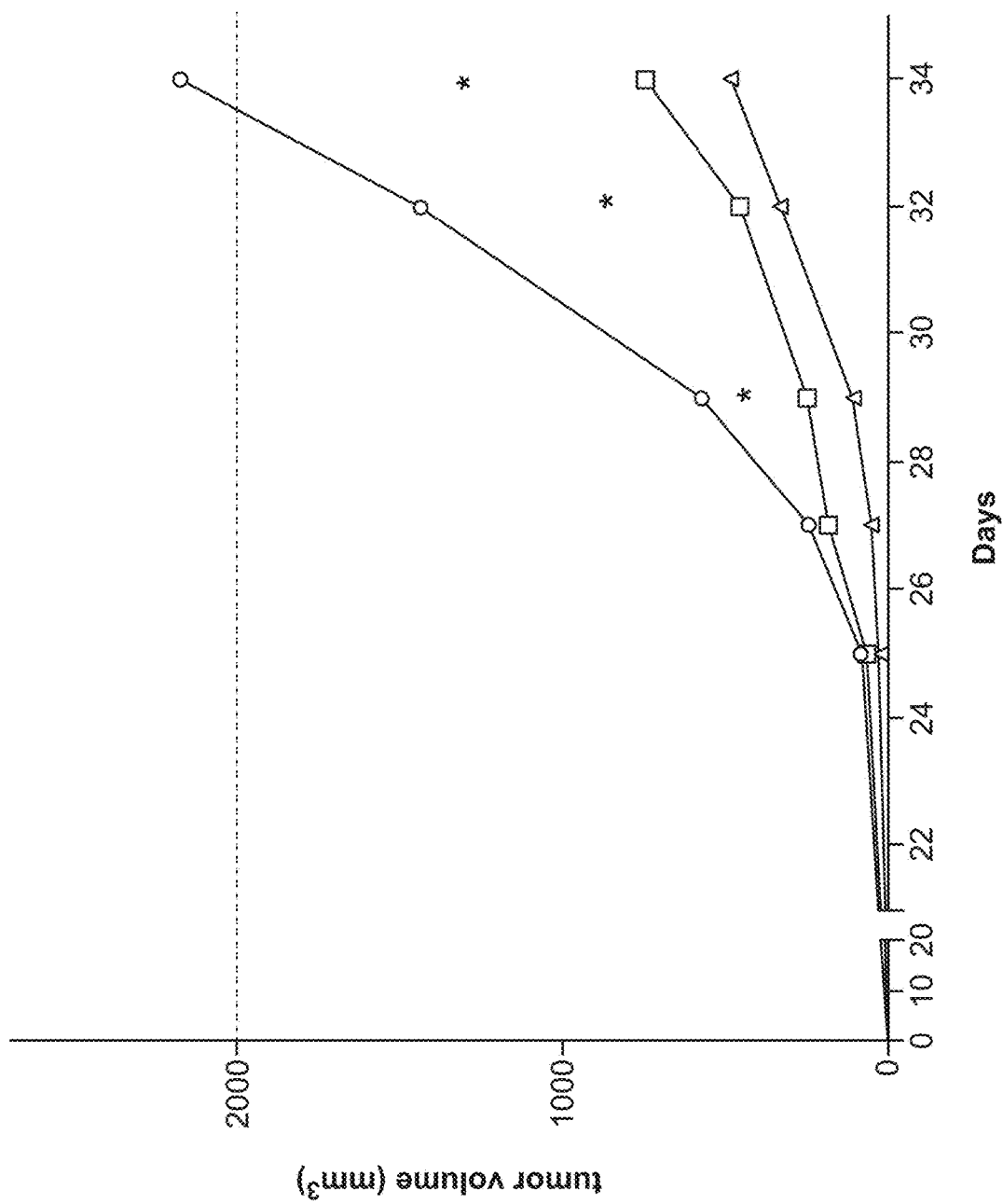

Methods:

In this experiment 15 NOD-SCID-g-chain-null (NSG) mice were engrafted subcutaneously with $5 \times 10^6$ HPB-ALL cells. Mice were then randomized to receive weekly intraperitoneal administration of 15 mg/kg of control IgG1, h-UMG1 or a-h-UMG1 starting from day 1 until either death, tumor volume >2000 mm^3, or unacceptable toxicity. Tumor volume was assessed every other day and the average volume of the tumor for each treatment group at each time point is reported and summarized in FIG. 11.

Results:

Starting from day 29, both the h-UMG1 (line with squares) and a-h-UMG1 (line with triangles) antibody treated cohorts presented a significantly reduced disease burden compared to the IgG1 control (line with circles) cohort. See, FIG. 11. These results suggest that both antibodies have strong anti-tumor activity.

7.17.18. Example 17: UMG1-Targeted Chimeric Antigen Receptor-T Cells (CAR-UMG1) Induce T-Cell Activation in the Presence of H9 Cells To further improve the potential of the UMG1 antibody as an immunotherapeutic tool, a third generation CAR was developed.

Figure 20:
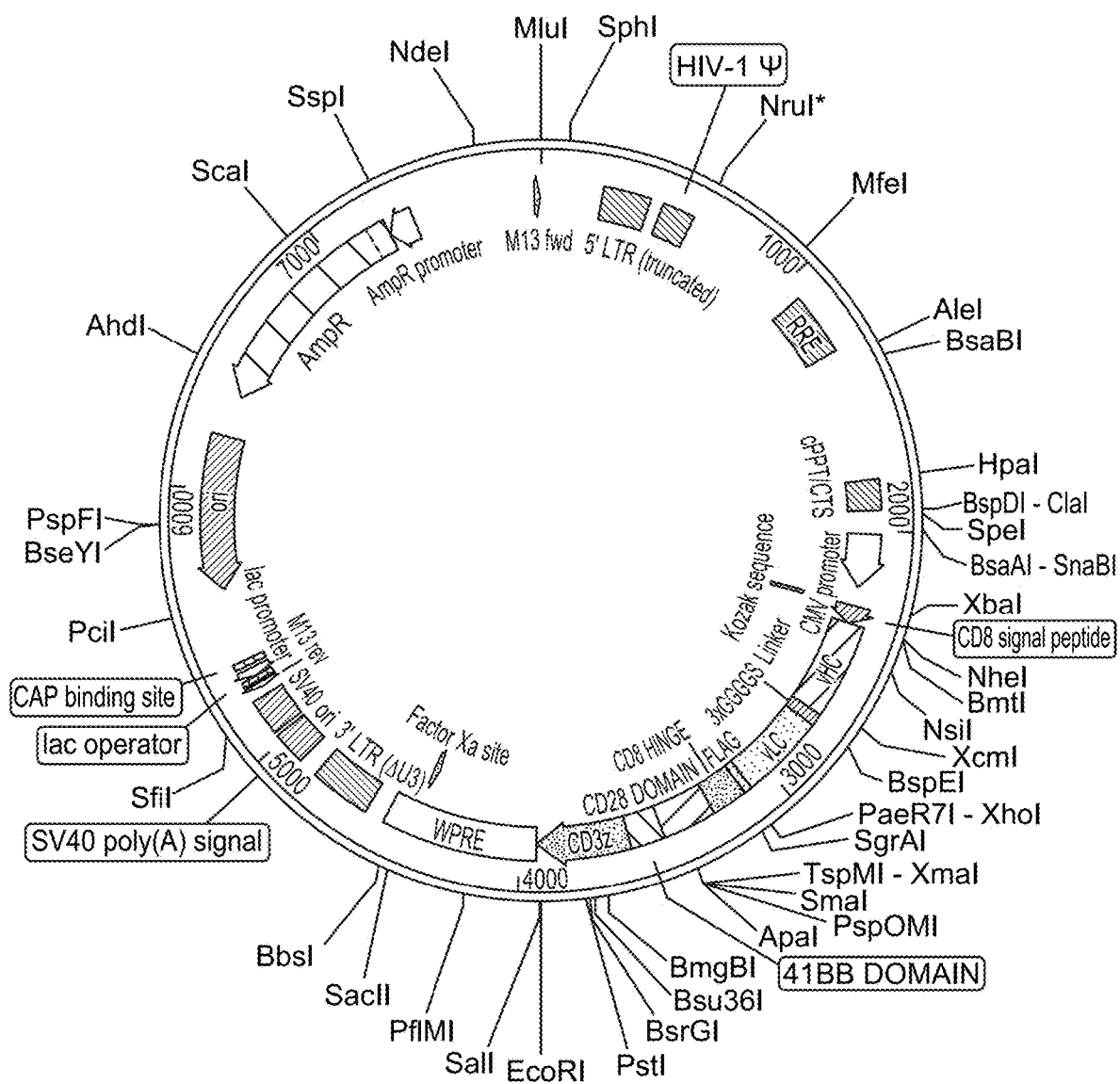
FIG. 20 depicts the plasmid map for the construct used to make various embodiments of the CAR-T provided herein.

Methods:

A third generation CAR was designed by coupling an extracellular domain consisting of a scFv derived from the sequence of the UMG1 antibody (SEQ ID NO: 7 for the heavy chain and SEQ ID NO: 12 for the light chain) with an intracellular region consisting of the CD3ζ chain (the signaling region of the TCR), and two co-stimulatory domains, CD28 and 4-1BB, thus mimicking physiological T-cell activation. A map of the CAR construct is provided in FIG. 20 (circularized map) and the complete sequence of the CAR construct is provided in SEQ ID NO: 41.

The construct was cloned as a CAR cassette in a lentivirus vector (Qin D Y et al., Anticancer Drugs. 2016 September; 27(8):711-22). Subsequently, viral particles were used to transduce $CD3^+$ lymphocytes from healthy donors at a multiplicity of infection (MOI) of 5 and transduction efficiency was evaluated by flow cytometry (about 38%). These CAR-T cells were assayed for their ability to release IFNγ and IL-2 in the presence of target cells and for their selective cytotoxicity capability.

Figure 10:
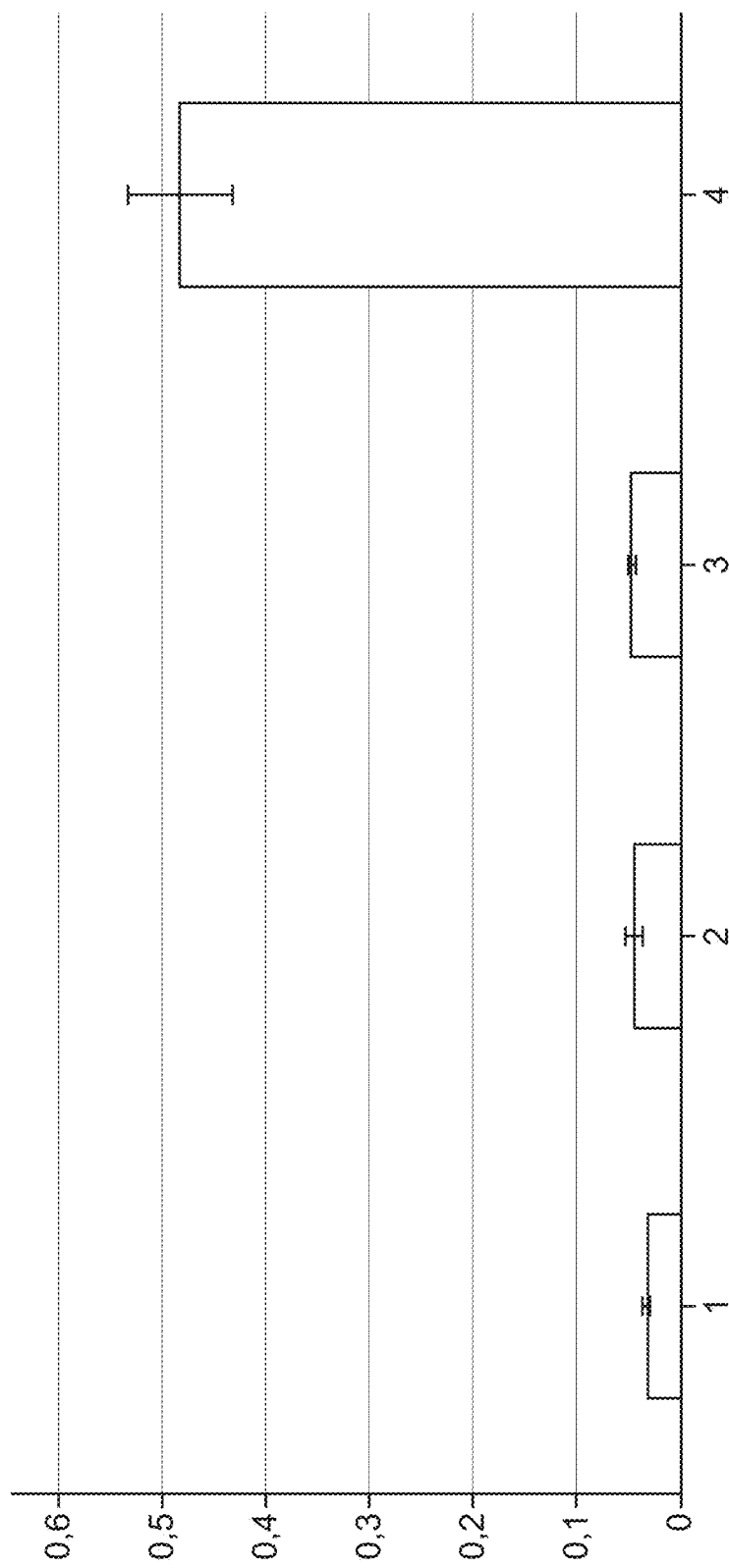

Results:

As shown in FIG. 8 and FIG. 9, CAR-UMG1 was able to release significantly higher amounts of Interferon gamma (IFNγ) and Interleukin 2 (IL-2) only in the presence of H9 T cell lymphoma cells. Additionally, only CAR-UMG1 was able to induce selective killing of H9 cells (see, FIG. 10). These results demonstrate the ability of CAR-UMG1 to recognize H9 cells and induce T-cell activation.

Chimeric antigen receptor CAR-UMG1 induces significant cytotoxicity against cells expressing the UMG1 epitope.

7.17.19. Example 18: UMG1-CD3 Bispecific

To test the specificity of a UMG1-CD3 bispecific antibody, and its ability to redirect T-cell cytotoxicity to UMG1 positive cells, assays were conducted on KE37 cell line which expresses the UMG1 CD43 epitope but is negative for CD3 ($UMG1^+$, $CD3^-$), and ALL-SIL cell line which is negative for both the UMG1 antigen and CD3 ($UMG1^-$, $CD3^-$).

Methods:

A UMG1-CD3 construct comprising SEQ ID NO: 40 was used to generate a UMG1-CD3 bispecific antibody. Redirected T-cell cytotoxicity was assayed by flow cytometry using human PBMCs (peripheral blood mononuclear cells) and the KE37 cell line ($UMG1^+$, $CD3^-$) and ALL-SIL cell line ($UMG1^-$, $CD3^-$).

Increasing concentrations of UMG1-CD3 bispecific antibody were incubated with CFSE (Invitrogen)-labeled target cells as well as effector cells at a PBMC E:T cell ratios of 10:1 or 20:1. Cell lysis was assessed after 72 hours treatment by flow cytometry as loss of target-cell membrane integrity, which is reflected by nuclear uptake of 7AAD.

Representative FACS images from experiments using 1 µg/ml UMG1-CD3 bispecific antibody and E:T cell ratios of 20:1 are showed in FIGS. 18A-18B.

Results:

Increased killing was observed in both cell lines, KE37 (see FIG. 18A) and ALL-SIL (see FIG. 18B) treated with UMG1-CD3 bispecific antibody compared to untreated cells (indicated as NT).

Further, the KE37 cell line expressing the UMG1 antigen showed higher cell death, ~86% of the cell population assayed, while ALL-SIL cell line which does not express the UMG1 antigen, has a lower cell death %, of ~22% of the cell population assayed. These results demonstrate that T cell killing can be directed to UMG1$^+$ cells with a UMG1-CD3 bispecific antibody. See, FIGS. 18A-18B.

7.18. Sequences

```
UMG1 heavy chain CDR1 [SEQ ID NO: 1]:
Gly Phe Thr Phe Ser Ser Phe Gly Met His UMG1 heavy chain CDR2 [SEQ ID NO: 2]:
Tyr Ile Ser Ser Gly Ser Gly Asn Phe Tyr Tyr Val Asp Thr Val Lys UMG1 heavy chain CDR3 [SEQ ID NO: 3]:
Ser Thr Tyr Tyr His Gly Ser Arg Gly Ala Met Asp Tyr UMG1 light chain CDR1 [SEQ ID NO: 4]:
Ser Ala Ser Ser Ser Val Ser Ser Met Tyr Trp Tyr UMG1 light chain CDR2 [SEQ ID NO: 5]:
Asp Thr Ser Lys Met Ala Ser UMG1 light chain CDR3 [SEQ ID NO: 6]:
Gln Gln Trp Ser Ser Tyr Pro Pro Ile Thr UMG1 VH (murine)(clone IGHV5-17*02) [SEQ ID NO: 7]:
DVQLVESGGGLVQPGGSRKLSCVAS_GFTFSSFGMH_WVRQAPEKGL

EWVA_YISSGSGNFYYVDTVK_GRFTISRDNPKNTLFLQMTSLRSEDTA

MYYCAR_STYYHGSRGAMDY_WGQGTSVTVSS

CDRs are underlined and italicized
Germ line mutations are in bold
V is A in germ line Humanized VH1 (clone IGHV3-48*01) [SEQ ID NO: 8]:
EVQLVESGGGLVQPGGSLRLSCAAS_GFTFSSFGMH_WVRQAPGK

GLEWVS_YISSGSGNFYYVDTVK_GRFTIS

RDNAKNSLYLQMNSLRAEDTAVYYCAR_STYYHGSRGAMDY_WGQ

GTLVTVSS

CDRs are underlined and italicized
Mutations vs. original mouse sequence are in bold Humanized VH2 (clone IGHV3-48*01 with germ line reversion) [SEQ ID NO: 9]:
EVQLVESGGGLVQPGGSLRLSCVAS_GFTFSSFGMH_WVRQAPGKG

LEWVS_YISSGSGNFYYVDTVK_GRFTISRDNAKNSLYLQMNSLRAEDT

AVYYCAR_STYYHGSRGAMDY_WGQGTLVTVSS

CDRs are underlined and italicized
Mutations vs. original mouse sequence are in bold Humanized VH3 (clone IGHV1-48*01 with germ line reversion and conserved
residues flanking CDRs) [SEQ ID NO: 10]:
EVQLVESGGGLVQPGGSLRLSCVAS_GFTFSSFGMH_WVRQAPGKG

LEWVA_YISSGSGNFYYVDTVK_GRFTISRDNAKNSLYLQMNSLRAEDT

AVYYCAR_STYYHGSRGAMDY_WGQGTLVTVSS

CDRs are underlined and italicized
Mutations vs. original mouse sequence are in bold
```

-continued

Humanized VH4 (clone IGHV3-30*02 with germ line reversion) [SEQ ID NO: 11]:
QVQLVESGGGVVQPGGSLRLSCVAS*GFTFSSFGMH*WVRQAPGKG

LEWVA*YISSGSGNFYYVDTVK*GRFTIS

RDNSKNTLYLQMNSLRAEDTAVYYCAR*STYYHGSRGAMDY*WGQG

TLVTVSS

CDRs are underlined and italicized
Mutations vs. original mouse sequence are in bold UMG1 VL(murine, kappa)(clone IG IGKV4-55*01) [SEQ ID NO: 12]:
QIALTQSPAIMSASPGEKVTMTC*SASSSVSSMYWY*QLKPGSSPRLLIY

*DTSKMAS*GVPIRFSGSGSGTSFSLTVSRVEAEDAATYYC*QQWSSYPP*

*IT*FGAGSKLELK

CDRs are underlined and italicized
Germ line mutations in bold
A as V in germ line
L as Q in germ line
I as V in germ line
F as Y in germ line
V as I in germ line
V as M in germ line Humanized VL1 (clone IGKV3D-20*01) [SEQ ID NO: 13]:
EIVLTQSPATLSLSPGERATLSC*SASSSVSSMY*WYQQKPGLAPRLLIY

*DTSKMAS*GIPDRFSGSGSGTDFT

LTISRLEPEDFAVYYC*QQWSSYPPIT*FGQGTRLEIK

CDRs are underlined an italicized
Mutations vs. original mouse sequence are in bold Humanized VL2 (IGKV3D-20*01 with germ line reversion) [SEQ ID NO: 14]:
EIALTQSPATLSLSPGERATLSC*SASSSVSSMY*WYQLKPGLAPRLLIY

*DTSKMAS*GIPIRFSGSGSGTDFT

LTVSRVEPEDFAVYYC*QQWSSYPPIT*FGQGTRLEIK

CDRs are underlined an italicized
Mutations vs. original mouse sequence are in bold Humanized VL3 (clone IGKV6D-41*01) [SEQ ID NO: 15]:
QVVMTQSPAFLSVTPGEKVTITC*SASSSVSSMY*WYQQKPDQAPKLL

IY*DTSKMAS*GVPSRFSGSGSGTDFT

FTISSLEAEDAATYYC*QQWSSYPPIT*FGGGTKVEIK

CDRs are underlined and italicized
Mutations vs. original mouse sequence are in bold Humanized VL4 (clone IGKV6D-41*01 partial germ line reversion) [SEQ ID NO: 16]:
QVVMTQSPAFLSVTPGEKVTITC*SASSSVSSMY*WYQLKPDQAPKLL

IY*DTSKAMAS*GVPIRFSGSGSGTDFT

FTVSSVEAEDAATYYC*QQWSSYPPIT*FGGGTKVEIK

CDRs are underlined and italicized
Mutations vs. original mouse sequence are in bold CD43 Clone #1 (wild-type CD43 with 400 aa) [SEQ ID NO: 17]:
MATLLLLLGVLVVSPDALGSTTAVQTPTSGEPLVSTSEPLSSKMYTTSI

TSDPKADSTGDQTSALPPSTSINEGSPLWTSIGASTGSPLPEPTTYQEVSI

KMSSVPQETPHATSHPAVPITANSLGSHTVTGGTITTNSPETSSRTSGAP

VTTAASSLETSRGTSGPPLTMATVSLETSKGTSGPPVTMATDSLETSTG

TTGPPVTMTTGSLEPSSGASGPQVSSVKLSTMMSPTTSTNASTVPFRNP

-continued
DENSRGMLPVAVLVALLAVIVLVALLLLWRRRQKRRTGALVLSRGGK

RNGVVDAWAGPAQVPEEGAVTVTVGGSGGDKGSGFPDGEGSSRRPT

LTTFFGRRKSRQGSLAMEELKSGSGPSLKGEEEPLVASEDGAVDAPAP

DEPEGGDGAAP

CD43 Clone #2 (truncated CD43)(aa 31 to 400) [SEQ ID NO: 18]:
EPLVSTSEPLSSKMYTTSITSDPKADSTGDQTSALPPSTSINEGSPLWTSI

GASTGSPLPEPTTYQEVSIKMSSVPQETPHATSHPAVPITANSLGSHTVT

GGTITTNSPETSSRTSGAPVTTAASSLETSRGTSGPPLTMATVSLETSKG

TSGPPVTMATDSLETSTGTTGPPVTMTTGSLEPSSGASGPQVSSVKLST

MMSPTTSTNASTVPFRNPDENSRGMLPVAVLVALLAVIVLVALLLLW

RRRQKRRTGALVLSRGGKRNGVVDAWAGPAQVPEEGAVTVTVGGSG

GDKGSGFPDGEGSSRRPTLTTFFGRRKSRQGSLAMEELKSGSGPSLKG

EEEPLVASEDGAVDAPAPDEPEGGDGAAP

CD43 Clone #3 truncated CD43 (aa 41 to 400) [SEQ ID NO: 19]:
QTSALPPSTSINEGSPLWTSIGASTGSPLPEPTTYQEVSIKMSSVPQETPH

ATSHPAVPITANSLGSHTVTGGTITTNSPETSSRTSGAPVTTAASSLETS

RGTSGPPLTMATVSLETSKGTSGPPVTMATDSLETSTGTTGPPVTMTT

GSLEPSSGASGPQVSSVKLSTMMSPTTSTNASTVPFRNPDENSRGMLP

VAVLVALLAVIVLVALLLLWRRRQKRRTGALVLSRGGKRNGVVDAW

AGPAQVPEEGAVTVTVGGSGGDKGSGFPDGEGSSRRPTLTTFFGRRKS

RQGSLAMEELKSGSGPSLKGEEEPLVASEDGAVDAPAPDEPEGGDGA

AP

CD43 Clone #4 truncated CD43 (aa 61 to 400) [SEQ ID NO: 20]:
QTSALPPSTSINEGSPLWTSIGASTGSPLPEPTTYQEVSIKMSSVPQETPH

ATSHPAVPITANSLGSHTVTGGTITTNSPETSSRTSGAPVTTAASSLETS

RGTSGPPLTMATVSLETSKGTSGPPVTMATDSLETSTGTTGPPVTMTT

GSLEPSSGASGPQVSSVKLSTMMSPTTSTNASTVPFRNPDENSRGMLP

VAVLVALLAVIVLVALLLLWRRRQKRRTGALVLSRGGKRNGVVDAW

AGPAQVPEEGAVTVTVGGSGGDKGSGFPDGEGSSRRPTLTTFFGRRKS

RQGSLAMEELKSGSGPSLKGEEEPLVASEDGAVDAPAPDEPEGGDGA

AP

CD43 Clone #5 truncated CD43 (aa 91 to 400) [SEQ ID NO: 21]:
EPTTYQEVSIKMSSVPQETPHATSHPAVPITANSLGSHTVTGGTITTNSP

ETSSRTSGAPVTTAASSLETSRGTSGPPLTMATVSLETSKGTSGPPVTM

ATDSLETSTGTTGPPVTMTTGSLEPSSGASGPQVSSVKLSTMMSPTTST

NASTVPFRNPDENSRGMLPVAVLVALLAVIVLVALLLLWRRRQKRRT

GALVLSRGGKRNGVVDAWAGPAQVPEEGAVTVTVGGSGGDKGSGFP

DGEGSSRRPTLTTFFGRRKSRQGSLAMEELKSGSGPSLKGEEEPLVASE

DGAVDAPAPDEPEGGDGAAP

CD43 Clone #6 deletion from aa 64 to78 [SEQ ID NO: 22]:
MATLLLLLGVLVVSPDALGSTTAVQTPTSGEPLVSTSEPLSSKMYTTSI

TSDPKADSTGDQTSTSIGASTGSPLPEPTTYQEVSIKMSSVPQETPHATS

HPAVPITANSLGSHTVTGGTITTNSPETSSRTSGAPVTTAASSLETSRGT

-continued

SGPPLTMATVSLETSKGTSGPPVTMATDSLETSTGTTGPPVTMTTGSLE

PSSGASGPQVSSVKLSTMMSPTTSTNASTVPFRNPDENSRGMLPVAVL

VALLAVIVLVALLLLWRRRQKRRTGALVLSRGGKRNGVVDAWAGPA

QVPEEGAVTVTVGGSGGDKGSGFPDGEGSSRRPTLTTFFGRRKSRQGS

LAMEELKSGSGPSLKGEEEPLVASEDGAVDAPAPDEPEGGDGAAP

CD43 Clone #7 deletion of aa 69 (O-glycosylation site for GalNac) [SEQ ID NO: 23]:
MATLLLLLGVLVVSPDALGSTTAVQTPTSGEPLVSTSEPLSSKMYT

TSITSDPKADSTGDQTSALPPSSINEGSPLWTSIGASTGSPLPEPTTY

QEVSIKMSSVPQETPHATSHPAVPITANSLGSHTVTGGTITTNSPETS

SRTSGAPVTTAASSLETSRGTSGPPLTMATVSLETSKGTSGPPVTM

ATDSLETSTGTTGPPVTMTTGSLEPSSGASGPQVSSVKLSTMMSPT

TSTNASTVPFRNPDENSRGMLPVAVLVALLAVIVLVALLLLWRRR

QKRRTGALVLSRGGKRNGVVDAWAGPAQVPEEGAVTVTVGGSG

GDKGSGFPDGEGSSRRPTLTTFFGRRKSRQGSLAMEELKSGSGPSL

KGEEEPLVASEDGAVDAPAPDEPEGGDGAAP

CD43 Clone #8 amino acidic substitution T69N [SEQ ID NO: 24]:
MATLLLLLGVLVVSPDALGSTTAVQTPTSGEPLVSTSEPLSSKMYTTSITS

DPKADSTGDQTSALPPSNSINEGSPLWTSIGASTGSPLPEPTTYQEVSIKMS

SVPQETPHATSHPAVPITANSLGSHTVTGGTITTNSPETSSRTSGAPVTTAA

SSLETSRGTSGPPLTMATVSLETSKGTSGPPVTMATDSLETSTGTTGPPVT

MTTGSLEPSSGASGPQVSSVKLSTMMSPTTSTNASTVPFRNPDENSRGML

PVAVLVALLAVIVLVALLLLWRRRQKRRTGALVLSRGGKRNGVVDAW

AGPAQVPEEGAVTVTVGGSGGDKGSGFPDGEGSSRRPTLTTFFGRRKSR

QGSLAMEELKSGSGPSLKGEEEPLVASEDGAVDAPAPDEPEGGDGAAP

Human nucleotide CD43 full-length [SEQ ID NO: 25]:
ATGGCCACG CTTCTCCTTCT CCTTGGGGTG CTGGTGGTAA

GCCCAGACGC TCTGGGGAGC ACAACAGCAG TGCAGACACC

CACCTCCGGA GAGCCTTTGG TCTCTACTAG CGAGCCCCTG

AGCTCAAAGA TGTACACCAC TTCAATAACA AGTGACCCTA

AGGCCGACAG CACTGGGGAC CAGACCTCAG CCCTACCTCC

CTCAACTTC CATCAATGAGG GATCCCCTCT TTGGACTTCC

ATTGGTGCCA GCACTGGTTC CCCTTTACCT GAGCCAACAA

CCTACCAGGA AGTTTCCATC AAGATGTCAT CAGTGCCCCA

GGAAACCCCT CATGCAACCA GTCATCCTGC TGTTCCCATA

ACAGCAAACT CTCTAGGATC CCACACCGTG ACAGGTGGAA

CCATAACAAC GAACTCTCCA GAAACCTCCA GTAGGACCAG

TGGAGCCCCT GTTACCACGG CAGCTAGCTC TCTGGAGACC

TCCAGAGGCA CCTCTGGACC CCCTCTTACC ATGGCAACTG

TCTCTCTGGA GACTTCCAAA GGCACCTCTG GACCCCCTGT

TACCATGGCA ACTGACTCTC TGGAGACCTC CACTGGGACC

ACTGGACCCC CTGTTACCAT GACAACTGGC TCTCTGGAGC

CCTCCAGCGG GGCCAGTGGA CCCCAGGTCT CTAGCGTAAA

-continued

```
ACTATCTACA ATGATGTCTC CAACGACCTC CACCAACGCA

AGCACTGTGC CCTTCCGGAA CCCAGATGAG AACTCACGAG

GCATGCTGCC AGTGGCTGTG CTTGTGGCCC TGCTGGCGGT

CATAGTCCTC GTGGCTCTGC TCCTGCTGTG GCGCCGGCGG

CAGAAGCGGC GGACTGGGGC CCTCGTGCTG AGCAGAGGCG

GCAAGCGTAA CGGGGTGGTG GACGCCTGGG CTGGGCCAGC

CCAGGTCCCT GAGGAGGGGG CCGTGACAGT GACCGTGGGA

GGGTCCGGGG GCGACAAGGG CTCTGGGTTC CCCGATGGGG

AGGGGTCTAG CCGTCGGCCC ACGCTCACCA CTTTCTTTGG

CAGACGGAAG TCTCGCCAGG GCTCCCTGGC GATGGAGGAG

CTGAAGTCTG GGTCAGGCCC CAGCCTCAAA GGGGAGGAGG

AGCCACTGGT GGCCAGTGAG GATGGGGCTG TGGACGCCCC

AGCTCCTGAT GAGCCCGAAG GGGGAGACGG GGCTGCCCCT

TAA

Human protein CD43 full-length [SEQ ID NO: 26]:
MATLLLLLGVLVVSPDALGSTTAVQTPTSGEPLVSTSEPLSSKMYTTSIT

SDPKADSTGDQTSALPPSTSINEGSPLWTSIGASTGSPLPEPTTYQEVSIK

MSSVPQETPHATSHPAVPITANSLGSHTVTGGTITTNSPETSSRTSGAPV

TTAASSLETSRGTSGPPLTMATVSLETSKGTSGPPVTMATDSLETSTGTT

GPPVTMTTGSLEPSSGASGPQVSSVKLSTMMSPTTSTNASTVPFRNPDE

NSRGMLPVAVLVALLAVIVLVALLLLWRRRQKRRTGALVLSRGGKRN

GVVDAWAGPAQVPEEGAVTVTVGGSGGDKGSGFPDGEGSSRRPTLTT

FFGRRKSRQGSLAMEELKSGSGPSLKGEEEPLVASEDGAVDAPAPDEPE

GGDGAAP

UMG1 Chimeric Heavy Chain, nucleic acid (clone NUC 7200_evi-5 UMG.1.CH-
hl.HC) [SEQ ID NO: 27]:
GCGGCCGCCATGAATTTTGGACTGAGGCTGATTTTCCTGGTGCTGA

CCCTGAAAGGCGTCCAGTGTGACGTGCAGCTGGTCGAGAGTGGCG

GAGGGCTGGTGCAGCCCGGTGGCAGCCGAAAGCTGTCTTGCGTCGC

TAGTGGTTTCACCTTTTCCAGCTTCGGCATGCACTGGGTGAGGCAG

GCACCTGAGAAAGGACTGGAATGGGTCGCCTACATCTCTAGTGGA

AGCGGGAACTTCTACTATGTGGACACTGTCAAGGGGAGGTTTACCA

TTTCTCGGGATAACCCAAAAAATACACTGTTTCTGCAAATGACTTC

ACTGAGATCCGAAGACACCGCCATGTACTATTGTGCTAGATCAACA

TACTACCACGGCTCCAGGGGCGCTATGGACTATTGGGGTCAGGGCA

CCTCTGTGACAGTCTCGAGCGCTAGCACAAAGGGCCCTAGTGTGTT

TCCTCTGGCTCCCTCTTCCAAATCCACTTCTGGTGGCACTGCTGCTC

TGGGATGCCTGGTGAAGGATTACTTTCCTGAACCTGTGACTGTCTC

ATGGAACTCTGGTGCTCTGACTTCTGGTGTCCACACTTTCCCTGCTG

TGCTGCAGTCTAGTGGACTGTACTCTCTGTCATCTGTGGTCACTGTG

CCCTCTTCATCTCTGGGAACCCAGACCTACATTTGTAATGTGAACC

ACAAACCATCCAACACTAAAGTGGACAAAAAAGTGGAACCCAAAT
```

```
CCTGTGACAAAACCCACACCTGCCCACCTTGTCCTGCCCCTGAACT
GCTGGGAGGACCTTCTGTGTTTCTGTTCCCCCCCAAACCAAAGGAT
ACCCTGATGATCTCTAGAACCCCTGAGGTGACATGTGTGGTGGTGG
ATGTGTCTCATGAGGACCCTGAGGTCAAATTCAACTGGTACGTGGA
TGGAGTGGAAGTCCACAATGCCAAAACCAAGCCTAGAGAGGAACA
GTACAATTCAACCTACAGAGTGGTCAGTGTGCTGACTGTGCTGCAT
CAGGATTGGCTGAATGGCAAGGAATACAAGTGTAAAGTCTCAAAC
AAGGCCCTGCCTGCTCCAATTGAGAAAACAATCTCAAAGGCCAAG
GGACAGCCTAGGGAACCCCAGGTCTACACCCTGCCACCTTCAAGAG
AGGAAATGACCAAAAACCAGGTGTCCCTGACATGCCTGGTCAAAG
GCTTCTACCCTTCTGACATTGCTGTGGAGTGGGAGTCAAATGGACA
GCCTGAGAACAACTACAAAACAACCCCCCCTGTGCTGGATTCTGAT
GGCTCTTTCTTTCTGTACTCCAAACTGACTGTGGACAAGTCTAGATG
GCAGCAGGGGAATGTCTTTTCTTGCTCTGTCATGCATGAGGCTCTG
CATAACCACTACACTCAGAAATCCCTGTCTCTGTCTCCCGGGAAAT
GATAGTAAAAGCTT

UMG1 Chimeric Light Chain, nucleic acid (clone NUC 7201_evi-5 UMG.1.CH-
hk.LC) [SEQ ID NO: 28]
GCGGCCGCCATGAATTTTGGACTGAGGCTGATTTTCCTGGTG
CTGACCCTGAAAGGCGTCCAGTGTCAGATCGCCCTGACCCA
GAGTCCTGCAATTATGTCAGCCTCCCCGGGCGAGAAGGTGA
CCATGACATGCTCCGCTTCCAGCTCTGTCAGTTCAATGTACT
GGTATCAGCTGAAGCCCGGCTCCTCCCCCAGGCTGCTGATCT
ACGACACAAGCAAAATGGCATCTGGCGTGCCCATTCGGTTC
AGCGGCTCTGGAAGTGGGACTTCATTTTCCCTGACCGTGTCC
AGAGTCGAGGCTGAAGATGCCGCTACATACTATTGTCAGCA
GTGGTCTAGTTATCCCCCTATCACTTTCGGTGCAGGCAGCAA
GCTCGAGCTGAAACGTACGGTCGCGGCGCCTTCTGTGTTCAT
TTTCCCCCCATCTGATGAACAGCTGAAATCTGGCACTGCTTC
TGTGGTCTGTCTGCTGAACAACTTCTACCCTAGAGAGGCCAA
AGTCCAGTGGAAAGTGGACAATGCTCTGCAGAGTGGGAATT
CCCAGGAATCTGTCACTGAGCAGGACTCTAAGGATAGCACA
TACTCCCTGTCCTCTACTCTGACACTGAGCAAGGCTGATTAC
GAGAAACACAAAGTGTACGCCTGTGAAGTCACACATCAGGG
GCTGTCTAGTCCTGTGACCAAATCCTTCAATAGGGGAGAGTG
CTGATAGTAAAAGCTT Humanized Heavy Chain (VH3), nucleic acid (clone NUC 7683 evi-5 UMG.HUM3-
h1.HC), nucleic acid [SEQ ID NO: 29]
GCGGCCGCCATGAATTTTGGACTGAGGCTGATTTTCCTGGTGCTGA
CCCTGAAAGGCGTCCAGTGTGAGGTGCAGCTGGTGGAATCTGGCG
GAGGGCTGGTGCAGCCCGGTGGCAGCCTGAGACTGTCTTGCGTCGC
CAGTGGATTCACCTTTTCCAGCTTCGGGATGCACTGGGTCAGGCAG
```

-continued

GCACCTGGAAAGGGGCTGGAGTGGGTGGCCTACATCTCTAGTGGTT

CCGGCAACTTCTACTATGTGGACACTGTCAAGGGCAGGTTTACCAT

TAGCCGGGATAACGCTAAAAATTCTCTGTATCTGCAAATGAATAGT

CTGAGAGCCGAAGACACAGCCGTGTACTATTGTGCTAGATCAACTT

ACTATCATGGTTCCCGCGGCGCAATGGATTACTGGGGACAGGGGAC

CCTGGTGACAGTCTCGAGCGCTAGCACAAAGGGCCCTAGTGTGTTT

CCTCTGGCTCCCTCTTCCAAATCCACTTCTGGTGGCACTGCTGCTCT

GGGATGCCTGGTGAAGGATTACTTTCCTGAACCTGTGACTGTCTCA

TGGAACTCTGGTGCTCTGACTTCTGGTGTCCACACTTTCCCTGCTGT

GCTGCAGTCTAGTGGACTGTACTCTCTGTCATCTGTGGTCACTGTGC

CCTCTTCATCTCTGGGAACCCAGACCTACATTTGTAATGTGAACCA

CAAACCATCCAACACTAAAGTGGACAAAAAAGTGGAACCCAAATC

CTGTGACAAAACCCACACCTGCCCACCTTGTCCTGCCCCTGAACTG

CTGGGAGGACCTTCTGTGTTTCTGTTCCCCCCCAAACCAAAGGATA

CCCTGATGATCTCTAGAACCCCTGAGGTGACATGTGTGGTGGTGGA

TGTGTCTCATGAGGACCCTGAGGTCAAATTCAACTGGTACGTGGAT

GGAGTGGAAGTCCACAATGCCAAAACCAAGCCTAGAGAGGAACAG

TACAATTCAACCTACAGAGTGGTCAGTGTGCTGACTGTGCTGCATC

AGGATTGGCTGAATGGCAAGGAATACAAGTGTAAAGTCTCAAACA

AGGCCCTGCCTGCTCCAATTGAGAAAACAATCTCAAAGGCCAAGG

GACAGCCTAGGGAACCCCAGGTCTACACCCTGCCACCTTCAAGAGA

GGAAATGACCAAAAACCAGGTGTCCCTGACATGCCTGGTCAAAGG

CTTCTACCCTTCTGACATTGCTGTGGAGTGGGAGTCAAATGGACAG

CCTGAGAACAACTACAAAACAACCCCCCCTGTGCTGGATTCTGATG

GCTCTTTCTTTCTGTACTCCAAACTGACTGTGGACAAGTCTAGATGG

CAGCAGGGGAATGTCTTTTCTTGCTCTGTCATGCATGAGGCTCTGC

ATAACCACTACACTCAGAAATCCCTGTCTCTGTCTCCCGGGAAATG

ATAGTAAAAGCTT

Humanized Light Chain (VL4), nucleic acid (clone NUC 7700_evi-5
UMG.HUM4-hk.LC) [SEQ ID NO: 30]
GCGGCCGCCATGAATTTTGGACTGAGGCTGATTTTCCTGGTG

CTGACCCTGAAAGGCGTCCAGTGTCAGGTGGTCATGACCCA

GTCTCCTGCTTTCCTGTCCGTGACACCGGGCGAGAAGGTCAC

CATCACATGCTCCGCATCCAGCTCTGTCAGTTCAATGTACTG

GTATCAGCTGAAGCCAGACCAGGCACCCAAACTGCTGATCT

ACGATACATCTAAAATGGCCAGTGGCGTCCCCATTAGGTTCT

CGGGATCGGGGAGCGGAACTGACTTCACTTTTACCGTGTCG

AGCGTCGAGGCCGAAGATGCCGCTACCTACTATTGTCAGCA

GTGGTCTAGTTATCCCCCTATCACATTTGGCGGAGGGACTAA

GGTGGAGATTAAGCGTACGGTCGCGGCGCCTTCTGTGTTCAT

TTTCCCCCCATCTGATGAACAGCTGAAATCTGGCACTGCTTC

TGTGGTCTGTCTGCTGAACAACTTCTACCCTAGAGAGGCCAA

AGTCCAGTGGAAAGTGGACAATGCTCTGCAGAGTGGGAATT

CCCAGGAATCTGTCACTGAGCAGGACTCTAAGGATAGCACA

TACTCCCTGTCCTCTACTCTGACACTGAGCAAGGCTGATTAC

GAGAAACACAAAGTGTACGCCTGTGAAGTCACACATCAGGG

GCTGTCTAGTCCTGTGACCAAATCCTTCAATAGGGGAGAGTG

CTGATAGTAAAAGCTT

Mouse Heavy Chain, nucleic acid (clone NUC 29709_evi-5 UMG.VH-ml.HC) [SEQ ID NO: 31]
GCGGCCGCCATGAATTTTGGACTGAGGCTGATTTTCCTGGTG

CTGACCCTGAAAGGCGTCCAGTGTGACGTGCAGCTGGTCGA

GAGTGGCGGAGGGCTGGTGCAGCCCGGTGGCAGCCGAAAGC

TGTCTTGCGTCGCTAGTGGTTTCACCTTTTCCAGCTTCGGCAT

GCACTGGGTGAGGCAGGCACCTGAGAAAGGACTGGAATGG

GTCGCCTACATCTCTAGTGGAAGCGGGAACTTCTACTATGTG

GACACTGTCAAGGGGAGGTTTACCATTTCTCGGGATAACCC

AAAAAATACACTGTTTCTGCAAATGACTTCACTGAGATCCGA

AGACACCGCCATGTACTATTGTGCTAGATCAACATACTACCA

CGGCTCCAGGGGCGCTATGGACTATTGGGGTCAGGGCACCT

CTGTGACAGTCTCGAGCGCAAAAACAACCCCTCCAAGCGTC

TACCCCCTGGCGCCTGGGAGCGCGGCGCAGACGAACTCGAT

GGTCACGTTGGGGTGCCTCGTCAAGGGATATTTCCCGGAGCC

AGTCACGGTCACGTGGAACTCGGGGAGCCTGTCGAGCGGCG

TCCACACGTTCCCGGCAGTCCTGCAAAGCGACCTGTACACGC

TGAGCTCGTCAGTCACGGTCCCGAGCTCGACGTGGCCGTCG

GAGACGGTCACGTGCAACGTGGCGCACCCGGCGAGCTCGAC

GAAAGTGGACAAGAAGATCGTGCCGCGGGACTGCGGGTGCA

AGCCATGCATATGCACGGTCCCGGAAGTGTCGAGCGTGTTC

ATCTTCCCGCCGAAGCCGAAGGACGTGCTGACGATCACGCT

GACGCCGAAAGTCACGTGCGTCGTCGTAGACATCTCGAAGG

ACGACCCGGAAGTCCAGTTCTCGTGGTTCGTCGACGACGTG

GAAGTCCACACGGCGCAGACGCAGCCGCGGGAGGAGCAGTT

CAACTCGACGTTCAGGAGCGTGTCGGAGCTGCCGATCATGC

ACCAGGACTGGCTGAACGGGAAGGAGTTCAAGTGCCGCGTC

AACTCGGCGGCGTTCCCAGCGCCAATTGAGAAGACGATCTC

GAAGACGAAGGGGCGGCCGAAAGCGCCGCAAGTCTACACG

ATCCCGCCGCCGAAGGAGCAGATGGCGAAGGACAAAGTCTC

GCTGACGTGCATGATCACGGACTTCTTCCCGGAGGACATCAC

GGTCGAGTGGCAGTGGAACGGGCAGCCTGCAGAGAACTACA

AGAACACGCAGCCGATCATGGACACGGACGGGAGCTACTTC

GTGTACTCGAAGCTGAACGTGCAGAAGTCGAACTGGGAGGC

GGGGAACACGTTCACGTGCTCAGTCCTGCACGAGGGGCTGC

ACAACCACCACACGGAGAAGAGCCTGTCGCACTCGCCCGGG

AAATGATAAGCTT

Mouse light chain, nucleic acid (clone NUC 29710_evi-5 UMG.VL-mk.LC) [SEQ ID NO: 32]
GCGGCCGCCATGAATTTTGGACTGAGGCTGATTTTCCTGGTG

CTGACCCTGAAAGGCGTCCAGTGTCAGATCGCCCTGACCCA

GAGTCCTGCAATTATGTCAGCCTCCCCGGGCGAGAAGGTGA

CCATGACATGCTCCGCTTCCAGCTCTGTCAGTTCAATGTACT

GGTATCAGCTGAAGCCCGGCTCCTCCCCCAGGCTGCTGATCT

ACGACACAAGCAAAATGGCATCTGGCGTGCCCATTCGGTTC

AGCGGCTCTGGAAGTGGGACTTCATTTTCCCTGACCGTGTCC

AGAGTCGAGGCTGAAGATGCCGCTACATACTATTGTCAGCA

GTGGTCTAGTTATCCCCCTATCACTTTCGGTGCAGGCAGCAA

GCTCGAGCTGAAACGGGCTGACGCGGCGCCTACAGTCTCCA

TTTTTCCACCTAGTAGCGAACAGCTGACATCCGGGGGGCTT

CCGTCGTCTGCTTTCTGAACAACTTTTACCCCAAGGACATCA

ACGTGAAGTGGAAAATTGATGGCTCCGAGAGGCAGAACGGA

GTCCTGAATTCTTGGACCGACCAGGATTCTAAGGACAGTAC

ATATTCAATGTCCAGCACCCTGACACTGACTAAAGATGAGT

ACGAACGGCACAATAGCTATACCTGCGAGGCAACCCATAAA

ACAAGCACAAGCCCAATCGTCAAATCCTTCAACCGTAATGA

GTGTTGATAAGCTT

Bispecific Human Heavy Chain, nucleic acid (NUC 32827_evi-5 UMG.VH3-hl.HC-CD3.scFv) [SEQ ID NO: 33]
GCGGCCGCCATGAATTTTGGACTGAGGCTGATTTTCCTGGTG

CTGACCCTGAAAGGCGTCCAGTGTGAGGTGCAGCTGGTGGA

ATCTGGCGGAGGGCTGGTGCAGCCCGGTGGCAGCCTGAGAC

TGTCTTGCGTCGCCAGTGGATTCACCTTTTCCAGCTTCGGGA

TGCACTGGGTCAGGCAGGCACCTGGAAAGGGGCTGGAGTGG

GTGGCCTACATCTCTAGTGGTTCCGGCAACTTCTACTATGTG

GACACTGTCAAGGGCAGGTTTACCATTAGCCGGGATAACGC

TAAAAATTCTCTGTATCTGCAAATGAATAGTCTGAGAGCCGA

AGACACAGCCGTGTACTATTGTGCTAGATCAACTTACTATCA

TGGTTCCCGCGGCGCAATGGATTACTGGGGACAGGGGACCC

TGGTGACAGTCTCGAGCGCTAGCACAAAGGGCCCTAGTGTG

TTTCCTCTGGCTCCCTCTTCCAAATCCACTTCTGGTGGCACTG

CTGCTCTGGGATGCCTGGTGAAGGATTACTTTCCTGAACCTG

TGACTGTCTCATGGAACTCTGGTGCTCTGACTTCTGGTGTCC

ACACTTTCCCTGCTGTGCTGCAGTCTAGTGGACTGTACTCTC

TGTCATCTGTGGTCACTGTGCCCTCTTCATCTCTGGGAACCC

AGACCTACATTTGTAATGTGAACCACAAACCATCCAACACT

AAAGTGGACAAAAAAGTGGAACCCAAATCCTGTGACAAAAC

CCACACCTGCCCACCTTGTCCTGCCCCTGAACTGCTGGGAGG

```
ACCTTCTGTGTTTCTGTTCCCACCAAAACCAAAAGATACCCT

GATGATCTCTAGAACCCCTGAGGTGACATGTGTGGTGGTGG

ATGTGTCTCATGAGGACCCTGAGGTCAAATTCAACTGGTACG

TGGATGGAGTGGAAGTCCACAATGCCAAAACCAAGCCTAGA

GAGGAACAGTACAATTCAACCTACAGAGTGGTCAGTGTGCT

GACTGTGCTGCATCAGGATTGGCTGAATGGCAAGGAATACA

AGTGTAAAGTCTCAAACAAGGCCCTGCCTGCTCCAATTGAG

AAAACAATCTCAAAGGCCAAGGGACAGCCTAGGGAACCCCA

GGTCTACACCCTGCCACCTTCAAGAGAGGAAATGACCAAAA

ACCAGGTGTCCCTGACATGCCTGGTCAAAGGCTTCTACCCTT

CTGACATTGCTGTGGAGTGGGAGTCAAATGGACAGCCTGAG

AACAACTACAAAACAACCCCCCCTGTGCTGGATTCTGATGG

CTCTTTCTTTCTGTACTCCAAACTGACTGTGGACAAGTCTAG

ATGGCAGCAGGGGAATGTCTTTTCTTGCTCTGTCATGCATGA

GGCTCTGCATAACCACTACACTCAGAAATCCCTGTCTCTGTC

TCCTGGCAAAGGCGGCGGAGGATCCGGGGGTGGGGAAGC

GGCGGAGGAGGTAGCGACATCAAACTGCAGCAGAGTGGAG

CCGAACTGGCTAGACCTGGTGCTTCTGTGAAAATGTCCTGTA

AAACCTCCGGTTACACCTTTACCCGGTACACAATGCATTGGG

TGAAACAGAGGCCTGGACAGGGGCTGGAATGGATCGGATAC

ATCAACCCTAGTCGGGGATACACAAACTACAACCAGAAATT

CAAAGACAAGGCCACCCTGACAACCGACAAATCTTCTTCTA

CTGCCTACATGCAGCTGTCATCTCTGACTTCCGAGGATAGTG

CCGTCTACTACTGTGCTCGGTACTACGATGATCATTACTGTC

TGGACTACTGGGGCCAGGGAACAACACTTACCGTTTCTAGC

GTCGAGGGCGGATCTGGCGGTAGCGGTGGATCTGGAGGCTC

TGGAGGAGTGGATGATATCCAGCTGACCCAGTCTCCTGCTAT

CATGTCCGCTTCACCTGGCGAAAAAGTGACCATGACCTGCC

GTGCTTCATCTTCCGTGTCATACATGAATTGGTACCAGCAGA

AATCTGGCACATCTCCCAAACGATGGATCTACGACACCTCA

AAAGTCGCTAGTGGCGTGCCTTACCGTTTCTCCGGTTCCGGA

TCTGGAACATCATACTCCCTGACCATCTCTTCTATGGAGGCT

GAGGATGCTGCCACATACTACTGTCAGCAGTGGAGTAGCAA

TCCTCTGACCTTTGGTGCTGGGACAAAACTGGAGCTGAAATG

ATAAGCTTTGA

Chimeric Heavy Chain, (clone PRO 7200_evi-5 UMG.1.CH-hl.HC) [SEQ ID
NO: 34]
DVQLVESGGGLVQPGGSRKLSCVASGFTFSSFGMHWVRQAPE

KGLEWVAYISSGSGNFYYVDTVKGRFTISRDNPKNTLFLQMTS

LRSEDTAMYYCARSTYYHGSRGAMDYWGQGTSVTVSSASTK

GPSVFPLAPSSKSTSGGTAALGCLVKDYFPEPVTVSWNSGALTS
```

```
GVHTFPAVLQSSGLYSLSSVVTVPSSSLGTQTYICNVNHKPSNT

KVDKKVEPKSCDKTHTCPPCPAPELLGGPSVFLFPPKPKDTLMI

SRTPEVTCVVVDVSHEDPEVKFNWYVDGVEVHNAKTKPREEQ

YNSTYRVVSVLTVLHQDWLNGKEYKCKVSNKALPAPIEKTISK

AKGQPREPQVYTLPPSREEMTKNQVSLTCLVKGFYPSDIAVEW

ESNGQPENNYKTTPPVLDSDGSFFLYSKLTVDKSRWQQGNVFS

CSVMHEALHNHYTQKSLSLSPGK

Chimeric Light Chain (clone PRO 7201_evi-5 UMG.1.CH-hk.LC) [SEQ ID
NO: 35]
QIALTQSPAIMSASPGEKVTMTCSASSSVSSMYWYQLKPGSSPR

LLIYDTSKMASGVPIRFSGSGSGTSFSLTVSRVEAEDAATYYCQ

QWSSYPPITFGAGSKLELKRTVAAPSVFIFPPSDEQLKSGTASVV

CLLNNFYPREAKVQWKVDNALQSGNSQESVTEQDSKDSTYSL

SSTLTLSKADYEKHKVYACEVTHQGLSSPVTKSFNRGEC

Human Heavy Chain (VH3)(clone PRO 7683_evi-5 UMG.HUM3-hl.HC)
[SEQ ID NO: 36]
EVQLVESGGGLVQPGGSLRLSCVASGFTFSSFGMHWVRQAPG

KGLEWVAYISSGSGNFYYVDTVKGRFTISRDNAKNSLYLQMNS

LRAEDTAVYYCARSTYYHGSRGAMDYWGQGTLVTVSSASTK

GPSVFPLAPSSKSTSGGTAALGCLVKDYFPEPVTVSWNSGALTS

GVHTFPAVLQSSGLYSLSSVVTVPSSSLGTQTYICNVNHKPSNT

KVDKKVEPKSCDKTHTCPPCPAPELLGGPSVFLFPPKPKDTLMI

SRTPEVTCVVVDVSHEDPEVKFNWYVDGVEVHNAKTKPREEQ

YNSTYRVVSVLTVLHQDWLNGKEYKCKVSNKALPAPIEKTISK

AKGQPREPQVYTLPPSREEMTKNQVSLTCLVKGFYPSDIAVEW

ESNGQPENNYKTTPPVLDSDGSFFLYSKLTVDKSRWQQGNVFS

CSVMHEALHNHYTQKSLSLSPGK

Human Light Chain (VL4)(clone PRO 7700_evi-5 UMG.VL4-hk.LC) [SEQ
ID NO: 37]
QVVMTQSPAFLSVTPGEKVTITCSASSSVSSMYWYQLKPDQAP

KLLIYDTSKMASGVPIRFSGSGSGTDFTFTVSSVEAEDAATYYC

QQWSSYPPITFGGGTKVEIKRTVAAPSVFIFPPSDEQLKSGTASV

VCLLNNFYPREAKVQWKVDNALQSGNSQESVTEQDSKDSTYS

LSSTLTLSKADYEKHKVYACEVTHQGLSSPVTKSFNRGEC

Mouse Heavy Chain (clone PRO 29709_evi-5 UMG.VH-ml.HC) [SEQ ID
NO: 38]
DVQLVESGGGLVQPGGSRKLSCVASGFTFSSFGMHWVRQAPE

KGLEWVAYISSGSGNFYYVDTVKGRFTISRDNPKNTLFLQMTS

LRSEDTAMYYCARSTYYHGSRGAMDYVVGQGTSVTVSSAKTTP

PSVYPLAPGSAAQTNSMVTLGCLVKGYFPEPVTVTWNSGSLSS

GVHTFPAVLQSDLYTLSSSVTVPSSTWPSETVTCNVAHPASSTK

VDKKIVPRDCGCKPCICTVPEVSSVFIFPPKPKDVLTITLTPKVTC

VVVDISKDDPEVQFSWFVDDVEVHTAQTQPREEQFNSTFRSVS

ELPIMHQDWLNGKEFKCRVNSAAFPAPIEKTISKTKGRPKAPQV

YTIPPPKEQMAKDKVSLTCMITDFFPEDITVEWQWNGQPAENY
```

KNTQPIMDTDGSYFVYSKLNVQKSNWEAGNTFTCSVLHEGLH

NHHTEKSLSHSPGK

Mouse Light Chain (clone PRO 29710_evi-5 UMG.VL-mk.LC) [SEQ ID NO: 39]
`QIALTQSPAIMSASPGEKVTMTCSASSSVSSMYWYQLKPGSSP

RLLIYDTSKMASGVPIRFSGSGSGTSFSLTVSRVEAEDAATYYC

QQWSSYPPITFGAGSKLELKRADAAPTVSIFPPSSEQLTSGGASV

VCFLNNFYPKDINVKWKIDGSERQNGVLNSWTDQDSKDSTYS

MSSTLTLTKDEYERHNSYTCEATHKTSTSPIVKSFNRNEC

Bispecific Human Heavy Chain-CD3 (clone PRO 32827_evi-5 UMG.VH3-hl.HC-CD3.scFv) [SEQ ID NO: 40]
EVQLVESGGGLVQPGGSLRLSCVASGFTFSSFGMHWVRQAPG

KGLEWVAYISSGSGNFYYVDTVKGRFTISRDNAKNSLYLQMNS

LRAEDTAVYYCARSTYYHGSRGAMDYWGQGTLVTVSSASTK

GPSVFPLAPSSKSTSGGTAALGCLVKDYFPEPVTVSWNSGALTS

GVHTFPAVLQSSGLYSLSSVVTVPSSSLGTQTYICNVNHKPSNT

KVDKKVEPKSCDKTHTCPPCPAPELLGGPSVFLFPPKPKDTLMI

SRTPEVTCVVVDVSHEDPEVKFNWYVDGVEVHNAKTKPREEQ

YNSTYRVVSVLTVLHQDWLNGKEYKCKVSNKALPAPIEKTISK

AKGQPREPQVYTLPPSREEMTKNQVSLTCLVKGFYPSDIAVEW

ESNGQPENNYKTTPPVLDSDGSFFLYSKLTVDKSRWQQGNVFS

CSVMHEALHNHYTQKSLSLSPGKGGGGSGGGGSGGGGSDIKL

QQSGAELARPGASVKMSCKTSGYTFTRYTMHWVKQRPGQGLE

WIGYINPSRGYTNYNQKFKDKATLTTDKSSSTAYMQLSSLTSE

DSAVYYCARYYDDHYCLDYWGQGTTLTVSSVEGGSGGSGGS

GGSGGVDDIQLTQSPAIMSASPGEKVTMTCRASSSVSYMNWY

QQKSGTSPKRWIYDTSKVASGVPYRFSGSGSGTSYSLTISSMEA

EDAATYYCQQWSSNPLTFGAGTKLELK

Plasmid sequence for CAR-T, nucleic acid [SEQ ID NO: 41]:
ACGCGTGTAGTCTTATGCAATACTCTTGTAGTCTTGCAACAT

GGTAACGATGAGTTAGCAACATGCCTTACAAGGAGAGAAAA

AGCACCGTGCATGCCGATTGGTGGAAGTAAGGTGGTACGAT

CGTGCCTTATTAGGAAGGCAACAGACGGGTCTGACATGGAT

TGGACGAACCACTGAATTGCCGCATTGCAGAGATATTGTATT

TAAGTGCCTAGCTCGATACAATAAACGGGTCTCTCTGGTTAG

ACCAGATCTGAGCCTGGGAGCTCTCTGGCTAACTAGGGAAC

CCACTGCTTAAGCCTCAATAAAGCTTGCCTTGAGTGCTTCAA

GTAGTGTGTGCCCGTCTGTTGTGTGACTCTGGTAACTAGAGA

TCCCTCAGACCCTTTTAGTCAGTGTGGAAAATCTCTAGCAGT

GGCGCCCGAACAGGGACCTGAAAGCGAAAGGGAAACCAGA

GCTCTCTCGACGCAGGACTCGGCTTGCTGAAGCGCGCACGG

CAAGAGGCGAGGGGCGGCGACTGGTGAGTACGCCAAAAATT

TTGACTAGCGGAGGCTAGAAGGAGAGAGATGGGTGCGAGA

```
GCGTCAGTATTAAGCGGGGGAGAATTAGATCGCGATGGGAA

AAAATTCGGTTAAGGCCAGGGGGAAAGAAAAAATATAAATT

AAAACATATAGTATGGGCAAGCAGGGAGCTAGAACGATTCG

CAGTTAATCCTGGCCTGTTAGAAACATCAGAAGGCTGTAGA

CAAATACTGGGACAGCTACAACCATCCCTTCAGACAGGATC

AGAAGAACTTAGATCATTATATAATACAGTAGCAACCCTCT

ATTGTGTGCATCAAAGGATAGAGATAAAAGACACCAAGGAA

GCTTTAGACAAGATAGAGGAAGAGCAAACAAAAGTAAGA

CCACCGCACAGCAAGCGGCCACTGATCTTCAGACCTGGAGG

AGGAGATATGAGGGACAATTGGAGAAGTGAATTATATAAAT

ATAAAGTAGTAAAAATTGAACCATTAGGAGTAGCACCCACC

AAGGCAAAGAGAAGAGTGGTGCAGAGAGAAAAAAGAGCAG

TGGGAATAGGAGCTTTGTTCCTTGGGTTCTTGGGAGCAGCAG

GAAGCACTATGGGCGCAGCCTCAATGACGCTGACGGTACAG

GCCAGACAATTATTGTCTGGTATAGTGCAGCAGCAGAACAA

TTTGCTGAGGGCTATTGAGGCGCAACAGCATCTGTTGCAACT

CACAGTCTGGGGCATCAAGCAGCTCCAGGCAAGAATCCTGG

CTGTGGAAAGATACCTAAAGGATCAACAGCTCCTGGGGATT

TGGGGTTGCTCTGGAAAACTCATTTGCACCACTGCTGTGCCT

TGGAATGCTAGTTGGAGTAATAAATCTCTGGAACAGATTGG

AATCACACGACCTGGATGGAGTGGGACAGAGAAATTAACAA

TTACACAAGCTTAATACACTCCTTAATTGAAGAATCGCAAAA

CCAGCAAGAAAAGAATGAACAAGAATTATTGGAATTAGATA

AATGGGCAAGTTTGTGGAATTGGTTTAACATAACAAATTGG

CTGTGGTATATAAAATTATTCATAATGATAGTAGGAGGCTTG

GTAGGTTTAAGAATAGTTTTTGCTGTACTTTCTATAGTGAAT

AGAGTTAGGCAGGGATATTCACCATTATCGTTTCAGACCCAC

CTCCCAACCCCGAGGGGACCCGACAGGCCCGAAGGAATAGA

AGAAGAAGGTGGAGAGAGAGACAGAGACAGATCCATTCGA

TTAGTGAACGGATCTCGACGGTATCGGTTAACTTTTAAAAGA

AAAGGGGGGATTGGGGGGTACAGTGCAGGGGAAAGAATAG

TAGACATAATAGCAACAGACATACAAACTAAAGAATTACAA

AAACAAATTACAAAATTCAAAATTTTATCGATACTAGTATTA

TGCCCAGTACATGACCTTATGGGACTTTCCTACTTGGCAGTA

CATCTACGTATTAGTCATCGCTATTACCATGGTGATGCGGTT

TTGGCAGTACATCAATGGGCGTGGATAGCGGTTTGACTCAC

GGGGATTTCCAAGTCTCCACCCCATTGACGTCAATGGGAGTT

TGTTTTGGCACCAAAATCAACGGGACTTTCCAAAATGTCGTA

ACAACTCCGCCCCATTGACGCAAATGGGCGGTAGGCGTGTA

CGGTGGGAGGTTTATATAAGCAGAGCTCGTTTAGTGAACCG
```

```
TCAGATCGCCTGGAGACGCCATCCACGCTGTTTTGACCTCCA

TAGAAGATTCTAGAGCCGCCACCATGGCCCTCCCAGTAACC

GCCCTCCTGCTCCCCCTTGCTTTGCTGCTGCACGCCGCACGG

CCCGCTAGCGAAGTTCAGCTTGTCGAATCTGGGGAGGGTT

GGTTCAGCCGGGAGGGAGTCTGCGCCTTTCTTGCGTGGCTTC

AGGCTTTACCTTTTCCAGTTTTGGGATGCATTGGGTACGACA

AGCACCTGGGAAAGGACTGGAGTGGGTGGCATATATATCAA

GCGGCAGCGGAAACTTCTACTACGTTGACACTGTAAAAGGG

AGATTCACCATCTCCCGAGACAACGCTAAAAACTCACTCTAT

CTTCAAATGAATAGCCTGCGAGCTGAGGATACGGCGGTTTA

CTACTGCGCGATCAACATATTACCACGGGTCCAGAGGCG

CGATGGACTACTGGGGCAAGGGACTTTGGTTACTGTGGGT

GGCGGAGGCAGCGGCGGTGGTGGTTCCGGAGGCGGCGGTTC

TCAAGTCGTTATGACCCAAAGCCCCGCATTTCTTTCTGTGAC

TCCAGGCGAGAAGGTGACGATAACCTGTTCAGCCAGTTCCA

GTGTCTCCAGTATGTATTGGTATCAACTGAAACCAGATCAGG

CACCGAAGCTTTTGATATATGACACATCTAAAATGGCATCAG

GGGTACCCATAAGGTTTAGCGGGTCCGGCTCAGGGACCGAT

TTTACGTTTACTGTCTCATCCGTCGAGGCGGAAGATGCAGCG

ACCTATTACTGCCAGCAGTGGAGTAGTTATCCCCCCATCACG

TTTGGCGGCGGTACGAAAGTGGAGATAAAGGACTACAAAGA

CGATGACGACAAGCTCGAGACCACGACGCCAGCGCCGCGAC

CACCAACACCGGCGCCCACCATCGCGTCGCAGCCCCTGTCCC

TGCGCCCAGAGGCGTGCCGGCCAGCGGCGGGGGCGCAGTG

CACACGAGGGGCTGGACTTCGCCTGTGATTTTTGGGTGCTG

GTGGTGGTTGGTGGAGTCCTGGCTTGCTATAGCTTGCTAGTA

ACAGTGGCCTTTATTATTTTCTGGGTGAGGAGTAAGAGGAGC

AGGCTCCTGCACAGTGACTACATGAACATGACTCCCCGCCG

CCCCGGGCCCACCCGCAAGCATTACCAGCCCTATGCCCCACC

ACGCGACTTCGCAGCCTATCGCTCCAAACGGGGCAGAAAGA

AACTCCTGTATATATTCAAACAACCATTTATGAGACCAGTAC

AAACTACTCAAGAGGAAGATGGCTGTAGCTGCCGATTTCCA

GAAGAAGAAGAAGGAGGATGTGAACTGAGAGTGAAGTTCA

GCAGGAGCGCAGACGCCCCCGCGTACCAGCAGGGCCAGAAC

CAGCTCTATAACGAGCTCAATCTAGGACGAAGAGAGGAGTA

CGATGTTTTGGACAAGAGACGTGGCCGGGACCCTGAGATGG

GGGGAAAGCCGAGAAGGAAGAACCCTCAGGAAGGCCTGTA

CAATGAACTGCAGAAAGATAAGATGGCGGAGGCCTACAGTG

AGATTGGGATGAAAGGCGAGCGCCGGAGGGGCAAGGGGCA

CGATGGCCTTTACCAGGGTCTCAGTACAGCCACCAAGGACA

CCTACGACGCCCTTCACATGCAGGCCCTGCCCCCTCGCTAAT
```

```
AGGAATTCGTCGACAATCAACCTCTGGATTACAAAATTTGTG

AAAGATTGACTGGTATTCTTAACTATGTTGCTCCTTTTACGCT

ATGTGGATACGCTGCTTTAATGCCTTTGTATCATGCTATTGCT

TCCCGTATGGCTTTCATTTTCTCCTCCTTGTATAAATCCTGGT

TGCTGTCTCTTTATGAGGAGTTGTGGCCCGTTGTCAGGCAAC

GTGGCGTGGTGTGCACTGTGTTTGCTGACGCAACCCCCACTG

GTTGGGCATTGCCACCACCTGTCAGCTCCTTTCCGGGACTT

TCGCTTTCCCCCTCCCTATTGCCACGGCGGAACTCATCGCCG

CCTGCCTTGCCCGCTGCTGGACAGGGGCTCGGCTGTTGGGCA

CTGACAATTCCGTGGTGTTGTCGGGGAAATCATCGTCCTTTC

CTTGGCTGCTCGCCTGTGTTGCCACCTGGATTCTGCGCGGGA

CGTCCTTCTGCTACGTCCCTTCGGCCCTCAATCCAGCGGACC

TTCCTTCCCGCGGCCTGCTGCCGGCTCTGCGGCCTCTTCCGC

GTCTTCGCCTTCGCCCTCAGACGAGTCGGATCTCCCTTTGGG

CCGCCTCCCCGCCTGGTACCTTTAAGACCAATGACTTACAAG

GCAGCTGTAGATCTTAGCCACTTTTTAAAAGAAAAGGGGGG

ACTGGAAGGGCTAATTCACTCCCAACGAAAATAAGATCTGC

TTTTTGCTTGTACTGGGTCTCTCTGGTTAGACCAGATCTGAG

CCTGGGAGCTCTCTGGCTAACTAGGGAACCCACTGCTTAAGC

CTCAATAAAGCTTGCCTTGAGTGCTTCAAGTAGTGTGTGCCC

GTCTGTTGTGTGACTCTGGTAACTAGAGATCCCTCAGACCCT

TTTAGTCAGTGTGGAAAATCTCTAGCAGTAGTAGTTCATGTC

ATCTTATTATTCAGTATTTATAACTTGCAAAGAAATGAATAT

CAGAGAGTGAGAGGAACTTGTTTATTGCAGCTTATAATGGTT

ACAAATAAAGCAATAGCATCACAAATTTCACAAATAAAGCA

TTTTTTTCACTGCATTCTAGTTGTGGTTTGTCCAAACTCATCA

ATGTATCTTATCATGTCTGGCTCTAGCTATCCCGCCCCTAACT

CCGCCCAGTTCCGCCCATTCTCCGCCCCATGGCTGACTAATT

TTTTTTATTTATGCAGAGGCCGAGGCCGCCTCGGCCTCTGAG

CTATTCCAGAAGTAGTGAGGAGGCTTTTTTGGAGGCCTAGAC

TTTTGCAGAGACGGCCCAAATTCGTAATCATGGTCATAGCTG

TTTCCTGTGTGAAATTGTTATCCGCTCACAATTCCACACAAC

ATACGAGCCGGAAGCATAAAGTGTAAAGCCTGGGGTGCCTA

ATGAGTGAGCTAACTCACATTAATTGCGTTGCGCTCACTGCC

CGCTTTCCAGTCGGGAAACCTGTCGTGCCAGCTGCATTAATG

AATCGGCCAACGCGCGGGGAGAGGCGGTTTGCGTATTGGGC

GCTCTTCCGCTTCCTCGCTCACTGACTCGCTGCGCTCGGTCGT

TCGGCTGCGGCGAGCGGTATCAGCTCACTCAAAGGCGGTAA

TACGGTTATCCACAGAATCAGGGGATAACGCAGGAAAGAAC

ATGTGAGCAAAAGGCCAGCAAAAGGCCAGGAACCGTAAAA
```

-continued

```
AGGCCGCGTTGCTGGCGTTTTTCCATAGGCTCCGCCCCCTG

ACGAGCATCACAAAAATCGACGCTCAAGTCAGAGGTGGCGA

AACCCGACAGGACTATAAAGATACCAGGCGTTTCCCCCTGG

AAGCTCCCTCGTGCGCTCTCCTGTTCCGACCCTGCCGCTTAC

CGGATACCTGTCCGCCTTTCTCCCTTCGGGAAGCGTGGCGCT

TTCTCATAGCTCACGCTGTAGGTATCTCAGTTCGGTGTAGGT

CGTTCGCTCCAAGCTGGGCTGTGTGCACGAACCCCCCGTTCA

GCCCGACCGCTGCGCCTTATCCGGTAACTATCGTCTTGAGTC

CAACCCGGTAAGACACGACTTATCGCCACTGGCAGCAGCCA

CTGGTAACAGGATTAGCAGAGCGAGGTATGTAGGCGGTGCT

ACAGAGTTCTTGAAGTGGTGGCCTAACTACGGCTACACTAG

AAGGACAGTATTTGGTATCTGCGCTCTGCTGAAGCCAGTTAC

CTTCGGAAAAAGAGTTGGTAGCTCTTGATCCGGCAAACAAA

CCACCGCTGGTAGCGGTGGTTTTTTTGTTTGCAAGCAGCAGA

TTACGCGCAGAAAAAAAGGATCTCAAGAAGATCCTTTGATC

TTTTCTACGGGGTCTGACGCTCAGTGGAACGAAAACTCACGT

TAAGGGATTTTGGTCATGAGATTATCAAAAAGGATCTTCACC

TAGATCCTTTTAAATTAAAAATGAAGTTTTAAATCAATCTAA

AGTATATATGAGTAAACTTGGTCTGACAGTTACCAATGCTTA

ATCAGTGAGGCACCTATCTCAGCGATCTGTCTATTTCGTTCA

TCCATAGTTGCCTGACTCCCCGTCGTGTAGATAACTACGATA

CGGGAGGGCTTACCATCTGGCCCCAGTGCTGCAATGATACC

GCGAGACCCACGCTCACCGGCTCCAGATTTATCAGCAATAA

ACCAGCCAGCCGGAAGGGCCGAGCGCAGAAGTGGTCCTGCA

ACTTTATCCGCCTCCATCCAGTCTATTAATTGTTGCCGGGAA

GCTAGAGTAAGTAGTTCGCCAGTTAATAGTTTGCGCAACGTT

GTTGCCATTGCTACAGGCATCGTGGTGTCACGCTCGTCGTTT

GGTATGGCTTCATTCAGCTCCGGTTCCCAACGATCAAGGCGA

GTTACATGATCCCCCATGTTGTGCAAAAAAGCGGTTAGCTCC

TTCGGTCCTCCGATCGTTGTCAGAAGTAAGTTGGCCGCAGTG

TTATCACTCATGGTTATGGCAGCACTGCATAATTCTCTTACT

GTCATGCCATCCGTAAGATGCTTTTCTGTGACTGGTGAGTAC

TCAACCAAGTCATTCTGAGAATAGTGTATGCGGCGACCGAG

TTGCTCTTGCCCGGCGTCAATACGGGATAATACCGCGCCACA

TAGCAGAACTTTAAAAGTGCTCATCATTGGAAAACGTTCTTC

GGGGCGAAAACTCTCAAGGATCTTACCGCTGTTGAGATCCA

GTTCGATGTAACCCACTCGTGCACCCAACTGATCTTCAGCAT

CTTTTACTTTCACCAGCGTTTCTGGGTGAGCAAAAACAGGAA

GGCAAAATGCCGCAAAAAAGGGAATAAGGGCGACACGGAA

ATGTTGAATACTCATACTCTTCCTTTTTCAATATTATTGAAGC

ATTTATCAGGGTTATTGTCTCATGAGCGGATACATATTTGAA
```

```
TGTATTTAGAAAAATAAACAAATAGGGGTTCCGCGCACATT

TCCCCGAAAAGTGCCACCTGACGTCTAAGAAACCATTATTAT

CATGACATTAACCTATAAAAATAGGCGTATCACGAGGCCCT

TTCGTCTCGCGCGTTTCGGTGATGACGGTGAAAACCTCTGAC

ACATGCAGCTCCCGGAGACGGTCACAGCTTGTCTGTAAGCG

GATGCCGGGAGCAGACAAGCCCGTCAGGGCGCGTCAGCGGG

TGTTGGCGGGTGTCGGGGCTGGCTTAACTATGCGGCATCAG

AGCAGATTGTACTGAGAGTGCACCATATGCGGTGTGAAATA

CCGCACAGATGCGTAAGGAGAAAATACCGCATCAGGCGCCA

TTCGCCATTCAGGCTGCGCAACTGTTGGGAAGGGCGATCGG

TGCGGGCCTCTTCGCTATTACGCCAGCTGGCGAAAGGGGGA

TGTGCTGCAAGGCGATTAAGTTGGGTAACGCCAGGGTTTTCC

CAGTCACGACGTTGTAAAACGACGGCCAGTGCCAAGCTG

Recombinant human protein CD43 (aa 20 to 253) [SEQ ID NO: 42]:
STTAVQTPTSGEPLVSTSEPLSSKMYTTSITSDPKADSTGDQTSA

LPPSTSINEGSPLWTSIGASTGSPLPEPTTYQEVSIKMSSVPQETP

HATSHPAVPITANSLGSHTVTGGTITTNSPETSSRTSGAPVTTAA

SSLETSRGTSGPPLTMATVSLETSKGTSGPPVTMATDSLETSTGT

TGPPVTMTTGSLEPSSGASGPQVSSVKLSTMMSPTTSTNASTVP

FRNPDENSR
```

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

9. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A CD43 binding protein, comprising: an antibody or antigen-binding fragment thereof, wherein the antibody or the antigen-binding fragment thereof comprises a heavy chain variable domain (VH) and a light chain variable domain (VL), wherein the VH comprises framework regions and complementarity determining regions (CDRs) having the sequences SEQ ID NO: 1; SEQ ID NO: 43; and SEQ ID NO: 3, and the VL comprises framework regions and CDRs having the sequences SEQ ID NO: 4; SEQ ID NO: 5; and SEQ ID NO: 6.

2. The CD43 binding protein of claim 1, wherein the antibody VH sequence is SEQ ID NO: 7 and VL sequence is SEQ ID NO: 12.

3. The CD43 binding protein of claim 2, wherein the antibody is a murine antibody UMG1 produced by the hybridoma cell line deposited under ICLC accession number ICLC PD number 16001.

4. The CD43 binding protein of claim 2, wherein the antibody is a chimeric antibody further comprising human constant region domains.

5. The CD43 binding protein of claim 4, wherein the human constant region domains are IgG domains.

6. The CD43 binding protein of claim 5, wherein the antibody heavy chain sequence is SEQ ID NO: 34 and the antibody light chain sequence is SEQ ID NO: 35.

7. The CD43 binding protein of claim 1, wherein the antibody or the antigen-binding fragment thereof further comprises human variable domain framework regions.

8. The CD43 binding protein of claim 7, selected from SEQ ID NO: 8, SEQ ID NO: 9, SEQ ID NO: 10, and SEQ ID NO: 11; and the VL has a sequence selected from SEQ ID NO: 13, SEQ ID NO: 14, SEQ ID NO: 15, and SEQ ID NO: 16.

9. The CD43 binding protein of claim 1, wherein the antibody or the antigen-binding fragment thereof is a bivalent monospecific monoclonal antibody, a bivalent bispecific antibody, a trivalent trispecific antibody, an Fab, an F(ab')2, a scFv, a diabody, a single domain antibody, a tandab, or a flexibody.

10. The CD43 binding protein of claim 9, wherein the antibody is a monoclonal antibody.

11. The CD43 binding protein of claim 9, wherein the antibody or the antigen-binding fragment thereof is a scFv.

12. The CD43 binding protein of claim 1, wherein the antibody binds an epitope within amino acids 61-91 of wild-type CD43.

13. The CD43 binding protein of claim 1, wherein the antibody is capable of inducing antibody dependent cellular cytotoxicity (ADCC) against EGIL T3 subgroup of T cell acute lymphoblastic leukemia (T-ALL) cells, against T cell lymphoblastic lymphoma cells, against Waldenströms macroglobulinemia (WM) cells, and against tumor-infiltrating macrophages.

14. A pharmaceutical composition comprising the CD43 binding protein of claim 1.

15. A chimeric antigen receptor (CAR), the CAR comprising the scFv of claim 11, at least one T cell signaling domain, and at least one costimulatory domain.

16. The CAR of claim 15, wherein the CAR comprises a CD3ζ signaling domain.

17. The CAR of claim 15, wherein the CAR comprises a CD28 costimulatory domain.

18. The CAR of claim 15, wherein the CAR comprises a 4-1BB costimulatory domain.

19. The CAR of claim 15, wherein the CAR comprises both a CD28 costimulatory domain and a 4-1BB costimulatory domain.

20. The CAR of claim 19, wherein the CAR is encoded by the sequence of SEQ ID NO: 41.

* * * * *

UNITED STATES PATENT AND TRADEMARK OFFICE
CERTIFICATE OF CORRECTION

PATENT NO. : 11,174,318 B2
APPLICATION NO. : 16/449255
DATED : November 16, 2021
INVENTOR(S) : Tassone Page 1 of 1

It is certified that error appears in the above-identified patent and that said Letters Patent is hereby corrected as shown below:

In the Claims

In Column 165, in Claim 8, Line 61, after "claim 7," insert -- wherein the VH has a sequence --.

In Column 166, in Claim 13, Line 47, delete "Waldenströms" and insert -- Waldenström's --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*